US012617756B2

(12) United States Patent
Scherrer et al.

(10) Patent No.: US 12,617,756 B2
(45) Date of Patent: May 5, 2026

(54) SUBSTITUTED IMIDAZOLIDINES FOR TREATING A RNA VIRUS INFECTION

(71) Applicants: ABIVAX, Paris (FR); CENTRE NATIONAL DE LA RECHERCHE SCIENTIFIQUE, Paris (FR); UNIVERSITE DE MONTPELLIER, Montpellier (FR); INSTITUT CURIE, Paris (FR)

(72) Inventors: Didier Scherrer, Castelnau le Lez (FR); Florence Mahuteau, Saint Remy-les-Chevreuse (FR); Romain Najman, L'hay-les-roses (FR); Jamal Tazi, Clapiers (FR); Julien Santo, Grabels (FR); Cécile Apolit, Grabels (FR); Frederic Labeguere, Toulouse (FR); Brice Sautier, Toulouse (FR); Natacha Bienvenu, Toulouse (FR); Elisa Azzali, Verona (IT)

(73) Assignees: ABIVAX, Paris (FR); CENTRE NATIONAL DE LA RECHERCHE SCIENTIFIQUE, Paris (FR); UNIVERSITE DE MONTPELLIER, Montpellier (FR); INSTITUT CURIE, Paris (FR)

( * ) Notice: Subject to any disclaimer, the term of this patent is extended or adjusted under 35 U.S.C. 154(b) by 1144 days.

(21) Appl. No.: 17/628,402

(22) PCT Filed: Jul. 17, 2020

(86) PCT No.: PCT/EP2020/070294
§ 371 (c)(1),
(2) Date: Jan. 19, 2022

(87) PCT Pub. No.: WO2021/013733
PCT Pub. Date: Jan. 28, 2021

(65) Prior Publication Data

US 2023/0106420 A1 Apr. 6, 2023

(30) Foreign Application Priority Data

Jul. 19, 2019 (EP) .................................... 19305964
Jan. 7, 2020 (EP) .................................... 20305004

(51) Int. Cl.
*A61K 31/4168* (2006.01)
*C07D 233/44* (2006.01)
(Continued)

(52) U.S. Cl.
CPC ......... *C07D 233/44* (2013.01); *C07D 233/68* (2013.01); *C07D 401/12* (2013.01);
(Continued)

(58) Field of Classification Search
CPC .......................... A61K 31/4168; C07D 233/44
(Continued)

(56) References Cited

U.S. PATENT DOCUMENTS 9,827,237 B2 11/2017 Tazi et al.
10,718,770 B2 7/2020 Scherrer et al.
(Continued)

FOREIGN PATENT DOCUMENTS

CN 101142208 A 3/2008
JP 2011-026251 A 2/2011
(Continued)

OTHER PUBLICATIONS

Registry(STN)[online ], date-of-search Jul. 11, 2023: Sep. 9, 2016 RN: 1990473-92-1, Sep. 2, 2016 RN:1985111-93-0, Sep. 2, 2016 RN: 1985111-90-7, Sep. 2, 2016 RN: 1991597-00-2, May 13, 2016 RN: 1909835-58-0, May 9, 2016 RN:1906298-82-5.
(Continued)

*Primary Examiner* — Douglas M Willis
(74) *Attorney, Agent, or Firm* — OLIFF PLC

(57) ABSTRACT

A compound of formula (I) is:

(I)

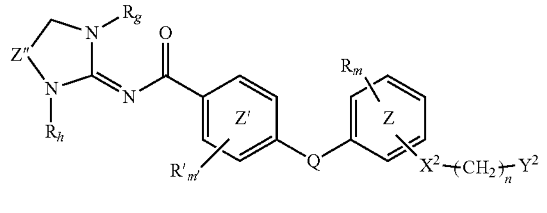

wherein: $X^2$ represents a —CO—$NR_k$— group, a —$NR'_k$—CO— group, a —O— group, a —CO— group, a —$SO_2$- group, a —CS—NH— group, a —$CH_2$—NH—, a

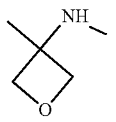

group, or a heterocyclyl, wherein the heterocyclyl is a 5- or 6-membered ring comprising 1, 2, 3 or 4 heteroatoms selected from O, S and/or N; $Y^2$ represents a hydrogen atom, a halogen atom, a hydroxyl group, a morpholinyl group, optionally substituted by a ($C_1$-$C_4$)alkyl group or a trifluoromethyl group, a bridged morpholinyl group, a ($C_5$-$C_{11}$) bicycloalkyl group, an adamantyl group, a piperidinyl group, a ($C_1$-$C_4$)alkenyl group, a —PO($OR_a$)($OR_b$) group, a 5-membered heteroaromatic ring or a —$CR^1R^2R^3$ group, or any of its pharmaceutically acceptable salt.

19 Claims, No Drawings

(51) Int. Cl.

| | |
|---|---|
| ***C07D 233/68*** | (2006.01) |
| ***C07D 401/12*** | (2006.01) |
| ***C07D 401/14*** | (2006.01) |
| ***C07D 403/12*** | (2006.01) |
| ***C07D 405/12*** | (2006.01) |
| ***C07D 405/14*** | (2006.01) |
| ***C07D 409/12*** | (2006.01) |
| ***C07D 413/12*** | (2006.01) |
| ***C07D 413/14*** | (2006.01) |
| ***C07D 417/12*** | (2006.01) |
| ***C07D 498/08*** | (2006.01) |
| ***C07F 9/6506*** | (2006.01) |

(52) U.S. Cl.
CPC ......... *C07D 401/14* (2013.01); *C07D 403/12* (2013.01); *C07D 405/12* (2013.01); *C07D 405/14* (2013.01); *C07D 409/12* (2013.01); *C07D 413/12* (2013.01); *C07D 413/14* (2013.01); *C07D 417/12* (2013.01); *C07D 498/08* (2013.01); *C07F 9/6506* (2013.01)

(58) Field of Classification Search
USPC ........................................ 514/398; 548/326.5
See application file for complete search history.

(56) References Cited

U.S. PATENT DOCUMENTS

| | | | |
|---|---|---|---|
| 12,084,422 | B2 | 9/2024 | Scherrer et al. |
| 2005/0154232 | A1 | 7/2005 | Lardy et al. |
| 2007/0197625 | A1 | 8/2007 | Casara et al. |
| 2007/0244120 | A1 | 10/2007 | Dumas et al. |
| 2014/0187641 | A1 | 7/2014 | Dalton et al. |
| 2014/0206690 | A1 | 7/2014 | Scherrer et al. |
| 2016/0031797 | A1 | 2/2016 | Dalton et al. |
| 2016/0143884 | A1 | 5/2016 | Orlemans et al. |

FOREIGN PATENT DOCUMENTS

| | | | |
|---|---|---|---|
| RU | 2379302 | C2 | 1/2010 |
| RU | 2008129807 | A | 2/2010 |
| RU | 2467007 | C2 | 11/2012 |
| RU | 2628800 | C2 | 8/2017 |
| WO | 2003/033467 | A1 | 4/2003 |
| WO | 2004/084901 | A1 | 10/2004 |
| WO | 2005/021544 | A2 | 3/2005 |
| WO | 2005/023255 | A2 | 3/2005 |
| WO | 2005058869 | A1 | 6/2005 |
| WO | 2006/037117 | A1 | 4/2006 |
| WO | 2006/097534 | A1 | 9/2006 |
| WO | 2007/081517 | A2 | 7/2007 |
| WO | 2007/135106 | A1 | 11/2007 |
| WO | 2009/087238 | A2 | 7/2009 |
| WO | 2010/143168 | A2 | 12/2010 |
| WO | 2010/143169 | A2 | 12/2010 |
| WO | 2011/163355 | A1 | 12/2011 |
| WO | 2012/080953 | A1 | 6/2012 |
| WO | 2012/131656 | A2 | 10/2012 |
| WO | 2014/164667 | A1 | 10/2014 |
| WO | 2015/001518 | A1 | 1/2015 |
| WO | 2016/135053 | A1 | 9/2016 |
| WO | 2016/135055 | A1 | 9/2016 |
| WO | 2017/158201 | A1 | 9/2017 |

OTHER PUBLICATIONS

R.I. Hernandez-Benitez et al, "Palladium-Catalyzed Synthesis of Diarylamines and 1- and 2-Oxy-genated Carbazoles: Total Syntheses of Natural Alkaloids Clauraila A, Clausenal, Clausine P, and 7-Methoxy-O-methylmukonal", Synthesis, Jul. 5, 2017, 49, A-O.
Suzuki et al, "Design, Synthesis, and Biological Activity of a Novel Series of Human Sirtuin-2-Selective Inhibitors", Journal of Medicinal Chemistry, 2012, 55(12), pp. 5760-5773.
Bianchi et al., "Compounds with antiulcer and antisecretory activity. I. 3-Aryl-benzimidazolin-2-ones and -thiones", Eur. J. Med. Chem. Chimica Therapeutica, Jul.-Aug. 16, 1981, No. 4, pp. 321-326.
May 1, 2024 Notice of Allowance issued in U.S. Appl. No. 17/259,364.
Apr. 18, 2024 Notice of Allowance issued in U.S. Appl. No. 17/259,451.
Yin et al., "Pd-Catalyzed Intermolecular Amidation of Aryl Halides: The Discovery that Xantphos Can Be Trans-Chelating in a Palladium Complex", J. Am. Chem. Soc., 2002, 124, 6043-6048.
Nov. 6, 2023 Office Action issued in U.S. Appl. No. 17/259,451.
Feb. 28, 2024 Office Action issued in U.S. Appl. No. 17/259,370.
Dardonville et al, "Bisguanidine, Bis(2-aminoimidazoline), and Polyamine Derivatives as Potent and Selective Chemotherapeutic Agents against Trypanosoma brucei rhodesiense. Synthesis and in vitro evaluation", J. Med. Chem. 2004, 47, 9, 2296-2307.
STN database; "Specific Compounds".
STN Database Search Results including the following compounds: CAS Registry No. 1542686-52-1, entered Feb. 13, 2014; CAS Registry No. 1367998-11-5, entered Apr. 15, 2012; and CAS Registry No. 1258454-37-3, entered Jan. 5, 2011.
Sep. 19, 2024 Notice of Allowance issued in U.S. Appl. No. 17/259,370.
Sep. 30, 2024 Office Action issued in U.S. Appl. No. 17/259,451.
Feb. 28, 2025 Office Action issued in U.S. Appl. No. 18/660,578.
Dec. 28, 2023 U.S. Office Action issued in U.S. Appl. No. 17/259,364.
Tazi et al (2015): STN International, CAPLUS database, Accession No. 2015 : 34989.
Scherrer et al (2016) : STN International, CAP LUS database, Accession No. 2016 : 1435309.
Oct. 7, 2019 Search Report Issued in International Patent Application No. PCT/EP2019/068465.
Schmidt et al.; "Transition metals in Organic Synthesis, Part 91: Palladium-catalyzed Approach to 2, 6-Dioxygenated Carbazole Alkaloids—First Total Synthesis of the Phytoalexin Carbalexin C"; Synlett; 2009; pp. 2,421-2,424.
Sep. 10, 2019 Search Report Issued in International Patent Application No. PCT/EP2019/068460.
Sep. 27, 2019 Search Report Issued in International Patent Application No. PCT/EP2019/068461.
Sep. 26, 2019 Search Report Issued in International Patent Application No. PCT/EP2019/068459.
U.S. Appl. No. 17/259,483, filed Jan. 11, 2021 in the name of Scherrer et al.
U.S. Appl. No. 17/259,364, filed Jan. 11, 2021 in the name of Scherrer et al.
U.S. Appl. No. 17/259,370, filed Jan. 11, 2021 in the name of Scherrer et al.
U.S. Appl. No. 17/259,451, filed Jan. 11, 2021 in the name of Scherrer et al.
Jul. 11, 2022 Office Action issued in Russian Patent Application No. 2020143617/04(081468).
Aug. 16, 2022 Office Action issued in Russian Patent Application No. 2020142702/04(079504).
Jan. 3, 2023 Office Action Issued In U.S. Appl. No. 17/259,483.
Aug. 20, 2020 Search Report Issued in International Patent Application No. PCT/EP2020/070294.
Rao et al., "Hypervalent iodine(III) catalyzed oxidative C—N bond formation in water: synthesis of benzimidazole-fused heterocycles," RSC Advances, 2014, vol. 4, No. 49, pp. 25600-25604.
Peng et al., Synthesis and antitumor activity evaluation of anilinoquinoline derivatives by the effect on the expression of polo-like kinase, Medicinal Chemistry Research, 2013, vol. 23, No. 3, pp. 1437-1446, DOI:10.1007/s00044-013-0749-3.
Venkatesh et al., Palladium-Catalyzed Intramolecular N-Arylation of Heteroarenes: A Novel and Efficient Route to Benzimdazol[1,2-a]quinolines, The Journal of Organic Chemistry, 2006, vol. 71, No. 3, pp. 1280-1283, DOI:10.1021/jo0522411.
Formulae of compounds having registry Nos. RN1875830-19-5, RN1216052-00-4, RN512834-81-0 and RN94631-91-1 found in "REGISTRY database" and "entered STN before Feb. 29, 2016".
Mar. 24, 2023 Office Action issued in Chinese Patent Application No. 201980045893.2.

(56) References Cited

OTHER PUBLICATIONS

Apr. 12, 2023 Notice Of Allowance issued in U.S. Appl. No. 17/259,483.
Apr. 26, 2023 Corrected Notice Of Allowance issued in U.S. Appl. No. 17/259,483.
STN compounds having registry Nos. RN 1990430-84-6, entered Sep. 9, 2016; RN 1988220-74-1, entered Sep. 7, 2016; and RN 1923315-23-4, entered Jun. 2, 2016.
Registry (STN) [online] date of search: Jul. 11, 2023, STN Compounds (1)-(83), entered on or before Sep. 2016.
Christophe Dardonville et al., "Bisguanidine, Bis(2-aminoimidazoline) and Polyamine Derivatives as Potent and Selective Chemotherapeutic Agents against Trypanosoma brucei rhodesiense. Synthesis and in vitro evaluation.", J. Med. Chem. (2004), 47, 2296-2307.
Apr. 11, 2023 Office Action issued in Chinese Patent Application No. 201980045913.6.
Berman Group IV viruses: Single-Stranded (+)Sense RNA; Chapter 42; pp. 237-246; 2012.
Berman Group V viruses: Single-Stranded (−)Sense RNA; Chapter 43; pp. 247-255; 2012.
Mar. 19, 2025 Notice of Allowance issued in U.S. Appl. No. 17/259,451.
Jul. 15, 2025 Notice of Allowance issued in U.S. Appl. No. 18/660,578.

SUBSTITUTED IMIDAZOLIDINES FOR TREATING A RNA VIRUS INFECTION

The present invention relates to new compounds useful for preventing and/or treating a RNA virus infection, and most preferably a RNA virus infection caused by RNA viruses belonging to group V of the Baltimore classification, more particularly Respiratory Syncytial Virus (RSV) infection.

The present invention further relates to the use of said compounds, in particular useful for preventing and/or treating a RNA virus infection, and most preferably a RNA virus infection caused by a RNA virus belonging to group V of the Baltimore classification, more particularly Respiratory Syncytial Virus (RSV) infection.

It further relates to the pharmaceutical compositions containing said new compounds and to the chemical synthesis processes for obtaining them.

BACKGROUND

Viruses are one of the major causes of diseases around the world. Viruses are generally defined as small, non-living, infectious agents that replicate only within living cells, as they do not possess a completely autonomous replication mechanism. Although diverse in shape and size, they typically consist of a virus particle (known as a "virion"), made from a protein coat which comprises at least one nucleic acid molecule and optionally, depending on the type of virus, one or more proteins or nucleoproteins.

Because viruses do not possess a completely autonomous replication mechanism, they must necessarily rely on the machinery and metabolism of the infected cell or host, in order to replicate and produce multiple copies of themselves.

Even though their replication cycle varies greatly between species, it is generally recognized that the life cycle of viruses includes six basic steps: attachment, penetration, uncoating, replication, assembly and release.

Depending on the nature of the targeted virus, therapeutic molecules have been designed which may interfere with one or more of those mechanisms.

Among those, the replication step involves not only the multiplication of the viral genome, but also the synthesis of viral messenger RNA, of viral protein, and the modulation of the transcription or translation machinery of the host. However, it is also clear that the type of genome (single-stranded, double-stranded, RNA, DNA . . . ) characterizes dramatically this replication step. For instance, most DNA viruses assemble in the nucleus while most RNA viruses develop solely in the cytoplasm. Also, there is increasing evidence that single-stranded RNA viruses such as Influenza use the host RNA splicing and maturation machinery.

Accordingly, and considering the implications of a given type of genome in the replication step, the Baltimore classification of viruses was developed. This classification clusters viruses into families (or "groups") depending on their type of genome. The present virus classification, as in 2018, comprises seven different groups:

Group I: double-stranded DNA viruses (dsDNA);

Group II: single-stranded DNA viruses (ssDNA);

Group III: double-stranded RNA viruses (dsRNA);

Group IV: (+)strand or sense RNA viruses ((+)ssRNA);

Group V: (−)strand or antisense RNA viruses ((−)ssRNA);

Group VI: single-stranded RNA viruses having DNA intermediates (ssRNA-RT);

Group VII: double-stranded DNA viruses having RNA intermediates (dsDNA-RT).

According to that classification, viruses belonging to the Group VI are not, stricto sensu, RNA viruses. For the same reasons, viruses belonging to the Group VII are not, stricto sensu, DNA viruses. One well-studied example of a virus family belonging to the Group VI is the family Retroviridae (retrovirus) which includes HIV. One well-studied example of a virus family belonging to the Group VII is the family Hepadnaviridae which includes the Hepatitis B virus (HBV).

As a representative of viruses pertaining to group V one may cite the Filoviridae virus family encompassing the Ebola virus, the Paramyxoviridae family encompassing the Respiratory Syncytial virus (RSV), the Rhabdoviridae family, the Orthomyxoviridae family encompassing the Influenzavirus A, Influenzavirus B and Influenzavirus C.

Groups within the virus families particularly focused in the framework of the present invention are the ones encompassing RNA viruses, especially single-stranded RNA viruses, and more specifically RNA viruses belonging to group V of the Baltimore classification.

There are few cures for diseases caused by RNA virus infections, in particular single-stranded RNA viruses, and more specifically RNA virus infections from viruses belonging to group V of the Baltimore classification. Treatment is focused on relieving the symptoms. Therefore, there is still a need to identify new antiviral drugs, in particular small chemical molecules, to treat RNA virus infections, such as RNA virus infections from group V, more particularly Respiratory Syncytial Virus (RSV) infection.

Definitions

As used herein, the term "patient" refers to either an animal, such as a valuable animal for breeding, company or preservation purposes, or preferably a human or a human child, which is afflicted with, or has the potential to be afflicted with, one or more diseases and conditions described herein.

In particular, as used in the present application, the term "patient" refers to a mammal such as a rodent, cat, dog, primate or human, preferably said subject is a human and also extends to birds.

The identification of those patients who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those patients who are in need of such treatment.

In the context of the invention, the term "treating" or "treatment", as used herein, means reversing, alleviating, inhibiting the progress of, or preventing the disease resulting from RNA virus infection, and more particularly RNA virus infection from group V, or one or more symptoms of such disease.

As used herein, an "effective amount" refers to an amount of a compound of the present invention which is effective in preventing, reducing, eliminating, treating or controlling the symptoms of the herein-described diseases and conditions, i.e. RNA virus infection, and more particularly RNA virus infection from group V. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

The term “effective amount” includes “prophylaxis-effective amount” as well as “treatment-effective amount”.

The term “preventing”, as used herein, means reducing the risk of onset or slowing the occurrence of a given phenomenon, namely in the present invention, a disease resulting from a RNA virus infection, and more particularly a RNA virus infection from group V, and even more particularly Respiratory Syncytial Virus (RSV) infection.

As used herein, «preventing» also encompasses «reducing the likelihood of occurrence» or «reducing the likelihood of reoccurrence».

The term “prophylaxis-effective amount” refers to a concentration of compound of this invention that is effective in inhibiting, preventing, decreasing the likelihood of the disease by RNA viruses, and more particularly by a RNA virus from group V of the Baltimore classification, and even more particularly by Respiratory Syncytial Virus (RSV) or preventing the RNA virus infection and in particular a RNA virus infection from group V or preventing the delayed onset of the disease by the RNA virus, and more particularly by a RNA virus from group V, and even more particularly by Respiratory Syncytial Virus (RSV), when administered before infection, i.e. before, during and/or slightly after the exposure period to the RNA virus, and in particular to the RNA virus from group V, and even more particularly to Respiratory Syncytial Virus (RSV).

Likewise, the term “treatment-effective amount” refers to a concentration of compound that is effective in treating the RNA virus infection, e.g. leads to a reduction in RNA viral infection, following examination when administered after infection has occurred.

As used herein, the term “pharmaceutically acceptable” refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, a “viral infection or related condition” refers to an infection of condition related to a virus, more particularly said virus having a RNA genome, and especially a RNA virus belonging to group V according to the Baltimore classification. Viruses may be further classified in distinct families, orders and genus.

For reference, the content of the “Baltimore classification” which is reported herein further references to the virus taxonomy as set forth in the database of the 2017 International Committee of Taxonomy of Viruses (ICTV) as released online on Mar. 12, 2018 at http://ictvonline.org/virusTaxonomy.asp. This taxonomy is incorporated herein in its entirety.

Viruses of the Mononegavirales order are also particularly considered by the invention. The order Mononegavirales includes viruses belonging to Group V of the Baltimore classification. As of 2018, this order includes mainly the following virus families: Bornaviridae, Mymonaviridae, Filoviridae, Nyamiviridae, Paramyxoviridae, Pneumoviridae, Rhabdoviridae, and Sunviridae.

Human respiratory syncytial virus (HRSV) is a syncytial virus that causes respiratory tract infections. It is a major cause of lower respiratory tract infections and hospital visits during infancy and childhood. HRSV virus may in particular be considered by the invention and pertain to the Group V of RNA viruses. More particularly, RSV virus is a (−)ssRNA virus belonging to group V of the Baltimore classification. It is a pneumovirus which is part of the Paramyxoviridae family, which belongs to the Mononegavirales order.

Among other viruses of the Mononegavirales order, those which are particularly considered by the invention include: measles virus, mumps virus, Nipah virus, rabies virus, and human parainfluenza virus (which includes HPIV-1, HPIV-2, HPIV-3 and HPIV-4). Of note, the Paramyxovirinae subfamily was conventionally merged into the Paramyxoviridae family, by reference to the taxonomy of the Mononegavirales order updated in 2016.

The virus genus which are particularly considered within the Paramyxoviridae family include: Aquaparamyxovirus, Avulavirus, Ferlavirus, Henipavirus, Morbillivirus, Respirovirus and Rubulavirus genus.

Viruses of the Orthomyxoviridae family are also particularly considered by the invention. The Orthomyxoviridae family belongs to an “Unassigned” order according to the 2017 Virus Taxonomy. The virus genus which are particularly considered within the Orthomyxoviridae family include: Alphainfluenzavirus, Betainfluenzavirus, Deltainfluenzavirus, Gammainfluenzavirus, Isavirus, Quaranjavirus, and Thogotovirus.

Influenzavirus A, Influenzavirus B, Influenzavirus C may in particular be considered by the invention and pertain to the Group V RNA viruses and the Orthomyxoviridae family, which can be defined as a negative-sense single-stranded RNA or (−)ss RNA viruses. Isavirus and Thogotovirus also belong to the Orthomyxoviridae order.

DETAILED DESCRIPTION

The inventors have surprisingly found that aryl-N-aryl compounds are endowed with a broad-spectrum activity against RNA viruses, and more particularly single-stranded RNA viruses belonging to Group V of the Baltimore classification. Groups IV and V include respectively (+)ssRNA viruses and (−)ssRNA viruses; which also refer to positive-sense single-stranded RNA viruses and negative-sense single-stranded RNA viruses.

For reference, the content of the «Baltimore classification» is considered in light of the Classification and Nomenclature of viruses as set forth in the 10th report on Virus Taxonomy dated 2017.

According to one aspect, the present invention relates to a compound of formula (I)

(I)

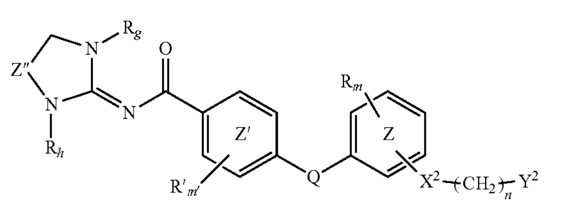

wherein:

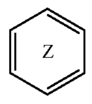

ring and

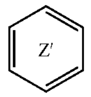

ring independently mean a phenylene or a pyridylene group,

Z" represents a —$CH_2$— group or a —CO— group, $R_g$ and $R_h$ independently represent a hydrogen atom, a ($C_1$-$C_4$)alkyl group, a ($C_3$-$C_6$)cycloalkyl group, a —$CH_2CHF_2$ group, or a —$COCH_3$ group, Q is NH or 0, $X^2$ represents

- a —CO—$NR_k$— group, wherein $R_k$ represents a hydrogen atom or a methyl group,
- a —$NR'_k$—CO— group, wherein $R'_k$ represents a hydrogen atom or a methyl group,
- a —O— group,
- a —CO— group,
- a —$SO_2$-group,
- a —CS—NH— group,
- a —$CH_2$—NH— group,
- a

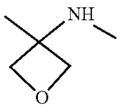

group, or

- a heterocyclyl, wherein the heterocyclyl is a 5- or 6-membered ring comprising 1, 2, 3 or 4 heteroatoms selected from 0, S and/or N, such as a triazole, a pyrazoline, an oxazole, an oxazoline, an oxazolidine, an imidazole, a pyrazole, an imidazoline, a tetrazole or an oxadiazole, said ring being optionally substituted by a ($C_1$-$C_4$)alkyl group, a halogen atom, or =O, n is 0, 1, 2 or 3, m and m' are independently 0, 1 or 2, $Y^2$ represents

- a hydrogen atom,
- a halogen atom,
- a hydroxyl group,
- a morpholinyl group, optionally substituted by a ($C_1$-$C_4$)alkyl group or a trifluoromethyl group,
- a bridged morpholinyl group, optionally substituted by a halogen atom,
- a ($C_5$-$C_{11}$)bicycloalkyl group,
- a piperidinyl group, optionally interrupted by a $SO_2$ group,
- a ($C_1$-$C_4$)alkenyl group,
- a —$PO(OR_a)(OR_b)$ group, or

- a —$CR^1R^2R^3$ group, wherein $R^1$, $R^2$ and $R^3$ independently represent a hydrogen atom, a fluorine atom or a ($C_1$-$C_4$)alkyl group, being understood that no more than one of $R^1$, $R^2$ and $R^3$ is a hydrogen atom, or $R^1$ and $R^2$ form together with the carbon atom bearing them a ($C_3$-$C_5$)cycloalkyl group, said ($C_3$-$C_5$)cycloalkyl group being optionally substituted by one or two ($C_1$-$C_4$)alkyl group, itself optionally substituted by a hydroxy group, halogen atom, trifluoromethyl group, cyano group, phosphonate group or ($C_1$-$C_4$) alkoxy group and said ($C_3$-$C_5$)cycloalkyl group being optionally interrupted on said $R^1$ and/or $R^2$ by one or two oxygen atom(s) or by a —$SO_2$-group, R and R' independently represent

- a ($C_1$-$C_4$)alkyl group, optionally substituted by a hydroxyl group, and optionally interrupted by a —$SO_2$— group or a —SO— group,
- a ($C_1$-$C_4$)alkenyl group,
- a ($C_3$-$C_6$)cycloalkyl group,
- a tetrahydrofuranyl group,
- a tetrahydropyranyl group,
- a trifluoromethyl group,
- a furanyl group,
- a halogen atom,
- a cyano group, or

- a ($C_1$-$C_5$)alkoxy group, $R_a$ and $R_b$ independently represent a hydrogen atom or a ($C_1$-$C_4$)alkyl group, or any of its pharmaceutically acceptable salt.

According to one aspect, the present invention relates to a compound of formula (I)

(I)

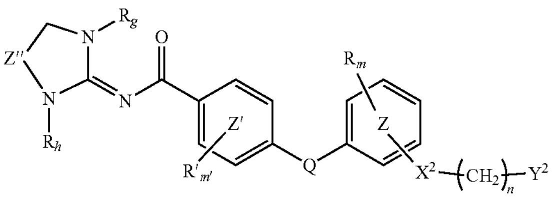

wherein:

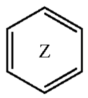

ring and

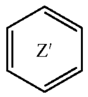

ring independently mean a phenylene or a pyridylene group,

Z" represents a —$CH_2$— group or a —CO— group, $R_g$ and $R_h$ independently represent a hydrogen atom, a ($C_1$-$C_4$)alkyl group, a ($C_3$-$C_6$)cycloalkyl group or a —$COCH_3$ group, Q is NH or 0, $X^2$ represents

- a —CO—$NR_k$— group, wherein $R_k$ represents a hydrogen atom or a methyl group,
- a —$NR'_k$—CO— group, wherein $R'_k$ represents a hydrogen atom or a methyl group,
- a —O— group,
- a —CO— group, a $-SO_2$-group,
a —CS—NH— group,
a $-CH_2-NH-$ group,
a

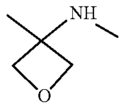

group,
or
a divalent 5-membered heteroaromatic ring comprising 1, 2, 3 or 4 heteroatoms, such as a triazole, an imidazole, a tetrazole or an oxadiazole, n is 0, 1, 2 or 3,
m and m' are independently 0, 1 or 2,
$Y^2$ represents
a hydrogen atom,
a halogen atom,
a hydroxyl group,
a morpholinyl group, optionally substituted by a $(C_1$-$C_4)$alkyl group,
a piperidinyl group, optionally interrupted by a $SO_2$ group,
a $(C_1$-$C_4)$alkenyl group,
a $-PO(OR_a)(OR_b)$ group,
or
a $-CR^1R^2R^3$ group, wherein $R^1$, $R^2$ and $R^3$ independently represent a hydrogen atom, a fluorine atom or a $(C_1$-$C_4)$alkyl group, being understood that no more than one of $R^1$, $R^2$ and $R^3$ is a hydrogen atom, or $R^1$ and $R^2$ form together with the carbon atom bearing them a $(C_3$-$C_5)$cycloalkyl group, said $(C_3$-$C_5)$cycloalkyl group being optionally substituted by one or two $(C_1$-$C_4)$alkyl group, halogen atom, trifluoromethyl group, cyano group or $(C_1$-$C_4)$alkoxy group and said $(C_3$-$C_5)$cycloalkyl group being optionally interrupted on said $R^1$ and/or $R^2$ by one or two oxygen atom(s) or by a $-SO_2$-group, R and R' independently represent
a $(C_1$-$C_4)$alkyl group, optionally substituted by a hydroxyl group, and optionally interrupted by a $-SO_2-$ group or a —SO— group,
a $(C_1$-$C_4)$alkenyl group,
a $(C_3$-$C_6)$cycloalkyl group,
a tetrahydrofuranyl group,
a tetrahydropyranyl group,
a trifluoromethyl group,
a furanyl group,
a halogen atom,
or
a $(C_1$-$C_5)$alkoxy group, $R_a$ and $R_b$ independently represent a hydrogen atom or a $(C_1$-$C_4)$alkyl group,
or any of its pharmaceutically acceptable salt.

In other words,

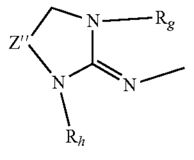

represents a group A (A)

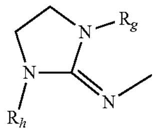

or a group (B)

(B)

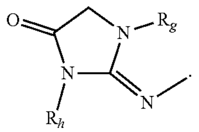

According to a first aspect, the present invention relates to a compound of formula (I):

(I)

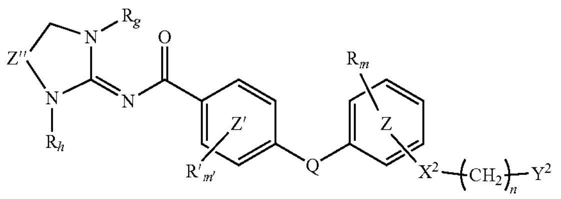

wherein:

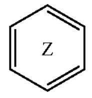

ring and

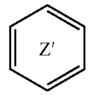

ring independently mean a phenylene or a pyridylene group,

Z" represents a $-CH_2-$ group or a —CO— group,
$R_g$ and $R_h$ independently represent a hydrogen atom, a $(C_1$-$C_4)$alkyl group, a $(C_3$-$C_6)$cycloalkyl group, a $-CH_2CHF_2$ group, or a $-COCH_3$ group,
Q is NH or 0,
$X^2$ represents
a $-CO-NR_k-$ group, wherein $R_k$ represents a hydrogen atom or a methyl group,
a $-NR'_k-CO-$ group, wherein $R'_k$ represents a hydrogen atom or a methyl group,
a —O— group,
a —CO— group,
a $-SO_2$-group,
a —CS—NH— group, a —$CH_2$—NH—, a

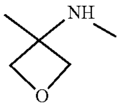

group, or a heterocyclyl, wherein the heterocyclyl is a 5- or 6-membered ring comprising 1, 2, 3 or 4 heteroatoms selected from O, S and/or N, such as a triazolyl, a pyrazolinyl, an oxazolyl, an oxazolinyl, an oxazolidinyl, an imidazolyl, a dihydroimidazolyl, a pyrazolyl, an imidazolinyl, a tetrazolyl or an oxadiazolyl, said ring being optionally substituted by a ($C_1$-$C_4$)alkyl group, a halogen atom, a —$COOR_p$ group or =O, with $R_p$ being a ($C_1$-$C_4$)alkyl group, n is 0, 1, 2 or 3, m and m' are independently 0, 1 or 2, $Y^2$ represents a hydrogen atom, a halogen atom, a hydroxyl group, a morpholinyl group, optionally substituted by a ($C_1$-$C_4$)alkyl group or a trifluoromethyl group, a bridged morpholinyl group, optionally substituted by a halogen atom, a ($C_5$-$C_{11}$)bicycloalkyl group, an adamantyl group, a piperidinyl group, optionally interrupted by a $SO_2$ group, a ($C_1$-$C_4$)alkenyl group, a —$PO(OR_a)(OR_b)$ group, a 5-membered heteroaromatic ring comprising one or two heteroatom(s) selected from an oxygen and a nitrogen atom, such as an oxazolyl, isoxazolyl, a pyrazolyl and an imidazolyl, in particular an oxazolyl, or a —$CR^1R^2R^3$ group, wherein $R^1$, $R^2$ and $R^3$ independently represent a hydrogen atom, a fluorine atom or a ($C_1$-$C_4$)alkyl group, being understood that no more than one of $R^1$, $R^2$ and $R^3$ is a hydrogen atom, or $R^1$ and $R^2$ form together with the carbon atom bearing them a ($C_3$-$C_5$)cycloalkyl group, said ($C_3$-$C_5$)cycloalkyl group being optionally substituted by one or two ($C_1$-$C_4$)alkyl group, itself optionally substituted by a hydroxy group, halogen atom, trifluoromethyl group, cyano group, phosphonate group, oxo group or ($C_1$-$C_4$)alkoxy group and said ($C_3$-$C_5$)cycloalkyl group being optionally interrupted on said $R^1$ and/or $R^2$ by one or two oxygen atom(s), by a sulfur atom, by a nitrogen atom or by a —$SO_2$— group, R and R' independently represent a ($C_1$-$C_4$)alkyl group, optionally substituted by a hydroxyl group, and optionally interrupted by a —$SO_2$— group or a —SO— group, a ($C_1$-$C_4$)alkenyl group, a ($C_3$-$C_6$)cycloalkyl group, a tetrahydrofuranyl group, a tetrahydropyranyl group, a trifluoromethyl group, a furanyl group, a halogen atom, a cyano group, or a ($C_1$-$C_5$)alkoxy group, $R_a$ and $R_b$ independently represent a hydrogen atom or a ($C_1$-$C_4$)alkyl group, or any of its pharmaceutically acceptable salt.

According to a second aspect, the present invention relates to a compound of formula (I) as defined above or any of its pharmaceutically acceptable salts, and any of compounds (1) to (181) as defined herein after or any of its pharmaceutically acceptable salts, for use as a medicament.

According to a third aspect, the present invention relates to compounds of formula (I) as defined above or any of its pharmaceutically acceptable salts, and any of compounds (1) to (181) as defined herein after or any of its pharmaceutically acceptable salts for use in the treatment and/or prevention of a RNA virus infection caused by a RNA virus belonging to group V of the Baltimore classification, and in particular a RSV viral infection or a virus-related condition.

The above-mentioned compounds (I) are particularly suitable for treating or preventing a virus infection or related condition, in particular a RNA virus infection caused by a RNA virus belonging to group V of the Baltimore classification or related condition, and most preferably a RSV viral infection or a virus-related condition.

According to a particular embodiment, the present invention relates to a compound of formula (I) as defined above, wherein

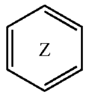

ring and

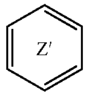

ring both represent a phenylene group or

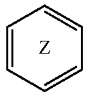

ring represents a pyridylene group and

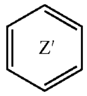

ring represents a phenylene group, or any of its pharmaceutically acceptable salt.

In another embodiment, the present invention relates to a compound of formula (I) as defined above, wherein Q is a NH group or any of its pharmaceutically acceptable salt.

In another embodiment, the present invention relates to a compound of formula (I) as defined above, wherein $R_g$ and $R_h$ represent a hydrogen atom or any of its pharmaceutically acceptable salt.

In another embodiment, the present invention relates to a compound of formula (I) as defined above, wherein $X^2$ represents

- a —CO—NH— group,
- a —NH—CO— group,
- a —O— group,
- a —CO— group,
- or
- a heterocyclyl, wherein the heterocyclyl is a 5- or 6-membered ring comprising 1, 2, 3 or 4 heteroatoms selected from O, S and/or N, such as a triazole, an imidazole, an imidazoline, an oxazoline, an oxazolidine, or a tetrazole, said ring being optionally substituted by a ($C_1$-$C_4$)alkyl group, a halogen atom or =O,
- or any of its pharmaceutically acceptable salt.

In another embodiment, the present invention relates to a compound of formula (I) as defined above, wherein $X^2$

- a —CO—NH— group,
- a —NH—CO— group,
- a —O— group,
- a —CO— group,
- or
- a divalent 5-membered heteroaromatic ring comprising at least 2 nitrogen atoms, such as a triazole, an imidazole or a tetrazole,
- or any of its pharmaceutically acceptable salt.

In another embodiment, the present invention relates to a compound of formula (I) as defined above, wherein $X^2$ represents

- a —CO—NH— group,
- a —NH—CO— group,
- a —O— group,
- a —CO— group,
- or
- a heterocyclyl, wherein the heterocyclyl is a 5- or 6-membered ring comprising 1, 2, 3 or 4 heteroatoms selected from 0, S and/or N, such as a triazolyl, an imidazolyl, an imidazolinyl, an oxazolyl, an oxazolinyl, an oxazolidinyl, a dihydroimidazolyl, or a tetrazolyl, said ring being optionally substituted by a ($C_1$-$C_4$)alkyl group, a halogen atom, a —$COOR_p$ group or =O, with $R_p$ being a ($C_1$-$C_4$)alkyl group, or any of its pharmaceutically acceptable salt.

In another embodiment, the present invention relates to a compound of formula (I) as defined above, wherein $Y^2$ represents

- a hydrogen atom,
- a halogen atom,
- a morpholinyl group, optionally substituted by a ($C_1$-$C_4$) alkyl group or a trifluoromethyl group,
- a bridged morpholinyl group, optionally substituted by a halogen atom,
- a ($C_5$-$C_{11}$)bicycloalkyl group,
- a ($C_1$-$C_4$)alkenyl group,
- a —$PO(OR_a)(OR_b)$ group,
- or
- a —$CR^1R^2R^3$ group, wherein $R^1$, $R^2$ and $R^3$ independently represent a hydrogen atom, a fluorine atom or a ($C_1$-$C_4$)alkyl group, being understood that no more than one of $R^1$, $R^2$ and $R^3$ is a hydrogen atom, or $R^1$ and $R^2$ form together with the carbon atom bearing them a ($C_3$-$C_5$)cycloalkyl group, said ($C_3$-$C_5$)cycloalkyl group being optionally substituted by one or two ($C_1$-$C_4$)alkyl group, itself optionally substituted by a hydroxy group, halogen atom, trifluoromethyl group or cyano group, phosphonate group and said ($C_3$-$C_5$)cycloalkyl group being optionally interrupted on said $R^1$ and/or $R^2$ by one or two oxygen atom(s) or by a —$SO_2$— group,
- with $R_a$ and $R_b$ being as defined above,
- or any of its pharmaceutically acceptable salt.

In another embodiment, the present invention relates to a compound of formula (I) as defined above, wherein $Y^2$ represents

- a hydrogen atom,
- a halogen atom,
- a morpholinyl group, optionally substituted by a ($C_1$-$C_4$) alkyl group,
- a ($C_1$-$C_4$)alkenyl group,
- a —$PO(OR_a)(OR_b)$ group,
- or
- a —$CR^1R^2R^3$ group, wherein $R^1$, $R^2$ and $R^3$ independently represent a hydrogen atom, a fluorine atom or a ($C_1$-$C_4$)alkyl group, being understood that no more than one of $R^1$, $R^2$ and $R^3$ is a hydrogen atom, or $R^1$ and $R^2$ form together with the carbon atom bearing them a ($C_3$-$C_5$)cycloalkyl group, said ($C_3$-$C_5$)cycloalkyl group being optionally substituted by one or two ($C_1$-$C_4$)alkyl group, halogen atom, trifluoromethyl group or cyano group and said ($C_3$-$C_5$)cycloalkyl group being optionally interrupted on said $R^1$ and/or $R^2$ by one or two oxygen atom(s) or by a —$SO_2$— group,
- with $R_a$ and $R_b$ being as defined in claim 1,
- or any of its pharmaceutically acceptable salt.

In another embodiment, the present invention relates to a compound of formula (I) as defined above, wherein $Y^2$ represents

- a hydrogen atom,
- a halogen atom,
- a morpholinyl group, optionally substituted by a ($C_1$-$C_4$) alkyl group or a trifluoromethyl group,
- a bridged morpholinyl group, optionally substituted by a halogen atom,
- a ($C_5$-$C_{11}$)bicycloalkyl group,
- an adamantyl group,
- a ($C_1$-$C_4$)alkenyl group,
- a —$PO(OR_a)(OR_b)$ group,
- an oxazolyl, an isoxazolyl, a pyrazolyl or an imidazolyl, in particular an oxazolyl,
- or
- a —$CR^1R^2R^3$ group, wherein $R^1$, $R^2$ and $R^3$ independently represent a hydrogen atom, a fluorine atom or a ($C_1$-$C_4$)alkyl group, being understood that no more than one of $R^1$, $R^2$ and $R^3$ is a hydrogen atom, or $R^1$ and $R^2$ form together with the carbon atom bearing them a ($C_3$-$C_5$)cycloalkyl group, said ($C_3$-$C_5$)cycloalkyl group being optionally substituted by one or two ($C_1$-$C_4$)alkyl group, itself optionally substituted by a hydroxy group, halogen atom, trifluoromethyl group or cyano group, phosphonate group oxo group and said ($C_3$-$C_5$)cycloalkyl group being optionally interrupted on said $R^1$ and/or $R^2$ by one or two oxygen atom(s), by a sulfur atom, by a nitrogen atom or by a —$SO_2$— group,
- with $R_a$ and $R_b$ being as defined in claim 1,
- or any of its pharmaceutically acceptable salt.

In a more particular embodiment, the polycyclic (bicyclic) alkyl group may be chosen in the group consisting in spiro[2.2]pentyl, spiro[5.5]undecanyl, spiro[3.4]octanyl, spiro[4.5]decanyl, bicyclo[1.1.0]butyl, bicyclo[2.1.1]hexyl, bicyclo[3.2.0]heptyl, bicyclo[3.3.0]octyl, bicyclo[4.3.0]nonyl, bicyclo[2.2.1]heptyl, bicyclo[2.2.2]octyl, bicyclo

[3.2.1]octyl, bicyclo[1.1.1]pentyl, oxabicyclo[1.1.1]pentyl, oxabicyclo[2.1.1]hexyl, oxabicyclo[2.2.1]heptyl, oxabicyclo[4.1.0]heptyl, oxabicyclo[3.2.1]octyl and cubyl, and more particularly consisting in bicyclo[1.1.1]pentyl, oxabicyclo[1.1.1]pentyl, bicyclo[2.1.1]hexyl, oxabicyclo[2.1.1]hexyl, and even more particularly is bicyclo[1.1.1]pentyl.

In another embodiment, the present invention relates to a compound of formula (I) as defined above, wherein R and R' independently represent a $(C_1-C_4)$alkyl group, optionally substituted by a hydroxyl group, and optionally interrupted by a —$SO_2$— group or a —SO— group, a $(C_3-C_6)$cycloalkyl group, a tetrahydrofuranyl group, a tetrahydropyranyl group, a trifluoromethyl group, a furanyl group, a chlorine or fluorine atom, a cyano group, or a $(C_1-C_5)$alkoxy group, or any of its pharmaceutically acceptable salt.

In another embodiment, the present invention relates to a compound of formula (I) as defined above, wherein R and R' independently represent a $(C_1-C_4)$alkyl group, optionally substituted by a hydroxyl group, and optionally interrupted by a —$SO_2$— group or a —SO— group, a $(C_3-C_6)$cycloalkyl group, a tetrahydrofuranyl group, a tetrahydropyranyl group, a trifluoromethyl group, a furanyl group, a chlorine or fluorine atom, or a $(C_1-C_5)$alkoxy group, or any of its pharmaceutically acceptable salt.

In another embodiment, the present invention relates to a compound of formula (I) as defined above, wherein R and R' independently represent a $(C_1-C_4)$alkyl group, optionally substituted by a hydroxyl group, and optionally interrupted by a —$SO_2$— group or a —SO— group, a $(C_3-C_6)$cycloalkyl group, a tetrahydrofuranyl group, a tetrahydropyranyl group, a trifluoromethyl group, a furanyl group, a chlorine or fluorine atom, a cyano group, or a $(C_1-C_5)$alkoxy group, or any of its pharmaceutically acceptable salt.

Any combination of the above-defined embodiments for R, R', Z", $R_g$, $R_h$, Q, m, m',

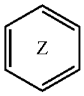

ring,

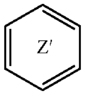

ring, $X^2$, n and $Y^2$ with each other does form part of the instant invention.

According to a preferred embodiment of the present invention, the compound of formula (I) is chosen from:

(1) 3-cyclopropyl-N-[(2Z)-imidazolidin-2-ylidene]-4-[(3-{[1-(propan-2-yl)cyclopropyl]carbamoyl}phenyl)amino]benzamide (2) 3-cyclopentyl-N-[(2E)-imidazolidin-2-ylidene]-4-{[3-(2-methylpropanamido)phenyl]amino}benzamide (3) 4-{[2-chloro-3-(morpholine-4-carbonyl)phenyl]amino}-3-cyclopentyl-N-[(2E)-imidazolidin-2-ylidene]benzamide (4) 4-{[2-chloro-3-(morpholine-4-carbonyl)phenyl]amino}-3-cyclopropyl-N-[(2E)-imidazolidin-2-ylidene]benzamide (5) 3-tert-butyl-N-[(2E)-imidazolidin-2-ylidene]-4-{[3-(4-methylpentanamido)phenyl]amino}benzamide (6) 3-tert-butyl-N-[(2E)-imidazolidin-2-ylidene]-4-({3-[(4-methylpentan-2-yl)carbamoyl]phenyl}amino)benzamide (7) 2-cyclopropyl-3-[(2-cyclopropyl-4-{[(2E)-imidazolidin-2-ylidene]carbamoyl}phenyl)amino]-N-(3-methylbutyl)benzamide (8) 3-tert-butyl-N-[(2E)-imidazolidin-2-ylidene]-4-({3-[(3-methylbutyl)carbamoyl]phenyl}amino)benzamide (9) 3-tert-butyl-4-{[2-cyclopropyl-3-(morpholine-4-carbonyl)phenyl]amino}-N-[(2E)-imidazolidin-2-ylidene]benzamide

(10) 4-({2-chloro-3-[(3-methylbutyl)carbamoyl]phenyl}amino)-3-cyclopropyl-N-[(2E)-imidazolidin-2-ylidene]benzamide

(11) 4-({2-chloro-3-[(propan-2-yl)carbamoyl]phenyl}amino)-3-cyclopropyl-N-[(2E)-imidazolidin-2-ylidene]benzamide

(12) 4-({2-chloro-3-[2-(1,4-dioxan-2-yl)ethoxy]phenyl}amino)-3-cyclopropyl-N-[(2E)-imidazolidin-2-ylidene]benzamide

(13) 4-[(3-cyclopropaneamidophenyl)amino]-3-cyclopropyl-N-[(2E)-imidazolidin-2-ylidene]benzamide

(14) 3-cyclopropyl-N-[(2Z)-imidazolidin-2-ylidene]-4-({3-[(1-methylcyclopropyl)carbamoyl]phenyl}amino)benzamide

(15) 4-{[2-chloro-3-(morpholine-4-carbonyl)phenyl]amino}-N-[(2E)-imidazolidin-2-ylidene]-3-(oxolan-3-yl)benzamide

(16) 4-{[2-chloro-3-(morpholine-4-carbonyl)phenyl]amino}-N-[(2E)-imidazolidin-2-ylidene]-3-(trifluoromethyl)benzamide

(17) 3-tert-butyl-N-[(2E)-1-methylimidazolidin-2-ylidene]-4-({3-[(propan-2-yl)carbamoyl]phenyl}amino)benzamide

(18) 3-cyclobutyl-N-[(2Z)-imidazolidin-2-ylidene]-4-({3-[(1-methylcyclopropyl)carbamoyl]phenyl}amino)benzamide

(19) 3-tert-butyl-N-[(2E)-imidazolidin-2-ylidene]-4-({3-[(propan-2-yl)carbamoyl]phenyl}amino)benzamide

(20) 3-tert-butyl-4-{[3-(2,2-dimethylpropanamido)phenyl]amino}-N-[(2Z)-imidazolidin-2-ylidene]benzamide

(21) 3-cyclopropyl-N-[(2Z)-imidazolidin-2-ylidene]-4-{[3-(1-methylcyclopropaneamido)phenyl]amino}benzamide

(22) 4-{[3-(3-cyclohexylpropoxy)phenyl]amino}-3-cyclopropyl-N-[(2E)-imidazolidin-2-ylidene]benzamide

(23) 4-({2-chloro-3-[(1,4-dioxan-2-yl)methoxy]phenyl}amino)-3-cyclopropyl-N-[(2E)-imidazolidin-2-ylidene]benzamide

(24) 3-tert-butyl-4-({3-[(1-methylcyclopropyl)carbamoyl]phenyl}amino)-N-[(2E)-1-methylimidazolidin-2-ylidene]benzamide

(25) 4-{[2-chloro-3-(cyclopropylcarbamoyl)phenyl]amino}-3-cyclopropyl-N-[(2Z)-imidazolidin-2-ylidene]benzamide

(26) 3-cyclopropyl-N-[(2E)-imidazolidin-2-ylidene]-4-{[3-(2-methylpropanamido)phenyl]amino}benzamide

(27) 3-cyclopropyl-N-[(2Z)-imidazolidin-2-ylidene]-4-({2-methoxy-3-[(3-methylbutyl)carbamoyl]phenyl}amino)benzamide

(28) 4-({2-chloro-3-[(oxolan-3-yl)carbamoyl]phenyl}amino)-3-cyclopropyl-N-[(2Z)-imidazolidin-2-ylidene]benzamide (29)N-[(2E)-imidazolidin-2-ylidene]-4-({3-[(3-methylbutyl)carbamoyl]phenyl}amino)-3-(prop-1-en-2-yl)benzamide

(30) 3-(2-hydroxypropan-2-yl)-N-[(2E)-imidazolidin-2-ylidene]-4-{[3-(morpholine-4-carbonyl)-2-(trifluoromethyl)phenyl]amino}benzamide

(31) 3-cyclopropyl-4-({3-[(1-ethylcyclopropyl)carbamoyl]phenyl}amino)-N-[(2Z)-imidazolidin-2-ylidene]benzamide

(32) 3-cyclopropyl-4-({3-fluoro-5-[(propan-2-yl)carbamoyl]phenyl}amino)-N-[(2Z)-imidazolidin-2-ylidene]benzamide

(33) 3-tert-butyl-N-[(2E)-imidazolidin-2-ylidene]-4-[(3-{[2-(oxan-3-yl)ethyl]carbamoyl}phenyl)amino]benzamide

(34) 3-cyclopropyl-N-[(2Z)-imidazolidin-2-ylidene]-4-({3-[(propan-2-yl)carbamothioyl]phenyl}amino)benzamide

(35) 3-tert-butyl-N-[(2E)-imidazolidin-2-ylidene]-4-[(3-{[2-(oxan-2-yl)ethyl]carbamoyl}phenyl)amino]benzamide

(36) 3-cyclopropyl-N-[(2E)-1-methylimidazolidin-2-ylidene]-4-({3-[(propan-2-yl)carbamoyl]phenyl}amino)benzamide

(37) 3-tert-butyl-N-[(2E)-imidazolidin-2-ylidene]-4-{[3-(2-methylpropanamido)phenyl]amino}benzamide

(38) 3-tert-butyl-N-[(2E)-imidazolidin-2-ylidene]-4-({3-[methyl(propan-2-yl)carbamoyl]phenyl}amino)benzamide

(39) 3-tert-butyl-N-[(2E)-imidazolidin-2-ylidene]-4-[(3-{[2-(oxan-4-yl)ethyl]carbamoyl}phenyl)amino]benzamide

(40) 2-[(2-cyclopropyl-4-{[(2E)-imidazolidin-2-ylidene]carbamoyl}phenyl)amino]-3-methyl-N-(3-methylbutyl)pyridine-4-carboxamide

(41) 4-{[3-(3-cyclohexylpropoxy)phenyl]amino}-3-cyclopropyl-N-[(2E)-4-oxoimidazolidin-2-ylidene]benzamide

(42) 4-{[2-cyclopropyl-3-(morpholine-4-carbonyl)phenyl]amino}-N-[(2Z)-imidazolidin-2-ylidene]-3-(trifluoromethyl)benzamide

(43) 3-cyclopropyl-N-[(2E)-1-cyclopropylimidazolidin-2-ylidene]-4-({3-[(propan-2-yl)carbamoyl]phenyl}amino)benzamide

(44) 3-(2-hydroxypropan-2-yl)-N-[(2E)-imidazolidin-2-ylidene]-4-({3-[(3-methylbutyl)carbamoyl]phenyl}amino)benzamide

(45) 4-{[2-chloro-3-(morpholine-4-carbonyl)phenyl]amino}-3-(2-hydroxypropan-2-yl)-N-[(2E)-imidazolidin-2-ylidene]benzamide (46)N-[(2E)-1-acetylimidazolidin-2-ylidene]-4-{[3-(3-cyclohexylpropoxy)phenyl]amino}-3-cyclopropylbenzamide

(47) 3-cyclopropyl-4-({3-fluoro-5-[(1-methylcyclopropyl)carbamoyl]phenyl}amino)-N-[(2Z)-imidazolidin-2-ylidene]benzamide

(48) 3-tert-butyl-N-[(2E)-imidazolidin-2-ylidene]-4-[(3-{[2-(oxolan-3-yl)ethyl]carbamoyl}phenyl)amino]benzamide

(49) 3-tert-butyl-N-[(2E)-4-oxoimidazolidin-2-ylidene]-4-({3-[(propan-2-yl)carbamoyl]phenyl}amino)benzamide

(50) 4-({2-chloro-3-[(oxan-4-yl)carbamoyl]phenyl}amino)-3-cyclopropyl-N-[(2E)-imidazolidin-2-ylidene]benzamide

(51) 3-cyclopentyl-4-({3-[(1,4-dioxan-2-yl)methoxy]phenyl}amino)-N-[(2E)-imidazolidin-2-ylidene]benzamide

(52) 3-tert-butyl-4-({3-[(1,4-dioxan-2-yl)methoxy]phenyl}amino)-N-[(2E)-imidazolidin-2-ylidene]benzamide

(53) 3-cyclopropyl-N-[(2Z)-imidazolidin-2-ylidene]-4-[(3-{[1-(trifluoromethyl)cyclopropyl]carbamoyl}phenyl)amino]benzamide

(54) 3-tert-butyl-N-[(2E)-imidazolidin-2-ylidene]-4-({2-[(propan-2-yl)carbamoyl]phenyl}amino)benzamide

(55) 2-[(2-tert-butyl-4-{[(2E)-imidazolidin-2-ylidene]carbamoyl}phenyl)amino]-N-(3-methylbutyl)pyridine-4-carboxamide

(56) 3-tert-butyl-N-[(2E)-imidazolidin-2-ylidene]-4-({2-[(2-methylpropyl)carbamoyl]phenyl}amino)benzamide

(57) 4-{[3-(5-chloro-1H-imidazol-2-yl)-2-methylphenyl]amino}-3-cyclopropyl-N-[(2Z)-imidazolidin-2-ylidene]benzamide

(58) 3-cyclopropyl-N-[(2E)-imidazolidin-2-ylidene]-4-[(3-{[2-(oxan-4-yl)ethyl]carbamoyl}phenyl)amino]benzamide (59)N-[(2E)-imidazolidin-2-ylidene]-3-(oxolan-3-yl)-4-({3-[(propan-2-yl)carbamoyl]phenyl}amino)benzamide

(60) 3-cyclopropyl-N-[(2Z)-imidazolidin-2-ylidene]-4-({3-[1-(3-methylbut-2-en-1-yl)-1H-1,2,3,4-tetrazol-5-yl]phenyl}amino)benzamide

(61) 3-cyclopropyl-N-[(2E)-1-methyl-5-oxoimidazolidin-2-ylidene]-4-({3-[(propan-2-yl)carbamoyl]phenyl}amino)benzamide

(62) 3-cyclopropyl-N-[(2E)-imidazolidin-2-ylidene]-4-({2-[(3-methylbutyl)carbamoyl]phenyl}amino)benzamide (63)N-[(2E)-imidazolidin-2-ylidene]-4-{[3-(2-methylpropanamido)phenyl]amino}-3-(oxolan-3-yl)benzamide

(64) 4-({3-[(1-cyanocyclopropyl)carbamoyl]-2-methylphenyl}amino)-3-cyclopropyl-N-[(2Z)-imidazolidin-2-ylidene]benzamide

(65) 3-cyclopropyl-N-[(2Z)-imidazolidin-2-ylidene]-4-({3-[(propan-2-yl)carbamoyl]-5-(trifluoromethyl)phenyl}amino)benzamide

(66) 3-cyclopropyl-4-({4-fluoro-3-[(propan-2-yl)carbamoyl]phenyl}amino)-N-[(2Z)-imidazolidin-2-ylidene]benzamide

(67) 3-(2-hydroxypropan-2-yl)-N-[(2E)-imidazolidin-2-ylidene]-4-({3-[3-(oxan-4-yl)propoxy]phenyl}amino)benzamide (68)N-{3-[(2-cyclopropyl-4-{[(2E)-imidazolidin-2-ylidene]carbamoyl}phenyl)amino]-2-methylphenyl}-3-methyloxetane-3-carboxamide (69)N-[(2Z)-imidazolidin-2-ylidene]-3-(oxan-4-yl)-4-({3-[(propan-2-yl)carbamoyl]phenyl}amino)benzamide

(70) 3-cyclopropyl-N-[(2E)-imidazolidin-2-ylidene]-4-({2-[(propan-2-yl)carbamoyl]phenyl}amino)benzamide

(71) 3-tert-butyl-N-[(2Z)-1,3-dimethylimidazolidin-2-ylidene]-4-({3-[(propan-2-yl)carbamoyl]phenyl}amino)benzamide

(72) 3-chloro-N-[(2E)-imidazolidin-2-ylidene]-4-{[3-(2-methylpropanamido)phenyl]amino}benzamide
(73) 3-cyclopropyl-4-{[3-fluoro-5-(morpholine-4-carbonyl)phenyl]amino}-N-[(2Z)-imidazolidin-2-ylidene]benzamide
(74) 2-[(2-tert-butyl-4-{[(2E)-imidazolidin-2-ylidene]carbamoyl}phenyl)amino]-N-[2-(oxan-4-yl)ethyl]pyridine-4-carboxamide
(75) 3-cyclopropyl-4-{[3-(N,2-dimethylpropanamido)phenyl]amino}-N-[(2E)-imidazolidin-2-ylidene]benzamide
(76) 3-cyclopropyl-N-[(2Z)-imidazolidin-2-ylidene]-4-[(3-{[(propan-2-yl)carbamoyl]methyl}phenyl)amino]benzamide
(77) 3-cyclopropyl-4-({2-fluoro-5-[(propan-2-yl)carbamoyl]phenyl}amino)-N-[(2Z)-imidazolidin-2-ylidene]benzamide
(78) 4-{[2-cyclopropyl-3-(morpholine-4-carbonyl)phenyl]amino}-3-(2-hydroxypropan-2-yl)-N-[(2E)-imidazolidin-2-ylidene]benzamide
(79) 3-(furan-3-yl)-N-[(2E)-imidazolidin-2-ylidene]-4-[(3-{[2-(oxan-4-yl)ethyl]carbamoyl}phenyl)amino]benzamide
(80) 3-cyclopropyl-N-[(2E)-imidazolidin-2-ylidene]-4-({2-[(2-methylpropyl)carbamoyl]phenyl}amino)benzamide
(81) 3-cyclopropyl-N-[(2E)-1-methyl-4-oxoimidazolidin-2-ylidene]-4-({3-[(propan-2-yl)carbamoyl]phenyl}amino)benzamide
(82) 3-cyclopropyl-N-[(2Z)-imidazolidin-2-ylidene]-4-[(3-{3-[(propan-2-yl)amino]oxetan-3-yl}phenyl)amino]benzamide
(83) 3-cyclopropyl-N-[(2Z)-imidazolidin-2-ylidene]-4-({3-[(2-methylpropanamido)methyl]phenyl}amino)benzamide
(84) 3-(2-hydroxypropan-2-yl)-N-[(2E)-imidazolidin-2-ylidene]-4-({3-[3-(oxan-4-yl)propanesulfonyl]phenyl}amino)benzamide
(85) 3-(2-hydroxypropan-2-yl)-N-[(2E)-imidazolidin-2-ylidene]-4-({3-[2-(oxan-4-yl)ethoxy]phenyl}amino)benzamide
(86) 3-cyclopropyl-N-[(2Z)-imidazolidin-2-ylidene]-4-({3-[(1-methylcyclopropyl)carbamoyl]-5-(trifluoromethyl)phenyl}amino)benzamide
(87) 3-cyclopropyl-N-[(2E)-imidazolidin-2-ylidene]-4-{2-[(3-methylbutyl)carbamoyl]phenoxy}benzamide
(88) 4-({3-[2-(1,4-dioxan-2-yl)ethoxy]phenyl}amino)-3-(2-hydroxypropan-2-yl)-N-[(2Z)-imidazolidin-2-ylidene]benzamide
(89) 3-[(2-cyclopropyl-4-{[(2Z)-imidazolidin-2-ylidene]carbamoyl}phenyl)amino]-2-methylphenyl diethyl phosphate
(90) 3-cyclopropyl-N-[(2Z)-imidazolidin-2-ylidene]-4-({3-[2-(3-methylbut-2-en-1-yl)-2H-1,2,3,4-tetrazol-5-yl]phenyl}amino)benzamide
(91) 3-cyclopropyl-5-fluoro-N-[(2Z)-imidazolidin-2-ylidene]-4-({3-[(propan-2-yl)carbamoyl]phenyl}amino)benzamide
(92) 3-[(2-cyclopropyl-4-{[(2Z)-imidazolidin-2-ylidene]carbamoyl}phenyl)amino]-2-(furan-3-yl)-N-(propan-2-yl)benzamide
(93) 3-tert-butyl-N-[(2E)-imidazolidin-2-ylidene]-4-[2-(4-methylpentanamido)phenoxy]benzamide
(94) 4-({2-chloro-3-[(1,1-dioxo-1λ$^6$-thian-4-yl)carbamoyl]phenyl}amino)-3-cyclopropyl-N-[(2E)-imidazolidin-2-ylidene]benzamide
(95) 3-cyclopentyl-N-[(2Z)-imidazolidin-2-ylidene]-4-({3-[(oxolan-3-yl)carbamoyl]phenyl}amino)benzamide
(96) 3-cyclopentyl-N-[(2Z)-imidazolidin-2-ylidene]-4-({3-[(oxan-4-yl)carbamoyl]phenyl}amino)benzamide
(97) 4-{[2-chloro-3-(morpholine-4-carbonyl)phenyl]amino}-N-[(2E)-imidazolidin-2-ylidene]-3-(oxolan-2-yl)benzamide
(98) 3-cyclopropyl-4-({2-fluoro-3-[(propan-2-yl)carbamoyl]phenyl}amino)-N-[(2Z)-imidazolidin-2-ylidene]benzamide
(99) 4-[(2-cyclopropyl-6-fluoro-4-{[(2Z)-imidazolidin-2-ylidene]carbamoyl}phenyl)amino]-3-fluoro-N-(1-methylcyclopropyl)pyridine-2-carboxamide
(100) 3-cyclopropyl-N-[(2E)-imidazolidin-2-ylidene]-4-[2-(4-methylpentanamido)phenoxy]benzamide
(101) 4-({2-chloro-3-[(1-methylcyclopropyl)carbamoyl]phenyl}amino)-N-[(2E)-imidazolidin-2-ylidene]-3-methanesulfinylbenzamide
(102) 2-chloro-3-[(4-{[(2Z)-imidazolidin-2-ylidene]carbamoyl}-2-methanesulfonylphenyl)amino]-N-(1-methylcyclopropyl)benzamide
(103) 4-{[2-chloro-3-(1,1-dioxo-1)$^6$-thiomorpholine-4-carbonyl)phenyl]amino}-3-cyclopropyl-N-[(2E)-imidazolidin-2-ylidene]benzamide
(104) 4-({2-chloro-3-[3-(propan-2-yl)morpholine-4-carbonyl]phenyl}amino)-3-cyclopropyl-N-[(2Z)-imidazolidin-2-ylidene]benzamide
(105) 4-({2-chloro-3-[2-(propan-2-yl)morpholine-4-carbonyl]phenyl}amino)-3-cyclopropyl-N-[(2Z)-imidazolidin-2-ylidene]benzamide
(106) 3-cyclopropyl-N-[(2Z)-imidazolidin-2-ylidene]-5-methyl-4-({3-[(propan-2-yl)carbamoyl]phenyl}amino)benzamide
(107) 3-cyclopropyl-N-[(2Z)-imidazolidin-2-ylidene]-4-[(3-{[1-(2-methylpropyl)cyclopropyl]carbamoyl}phenyl)amino]benzamide
(108)N-{3-[(2-cyclopropyl-4-{[(2E)-imidazolidin-2-ylidene]carbamoyl}phenyl)amino]phenyl}oxolane-2-carboxamide
(109) 4-[(2-chloro-3-{[(oxolan-2-yl)methyl]carbamoyl}phenyl)amino]-3-cyclopropyl-N-[(2E)-imidazolidin-2-ylidene]benzamide
(110)N-[(2E)-1-acetylimidazolidin-2-ylidene]-3-cyclopropyl-4-{[3-(2-methylpropanamido)phenyl]amino}benzamide
(111) 4-({3-[(1-tert-butylcyclopropyl)carbamoyl]phenyl}amino)-3-cyclopropyl-N-[(2Z)-imidazolidin-2-ylidene]benzamide
(112) 4-({3-cyano-5-[(propan-2-yl)carbamoyl]phenyl}amino)-3-cyclopropyl-N-[imidazolidin-2-ylidene]benzamide,
(113) 3-cyclopropyl-N-[1-(2,2-difluoroethyl)imidazolidin-2-ylidene]-4-{[3-(2-methylpropanamido)phenyl]amino}benzamide,
(114) 4-[(2-chloro-3-{[1-(trifluoromethyl)cyclopropyl]carbamoyl}phenyl)amino]-3-cyclopropyl-N-[imidazolidin-2-ylidene]benzamide,
(115) 3-cyclopropyl-N-[imidazolidin-2-ylidene]-4-{[3-(morpholine-4-carbonyl)-2-(trifluoromethyl)phenyl]amino}benzamide,
(116) 3-cyclopropyl-4-f{[3-(cyclopropylcarbamoyl)-2-(trifluoromethyl)phenyl]amino}-N—[imidazolidin-2-ylidene]benzamide,
(117) 3-cyclopropyl-5-fluoro-N-[imidazolidin-2-ylidene]-4-({3-[(1-methylcyclopropyl)carbamoyl]phenyl}amino)benzamide,
(118) 4-{[2-chloro-5-fluoro-3-(morpholine-4-carbonyl)phenyl]amino}-3-cyclopropyl-N-[imidazolidin-2-ylidene]benzamide,
(119) 3-cyclopropyl-5-fluoro-N-[imidazolidin-2-ylidene]-4-{[3-(morpholine-4-carbonyl)phenyl]amino}benzamide, (120) 4-({2-chloro-3-[(1S,4S)-2-oxa-5-azabicyclo[2.2.1]heptane-5-carbonyl]phenyl}amino)-3-cyclopropyl-N—[imidazolidin-2-ylidene]benzamide,
(121) 4-({2-chloro-3-[2-(trifluoromethyl)morpholine-4-carbonyl]phenyl}amino)-3-cyclopropyl-N—[imidazolidin-2-ylidene]benzamide,
(122) 4-({2-chloro-3-[3-(trifluoromethyl)morpholine-4-carbonyl]phenyl}amino)-3-cyclopropyl-N—[imidazolidin-2-ylidene]benzamide,
(123) 3-chloro-2-[(2-cyclopropyl-4-{[imidazolidin-2-ylidene]carbamoyl}phenyl)amino]-N-(1-methylcyclopropyl)pyridine-4-carboxamide,
(124)N-{3-[(2-cyclopropyl-4-{[imidazolidin-2-ylidene]carbamoyl}phenyl)amino]phenyl}-1,1-dioxo-1$\lambda^6$-thiane-4-carboxamide,
(125) 3-fluoro-N—[imidazolidin-2-ylidene]-4-({3-[(1-methylcyclopropyl)carbamoyl]phenyl}amino)-5-(oxolan-2-yl)benzamide,
(126) 4-{[2-chloro-3-(morpholine-4-sulfonyl)phenyl]amino}-3-cyclopropyl-N-[imidazolidin-2-ylidene]benzamide,
(127) 4-({3-[(1-cyanocyclopropyl)carbamoyl]phenyl}amino)-3-cyclopropyl-5-fluoro-N-[imidazolidin-2-ylidene]benzamide,
(128) 3-cyclopropyl-5-fluoro-4-({3-fluoro-5-[(propan-2-yl)carbamoyl]phenyl}amino)-N-[imidazolidin-2-ylidene]benzamide,
(129) 4-({2-chloro-3-[(1-methylcyclopropyl)carbamoyl]phenyl}amino)-3-cyclopropyl-5-fluoro-N-[imidazolidin-2-ylidene]benzamide,
(130) 3-cyclopropyl-5-fluoro-4-({2-fluoro-3-[(propan-2-yl)carbamoyl]phenyl}amino)-N-[imidazolidin-2-ylidene]benzamide,
(131) 5-cyclopropyl-2-fluoro-N-[imidazolidin-2-ylidene]-4-({3-[(propan-2-yl)carbamoyl]phenyl}amino)benzamide,
(132) 3-tert-butyl-4-({2-chloro-3-[(1-methylcyclopropyl)carbamoyl]phenyl}amino)-N-[imidazolidin-2-ylidene]benzamide,
(133) 5-cyclopropyl-N-[imidazolidin-2-ylidene]-6-({3-[(propan-2-yl)carbamoyl]phenyl}amino)pyridine-3-carboxamide,
(134) 4-{[2-chloro-3-(morpholine-4-carbonyl)phenyl]amino}-3-fluoro-N-[imidazolidin-2-ylidene]-5-(oxolan-3-yl)benzamide,
(135) 4-({2-chloro-3-[(1-methylcyclopropyl)carbamoyl]phenyl}amino)-3-fluoro-N-[imidazolidin-2-ylidene]-5-(oxolan-2-yl)benzamide,
(136) 3-chloro-2-[(2-cyclopropyl-6-fluoro-4-{[imidazolidin-2-ylidene]carbamoyl}phenyl)amino]-N-(1-methylcyclopropyl)pyridine-4-carboxamide,
(137) 4-({2-chloro-3-[(1-methylcyclopropyl)carbamoyl]phenyl}amino)-N-[imidazolidin-2-ylidene]-3-(oxolan-2-yl)benzamide,
(138) 3-[(2-cyclopropyl-4-{[imidazolidin-2-ylidene]carbamoyl}phenyl)amino]-2,5-difluoro-N-(propan-2-yl)benzamide,
(139) 3-[(2-cyclopropyl-4-{[imidazolidin-2-ylidene]carbamoyl}phenyl)amino]-2,5-difluoro-N-(1-methylcyclopropyl)benzamide,
(140)N-[imidazolidin-2-ylidene]-4-({3-[(1-methylcyclopropyl)carbamoyl]phenyl}amino)-3-(oxolan-2-yl)benzamide,
(141) 4-{[3-(1-cyanocyclopropaneamido)phenyl]amino}-3-cyclopropyl-N-[imidazolidin-2-ylidene]benzamide,
(142) 3-cyclopropyl-5-fluoro-N-[imidazolidin-2-ylidene]-4-({3-[3-(trifluoromethyl)morpholine-4-carbonyl]phenyl}amino)benzamide,
(143) 3-cyclopropyl-5-fluoro-4-({2-fluoro-3-[(1-methylcyclopropyl)carbamoyl]phenyl}amino)-N-[imidazolidin-2-ylidene]benzamide,
(144) 3-cyclopropyl-5-fluoro-N-[imidazolidin-2-ylidene]-4-({3-[2-(trifluoromethyl)morpholine-4-carbonyl]phenyl}amino)benzamide,
(145) 3-fluoro-N-[imidazolidin-2-ylidene]-4-{[3-(morpholine-4-carbonyl)phenyl]amino}-5-(oxolan-2-yl)benzamide,
(146) 6-({2-chloro-3-[(1-methylcyclopropyl)carbamoyl]phenyl}amino)-5-cyclopropyl-N-[imidazolidin-2-ylidene]pyridine-3-carboxamide,
(147) 2-[(2-cyclopropyl-6-fluoro-4-{[imidazolidin-2-ylidene]carbamoyl}phenyl)amino]-3-fluoro-N-(1-methylcyclopropyl)pyridine-4-carboxamide,
(148) 2-cyclopropyl-3-[(2-cyclopropyl-4-{[imidazolidin-2-ylidene]carbamoyl}phenyl)amino]-5-fluoro-N-(propan-2-yl)benzamide,
(149) 3-cyano-5-cyclopropyl-N-[imidazolidin-2-ylidene]-4-({3-[(1-methylcyclopropyl)carbamoyl]phenyl}amino)benzamide,
(150) 3-chloro-4-[(2-cyclopropyl-4-{[imidazolidin-2-ylidene]carbamoyl}phenyl)amino]-N-(1-methylcyclopropyl)pyridine-2-carboxamide,
(151) 4-chloro-5-[(2-cyclopropyl-4-{[imidazolidin-2-ylidene]carbamoyl}phenyl)amino]-N-(1-methylcyclopropyl)pyridine-3-carboxamide
(152)N-(1-cyanocyclopropyl)-2-[(2-cyclopropyl-6-fluoro-4-{[imidazolidin-2-ylidene]carbamoyl}phenyl)amino]-3-fluoropyridine-4-carboxamide,
(153) 4-{[3-chloro-4-(morpholine-4-carbonyl)pyridin-2-yl]amino}-3-cyclopropyl-5-fluoro-N-[imidazolidin-2-ylidene]benzamide,
(154) 4-({3-chloro-4-[(1R,4R)-2-oxa-5-azabicyclo[2.2.1]heptane-5-carbonyl]pyridin-2-yl}amino)-3-cyclopropyl-5-fluoro-N-[imidazolidin-2-ylidene]benzamide,
(155) 4-({3-chloro-4-[(1S,4S)-2-oxa-5-azabicyclo[2.2.1]heptane-5-carbonyl]pyridin-2-yl}amino)-3-cyclopropyl-5-fluoro-N-[imidazolidin-2-ylidene]benzamide,
(156) 3-cyclopropyl-5-fluoro-4-{[3-fluoro-4-(morpholine-4-carbonyl)pyridin-2-yl]amino}-N-[imidazolidin-2-ylidene]benzamide,
(157) 3-chloro-4-[(2-cyclopropyl-6-fluoro-4-{[imidazolidin-2-ylidene]carbamoyl}phenyl)amino]-N-(1-methylcyclopropyl)pyridine-2-carboxamide,
(158) 3-cyclopropyl-5-fluoro-4-{[2-fluoro-3-(morpholine-4-carbonyl)phenyl]amino}-N—[imidazolidin-2-ylidene]benzamide,
(159) 3-cyclopropyl-5-fluoro-4-({3-fluoro-4-[(1S,4S)-2-oxa-5-azabicyclo[2.2.1]heptane-5-carbonyl]pyridin-2-yl}amino)-N—[imidazolidin-2-ylidene]benzamide,
(160) 3-cyclopropyl-4-({3-[2-(3-methylbut-2-en-1-yl)-2H-1,2,3,4-tetrazol-5-yl]phenyl}amino)-N-[1-methylimidazolidin-2-ylidene]benzamide,
(161)N-{3-[(2-cyclopropyl-4-{[imidazolidin-2-ylidene]carbamoyl}phenyl)amino]phenyl}-3-methyloxetane-3-carboxamide,
(162) 3-cyclopropyl-4-[(3-{[1-(hydroxymethyl)cyclopropyl]carbamoyl}phenyl)amino]-N-[imidazolidin-2-ylidene]benzamide,
(163)N-{3-[(2-cyclopropyl-6-fluoro-4-{[imidazolidin-2-ylidene]carbamoyl}phenyl)amino]phenyl}-3-methyloxetane-3-carboxamide,
(164)N-{bicyclo[1.1.1]pentan-2-yl}-3-chloro-2-[(2-cyclopropyl-6-fluoro-4-{[imidazolidin-2-ylidene]carbamoyl}phenyl)amino]pyridine-4-carboxamide, (165) 3-cyclopropyl-4-{[3-(4,5-dihydro-1,3-oxazol-2-yl)phenyl]amino}-5-fluoro-N-[imidazolidin-2-ylidene]benzamide, (166) 3-chloro-2-[(2-cyclopropyl-6-fluoro-4-{[(2Z)-imidazolidin-2-ylidene]carbamoyl}phenyl)amino]-N-{3-fluorobicyclo[1.1.1]pentan-1-yl}pyridine-4-carboxamide, (167) 4-({2-chloro-3-[(1-methylcyclopropyl)carbamoyl]phenyl}amino)-3-cyclopropyl-N-[imidazolidin-2-ylidene]benzamide, (168) tert-butyl 2-{3-chloro-2-[(2-cyclopropyl-6-fluoro-4-{[(2Z)-imidazolidin-2-ylidene]carbamoyl}phenyl)amino]pyridin-4-yl}-4,5-dihydro-1H-imidazole-1-carboxylate, (169) 3-cyclopropyl-4-{[3-(4,5-dihydro-1H-imidazol-2-yl)phenyl]amino}-5-fluoro-N-[(2Z)-imidazolidin-2-ylidene]benzamide, (170) 3-cyclopropyl-5-fluoro-N-[(2Z)-imidazolidin-2-ylidene]-4-{[3-(2-oxo-1,3-oxazolidin-3-yl)phenyl]amino}benzamide, (171) 3-cyclopropyl-5-fluoro-N-[(2Z)-imidazolidin-2-ylidene]-4-{[3-(thiomorpholine-4-carbonyl)phenyl]amino}benzamide, (172) 3-chloro-2-[(2-cyclopropyl-6-fluoro-4-{[(2Z)-imidazolidin-2-ylidene]carbamoyl}phenyl)amino]-N-[(1s,3R,5S,7s)-adamantan-1-yl]pyridine-4-carboxamide, (173) 3-cyclopropyl-5-fluoro-N-[(2Z)-imidazolidin-2-ylidene]-4-[(3-{[(1s,3R,5S,7s)-adamantan-1-yl]carbamoyl}phenyl)amino]benzamide, (174) 3-cyclopropyl-5-fluoro-N-[(2E)-1-methylimidazolidin-2-ylidene]-4-[(3-{[(1s,3R,5S,7s)-adamantan-1-yl]carbamoyl}phenyl)amino]benzamide, (175) (R)—N-(3-((2-cyclopropyl-6-fluoro-4-(imidazolidin-2-ylidenecarbamoyl)phenyl)amino)phenyl)pyrrolidine-2-carboxamide, (176) 3-cyclopropyl-5-fluoro-N-[(2E)-1-methylimidazolidin-2-ylidene]-4-({3-[(oxetan-3-yl)carbamoyl]phenyl}amino)benzamide, (177) 3-cyclopropyl-5-fluoro-N-[(2Z)-imidazolidin-2-ylidene]-4-({3-[(oxetan-3-yl)carbamoyl]phenyl}amino)benzamide, (178) 3-cyclopropyl-5-fluoro-N-[(2Z)-imidazolidin-2-ylidene]-4-({3-[(1,3-oxazol-2-yl)carbamoyl]phenyl}amino)benzamide, (179) (2R)—N-{3-[(2-cyclopropyl-6-fluoro-4-{[(2Z)-imidazolidin-2-ylidene]carbamoyl}phenyl)amino]phenyl}-5-oxopyrrolidine-2-carboxamide, (180)N-{3-[(2-cyclopropyl-6-fluoro-4-{[(2Z)-imidazolidin-2-ylidene]carbamoyl}phenyl)amino]phenyl}-2-oxabicyclo[2.1.1]hexane-1-carboxamide, (181) 4-({2-chloro-3-[(1-cyanocyclopropyl)carbamoyl]phenyl}amino)-3-cyclopropyl-5-fluoro-N-[(2E)-imidazolidin-2-ylidene]benzamide, and their pharmaceutically acceptable salts.

The present invention therefore extends to compounds (1) to (181) and their pharmaceutically acceptable salts, such as hydrobromide, tartrate, citrate, trifluoroacetate, ascorbate, hydrochloride, tosylate, triflate, maleate, mesylate, formate, acetate and fumarate.

According to another aspect, a subject-matter of the present invention relates to compounds (1) to (181) or any of its pharmaceutically acceptable salts, for use as a medicament.

According to another aspect, a subject-matter of the present invention relates to a compound of formula (I) as defined above or any of its pharmaceutically acceptable salts, and any of compounds (1) to (181) or any of its pharmaceutically acceptable salts, for use as an agent for preventing, inhibiting or treating a RNA virus infection caused by a RNA virus belonging to group V of the Baltimore classification, and in particular a RSV viral infection or a virus-related condition.

The compounds of the invention may exist in the form of free bases or of addition salts with pharmaceutically acceptable acids. «Pharmaceutically acceptable salt thereof» refers to salts which are formed from acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

Suitable physiologically acceptable acid addition salts of compounds of formula (I) include hydrobromide, tartrate, citrate, trifluoroacetate, ascorbate, hydrochloride, tosylate, triflate, maleate, mesylate, formate, acetate and fumarate.

The compounds of formula (I) and any of compounds (1) to (181) or any of their pharmaceutically acceptable salts may form solvates or hydrates and the invention includes all such solvates and hydrates.

The compounds of formula (I) may be present as well under tautomer forms and are part of the invention. The terms "hydrates" and "solvates" simply mean that the compounds (I) according to the invention can be in the form of a hydrate or solvate, i.e. combined or associated with one or more water or solvent molecules. This is only a chemical characteristic of such compounds, which can be applied for all organic compounds of this type.

In the context of the present invention, the term:

"halogen" is understood to mean chlorine, fluorine, bromine, or iodine, and in particular denotes chlorine, fluorine or bromine, "$(C_1\text{-}C_x)$alkyl", as used herein, respectively refers to a $C_1\text{-}C_x$ normal, secondary or tertiary saturated hydrocarbon, for example $(C_1\text{-}C_6)$alkyl. Examples are, but are not limited to, methyl, ethyl, 1-propyl, 2-propyl, butyl, pentyl, an "alkenylene" means a divalent $(C_1\text{-}C_x)$alkyl group comprising a double bond, and more particularly a ethenylene group, also known as vinylene or 1,2-ethenediyl, "$(C_3\text{-}C_6)$cycloalkyl", as used herein, refers to a cyclic saturated hydrocarbon. Examples are, but are not limited to, cyclopropyl, cyclobutyl, cyclopentyl, cyclohexyl, "$(C_1\text{-}C_x)$alkoxy", as used herein, refers to a O—$(C_1\text{-}C_x)$ alkyl moiety, wherein alkyl is as defined above, for example $(C_1\text{-}C_6)$alkoxy. Examples are, but are not limited to, methoxy, ethoxy, 1-propoxy, 2-propoxy, butoxy, pentoxy, a "5- or 6-membered heterocyclic ring comprising 1, 2, 3 or 4 heteroatoms" as used herein, means an aromatic or non aromatic ring comprising 5 or 6 bonds and 1, 2, 3 or 4 heteroatoms selected from oxygen, sulfur and nitrogen atoms. In one particular embodiment, it is a "5-membered heterocyclic ring comprising 1, 2, 3 or 4 heteroatoms". In one embodiment, it comprises at least 1 heteroatom, and preferably at least one nitrogen atom. In another embodiment, it comprises at least 2 heteroatoms, with for example at least one nitrogen atom. According to a further embodiment, it comprises 2, 3 or 4 nitrogen atoms. According to an even further embodiment, it comprises one nitrogen atom and one oxygen atom or two nitrogen atoms and one oxygen atom. Examples are, but not limited to, tetrazoles, triazoles, such as 1,2,3- or 1,2,4-triazoles, and diazoles, such as imidazole, pyrazole, 2- or 3-pyrazoline, dihydroimidazole or imidazoline, oxadiazoles, such as 1,2,4-oxadiazole or 1,2,3-oxadiazoles, oxazoles, oxazolines, oxazolidines, oxazolidinones. According to a preferred embodiment, such 5-membered heterocyclic ring comprising 2, 3 or 4 heteroatoms is a triazole, a tetrazole, an imidazoline or an oxazoline. In one embodiment, a 5-membered heteroaromatic ring may comprise one or two heteroatoms selected from a oxygen atom and a nitrogen atom, and may in particular be selected from a oxazolyl group, a isoxazolyl group, a pyrazolyl group and an imidazolyl group, a "bicyclic alkyl" or "($C_5$-$C_{11}$)bicyclic alkyl" compound means a bicyclic saturated hydrocarbon monovalent group that may be chosen among spirocyclic alkyl, fused bicyclic alkyl and bridged bicyclic alkyl. Such bicyclic alkyl generally comprises 5 to 11 carbon atoms. Examples are, but are not limited to, spiro[2.2]pentyl, spiro[5.5]undecanyl, spiro[3.4]octanyl, spiro[4.5]decanyl, bicyclo[1.1.0]butyl, bicyclo[2.1.1]hexyl, bicyclo[3.2.0]heptyl, bicyclo[3.3.0]octyl, bicyclo[4.3.0]nonyl, bicyclo[2.2.1]heptyl, bicyclo[2.2.2]octyl, bicyclo[3.2.1]octyl, bicyclo[1.1.1]pentyl, oxabicyclo[1.1.1]pentyl, oxabicyclo[2.1.1]hexyl, oxabicyclo[2.2.1]heptyl, oxabicyclo[4.1.0]heptyl, oxabicyclo[3.2.1]octyl and cubyl, and a "bridged morpholinyl group" means a bicyclic compound where one of the cycles is a morpholinyl group, the two rings share three or more atoms and the bridge contains at least one atom, for example 1, 2 or three atoms. Examples are, but are not limited to, as depicted herein after:

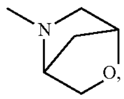,
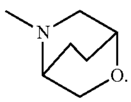.

The compounds of formula (I) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

The compounds of the present invention can be prepared by conventional methods of organic synthesis practiced by those skilled in the art. The general reaction sequences outlined below represent a general method useful for preparing the compounds of the present invention and are not meant to be limiting in scope or utility.

The compounds of general formula (I) when Q is NH can be prepared according to scheme 1 below.

Scheme 1

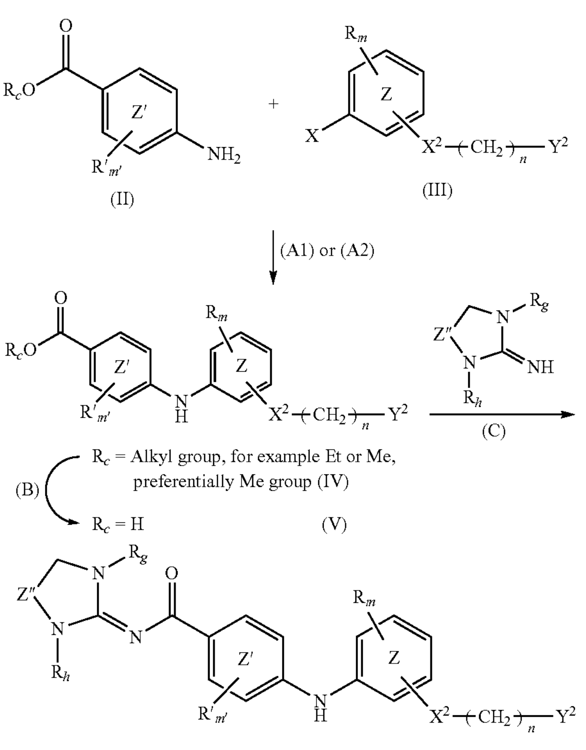

The synthesis is based on a coupling reaction of a halogeno aromatic compound of formula (III) with an aniline derivative (II), wherein R, R', $R_c$, $R_g$, $R_h$, m, m',

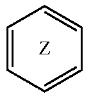

ring,

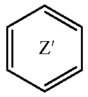

ring, $X^2$, n, $Y^2$ are as defined above and X is a chlorine atom, an iodine atom or a bromine atom, following procedure (A1) or (A2), followed by at least a further step reacting the carboxylic acid derivative of the compound obtained after said coupling step with a compound of formula

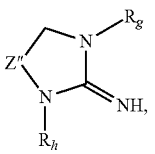, wherein Z", $R_g$ and $R_h$ are as defined above.

In the case where $R_g$=$R_h$=H and Z" is —CO—, the procedure may consist firstly in reacting compound (V) with guanidine and secondly in a cyclisation step to afford final cyclised derivative (I) where $R_g=R_h=H$ and Z" is —CO—.

According to one embodiment, procedure (A1) may advantageously be used when the group $$-X^2-(CH_2)_n-Y^2$$

is in meta or para position on the

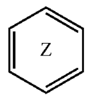

ring, with respect to the —NH— group.

According to procedure (A1), the compound of formula (III) may be placed in a protic solvent such as tert-butanol. The compound of formula (II) may then be added, for example in a molar ratio ranging from 1 to 1.5 with respect to the compound of formula (III) in presence of an inorganic base, such as $Cs_2CO_3$ or $K_2CO_3$, for example in a molar ratio ranging from 1 to 5 still with respect to the compound of formula (III), in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) or rac-BINAP in particular in an amount ranging from 2 mol % to 15 mol % relative to the total amount of compound of formula (III), and in the presence of an organometallic catalyst, such as $Pd(OAc)_2$ or $Pd_2dba_3$, or BrettPhos Pd G3 in an amount ranging from 2 mol % to 25 mol % relative to the total amount of compound of formula (III). The reaction mixture can then be heated at a temperature ranging from 80 to 130° C., for example at 90° C., and stirred for a time ranging from 15 to 25 hours, for example during 20 hours, under inert gas and for example argon. The reaction mixture can be concentrated under reduced pressure and the residue can be diluted with an organic solvent such as ethyl acetate. The organic phase can be washed with water, decanted, dried over magnesium sulphate, filtered and then concentrated under reduced pressure to give a compound of formula (IV).

According to one embodiment, procedure (A2) may advantageously be used when the group $$-X^2-(CH_2)_n-Y^2$$

is in ortho position on the

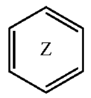

ring, with respect to the —NH— group.

According to procedure (A2), the compound of formula (II) may be placed in a polar aprotic solvent such as dimethylsulfoxide. The compound of formula (III) may then be added, for example in a molar ratio ranging from 1 to 1.5 with respect to the compound of formula (II) in presence of an inorganic base, such as $Cs_2CO_3$ or $K_2CO_3$, for example in a molar ratio ranging from 1 to 5 still with respect to the compound of formula (II), in the presence of a ligand, such as L-proline in particular in an amount ranging from 2 mol % to 25 mol % relative to the total amount of compound of formula (II), and in the presence of an organometallic catalyst, such as CuI, in an amount ranging from 2 mol % to 25 mol % relative to the total amount of compound of formula (II). The reaction mixture can then be heated at a temperature ranging from 80 to 130° C., for example at 90° C., and stirred for a time ranging from 15 to 25 hours, for example during 20 hours, under inert gas and for example argon. The reaction mixture can be diluted with an organic solvent such as ethyl acetate. The organic phase can be washed with water, decanted, dried over magnesium sulphate, filtered and then concentrated under reduced pressure to give a compound of formula (IV).

The starting compounds of formula (II), (III) are available or can be prepared according to methods known to the person skilled in the art. In particular, the method used to afford the building block of formula (III) which further leads to compound (166) is based on the synthesis of intermediate (3-fluorobicyclo[1.1.1]pentan-1-aminium chloride) described in *Org. Biomol. Chem.* 2015, 13, 11597-11601. In addition, the method used to afford the building block of formula (III) which further leads to compound (180) is based on the synthesis of intermediate (2-oxabicyclo[2.1.1]hexane-1-carboxylic acid) described in *Angew. Chem. Int. Ed.* 2020, 59, 7161-7167. In addition, the method used to afford the required building blocks of formula (III) which further lead to compounds (165), (168) and (169) is based on the method described in *Synlett* 2006, 10, 1479-1484.

Accordingly, the present invention further relates to the synthesis process for manufacturing new compounds of formula (I) as defined above, when Q is NH, comprising at least (i) a step of coupling a compound of formula (II)

(II)

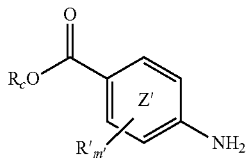

with a compound of formula (III)

(III)

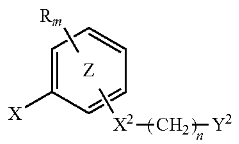

wherein R, R', m, m', n,

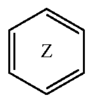

ring,

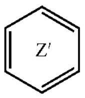

ring, $X^2$, $Y^2$ are as defined above, $R_c$ is an alkyl group, such as a ethyl or methyl group and X is a chlorine atom, an iodine atom or a bromine atom, in presence of an inorganic base and a ligand and in the presence of an organometallic catalyst, to obtain a compound of formula (IV)

(IV)

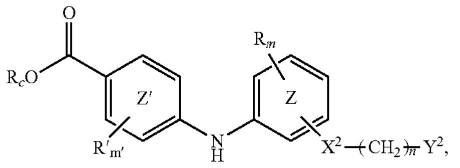

wherein $R_e$ means an alkyl group, such as an ethyl group or a methyl group, preferentially a methyl group and R, R', m, m', n,

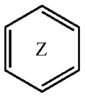

ring,

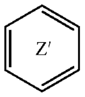

ring, $X^2$, $Y^2$ are as defined above, followed by a hydrolysis leading to a compound of formula (V)

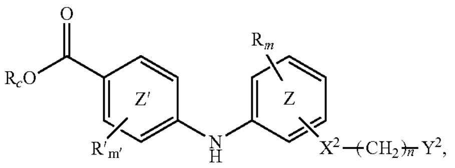

wherein $R_c$ is a hydrogen atom and R, R', m, m', n,

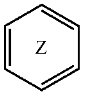

ring,

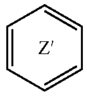

ring, $X^2$, $Y^2$ are as defined above, and (ii) a step of reacting a compound of formula (V) with a compound of formula

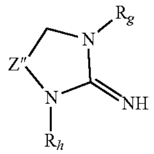

wherein Z", $R_g$ and $R_h$ are as defined above in presence of an organic base such as N,N-diisopropylethylamine and in presence of a coupling agent such as 1,1'-carbonyldiimidazole, to obtain a compound for formula (I) wherein Q is NH, as defined above.

The compounds of general formula (I) when Q is O can be prepared according to scheme 1' below.

Scheme 1'

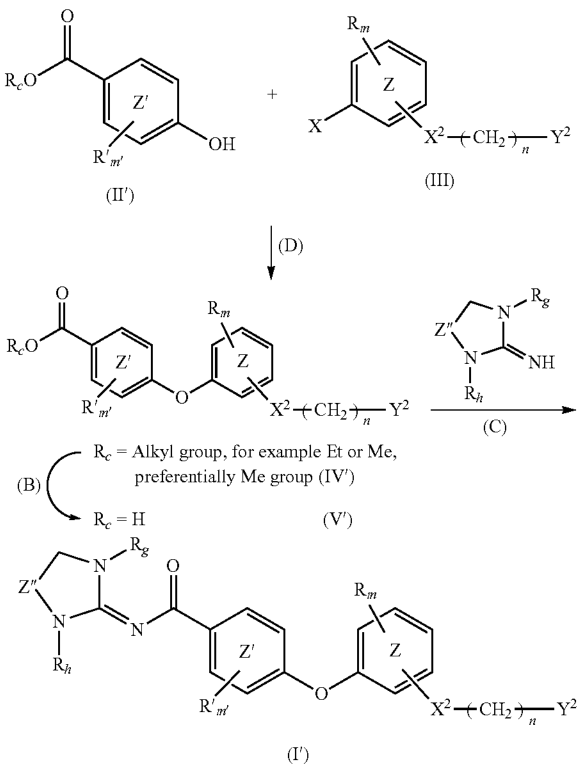

The synthesis is based on a coupling reaction starting from a halogeno aromatic compound of formula (III) with a phenol derivative of formula (II'), wherein R, R', $R_c$, $R_g$, $R_h$, Z", m, m',

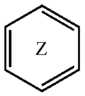

ring,

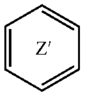

ring, $X^2$, n, $Y^2$ are as defined above and X is a fluorine atom.

According to procedure (D), the fluoroaryl derivative (III) may be placed in a polar solvent such as N,N-dimethylformamide. Phenol derivative (II') may then be added in a molar ratio ranging from 1 to 2 with respect to the fluoroaryl derivative (III) in presence of an inorganic base, such as $Cs_2CO_3$ or $K_2CO_3$, in particular in a molar ratio ranging from 1 to 5. The reaction mixture can then be heated at a temperature ranging from 50 to 150° C., for example at 70° C. and stirred for a time ranging from 5 to 90 hours, for example during 16 hours, under inert gas and for example argon. The reaction mixture can be concentrated under reduced pressure and the residue can be partitioned between an organic solvent, such as dichloromethane, and water. The organic phase can be washed with water, decanted, dried over magnesium sulphate, filtered, concentrated under reduced pressure and purified to give a compound of formula (IV').

Accordingly, the present invention further relates to the synthesis process for manufacturing new compounds of formula (I) as defined above, wherein Q is O, comprising (i) at least a step of coupling a compound of formula (II')

(II')

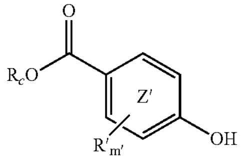

with a compound of formula (III)

(III)

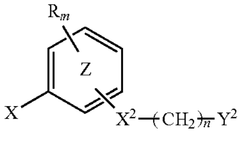

wherein R, R', $R_c$, $R_h$, $R_g$, m, m', n,

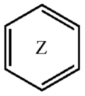

ring,

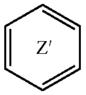

ring, $X^2$, $Y^2$ are as defined above and X is a fluorine atom, in presence of an inorganic base, to obtain a compound of formula (IV')

(IV')

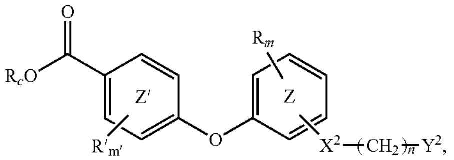

wherein $R_e$ means an alkyl group, such as an ethyl group or a methyl group, preferentially a methyl group and R, R', m, m', n,

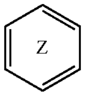

ring,

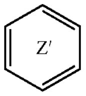

ring, $X^2$, $Y^2$ are as defined above, followed by a hydrolysis leading to a compound of formula (V')

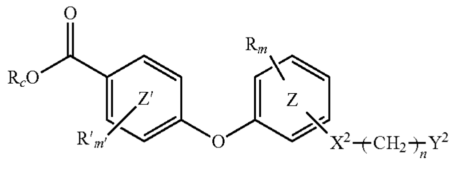

wherein $R_c$ is a hydrogen atom and R, R', m, m', n,

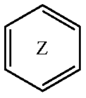

ring,

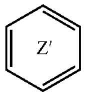

ring, $X^2$, $Y^2$ are as defined above, and (ii) a step of reacting a compound of formula (V') with a compound or formula

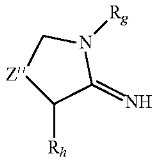

wherein $R_g$ and $R_h$ are as defined above, wherein Q is O, as defined above.

The starting compounds of formula (II), (II'), (III) are available or can be prepared according to methods known to the person skilled in the art.

More particularly, compounds of formula (II), when used to prepare compounds of formula (I), can be prepared according to scheme 2 below.

Scheme 2

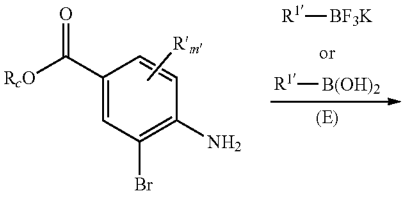

(VI)

-continued

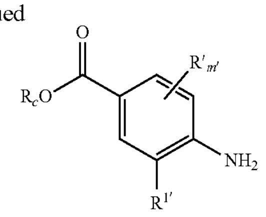

(II)

According to procedure (E), the compound of formula (VI) and an organometallic catalyst such as Pd(dppf)$Cl_2 \cdot CH_2Cl_2$ or $Pd(OAc)_2$ in an amount ranging from 2 mol % to 20 mol % relative to the amount of the compound of formula (VI) may be placed in a solvent such as 1,4-dioxane or a solvent mixture such as toluene and water. A boronic acid $R^{1'}$—$B(OH)_2$ or an organotrifluoroborate derivative $R^{1'}$—$BF_3K$ may then be added in a molar ratio ranging from 1 to 5 with respect to the compound of formula (VI), in presence of an inorganic base, such as $K_2CO_3$ or $K_3PO_4$, in particular in a molar ratio ranging from 2 to 5, and in presence of a ligand, such as RuPhos, in particular in a molar ratio ranging from 2 to 5. The reaction mixture can then be heated at a temperature ranging from 50 to 150° C., for example at 110° C., and stirred for a time ranging from 2 to 70 hours, for example during 3 hours, under inert gas and for example argon. The reaction mixture can be concentrated under reduced pressure and purified to give a compound of formula (II).

More particularly, compounds of formula (II'), when used to prepare compounds of formula (I), can be prepared with a procedure similar to procedure (E) described above.

The chemical structures and spectroscopic data of some compounds of formula (I) of the invention are illustrated respectively in the following Table I and Table II.

TABLE I

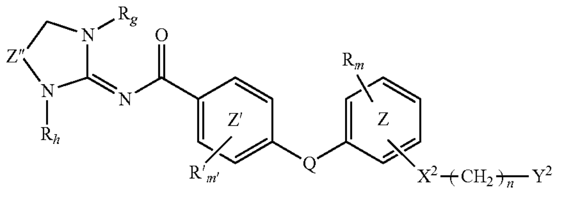

(I)

| No | Structure |
| --- | --- |
| 1 | 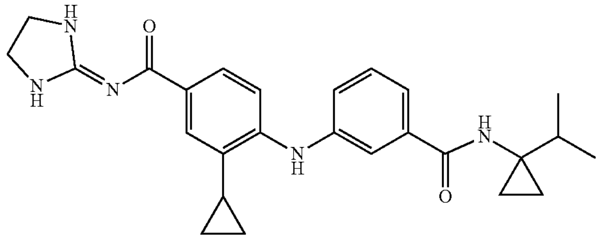 [SMILES: CC(C)C1(NC(=O)c2cccc(Nc3ccc(C(=O)N=C4NCCN4)cc3C3CC3)c2)CC1] |

TABLE I-continued
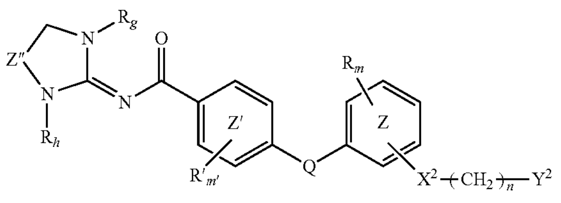
(I)
| No | Structure |
|---|---|
| 2 | 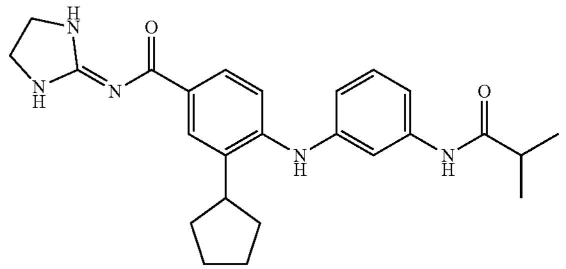 [SMILES: CC(C)C(=O)Nc1cccc(Nc2ccc(C(=O)N=C3NCCN3)cc2C2CCCC2)c1] |
| 3 | 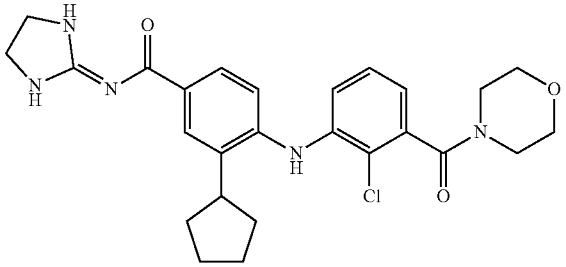 |
| 4 | 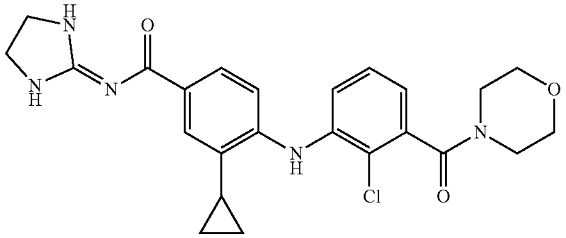 [SMILES: O=C(N=C1NCCN1)c1ccc(Nc2cccc(C(=O)N3CCOCC3)c2Cl)c(C2CC2)c1] |
| 5 | 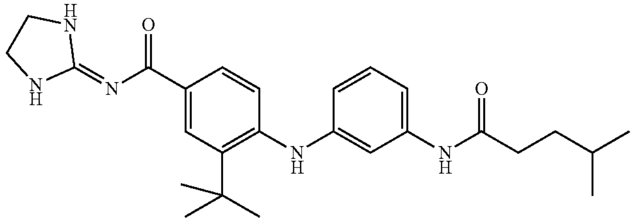 [SMILES: CC(C)CCC(=O)Nc1cccc(Nc2ccc(C(=O)N=C3NCCN3)cc2C(C)(C)C)c1] |
| 6 | 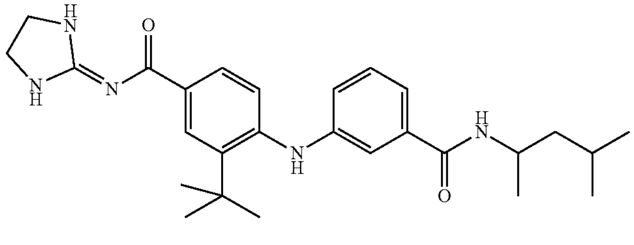 [SMILES: CC(C)CC(C)NC(=O)c1cccc(Nc2ccc(C(=O)N=C3NCCN3)cc2C(C)(C)C)c1] |

TABLE I-continued
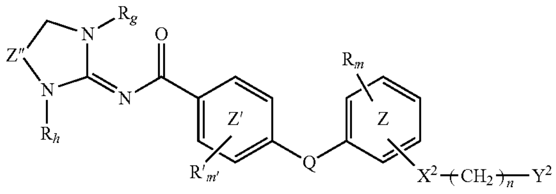
(I)
| No | Structure |
| --- | --- |
| 7 | 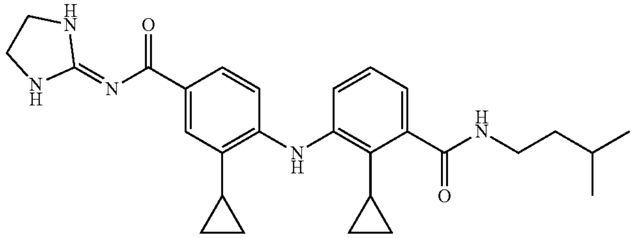 [SMILES: CC(C)CCNC(=O)c1cccc(Nc2ccc(C(=O)N=C3NCCN3)cc2C2CC2)c1C1CC1] |
| 8 | 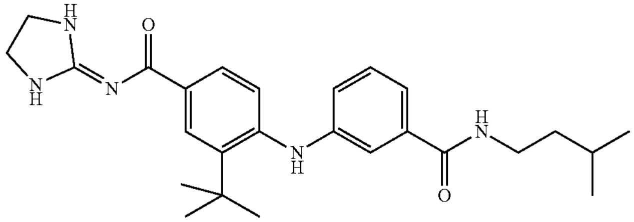 |
| 9 | 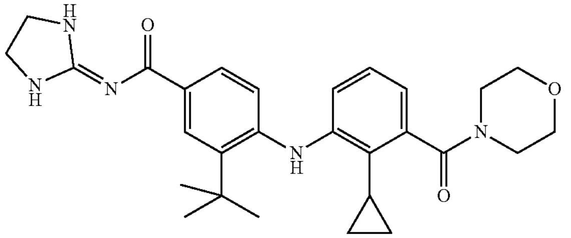 [SMILES: CC(C)(C)c1cc(C(=O)N=C2NCCN2)ccc1Nc1cccc(C(=O)N2CCOCC2)c1C1CC1] |
| 10 | 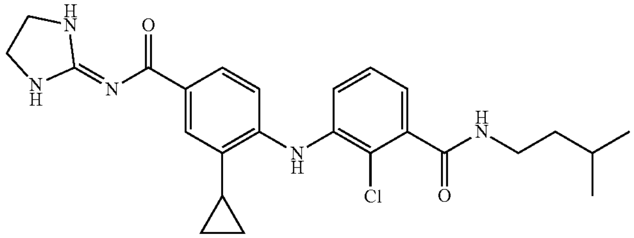 |
| 11 | 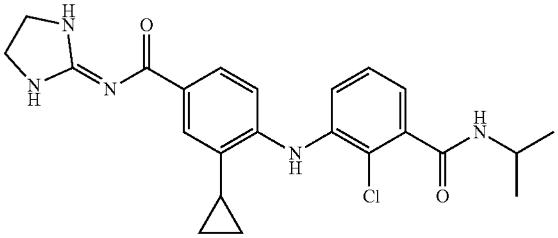 |

TABLE I-continued
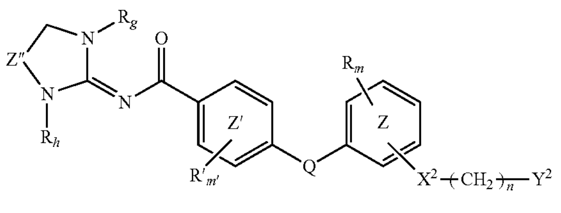
(I)
| No | Structure |
|---|---|
| 12 | 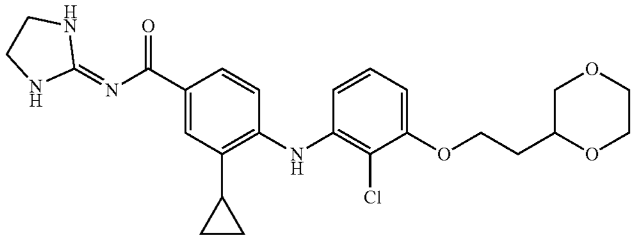 [SMILES: O=C(N=C1NCCN1)c1ccc(Nc2cccc(OCCC3COCCO3)c2Cl)c(C2CC2)c1] |
| 13 | 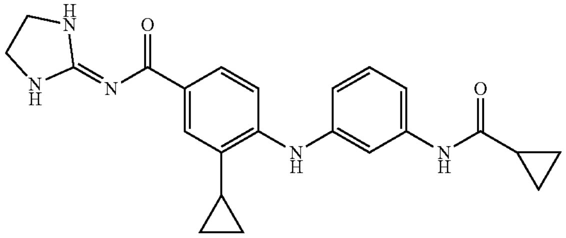 [SMILES: O=C(N=C1NCCN1)c1ccc(Nc2cccc(NC(=O)C3CC3)c2)c(C2CC2)c1] |
| 14 | 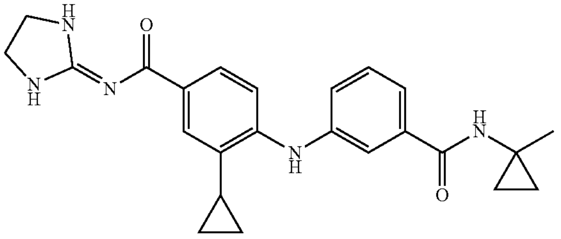 [SMILES: CC1(NC(=O)c2cccc(Nc3ccc(C(=O)N=C4NCCN4)cc3C3CC3)c2)CC1] |
| 15 | 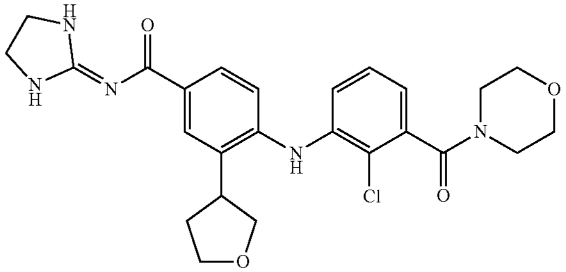 [SMILES: O=C(N=C1NCCN1)c1ccc(Nc2cccc(C(=O)N3CCOCC3)c2Cl)c(C2CCOC2)c1] |
| 16 | 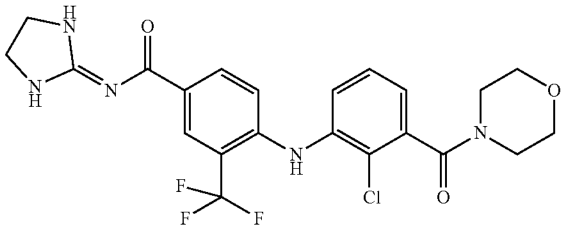 [SMILES: O=C(N=C1NCCN1)c1ccc(Nc2cccc(C(=O)N3CCOCC3)c2Cl)c(C(F)(F)F)c1] |

TABLE I-continued
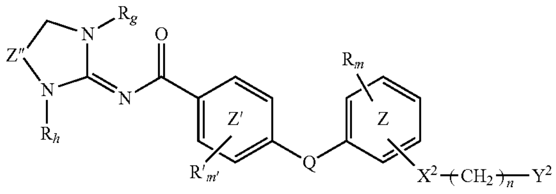
(I)
| No | Structure |
|---|---|
| 17 | 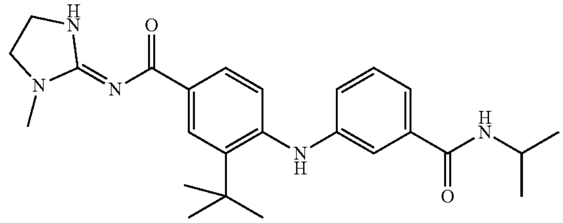 [SMILES: CC(C)NC(=O)c1cccc(Nc2ccc(C(=O)/N=C3\NCCN3C)cc2C(C)(C)C)c1] |
| 18 | 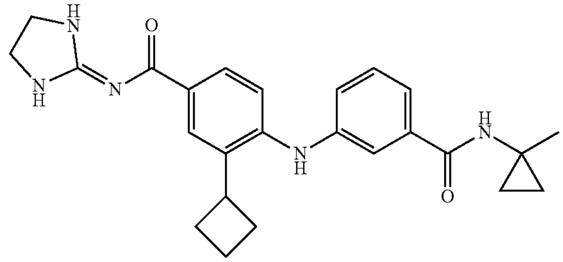 [SMILES: CC1(NC(=O)c2cccc(Nc3ccc(C(=O)N=C4NCCN4)cc3C3CCC3)c2)CC1] |
| 19 | 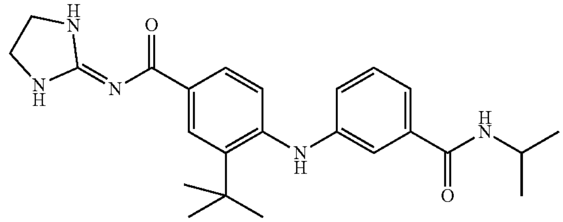 |
| 20 | 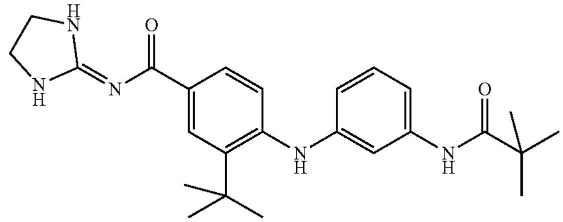 [SMILES: CC(C)(C)C(=O)Nc1cccc(Nc2ccc(C(=O)N=C3NCCN3)cc2C(C)(C)C)c1] |
| 21 | 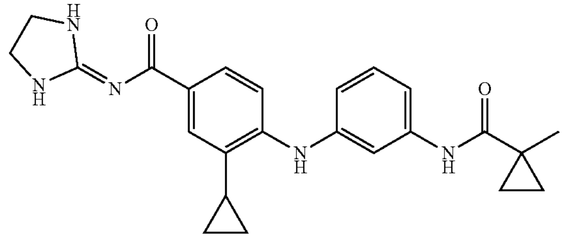 [SMILES: CC1(C(=O)Nc2cccc(Nc3ccc(C(=O)N=C4NCCN4)cc3C3CC3)c2)CC1] |

TABLE I-continued
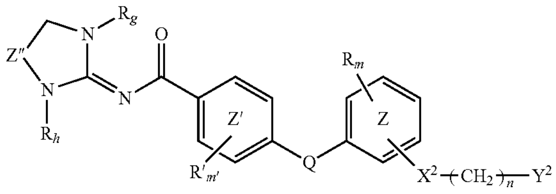
(I)
| No | Structure |
|---|---|
| 22 | 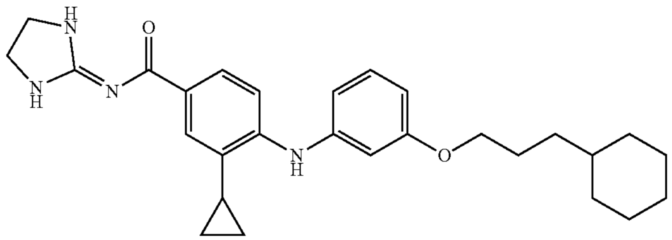 [SMILES: O=C(N=C1NCCN1)c1ccc(Nc2cccc(OCCCC3CCCCC3)c2)c(C2CC2)c1] |
| 23 | 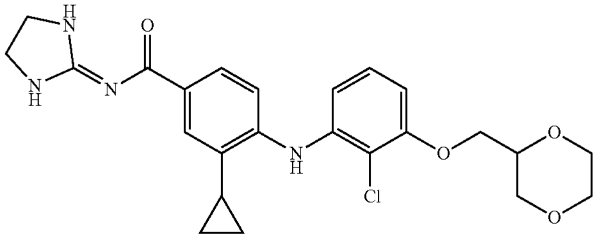 [SMILES: O=C(N=C1NCCN1)c1ccc(Nc2cccc(OCC3COCCO3)c2Cl)c(C2CC2)c1] |
| 24 | 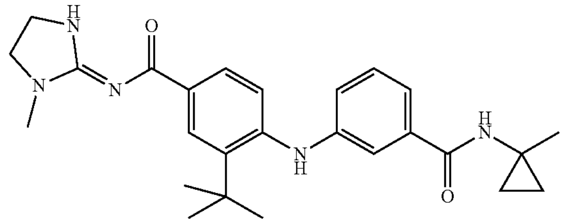 [SMILES: CN1CCN/C1=N\C(=O)c1ccc(Nc2cccc(C(=O)NC3(C)CC3)c2)c(C(C)(C)C)c1] |
| 25 | 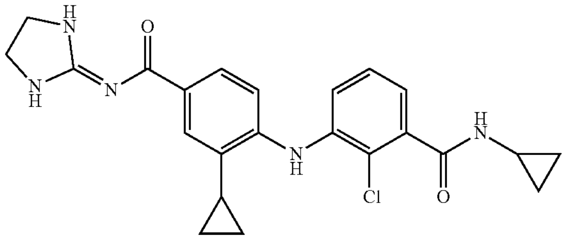 [SMILES: O=C(N=C1NCCN1)c1ccc(Nc2cccc(C(=O)NC3CC3)c2Cl)c(C2CC2)c1] |
| 26 | 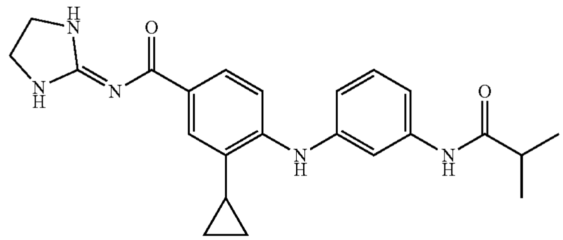 [SMILES: CC(C)C(=O)Nc1cccc(Nc2ccc(C(=O)N=C3NCCN3)cc2C2CC2)c1] |

TABLE I-continued
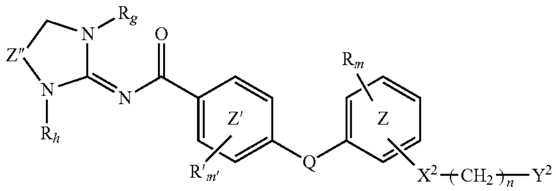
(I)
| No | Structure |
|---|---|
| 27 | 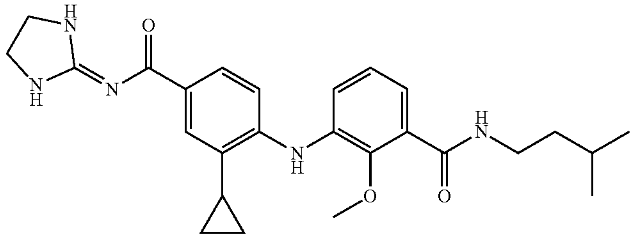 [SMILES: COc1c(Nc2ccc(C(=O)N=C3NCCN3)cc2C2CC2)cccc1C(=O)NCCC(C)C] |
| 28 | 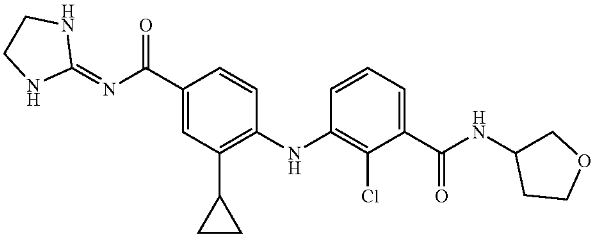 [SMILES: O=C(N=C1NCCN1)c1ccc(Nc2cccc(C(=O)NC3CCOC3)c2Cl)c(C2CC2)c1] |
| 29 | 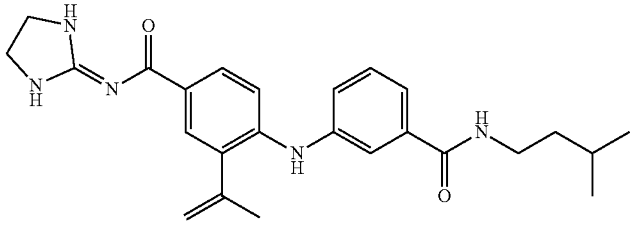 [SMILES: C=C(C)c1cc(C(=O)N=C2NCCN2)ccc1Nc1cccc(C(=O)NCCC(C)C)c1] |
| 30 | 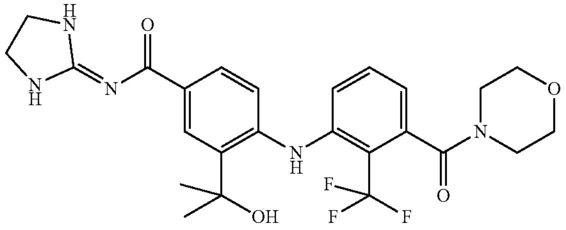 [SMILES: CC(C)(O)c1cc(C(=O)N=C2NCCN2)ccc1Nc1cccc(C(=O)N2CCOCC2)c1C(F)(F)F] |
| 31 | 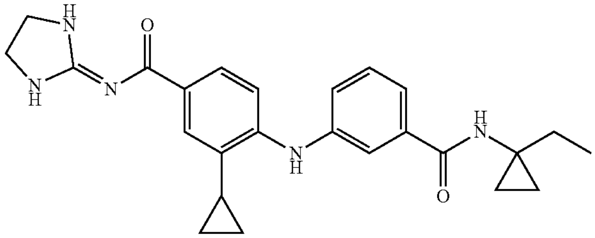 [SMILES: CCC1(NC(=O)c2cccc(Nc3ccc(C(=O)N=C4NCCN4)cc3C3CC3)c2)CC1] |

TABLE I-continued
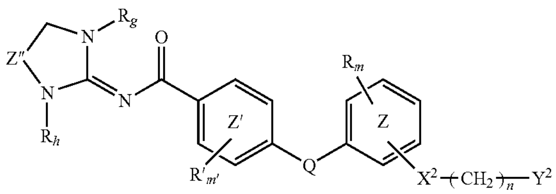
(I)
| No | Structure |
|---|---|
| 32 | 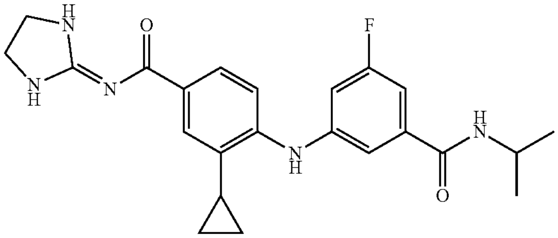 [SMILES: CC(C)NC(=O)c1cc(F)cc(Nc2ccc(C(=O)N=C3NCCN3)cc2C2CC2)c1] |
| 33 | 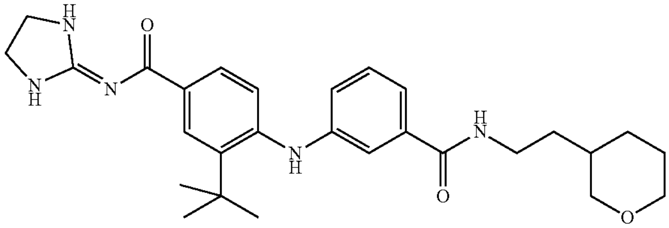 [SMILES: CC(C)(C)c1cc(C(=O)N=C2NCCN2)ccc1Nc1cccc(C(=O)NCCC2CCCOC2)c1] |
| 34 | 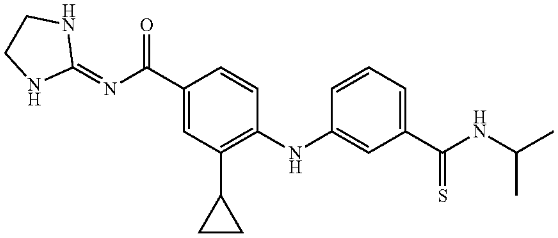 |
| 35 | 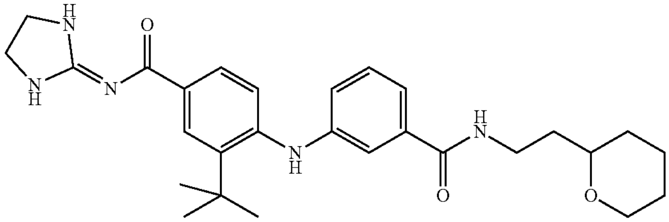 [SMILES: CC(C)(C)c1cc(C(=O)N=C2NCCN2)ccc1Nc1cccc(C(=O)NCCC2CCCCO2)c1] |
| 36 | 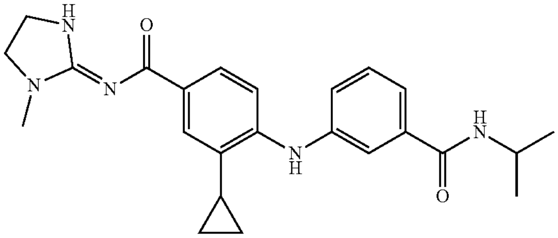 [SMILES: CC(C)NC(=O)c1cccc(Nc2ccc(C(=O)/N=C3\NCCN3C)cc2C2CC2)c1] |

TABLE I-continued
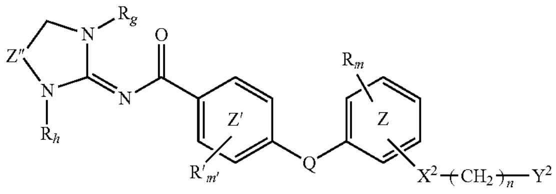
(I)
| No | Structure |
|---|---|
| 37 | 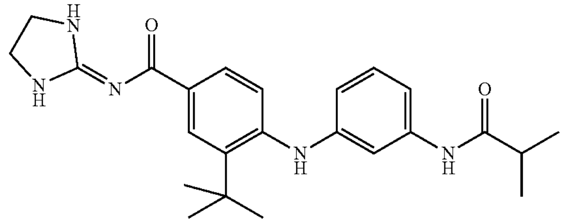 [SMILES: CC(C)C(=O)Nc1cccc(Nc2ccc(C(=O)N=C3NCCN3)cc2C(C)(C)C)c1] |
| 38 | 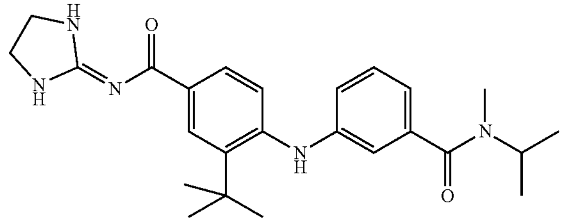 |
| 39 | 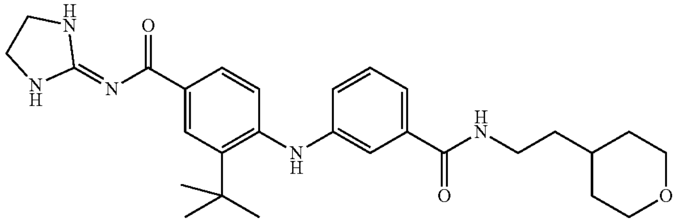 |
| 40 | 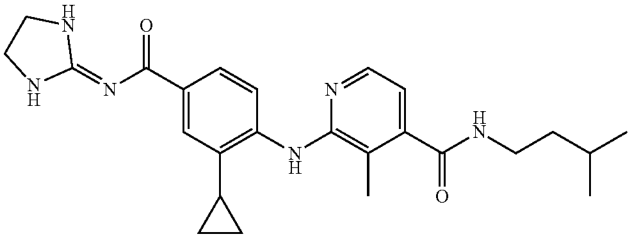 [SMILES: Cc1c(C(=O)NCCC(C)C)ccnc1Nc1ccc(C(=O)N=C2NCCN2)cc1C1CC1] |
| 41 | 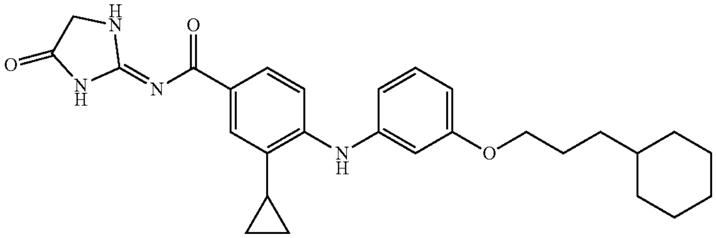 [SMILES: O=C1CN/C(=N\C(=O)c2ccc(Nc3cccc(OCCCC4CCCCC4)c3)c(C3CC3)c2)N1] |

TABLE I-continued
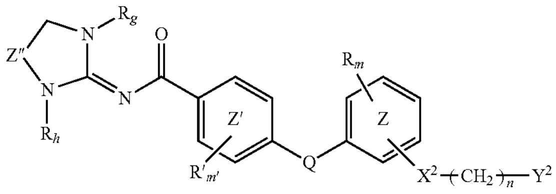
(I)
| No | Structure |
| --- | --- |
| 42 | 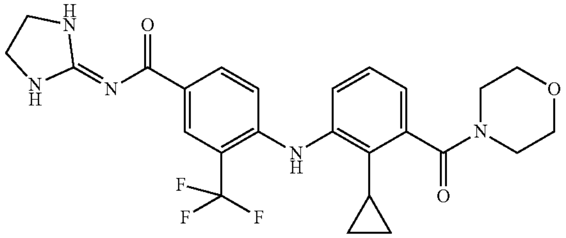 [SMILES: O=C(N=C1NCCN1)c1ccc(Nc2cccc(C(=O)N3CCOCC3)c2C2CC2)c(C(F)(F)F)c1] |
| 43 | 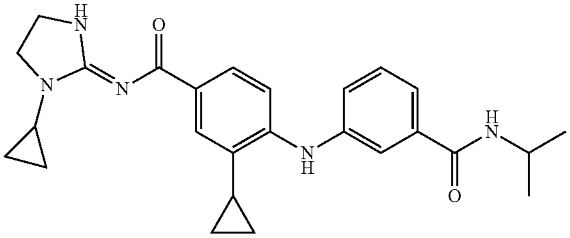 [SMILES: CC(C)NC(=O)c1cccc(Nc2ccc(C(=O)/N=C3\NCCN3C3CC3)cc2C2CC2)c1] |
| 44 | 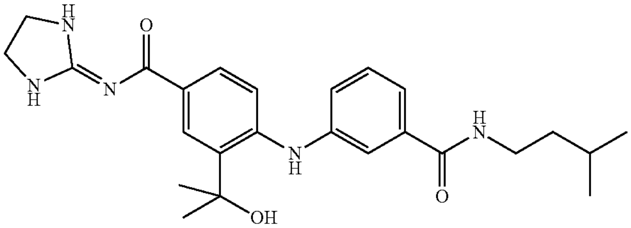 [SMILES: CC(C)CCNC(=O)c1cccc(Nc2ccc(C(=O)N=C3NCCN3)cc2C(C)(C)O)c1] |
| 45 | 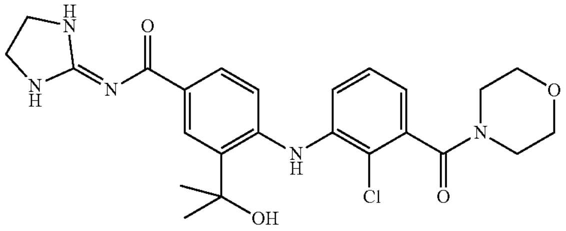 [SMILES: CC(C)(O)c1cc(C(=O)N=C2NCCN2)ccc1Nc1cccc(C(=O)N2CCOCC2)c1Cl] |
| 46 | 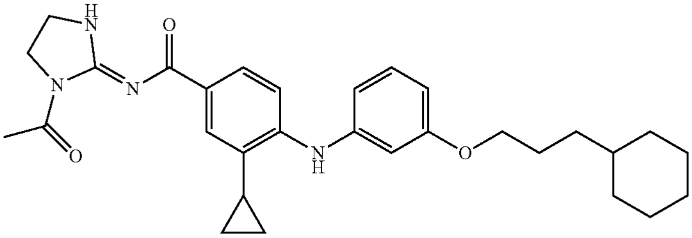 [SMILES: CC(=O)N1CCN/C1=N\C(=O)c1ccc(Nc2cccc(OCCCC3CCCCC3)c2)c(C2CC2)c1] |

TABLE I-continued
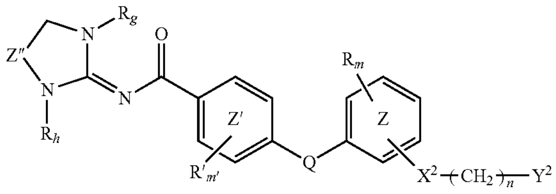
(I)
| No | Structure |
|---|---|
| 47 | 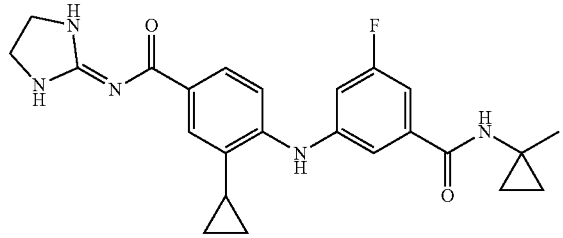 [SMILES: CC1(NC(=O)c2cc(F)cc(Nc3ccc(C(=O)N=C4NCCN4)cc3C3CC3)c2)CC1] |
| 48 | 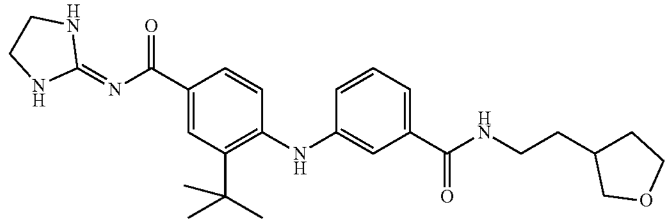 [SMILES: CC(C)(C)c1cc(C(=O)N=C2NCCN2)ccc1Nc1cccc(C(=O)NCCC2CCOC2)c1] |
| 49 | 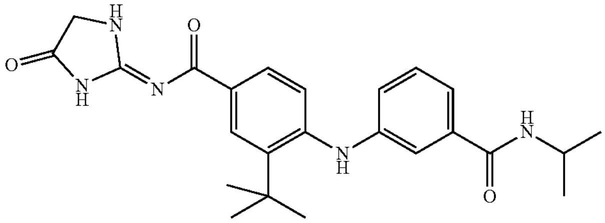 [SMILES: CC(C)NC(=O)c1cccc(Nc2ccc(C(=O)/N=C3\NCC(=O)N3)cc2C(C)(C)C)c1] |
| 50 | 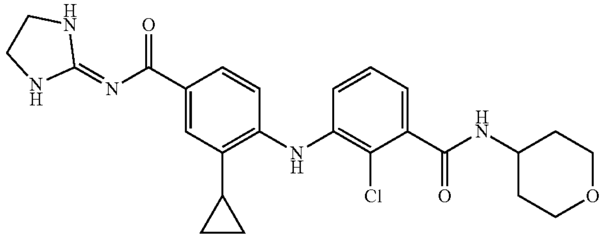 [SMILES: O=C(N=C1NCCN1)c1ccc(Nc2cccc(C(=O)NC3CCOCC3)c2Cl)c(C2CC2)c1] |
| 51 | 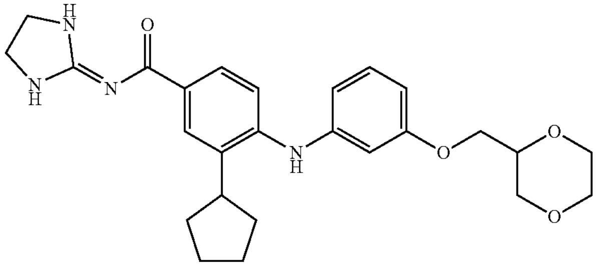 [SMILES: O=C(N=C1NCCN1)c1ccc(Nc2cccc(OCC3COCCO3)c2)c(C2CCCC2)c1] |

TABLE I-continued
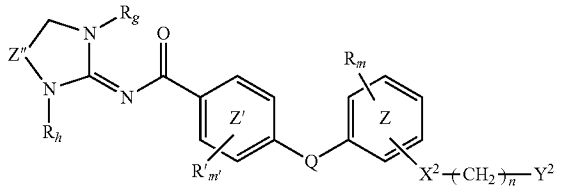
(I)
| No | Structure |
| --- | --- |
| 52 | 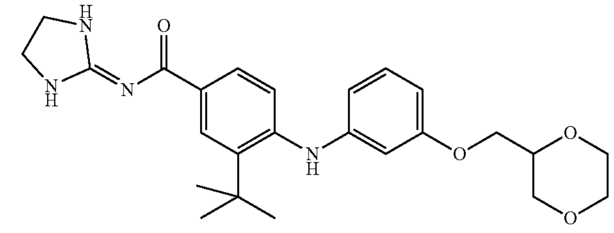 [SMILES: CC(C)(C)c1cc(C(=O)N=C2NCCN2)ccc1Nc1cccc(OCC2COCCO2)c1] |
| 53 | 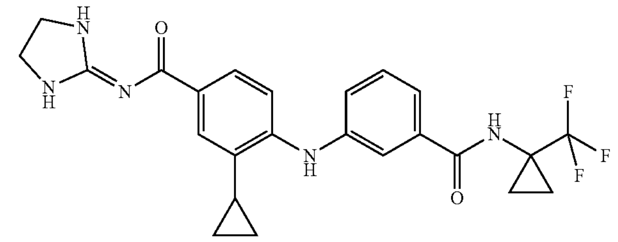 [SMILES: O=C(N=C1NCCN1)c1ccc(Nc2cccc(C(=O)NC3(C(F)(F)F)CC3)c2)c(C2CC2)c1] |
| 54 | 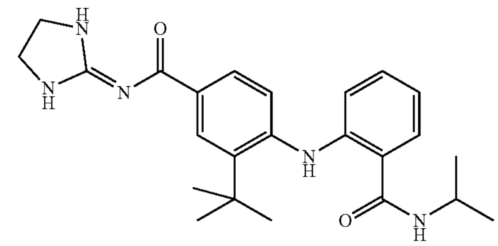 [SMILES: CC(C)NC(=O)c1ccccc1Nc1ccc(C(=O)N=C2NCCN2)cc1C(C)(C)C] |
| 55 | 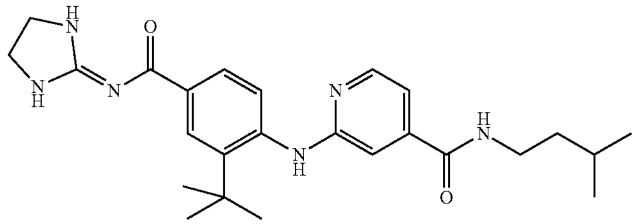 |
| 56 | 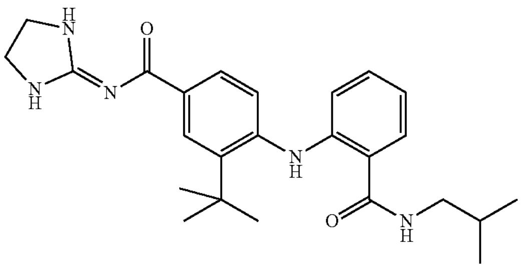 [SMILES: CC(C)CNC(=O)c1ccccc1Nc1ccc(C(=O)N=C2NCCN2)cc1C(C)(C)C] |

TABLE I-continued
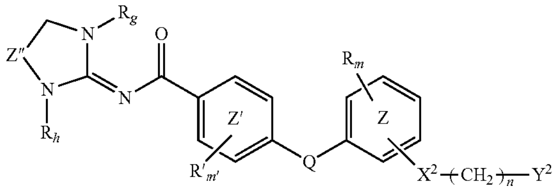
(I)
| No | Structure |
|---|---|
| 57 | 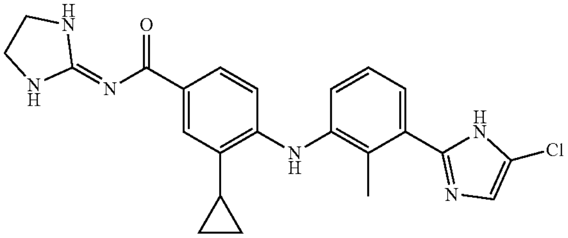 [SMILES: Cc1c(Nc2ccc(C(=O)N=C3NCCN3)cc2C2CC2)cccc1-c1ncc(Cl)[nH]1] |
| 58 | 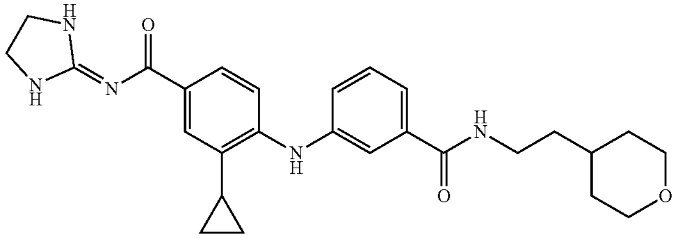 [SMILES: O=C(N=C1NCCN1)c1ccc(Nc2cccc(C(=O)NCCC3CCOCC3)c2)c(C2CC2)c1] |
| 59 | 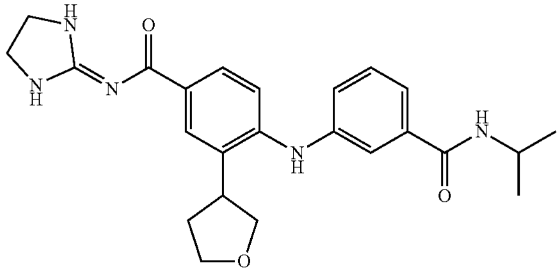 [SMILES: CC(C)NC(=O)c1cccc(Nc2ccc(C(=O)N=C3NCCN3)cc2C2CCOC2)c1] |
| 60 | 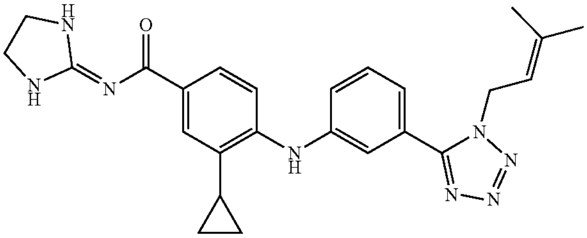 [SMILES: CC(C)=CCn1nnnc1-c1cccc(Nc2ccc(C(=O)N=C3NCCN3)cc2C2CC2)c1] |
| 61 | 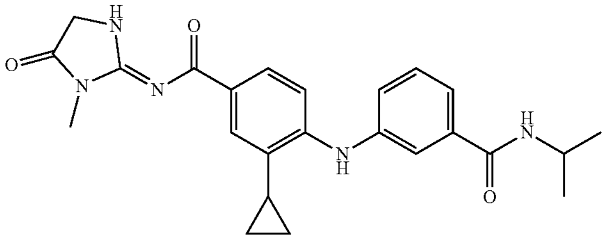 [SMILES: CC(C)NC(=O)c1cccc(Nc2ccc(C(=O)/N=C3\NCC(=O)N3C)cc2C2CC2)c1] |

TABLE I-continued
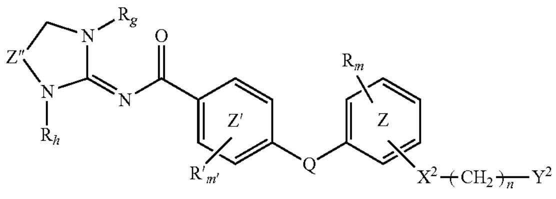
(I)
| No | Structure |
|---|---|
| 62 | 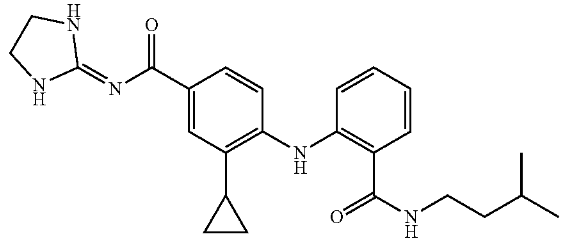 |
| 63 | 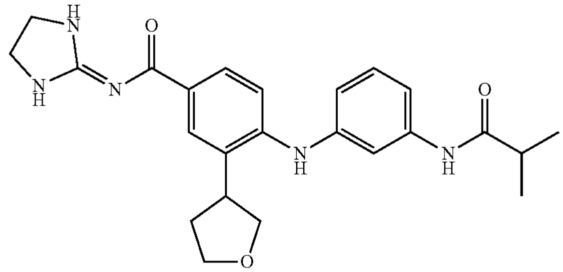 [SMILES: CC(C)C(=O)Nc1cccc(Nc2ccc(C(=O)N=C3NCCN3)cc2C2CCOC2)c1] |
| 64 | 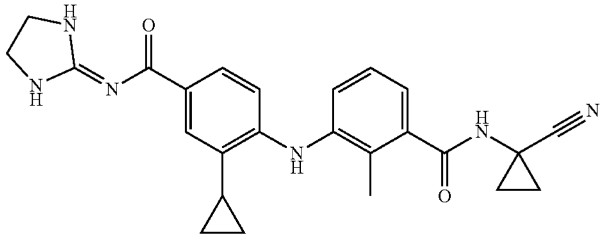 [SMILES: Cc1c(Nc2ccc(C(=O)N=C3NCCN3)cc2C2CC2)cccc1C(=O)NC1(C#N)CC1] |
| 65 | 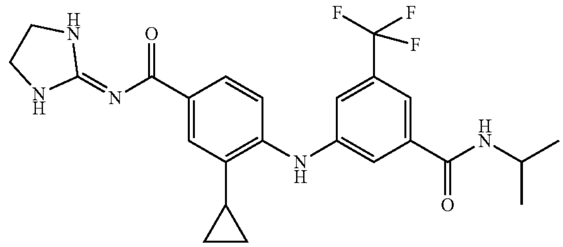 [SMILES: CC(C)NC(=O)c1cc(Nc2ccc(C(=O)N=C3NCCN3)cc2C2CC2)cc(C(F)(F)F)c1] |
| 66 | 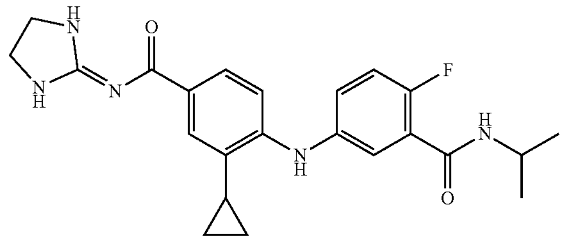 [SMILES: CC(C)NC(=O)c1cc(Nc2ccc(C(=O)N=C3NCCN3)cc2C2CC2)ccc1F] |

TABLE I-continued
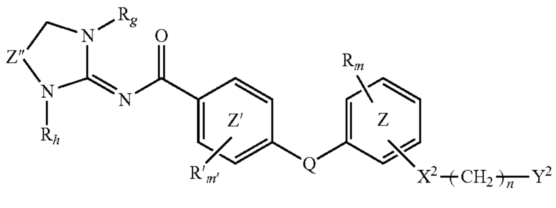
(I)
| No | Structure |
|---|---|
| 67 | 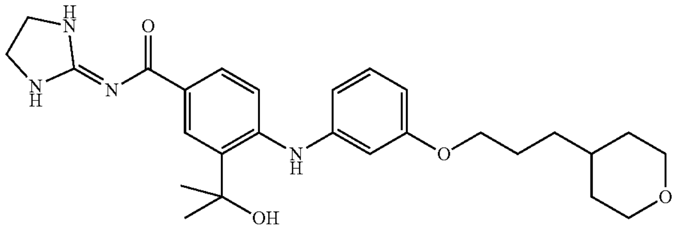 [SMILES: CC(C)(O)c1cc(C(=O)N=C2NCCN2)ccc1Nc1cccc(OCCCC2CCOCC2)c1] |
| 68 | 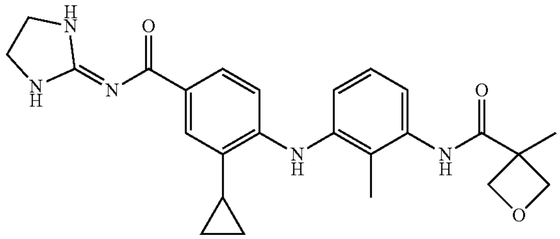 [SMILES: Cc1c(NC(=O)C2(C)COC2)cccc1Nc1ccc(C(=O)N=C2NCCN2)cc1C1CC1] |
| 69 | 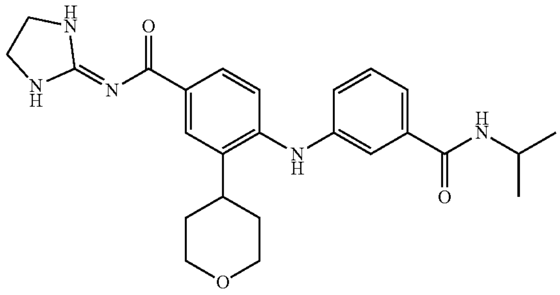 [SMILES: CC(C)NC(=O)c1cccc(Nc2ccc(C(=O)N=C3NCCN3)cc2C2CCOCC2)c1] |
| 70 | 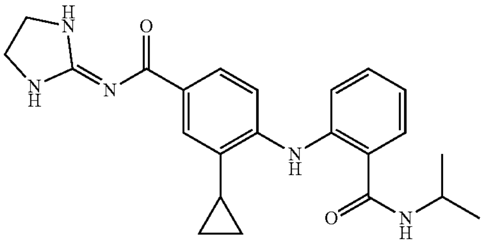 [SMILES: CC(C)NC(=O)c1ccccc1Nc1ccc(C(=O)N=C2NCCN2)cc1C1CC1] |
| 71 | 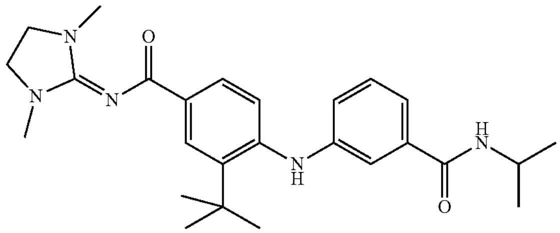 [SMILES: CC(C)NC(=O)c1cccc(Nc2ccc(C(=O)N=C3N(C)CCN3C)cc2C(C)(C)C)c1] |

TABLE I-continued
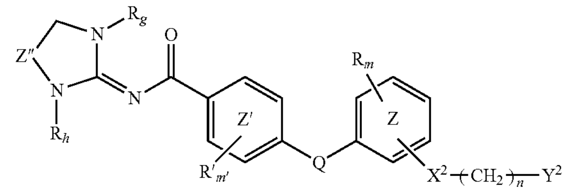
(I)
| No | Structure |
| --- | --- |
| 72 | 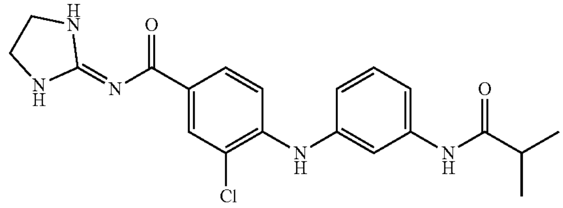 [SMILES: CC(C)C(=O)Nc1cccc(Nc2ccc(C(=O)N=C3NCCN3)cc2Cl)c1] |
| 73 | 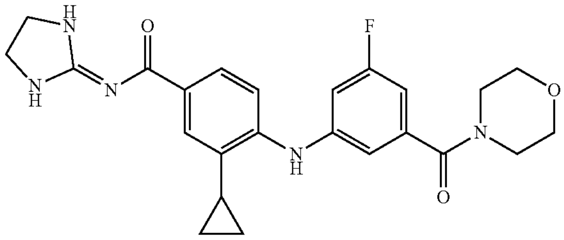 [SMILES: O=C(N=C1NCCN1)c1ccc(Nc2cc(F)cc(C(=O)N3CCOCC3)c2)c(C2CC2)c1] |
| 74 | 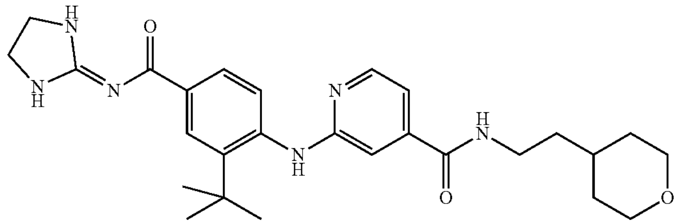 |
| 75 | 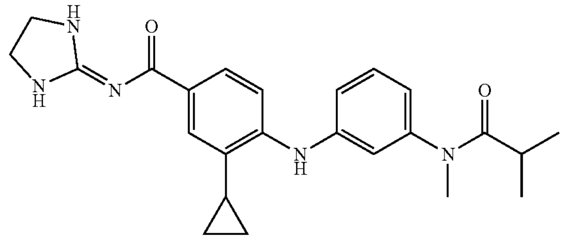 [SMILES: CC(C)C(=O)N(C)c1cccc(Nc2ccc(C(=O)N=C3NCCN3)cc2C2CC2)c1] |
| 76 | 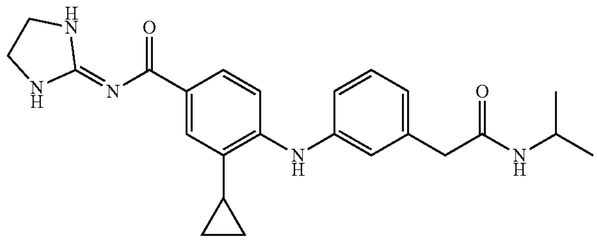 [SMILES: CC(C)NC(=O)Cc1cccc(Nc2ccc(C(=O)N=C3NCCN3)cc2C2CC2)c1] |

TABLE I-continued
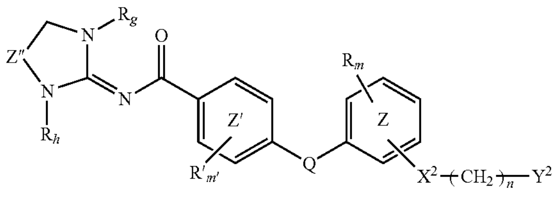
(I)
| No | Structure |
|---|---|
| 77 | 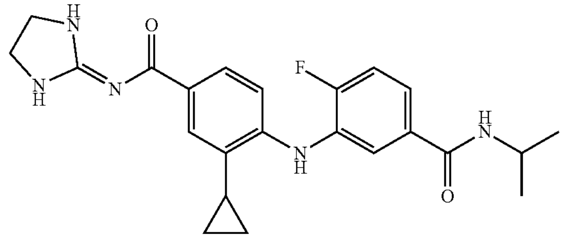 [SMILES: CC(C)NC(=O)c1ccc(F)c(Nc2ccc(C(=O)N=C3NCCN3)cc2C2CC2)c1] |
| 78 | 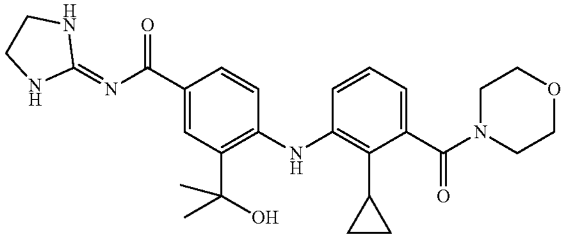 [SMILES: CC(C)(O)c1cc(C(=O)N=C2NCCN2)ccc1Nc1cccc(C(=O)N2CCOCC2)c1C1CC1] |
| 79 | 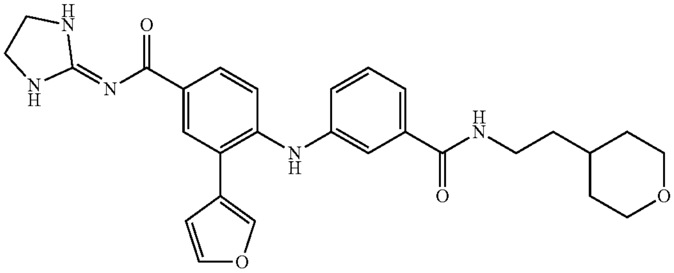 [SMILES: O=C(N=C1NCCN1)c1ccc(Nc2cccc(C(=O)NCCC3CCOCC3)c2)c(-c2ccoc2)c1] |
| 80 | 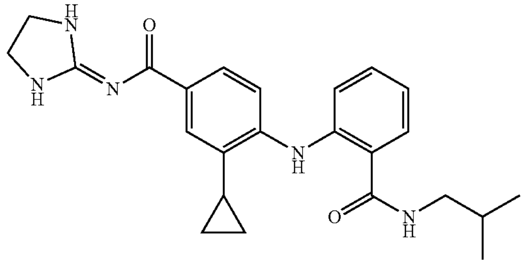 [SMILES: CC(C)CNC(=O)c1ccccc1Nc1ccc(C(=O)N=C2NCCN2)cc1C1CC1] |
| 81 | 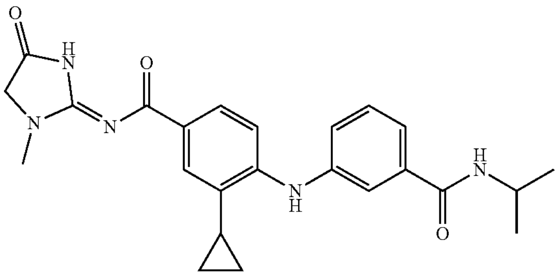 [SMILES: CC(C)NC(=O)c1cccc(Nc2ccc(C(=O)/N=C3\NC(=O)CN3C)cc2C2CC2)c1] |

TABLE I-continued
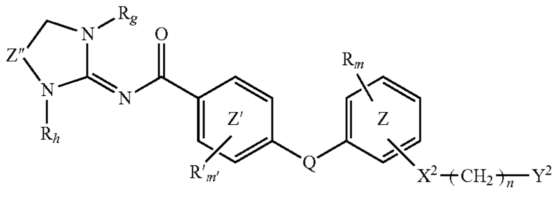
(I)
| No | Structure |
|---|---|
| 82 | 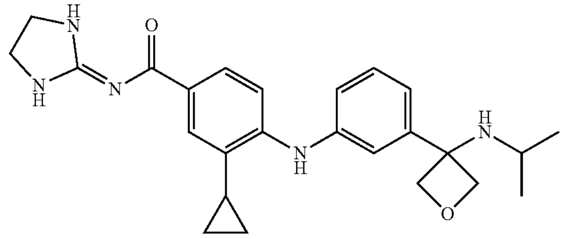 [SMILES: CC(C)NC1(c2cccc(Nc3ccc(C(=O)N=C4NCCN4)cc3C3CC3)c2)COC1] |
| 83 | 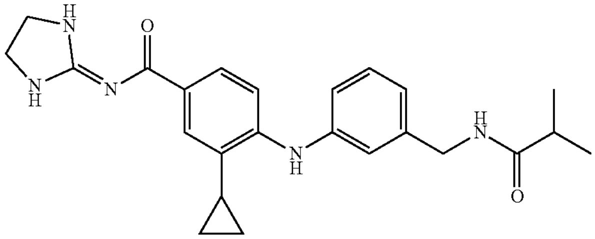 [SMILES: CC(C)C(=O)NCc1cccc(Nc2ccc(C(=O)N=C3NCCN3)cc2C2CC2)c1] |
| 84 | 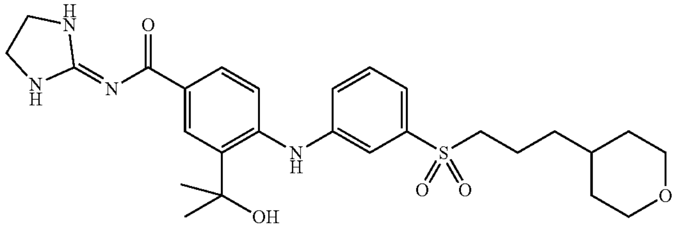 [SMILES: CC(C)(O)c1cc(C(=O)N=C2NCCN2)ccc1Nc1cccc(S(=O)(=O)CCCC2CCOCC2)c1] |
| 85 | 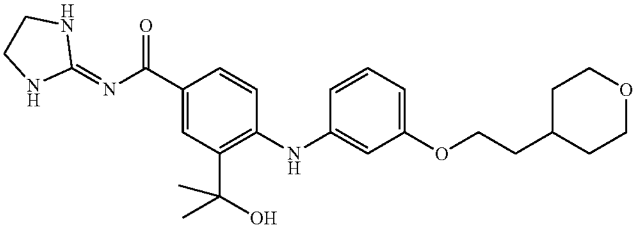 [SMILES: CC(C)(O)c1cc(C(=O)N=C2NCCN2)ccc1Nc1cccc(OCCC2CCOCC2)c1] |
| 86 | 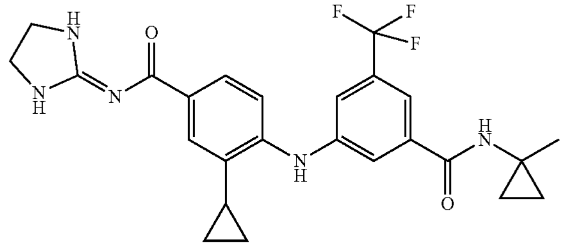 [SMILES: CC1(NC(=O)c2cc(Nc3ccc(C(=O)N=C4NCCN4)cc3C3CC3)cc(C(F)(F)F)c2)CC1] |

TABLE I-continued
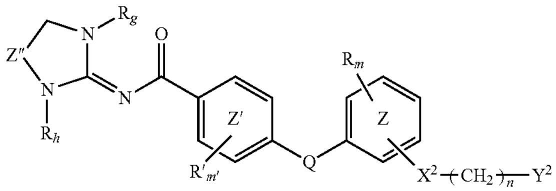
(I)
| No | Structure |
|---|---|
| 87 | 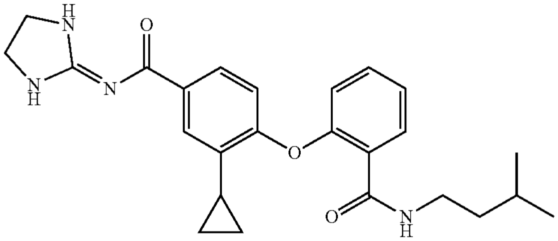 [SMILES: CC(C)CCNC(=O)c1ccccc1Oc1ccc(C(=O)N=C2NCCN2)cc1C1CC1] |
| 88 | 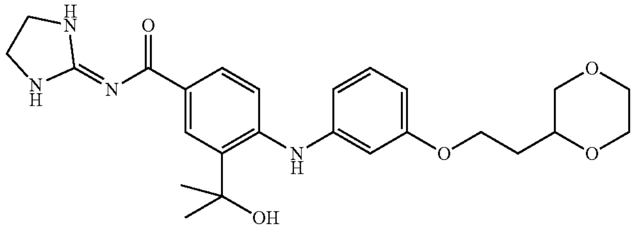 [SMILES: CC(C)(O)c1cc(C(=O)N=C2NCCN2)ccc1Nc1cccc(OCCC2COCCO2)c1] |
| 89 | 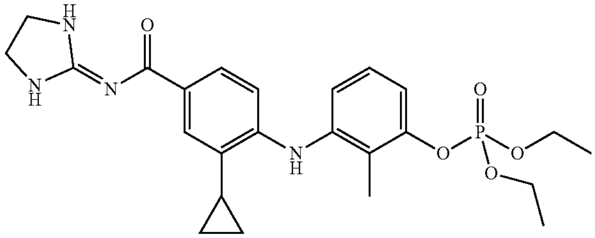 [SMILES: CCOP(=O)(OCC)Oc1cccc(Nc2ccc(C(=O)N=C3NCCN3)cc2C2CC2)c1C] |
| 90 | 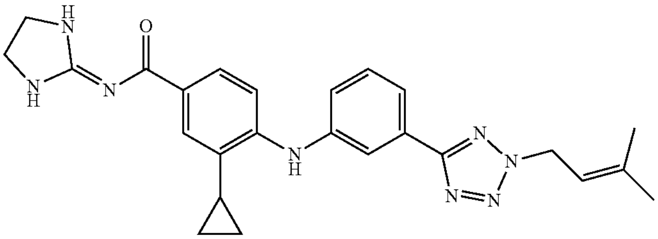 [SMILES: CC(C)=CCn1nnc(-c2cccc(Nc3ccc(C(=O)N=C4NCCN4)cc3C3CC3)c2)n1] |
| 91 | 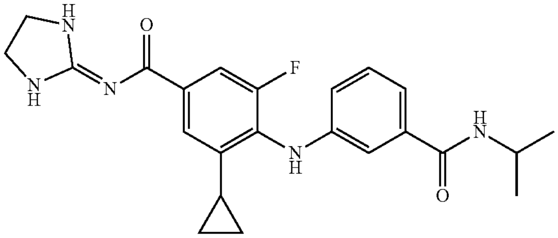 |

TABLE I-continued
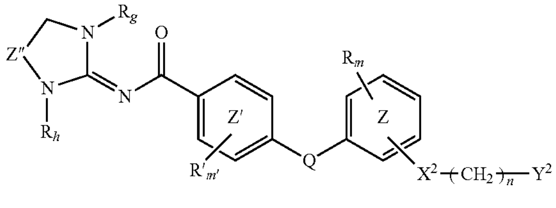
(I)
| No | Structure |
|---|---|
| 92 | 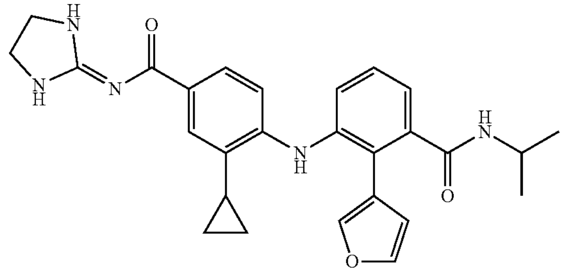 [SMILES: CC(C)NC(=O)c1cccc(Nc2ccc(C(=O)N=C3NCCN3)cc2C2CC2)c1-c1ccoc1] |
| 93 | 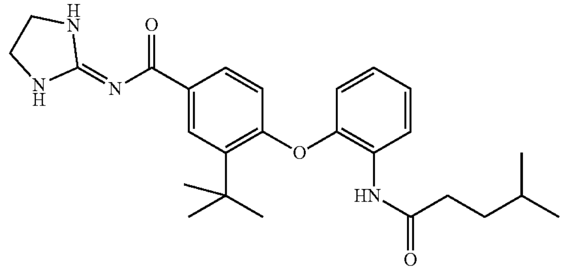 [SMILES: CC(C)CCC(=O)Nc1ccccc1Oc1ccc(C(=O)N=C2NCCN2)cc1C(C)(C)C] |
| 94 | 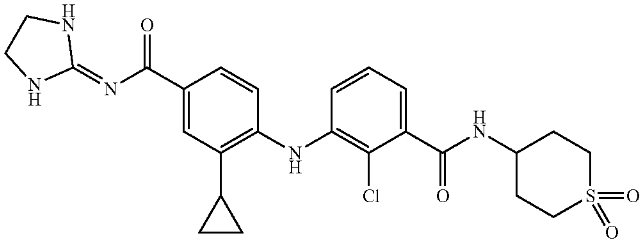 [SMILES: O=C(N=C1NCCN1)c1ccc(Nc2cccc(C(=O)NC3CCS(=O)(=O)CC3)c2Cl)c(C2CC2)c1] |
| 95 | 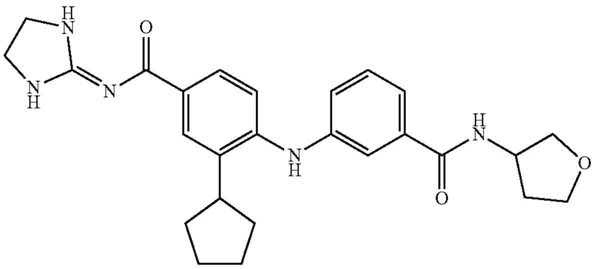 [SMILES: O=C(N=C1NCCN1)c1ccc(Nc2cccc(C(=O)NC3CCOC3)c2)c(C2CCCC2)c1] |
| 96 | 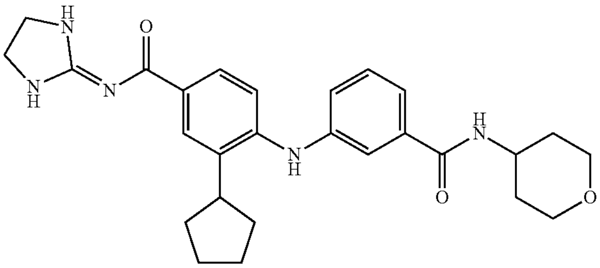 [SMILES: O=C(N=C1NCCN1)c1ccc(Nc2cccc(C(=O)NC3CCOCC3)c2)c(C2CCCC2)c1] |

TABLE I-continued
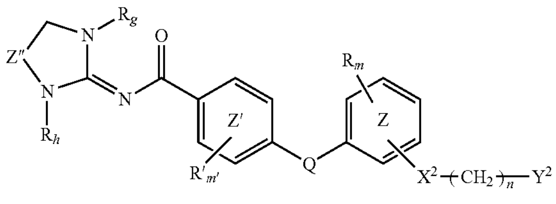
(I)
| No | Structure |
| --- | --- |
| 97 | 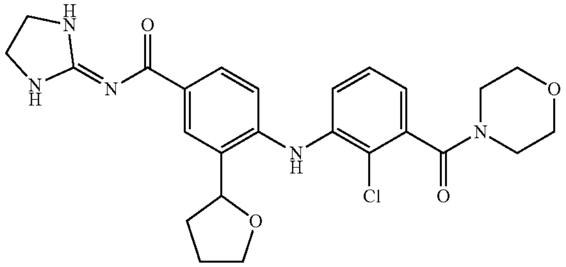 |
| 98 | 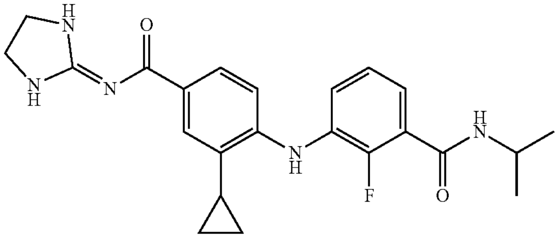 |
| 99 | 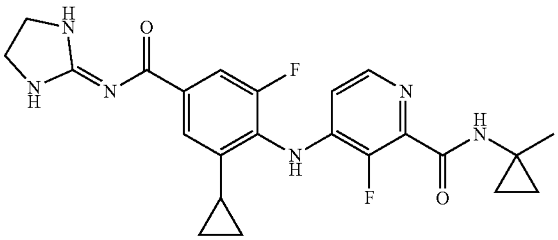 |
| 100 | 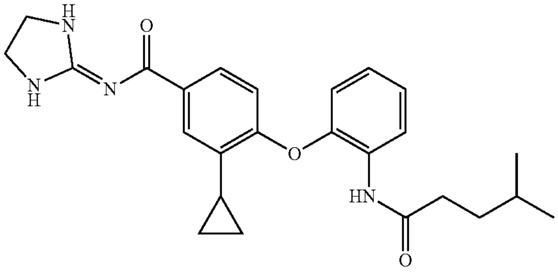 [SMILES: CC(C)CCC(=O)Nc1ccccc1Oc1ccc(C(=O)N=C2NCCN2)cc1C1CC1] |
| 101 | 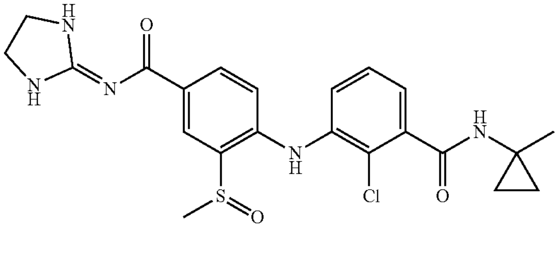 [SMILES: CS(=O)c1cc(C(=O)N=C2NCCN2)ccc1Nc1cccc(C(=O)NC2(C)CC2)c1Cl] |

TABLE I-continued
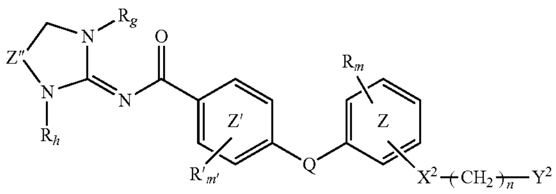
(I)
| No | Structure |
|---|---|
| 102 | 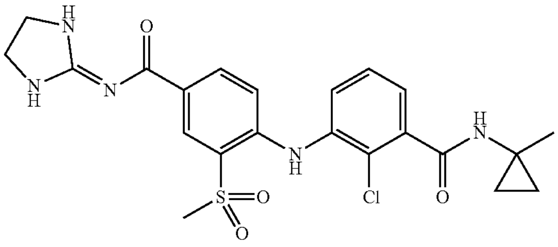 [SMILES: CC1(NC(=O)c2cccc(Nc3ccc(C(=O)N=C4NCCN4)cc3S(C)(=O)=O)c2Cl)CC1] |
| 103 | 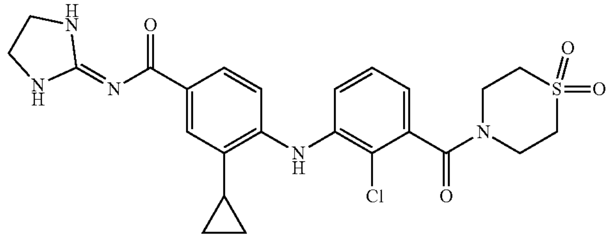 [SMILES: O=C(N=C1NCCN1)c1ccc(Nc2cccc(C(=O)N3CCS(=O)(=O)CC3)c2Cl)c(C2CC2)c1] |
| 104 | 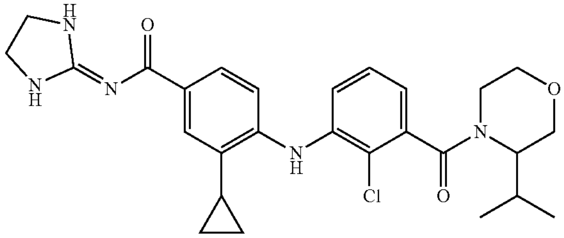 [SMILES: CC(C)C1COCCN1C(=O)c1cccc(Nc2ccc(C(=O)N=C3NCCN3)cc2C2CC2)c1Cl] |
| 105 | 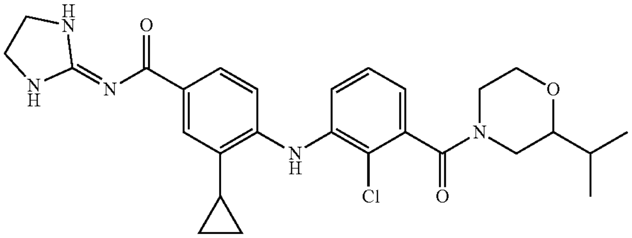 [SMILES: CC(C)C1CN(C(=O)c2cccc(Nc3ccc(C(=O)N=C4NCCN4)cc3C3CC3)c2Cl)CCO1] |
| 106 | 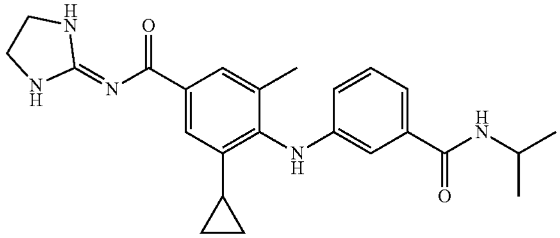 |

TABLE I-continued
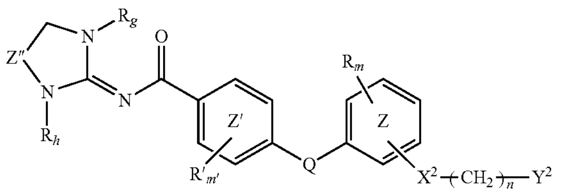
(I)
| No | Structure |
|---|---|
| 107 | 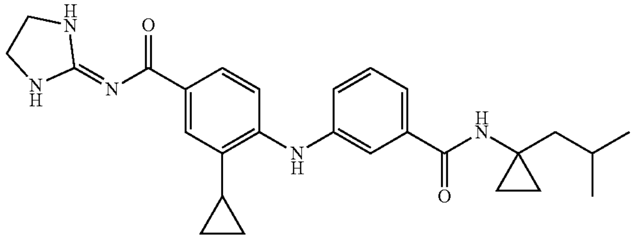 [SMILES: CC(C)CC1(NC(=O)c2cccc(Nc3ccc(C(=O)N=C4NCCN4)cc3C3CC3)c2)CC1] |
| 108 | 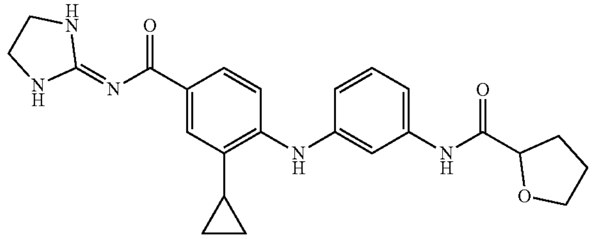 [SMILES: O=C(N=C1NCCN1)c1ccc(Nc2cccc(NC(=O)C3CCCO3)c2)c(C2CC2)c1] |
| 109 | 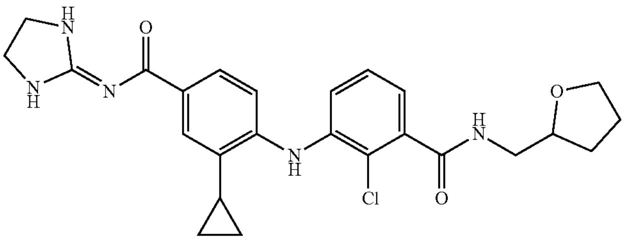 [SMILES: O=C(N=C1NCCN1)c1ccc(Nc2cccc(C(=O)NCC3CCCO3)c2Cl)c(C2CC2)c1] |
| 110 | 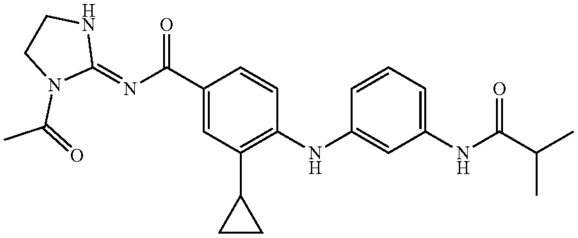 [SMILES: CC(=O)N1CCN/C1=N\C(=O)c1ccc(Nc2cccc(NC(=O)C(C)C)c2)c(C2CC2)c1] |
| 111 | 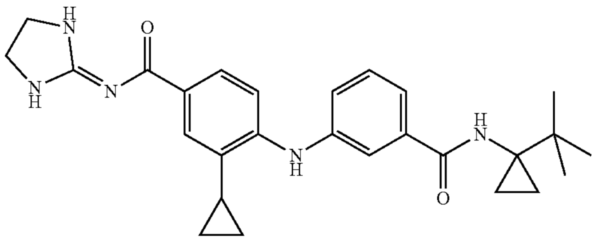 [SMILES: CC(C)(C)C1(NC(=O)c2cccc(Nc3ccc(C(=O)N=C4NCCN4)cc3C3CC3)c2)CC1] |

TABLE I-continued
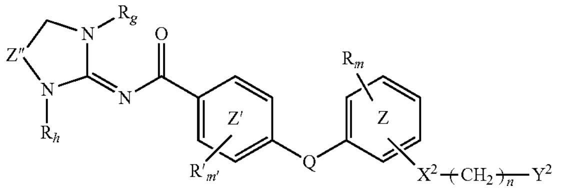
(I)
| No | Structure |
|---|---|
| 112 | 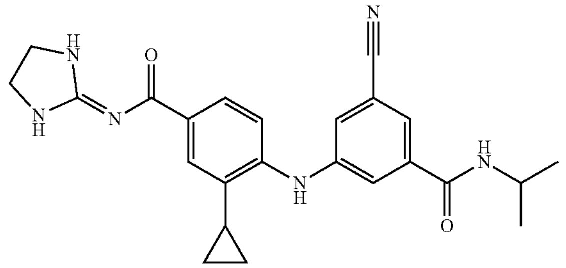 [SMILES: CC(C)NC(=O)c1cc(C#N)cc(Nc2ccc(C(=O)N=C3NCCN3)cc2C2CC2)c1] |
| 113 | 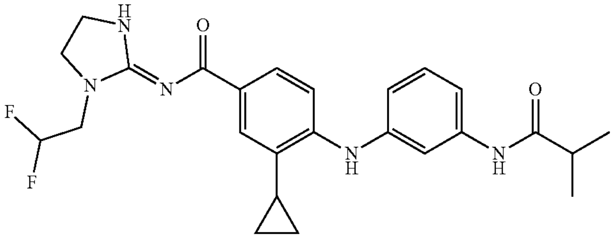 [SMILES: CC(C)C(=O)Nc1cccc(Nc2ccc(C(=O)/N=C3\NCCN3CC(F)F)cc2C2CC2)c1] |
| 114 | 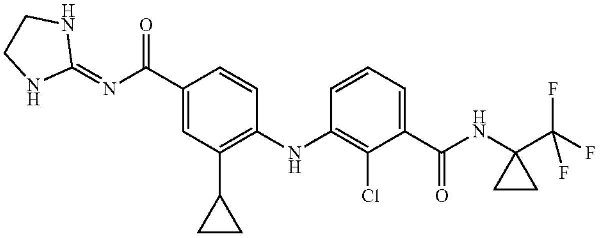 [SMILES: O=C(N=C1NCCN1)c1ccc(Nc2cccc(C(=O)NC3(C(F)(F)F)CC3)c2Cl)c(C2CC2)c1] |
| 115 | 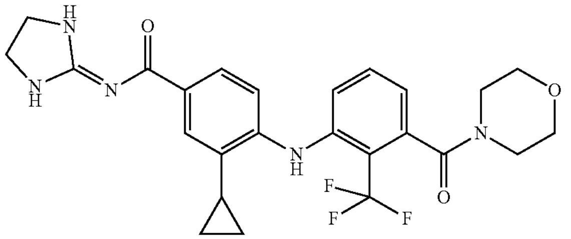 [SMILES: O=C(N=C1NCCN1)c1ccc(Nc2cccc(C(=O)N3CCOCC3)c2C(F)(F)F)c(C2CC2)c1] |
| 116 | 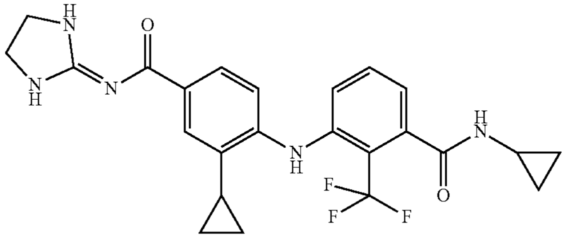 [SMILES: O=C(N=C1NCCN1)c1ccc(Nc2cccc(C(=O)NC3CC3)c2C(F)(F)F)c(C2CC2)c1] |

TABLE I-continued
| No | Structure |
|---|---|
| | 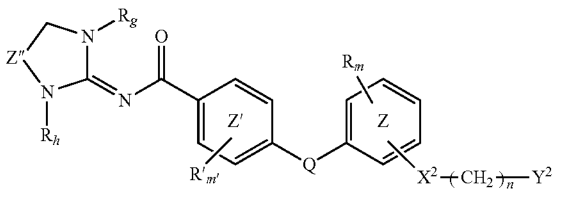 (I) |
| 117 | 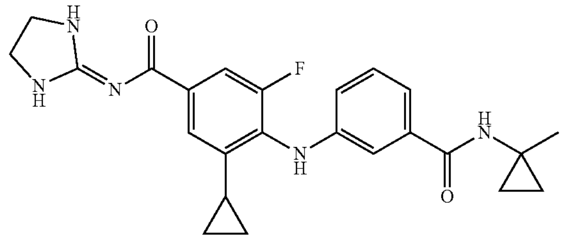 |
| 118 | 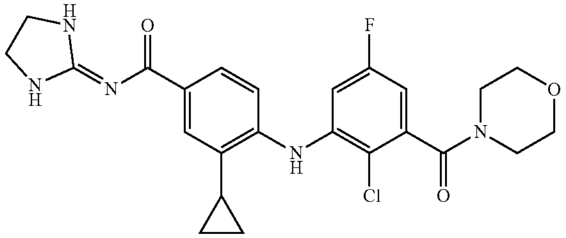 |
| 119 | 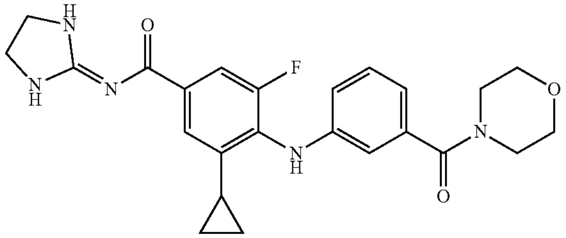 |
| 120 | 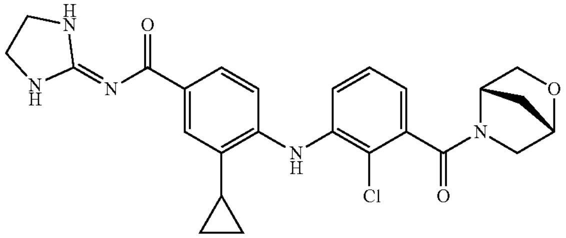 |
| 121 | 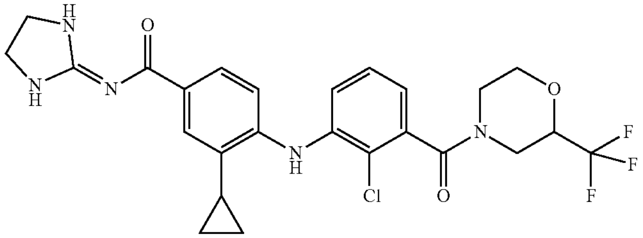 |

TABLE I-continued
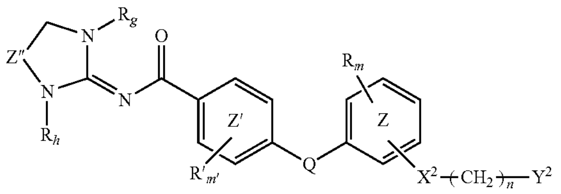
(I)
| No | Structure |
| --- | --- |
| 122 | 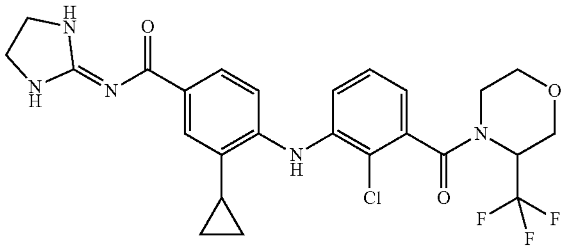 [SMILES: O=C(N=C1NCCN1)c1ccc(Nc2cccc(C(=O)N3CCOCC3C(F)(F)F)c2Cl)c(C2CC2)c1] |
| 123 | 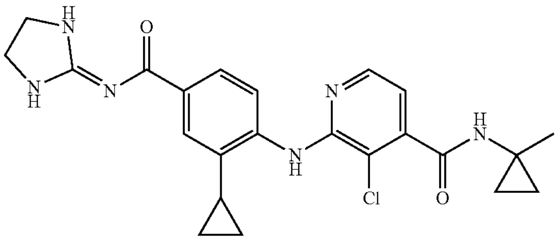 [SMILES: CC1(NC(=O)c2ccnc(Nc3ccc(C(=O)N=C4NCCN4)cc3C3CC3)c2Cl)CC1] |
| 124 | 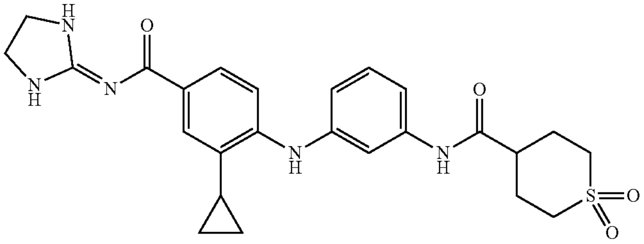 [SMILES: O=C(N=C1NCCN1)c1ccc(Nc2cccc(NC(=O)C3CCS(=O)(=O)CC3)c2)c(C2CC2)c1] |
| 125 | 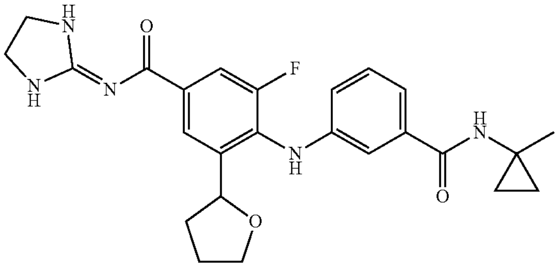 [SMILES: CC1(NC(=O)c2cccc(Nc3c(F)cc(C(=O)N=C4NCCN4)cc3C3CCCO3)c2)CC1] |
| 126 | 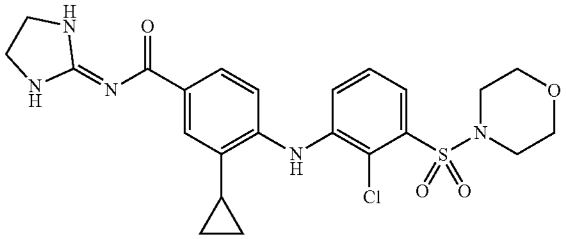 [SMILES: O=C(N=C1NCCN1)c1ccc(Nc2cccc(S(=O)(=O)N3CCOCC3)c2Cl)c(C2CC2)c1] |

TABLE I-continued
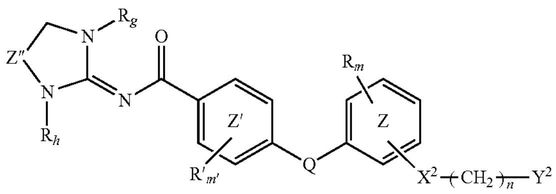
(I)
| No | Structure |
|---|---|
| 127 | 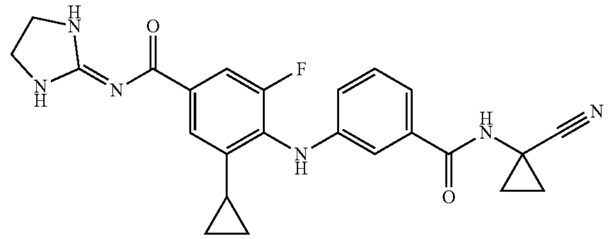 [SMILES: N#CC1(NC(=O)c2cccc(Nc3c(F)cc(C(=O)N=C4NCCN4)cc3C3CC3)c2)CC1] |
| 128 | 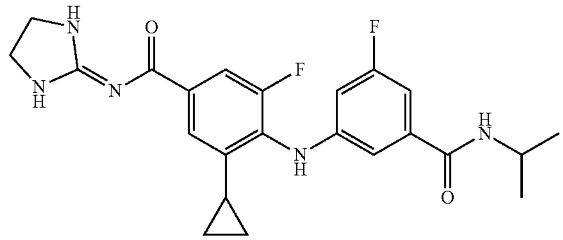 [SMILES: CC(C)NC(=O)c1cc(F)cc(Nc2c(F)cc(C(=O)N=C3NCCN3)cc2C2CC2)c1] |
| 129 | 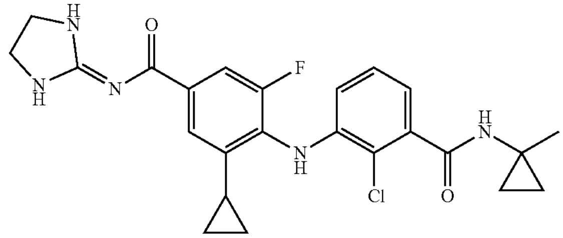 |
| 130 | 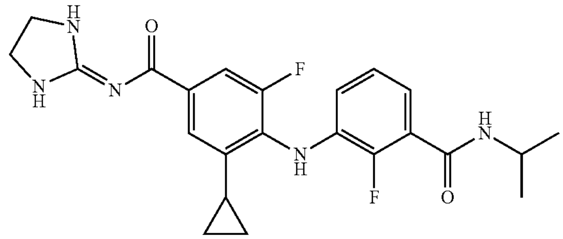 [SMILES: CC(C)NC(=O)c1cccc(Nc2c(F)cc(C(=O)N=C3NCCN3)cc2C2CC2)c1F] |
| 131 | 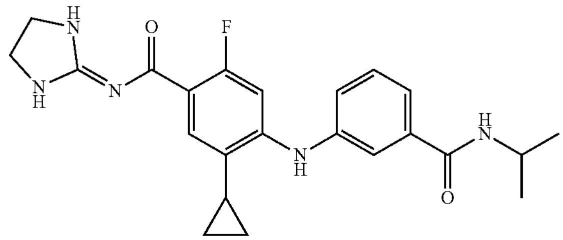 [SMILES: CC(C)NC(=O)c1cccc(Nc2cc(F)c(C(=O)N=C3NCCN3)cc2C2CC2)c1] |

TABLE I-continued
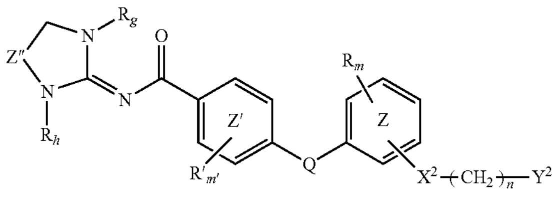
(I)
| No | Structure |
|---|---|
| 132 | 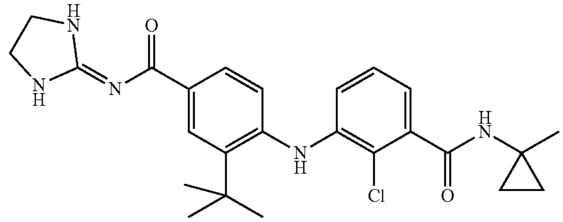 [SMILES: CC1(NC(=O)c2cccc(Nc3ccc(C(=O)N=C4NCCN4)cc3C(C)(C)C)c2Cl)CC1] |
| 133 | 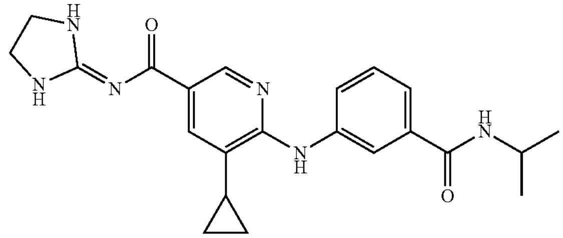 [SMILES: CC(C)NC(=O)c1cccc(Nc2ncc(C(=O)N=C3NCCN3)cc2C2CC2)c1] |
| 134 | 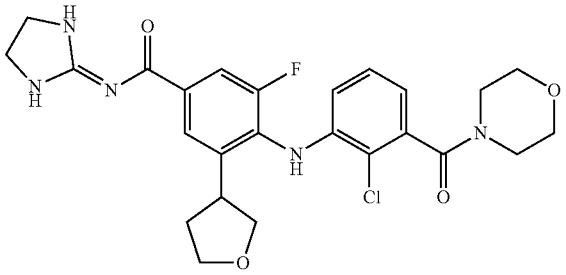 [SMILES: O=C(N=C1NCCN1)c1cc(F)c(Nc2cccc(C(=O)N3CCOCC3)c2Cl)c(C2CCOC2)c1] |
| 135 | 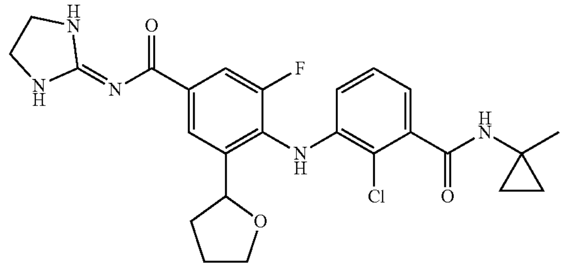 [SMILES: CC1(NC(=O)c2cccc(Nc3c(F)cc(C(=O)N=C4NCCN4)cc3C3CCCO3)c2Cl)CC1] |
| 136 | 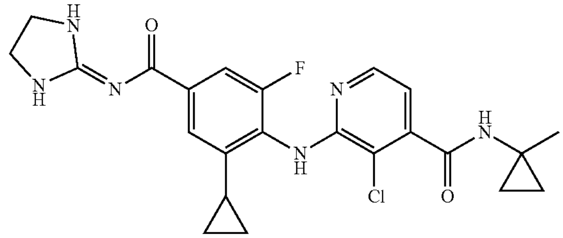 [SMILES: CC1(NC(=O)c2ccnc(Nc3c(F)cc(C(=O)N=C4NCCN4)cc3C3CC3)c2Cl)CC1] |

TABLE I-continued
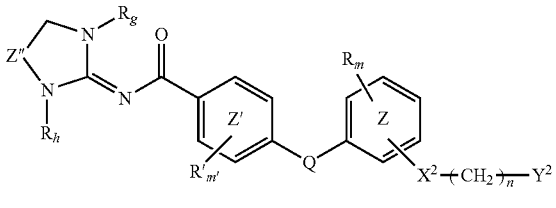
(I)
| No | Structure |
| --- | --- |
| 137 | 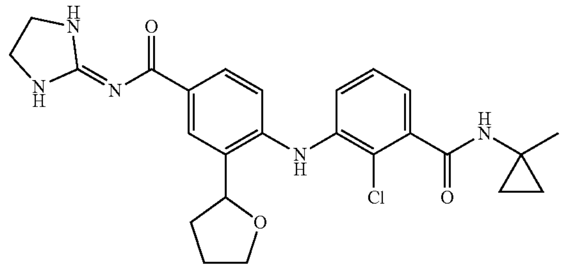 [SMILES: CC1(NC(=O)c2cccc(Nc3ccc(C(=O)N=C4NCCN4)cc3C3CCCO3)c2Cl)CC1] |
| 138 | 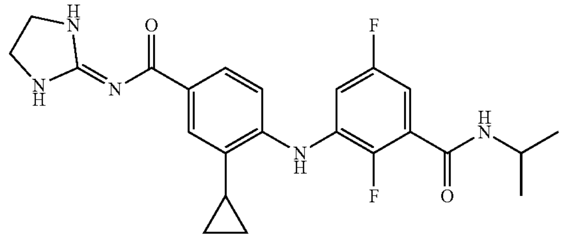 [SMILES: CC(C)NC(=O)c1cc(F)cc(Nc2ccc(C(=O)N=C3NCCN3)cc2C2CC2)c1F] |
| 139 | 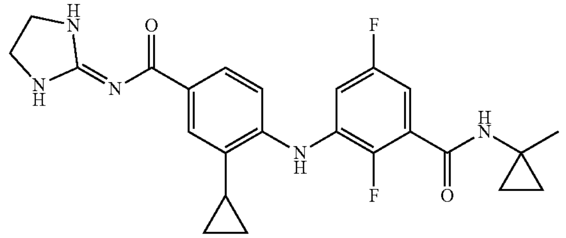 [SMILES: CC1(NC(=O)c2cc(F)cc(Nc3ccc(C(=O)N=C4NCCN4)cc3C3CC3)c2F)CC1] |
| 140 | 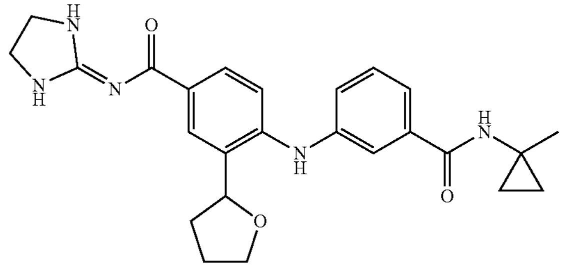 [SMILES: CC1(NC(=O)c2cccc(Nc3ccc(C(=O)N=C4NCCN4)cc3C3CCCO3)c2)CC1] |
| 141 | 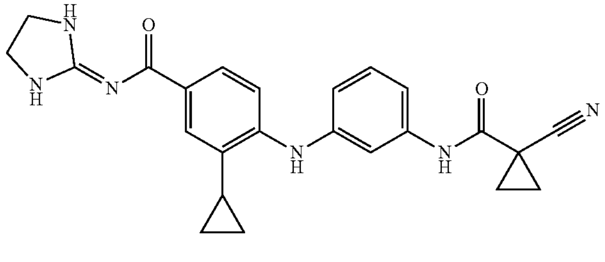 [SMILES: N#CC1(C(=O)Nc2cccc(Nc3ccc(C(=O)N=C4NCCN4)cc3C3CC3)c2)CC1] |

TABLE I-continued
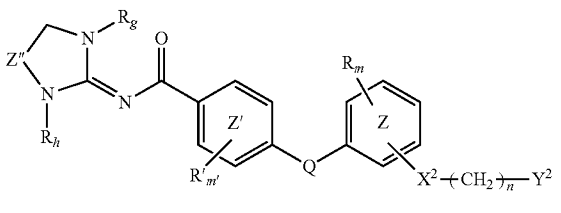
(I)
| No | Structure |
| --- | --- |
| 142 | 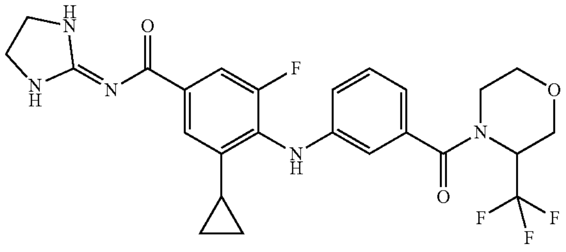 [SMILES: O=C(N=C1NCCN1)c1cc(F)c(Nc2cccc(C(=O)N3CCOCC3C(F)(F)F)c2)c(C2CC2)c1] |
| 143 | 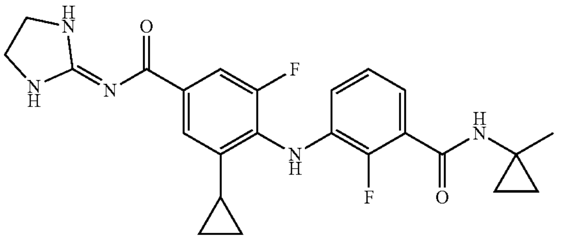 |
| 144 | 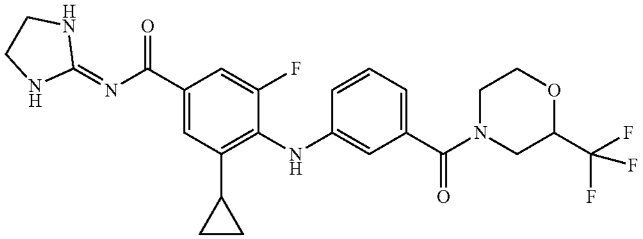 [SMILES: O=C(N=C1NCCN1)c1cc(F)c(Nc2cccc(C(=O)N3CCOC(C(F)(F)F)C3)c2)c(C2CC2)c1] |
| 145 | 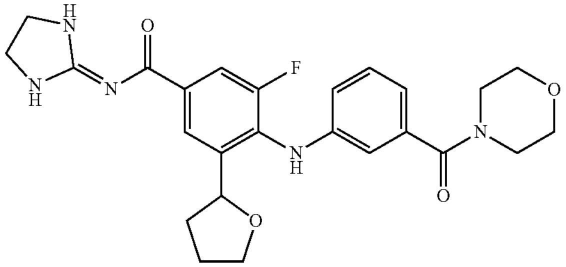 [SMILES: O=C(N=C1NCCN1)c1cc(F)c(Nc2cccc(C(=O)N3CCOCC3)c2)c(C2CCCO2)c1] |
| 146 | 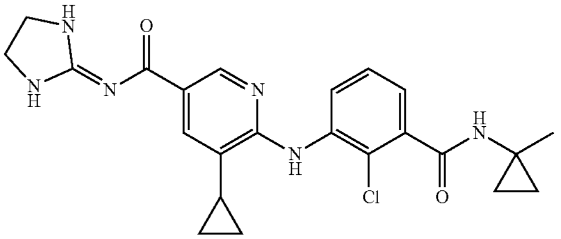 [SMILES: CC1(NC(=O)c2cccc(Nc3ncc(C(=O)N=C4NCCN4)cc3C3CC3)c2Cl)CC1] |

TABLE I-continued
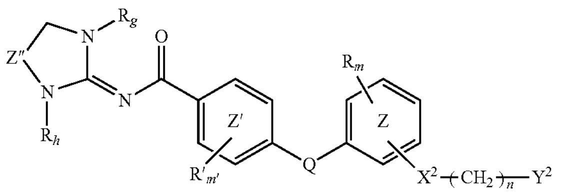
(I)
| No | Structure |
|---|---|
| 147 | 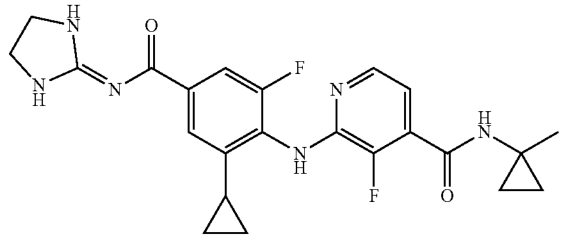 |
| 148 | 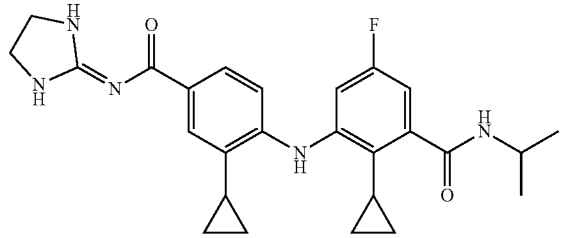 [SMILES: CC(C)NC(=O)c1cc(F)cc(Nc2ccc(C(=O)N=C3NCCN3)cc2C2CC2)c1C1CC1] |
| 149 | 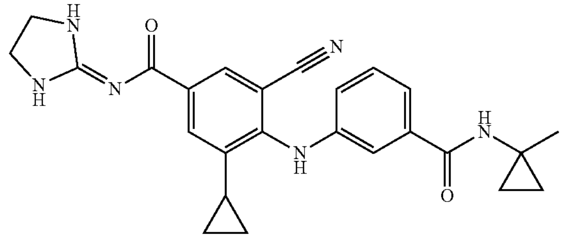 [SMILES: CC1(NC(=O)c2cccc(Nc3c(C#N)cc(C(=O)N=C4NCCN4)cc3C3CC3)c2)CC1] |
| 150 | 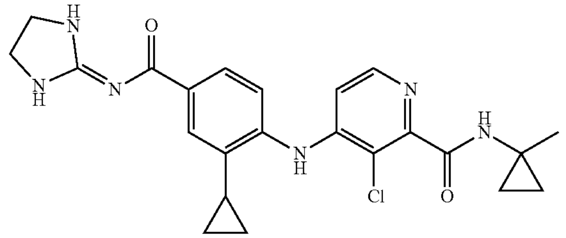 [SMILES: CC1(NC(=O)c2nccc(Nc3ccc(C(=O)N=C4NCCN4)cc3C3CC3)c2Cl)CC1] |
| 151 | 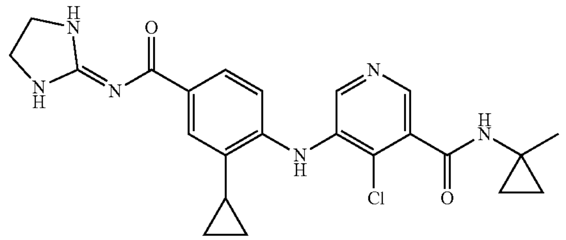 [SMILES: CC1(NC(=O)c2cncc(Nc3ccc(C(=O)N=C4NCCN4)cc3C3CC3)c2Cl)CC1] |

TABLE I-continued
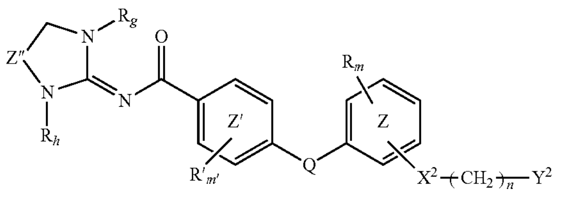
(I)
| No | Structure |
|---|---|
| 152 | 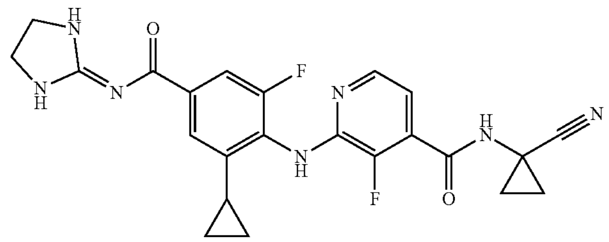 [SMILES: N#CC1(NC(=O)c2ccnc(Nc3c(F)cc(C(=O)N=C4NCCN4)cc3C3CC3)c2F)CC1] |
| 153 | 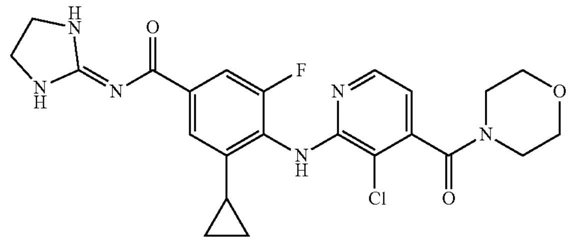 |
| 154 | 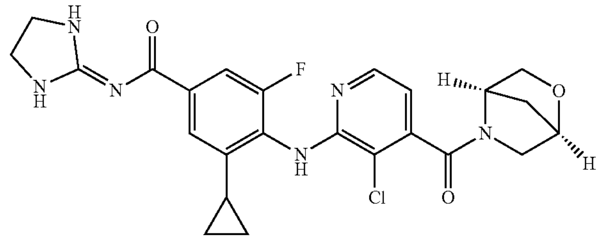 [SMILES: O=C(N=C1NCCN1)c1cc(F)c(Nc2nccc(C(=O)N3C[C@H]4C[C@@H]3CO4)c2Cl)c(C2CC2)c1] |
| 155 | 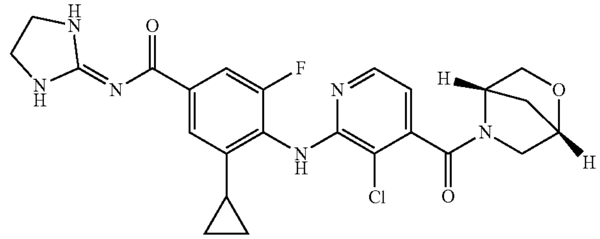 [SMILES: O=C(N=C1NCCN1)c1cc(F)c(Nc2nccc(C(=O)N3C[C@@H]4C[C@H]3CO4)c2Cl)c(C2CC2)c1] |
| 156 | 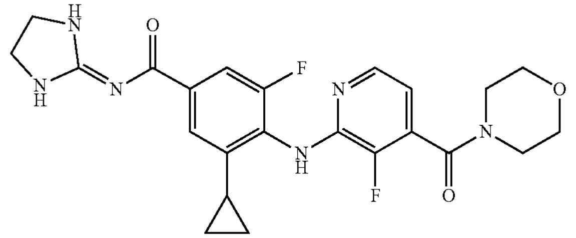 |

TABLE I-continued
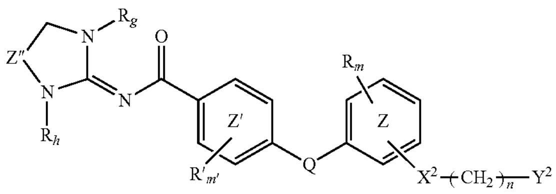
(I)
| No | Structure |
|---|---|
| 157 | 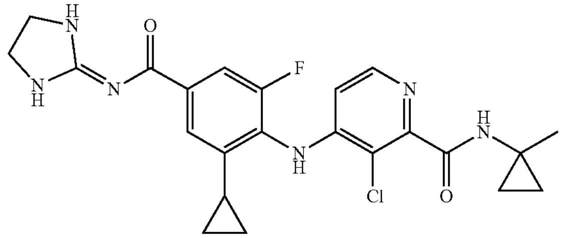 [SMILES: CC1(NC(=O)c2nccc(Nc3c(F)cc(C(=O)N=C4NCCN4)cc3C3CC3)c2Cl)CC1] |
| 158 | 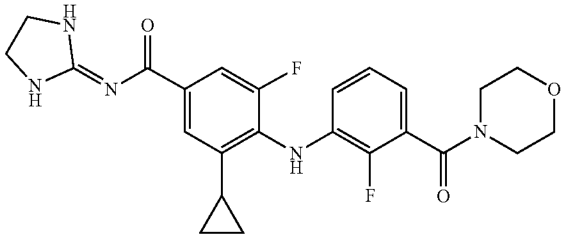 [SMILES: O=C(N=C1NCCN1)c1cc(F)c(Nc2cccc(C(=O)N3CCOCC3)c2F)c(C2CC2)c1] |
| 159 | 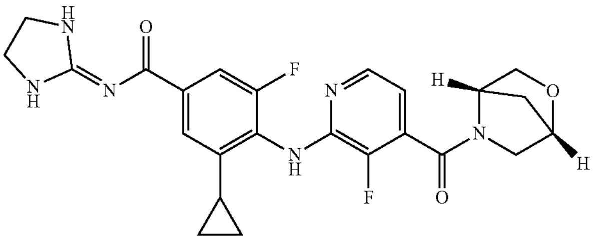 [SMILES: O=C(N=C1NCCN1)c1cc(F)c(Nc2nccc(C(=O)N3C[C@@H]4C[C@H]3CO4)c2F)c(C2CC2)c1] |
| 160 | 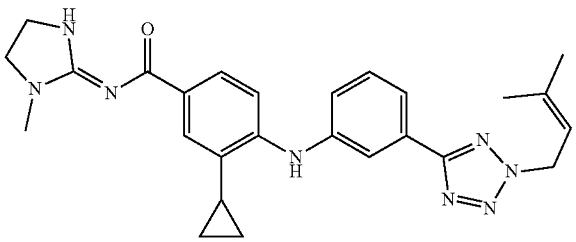 |
| 161 | 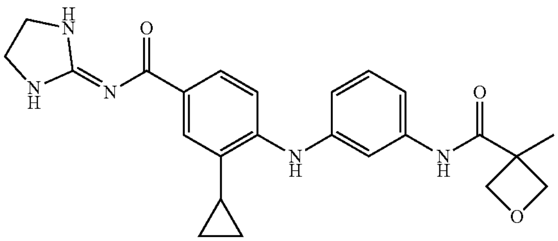 |

TABLE I-continued
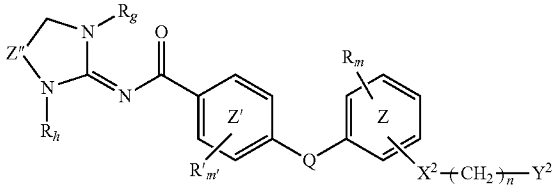
(I)
| No | Structure |
|---|---|
| 162 | 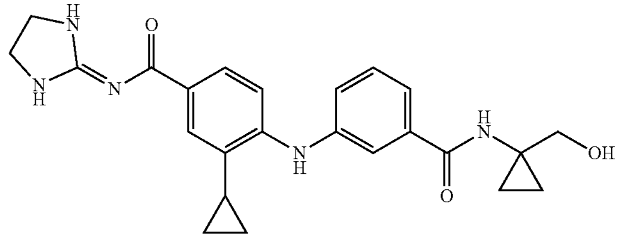 [SMILES: O=C(N=C1NCCN1)c1ccc(Nc2cccc(C(=O)NC3(CO)CC3)c2)c(C2CC2)c1] |
| 163 | 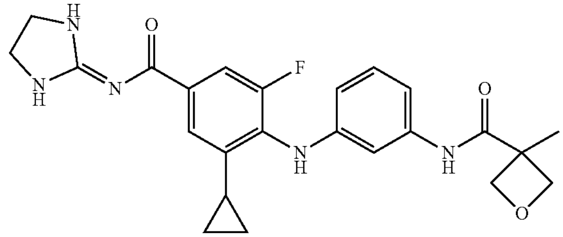 [SMILES: CC1(C(=O)Nc2cccc(Nc3c(F)cc(C(=O)N=C4NCCN4)cc3C3CC3)c2)COC1] |
| 164 | 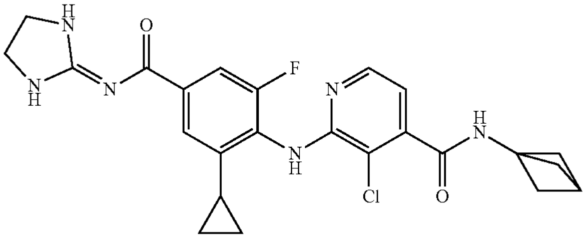 [SMILES: O=C(N=C1NCCN1)c1cc(F)c(Nc2nccc(C(=O)NC34CC(C3)C4)c2Cl)c(C2CC2)c1] |
| 165 | 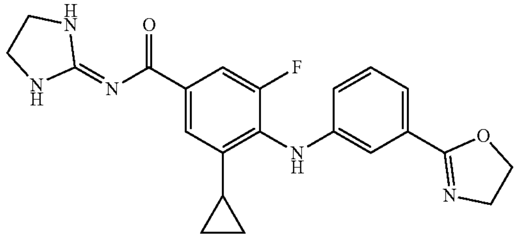 [SMILES: O=C(N=C1NCCN1)c1cc(F)c(Nc2cccc(C3=NCCO3)c2)c(C2CC2)c1] |
| 166 | 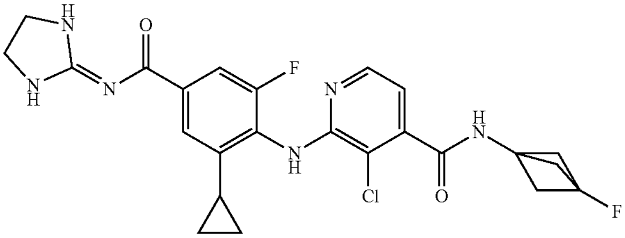 [SMILES: O=C(N=C1NCCN1)c1cc(F)c(Nc2nccc(C(=O)NC34CC(F)(C3)C4)c2Cl)c(C2CC2)c1] |

TABLE I-continued
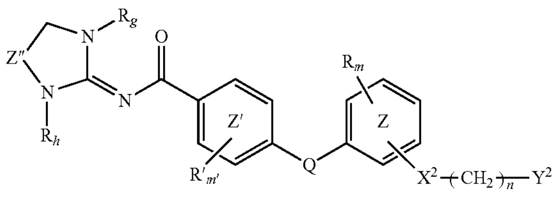
(I)
| No | Structure |
|---|---|
| 167 | 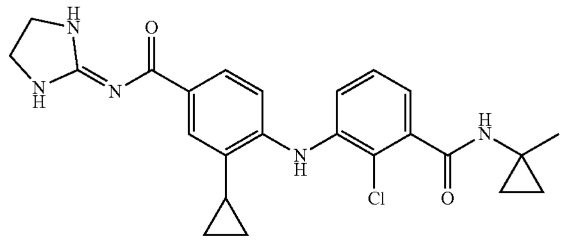 [SMILES: CC1(NC(=O)c2cccc(Nc3ccc(C(=O)N=C4NCCN4)cc3C3CC3)c2Cl)CC1] |
| 168 | 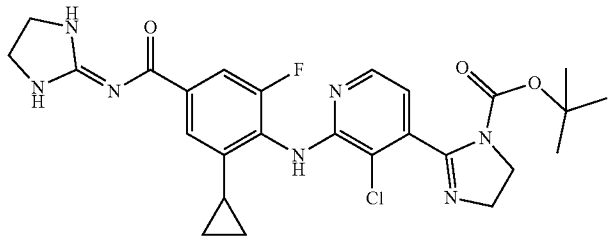 [SMILES: CC(C)(C)OC(=O)N1CCN=C1c1ccnc(Nc2c(F)cc(C(=O)N=C3NCCN3)cc2C2CC2)c1Cl] |
| 169 | 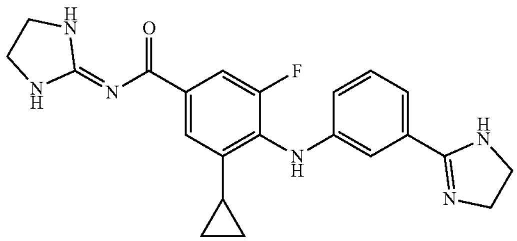 [SMILES: O=C(N=C1NCCN1)c1cc(F)c(Nc2cccc(C3=NCCN3)c2)c(C2CC2)c1] |
| 170 | 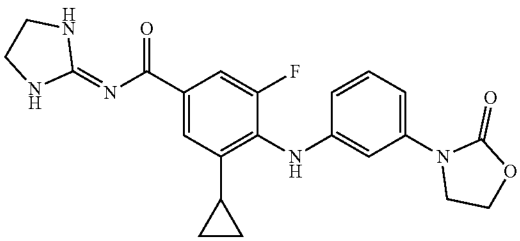 [SMILES: O=C(N=C1NCCN1)c1cc(F)c(Nc2cccc(N3CCOC3=O)c2)c(C2CC2)c1] |
| 171 | 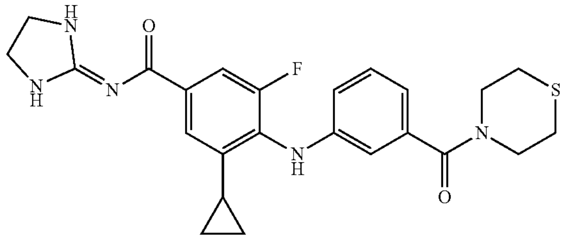 [SMILES: O=C(N=C1NCCN1)c1cc(F)c(Nc2cccc(C(=O)N3CCSCC3)c2)c(C2CC2)c1] |

TABLE I-continued
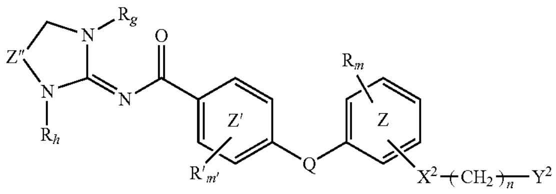
(I)
| No | Structure |
| --- | --- |
| 172 | 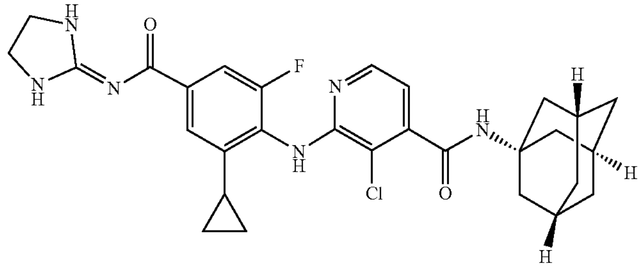 [SMILES: O=C(N=C1NCCN1)c1cc(F)c(Nc2nccc(C(=O)N[C@]34C[C@H]5C[C@H](C[C@H](C5)C3)C4)c2Cl)c(C2CC2)c1] |
| 173 | 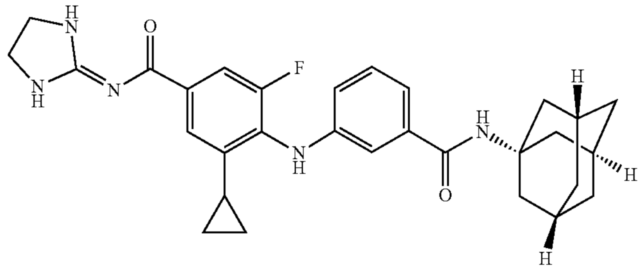 |
| 174 | 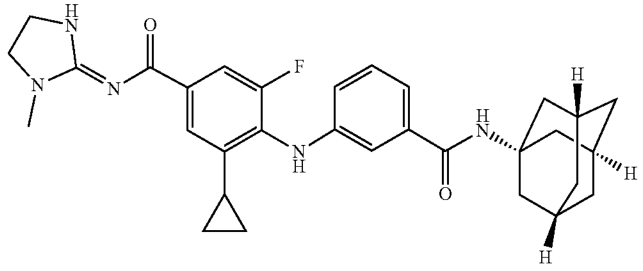 [SMILES: CN1CCN/C1=N\C(=O)c1cc(F)c(Nc2cccc(C(=O)N[C@]34C[C@H]5C[C@H](C[C@H](C5)C3)C4)c2)c(C2CC2)c1] |
| 175 | 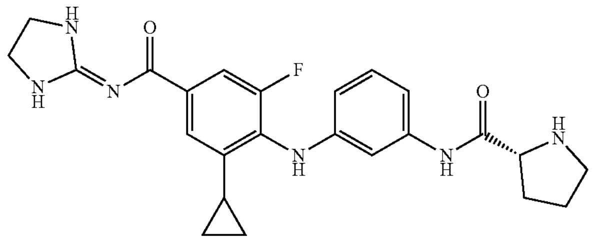 [SMILES: O=C(N=C1NCCN1)c1cc(F)c(Nc2cccc(NC(=O)[C@H]3CCCN3)c2)c(C2CC2)c1] |
| 176 | 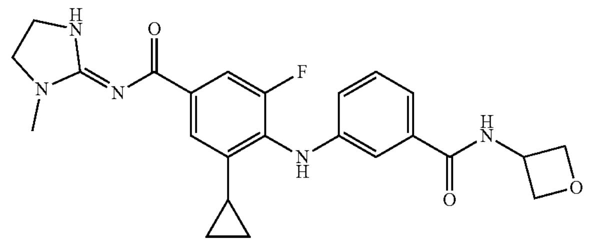 [SMILES: CN1CCN/C1=N\C(=O)c1cc(F)c(Nc2cccc(C(=O)NC3COC3)c2)c(C2CC2)c1] |

TABLE I-continued
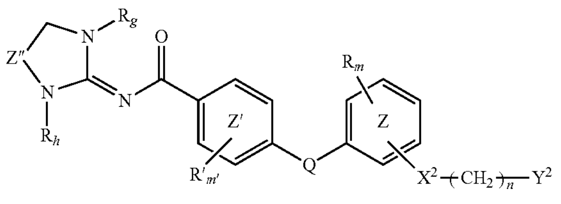
(I)
| No | Structure |
|---|---|
| 177 | 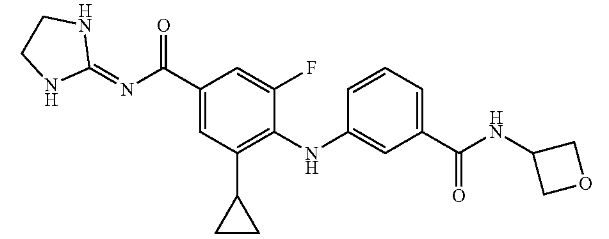 [SMILES: O=C(N=C1NCCN1)c1cc(F)c(Nc2cccc(C(=O)NC3COC3)c2)c(C2CC2)c1] |
| 178 | 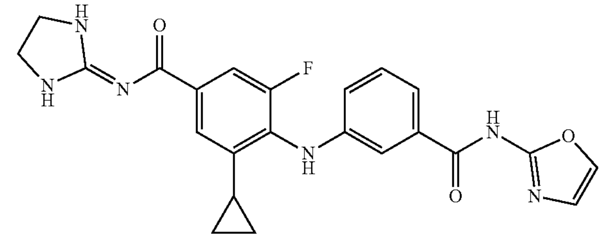 [SMILES: O=C(N=C1NCCN1)c1cc(F)c(Nc2cccc(C(=O)Nc3ncco3)c2)c(C2CC2)c1] |
| 179 | 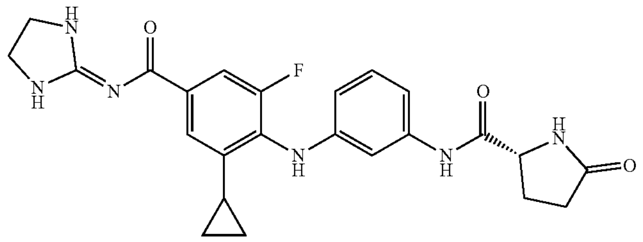 [SMILES: O=C1CC[C@H](C(=O)Nc2cccc(Nc3c(F)cc(C(=O)N=C4NCCN4)cc3C3CC3)c2)N1] |
| 180 | 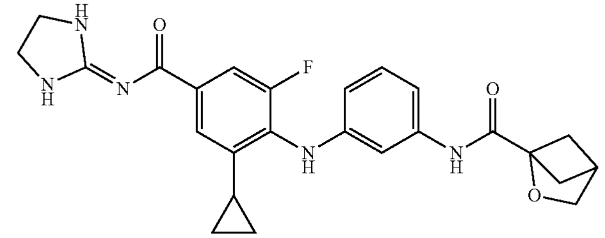 [SMILES: O=C(N=C1NCCN1)c1cc(F)c(Nc2cccc(NC(=O)C34CC(CO3)C4)c2)c(C2CC2)c1] |
| 181 | 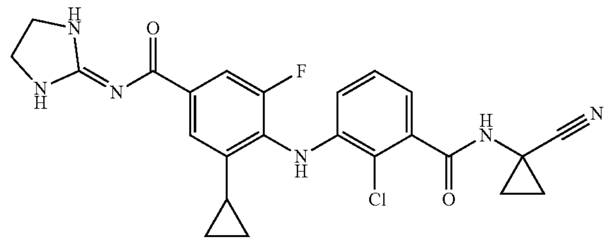 [SMILES: N#CC1(NC(=O)c2cccc(Nc3c(F)cc(C(=O)N=C4NCCN4)cc3C3CC3)c2Cl)CC1] |

TABLE II

| No | Characterizations |
|---|---|
| 1 | $^1$H NMR (400 MHz, $d_6$-DMSO) δ 8.38 (s, 1H), 8.09 (s, 2H), 7.79 (dd, J = 1.9, 8.4 Hz, 1H), 7.76 (s, 1H), 7.72 (d, J = 1.9 Hz, 1H), 7.53-7.49 (m, 1H), 7.31-7.26 (m, 2H), 7.21-7.15 (m, 1H), 7.11 (d, J = 8.5 Hz, 1H), 3.52 (s, 4H), 1.98-1.90 (m, 1H), 1.71-1.62 (m, 1H), 0.98-0.92 (m, 2H), 0.90 (d, J = 6.8 Hz, 6H), 0.70-0.65 (m, 4H), 0.61-0.55 (m, 2H).<br>$[M + H]^+$ = 446.2 |
| 2 | $^1$H NMR (400 MHz, $d_6$-DMSO) δ 9.64 (s, 1H), 8.12 (s, 2H), 8.03 (d, J = 1.9 Hz, 1H), 7.80 (dd, J = 8.4, 1.9 Hz, 1H), 7.51 (s, 1H), 7.33 (s, 1H), 7.16-7.05 (m, 2H), 7.02 (d, J = 8.4 Hz, 1H), 6.63 (d, J = 7.9 Hz, 1H), 3.53 (s, 4H), 3.29 (s, 1H), 2.61-2.52 (m, 1H), 2.00 (d, J = 8.0 Hz, 2H), 1.84-1.71 (m, 2H), 1.64 (dd, J = 7.2, 4.7 Hz, 2H), 1.55-1.41 (m, 2H), 1.07 (d, J = 6.8 Hz, 6H).<br>$[M + H]^+$ = 434.0 |
| 3 | $^1$H NMR (400 MHz, $d_6$-DMSO) δ 8.14 (s, 2H), 8.08 (s, 1H), 7.85 (d, J = 8.5 Hz, 1H), 7.29 (s, 1H), 7.20 (t, J = 7.8 Hz, 1H), 6.96 (d, J = 8.3 Hz, 1H), 6.78 (s, 2H), 3.66 (s, 4H), 3.56 (t, J = 4.7 Hz, 2H), 3.53 (s, 4H), 3.23 (d, J = 8.3 Hz, 1H), 3.19 (d, J = 5.1 Hz, 2H), 1.99 (s, 2H), 1.76 (s, 2H), 1.60 (d, J = 4.8 Hz, 2H), 1.52 (s, 2H).<br>$[M + H]^+$ = 496.0 |
| 4 | $^1$H NMR (400 MHz, $d_6$-DMSO) δ 8.15 (s, 2H), 7.83 (d, J = 8.7 Hz, 1H), 7.77 (s, 1H), 7.44 (s, 1H), 7.31 (s, 1H), 7.13 (s, 1H), 7.03 (s, 1H), 6.92 (s, 1H), 3.67 (s, 4H), 3.61-3.49 (m, 6H), 3.20 (d, J = 5.5 Hz, 2H), 1.90 (d, J = 10.4 Hz, 1H), 0.95 (d, J = 8.3 Hz, 2H), 0.61 (s, 2H).<br>$[M + H]^+$ = 468.0 |
| 5 | $^1$H NMR (400 MHz, $d_6$-DMSO) δ 8 9.61 (s, 1H), 8.18 (s, 1H), 8.13 (s, 2H), 7.86 (d, J = 8.1 Hz, 1H), 7.11 (d, J = 8.2 Hz, 1H), 7.01 (dd, J = 14.6, 6.9 Hz, 4H), 6.45 (d, J = 7.7 Hz, 1H), 3.54 (s, 4H), 2.26-2.20 (m, 2H), 1.52 (dd, J = 13.2, 6.4 Hz, 1H), 1.47-1.42 (m, 2H), 1.39 (s, 9H), 0.87 (d, J = 6.5 Hz, 6H).<br>$[M + H]^+$ = 450.2 |
| 6 | $^1$H NMR (400 MHz, $d_6$-DMSO) δ 8.21 (d, J = 1.9 Hz, 1H), 8.13 (s, 2H), 7.95 (d, J = 8.5 Hz, 1H), 7.87 (dd, J = 8.2, 1.9 Hz, 1H), 7.25-7.21 (m, 1H), 7.21-7.06 (m, 4H), 6.81-6.76 (m, 1H), 4.16-3.99 (m, 1H), 3.53 (s, 4H), 1.63-1.46 (m, 2H), 1.39 (s, 9H), 1.22 (ddd, J = 13.5, 8.3, 5.4 Hz, 1H), 1.09 (d, J = 6.6 Hz, 3H), 0.87 (dd, J = 6.5, 1.9 Hz, 6H).<br>$[M + H]^+$ = 464.3 |
| 7 | $^1$H NMR (400 MHz, $d_6$-DMSO) δ 8.14 (t, J = 5.5 Hz, 1H), 8.08 (s, 2H), 7.82 (d, J = 8.5 Hz, 2H), 7.26-7.15 (m, 3H), 7.03 (d, J = 8.2 Hz, 1H), 6.84 (d, J = 6.2 Hz, 1H), 3.51 (s, 4H), 3.25 (q, J = 6.5 Hz, 2H), 1.96-1.78 (m, 2H), 1.67 (dp, J = 13.3, 6.7 Hz, 1H), 1.43 (q, J = 7.0 Hz, 2H), 1.04-0.95 (m, 2H), 0.92 (d, J = 6.6 Hz, 6H), 0.87 (d, J = 8.6 Hz, 2H), 0.62 (q, J = 5.4 Hz, 2H), 0.45 (q, J = 5.4 Hz, 2H).<br>$^{13}$C NMR (151 MHz, $d_6$-DMSO) δ 175.7, 169.6, 165.7, 145.6, 143.1, 141.8, 130.6, 129.6, 129.0, 128.7, 128.2, 127.1, 120.5, 119.0, 114.2, 41.7, 38.4, 37.7, 25.8, 22.9, 11.9, 11.0, 7.27, 6.5<br>$[M + H]^+$ = 474.2 |
| 8 | $^1$H NMR (400 MHz, $d_6$-DMSO) δ 8.21 (d, J = 8.0 Hz, 2H), 8.14 (s, 2H), 7.87 (d, J = 8.3 Hz, 1H), 7.23-7.09 (m, 5H), 6.83 (s, 1H), 3.54 (s, 4H), 3.23 (q, J = 6.5 Hz, 2H), 1.60 (dt, J = 13.6, 6.8 Hz, 1H), 1.40 (s, 11H), 0.89 (d, J = 6.6 Hz, 6H).<br>$[M + H]^+$ = 450.2 |
| 9 | $^1$H NMR (400 MHz, $d_6$-DMSO) δ 8.21 (d, J = 1.9 Hz, 1H), 8.12 (s, 2H), 7.87 (dd, J = 8.2, 1.9 Hz, 1H), 7.09 (dt, J = 7.8, 3.7 Hz, 2H), 6.67 (dd, J = 8.2, 1.1 Hz, 1H), 6.60 (dd, J = 7.5, 1.1 Hz, 1H), 6.55 (s, 1H), 3.77-3.47 (m, 10H), 3.26 (dt, J = 7.1, 4.3 Hz, 2H), 1.77 (ddd, J = 14.0, 8.3, 5.8 Hz, 1H), 1.43 (s, 9H), 1.00-0.89 (m, 2H), 0.69 (s, 1H), 0.34 (dd, J = 8.9, 4.0 Hz, 1H).<br>$[M + H]^+$ = 490.3 |
| 10 | $^1$H NMR (500 MHz, $d_6$-DMSO) δ 8.36 (t, J = 5.7 Hz, 1H), 8.10 (s, 2H), 7.87-7.77 (m, 2H), 7.32 (s, 1H), 7.27-7.20 (m, 1H), 7.10 (dd, J = 8.2, 1.4 Hz, 1H), 7.04 (d, J = 8.3 Hz, 1H), 6.88 (dd, J = 7.4, 1.5 Hz, 1H), 3.52 (s, 4H), 3.27-3.20 (m, 2H), 1.87 (ddd, J = 13.7, 8.3, 5.4 Hz, 1H), 1.68 (dp, J = 13.4, 6.7 Hz, 1H), 1.41 (q, J = 7.0 Hz, 2H), 0.98-0.88 (m, 8H), 0.63-0.56 (m, 2H).<br>$[M + H]^+$ = 468.1 |
| 11 | $^1$H NMR (400 MHz, $d_6$-DMSO) δ 8.28 (d, J = 7.8 Hz, 1H), 8.11 (s, 2H), 7.85 (dd, J = 8.3, 1.9 Hz, 1H), 7.80 (d, J = 1.8 Hz, 1H), 7.32 (s, 1H), 7.28-7.20 (m, 1H), 7.10 (dd, J = 8.2, 1.5 Hz, 1H), 7.05 (d, J = 8.3 Hz, 1H), 6.89 (dd, J = 7.4, 1.5 Hz, 1H), 4.05 (d, J = 7.7 Hz, 1H), 3.52 (s, 4H), 1.94-1.82 (m, 1H), 1.15 (d, J = 6.6 Hz, 6H), 0.99-0.90 (m, 2H), 0.65-0.57 (m, 2H).<br>$[M + H]^+$ = 440.0 |
| 12 | $^1$H NMR (400 MHz, $d_6$-DMSO) δ 8.11 (s, 2H), 7.83 (dd, J = 8.3, 1.9 Hz, 1H), 7.80 (d, J = 1.8 Hz, 1H), 7.21 (s, 1H), 7.17 (t, J = 8.3 Hz, 1H), 7.04 (d, J = 8.3 Hz, 1H), 6.81-6.75 (m, 1H), 6.75-6.69 (m, 1H), 4.19-4.08 (m, 2H), 3.80 (dd, J = 11.4, 2.5 Hz, 1H), 3.76-3.70 (m, 2H), 3.65 (d, J = 11.2 Hz, 1H), 3.56 (dd, J = 11.4, 2.4 Hz, 1H), 3.52 (s, 4H), 3.47 (id, J = 11.0, 2.6 Hz, 1H), 3.27 (dd, J = 11.4, 9.9 Hz, 1H), 1.92-1.82 (m, 2H), 1.79 (dd, J = 13.8, 8.2 Hz, 1H), 0.98-0.92 (m, 2H), 0.62-0.56 (m, 2H).<br>$[M + H]^+$ = 485.0 |
| 13 | $^1$H NMR (400 MHz, $d_6$-DMSO) δ 10.05 (s, 1H), 8.10 (s, 2H), 7.78 (dd, J = 8.4, 2.0 Hz, 1H), 7.70 (d, J = 1.9 Hz, 1H), 7.62 (s, 1H), 7.44 (s, 1H), 7.17-7.10 (m, 2H), 7.08 (s, 1H), 6.75 (d, J = 8.9 Hz, 1H), 3.52 (s, 4H), 1.96 (ddd, J = 13.7, 8.3, 5.3 Hz, 1H), 1.81-1.70 (m, 1H), 0.99-0.89 (m, 2H), 0.76 (dt, J = 8.6, 2.5 Hz, 4H), 0.61-0.52 (m, 2H).<br>$[M + H]^+$ = 404.0 |
| 14 | $^1$H NMR (400 MHz, $d_6$-DMSO) δ 8.53 (s, 1H), 8.11 (s, 2H), 7.79 (dd, J = 8.4, 1.9 Hz, 2H), 7.72 (d, J = 1.8 Hz, 1H), 7.52 (s, 1H), 7.28 (d, J = 5.0 Hz, 2H), 7.22-7.14 (m, 1H), 7.11 (d, J = 8.4 Hz, 1H), 3.52 (s, 4H), 1.94 (ddd, J = 13.8, 8.3, 5.4 Hz, 1H), 1.35 (s, 3H), 0.98-0.91 (m, 2H), 0.75-0.68 (m, 2H), 0.58 (td, J = 6.3, 4.3 Hz, 4H).<br>$[M + H]^+$ = 418.0 |
| 15 | $^1$H NMR (400 MHz, $d_6$-DMSO) δ 8.15 (s, 2H), 8.08 (d, J = 1.9 Hz, 1H), 7.88 (dd, J = 8.3, 1.8 Hz, 1H), 7.47 (s, 1H), 7.24-7.17 (m, 1H), 6.98 (d, J = 7.7 Hz, 1H), 6.81 (dd, J = 7.5, 1.3 Hz, 1H), 6.74 (dd, J = 8.2, 1.4 Hz, 1H), 3.95 (td, J = 8.7, 8.3, 4.9 Hz, 2H), 3.74 (t, J = 7.6 Hz, 1H), 3.66 (s, 4H), |

TABLE II-continued

| No | Characterizations |
| --- | --- |
| | 3.61 (dt, J = 5.3, 3.3 Hz, 2H), 3.56 (t, J = 4.9 Hz, 2H), 3.53 (s, 4H), 3.23-3.14 (m, 2H), 2.28 (dd, J = 11.9, 7.0 Hz, 1H), 1.93-1.83 (m, 1H).<br>$[M + H]^+$ = 497.9 |
| 16 | $^1$H NMR (400 MHz, $d_6$-DMSO) δ 8.35 (d, J = 1.9 Hz, 1H), 8.17 (s, 2H), 8.10 (d, J = 8.6 Hz, 1H), 7.56 (s, 1H), 7.43-7.37 (m, 1H), 7.30 (dd, J = 8.1, 1.6 Hz, 1H), 7.13 (dd, J = 7.5, 1.6 Hz, 1H), 6.88 (d, J = 8.6 Hz, 1H), 3.66 (d, J = 2.7 Hz, 4H), 3.57-3.54 (m, 2H), 3.53 (s, 4H), 3.18 (d, J = 3.3 Hz, 2H).<br>$[M + H]^+$ = 495.9 |
| 17 | $^1$H NMR (500 MHz, $d_6$-DMSO) δ 8.64 (s, 1 H), 8.28 (d, J = 2.2 Hz, 1 H), 8.04 (d, J = 8.0 Hz, 1 H), 7.94 (dd, J = 8.2, 1.9 Hz, 1 H), 7.23 (t, J = 1.9 Hz, 1 H), 7.20-7.17 (m, 1 H), 7.17-7.15 (m, 1 H), 7.14-7.12 (m, 1H), 7.11 (d, J = 8.0 Hz, 1 H), 6.85-6.76 (m, 1 H), 4.13-3.97 (m, 1 H), 3.62-3.51 (m, 2H), 3.49-3.41 (m, 2 H), 2.95 (s, 3 H), 1.39 (s, 9 H), 1.13 (d, J = 6.6 Hz, 6 H).<br>$[M + H]^+$ = 436.5 |
| 18 | $^1$H NMR (400 MHz, $d_6$-DMSO) δ 8.52 (s, 1H), 8.12 (s, 2H), 8.02 (d, J = 1.8 Hz, 1H), 7.82 (dd, J = 8.4, 1.9 Hz, 1H), 7.48 (s, 1H), 7.43-7.37 (m, 1H), 7.22 (s, 2H), 7.13-7.02 (m, 2H), 3.70 (q, J = 8.5 Hz, 1H), 3.53 (s, 4H), 2.39-2.28 (m, 2H), 2.05-1.86 (m, 3H), 1.82-1.74 (m, 1H), 1.35 (s, 3H), 0.75-0.67 (m, 2H), 0.62-0.54 (m, 2H).<br>$[M + H]^+$ = 432.0 |
| 19 | $^1$H NMR (400 MHz, $d_6$-DMSO) δ 8.20 (d, J = 1.7 Hz, 1H), 8.13 (s, 2H), 8.03 (d, J = 7.7 Hz, 1H), 7.87 (dd, J = 8.2, 1.8 Hz, 1H), 7.24 (s, 1H), 7.16 (t, J = 6.0 Hz, 3H), 7.10 (d, J = 8.2 Hz, 1H), 6.80 (s, 1H), 4.11-4.00 (m, 1H), 3.54 (s, 4H), 1.39 (s, 9H), 1.14 (d, J = 6.6 Hz, 6H).<br>$[M + H]^+$ = 422.1 |
| 20 | $^1$H NMR (400 MHz, $d_6$-DMSO) δ 8.96 (s, 1H), 8.25-8.04 (m, 3H), 7.87 (dd, J = 8.2, 1.9 Hz, 1H), 7.17-6.96 (m, 4H), 6.92 (s, 1H), 6.47 (dt, J = 7.2, 2.0 Hz, 1H), 3.53 (s, 4H), 1.40 (s, 9H), 1.18 (s, 9H).<br>$[M + H]^+$ = 436.3 |
| 21 | $^1$H NMR (400 MHz, $d_6$-DMSO) δ 8.11 (s, 2H), 7.80 (s, 2H), 7.22 (s, 1H), 7.17 (t, J = 8.3 Hz, 1H), 7.03 (d, J = 8.3 Hz, 1H), 6.77 (d, J = 8.2 Hz, 1H), 6.73 (d, J = 8.2 Hz, 1H), 4.06 (qd, J = 10.5, 4.8 Hz, 2H), 3.96-3.83 (m, 2H), 3.83-3.75 (m, 1H), 3.72-3.60 (m, 2H), 3.49 (q, J = 11.7, 10.6 Hz, 6H), 1.87 (ddd, J = 13.8, 8.4, 5.5 Hz, 1H), 0.99-0.90 (m, 2H), 0.59 (q, J = 5.6 Hz, 2H).<br>$[M + H]^+$ = 418.3 |
| 22 | $^1$H NMR (400 MHz, $d_6$-DMSO) δ 8.08 (s, 2H), 7.78 (dd, J = 8.4, 1.9 Hz, 1H), 7.70 (d, J = 1.9 Hz, 1H), 7.58 (s, 1H), 7.17-7.07 (m, 2H), 6.65 (dd, J = 8.0, 1.5 Hz, 1H), 6.61 (t, J = 2.1 Hz, 1H), 6.42 (dd, J = 8.0, 2.1 Hz, 1H), 3.89 (t, J = 6.5 Hz, 2H), 3.51 (s, 4H), 1.94 (ddd, J = 13.7, 8.4, 5.4 Hz, 1H), 1.67 (dd, J = 18.2, 8.9 Hz, 7H), 1.31-1.12 (m, 6H), 0.96-0.81 (m, 4H), 0.61-0.52 (m, 2H).<br>$[M + H]^+$ = 461.2 |
| 23 | $^1$H NMR (400 MHz, $d_6$-DMSO) δ 8.11 (s, 2H), 7.80 (s, 2H), 7.22 (s, 1H), 7.17 (t, J = 8.3 Hz, 1H), 7.03 (d, J = 8.3 Hz, 1H), 6.77 (d, J = 8.2 Hz, 1H), 6.73 (d, J = 8.2 Hz, 1H), 4.06 (qd, J = 10.5, 4.8 Hz, 2H), 3.96-3.83 (m, 2H), 3.83-3.75 (m, 1H), 3.72-3.60 (m, 2H), 3.49 (q, J = 11.7, 10.6 Hz, 6H), 1.87 (ddd, J = 13.8, 8.4, 5.5 Hz, 1H), 0.99-0.90 (m, 2H), 0.59 (q, J = 5.6 Hz, 2H).<br>$[M + H]^+$ = 471.0 |
| 24 | $^1$H NMR (400 MHz, $d_6$-DMSO) δ 8.66 (s, 1H), 8.48 (s, 1H), 8.31 (d, J = 1.9 Hz, 1H), 7.96 (dd, J = 8.1, 1.9 Hz, 1H), 7.25-7.05 (m, 5H), 6.83 (dd, J = 1.1, 2.3 Hz, 1H), 3.68-3.53 (m, 2H), 3.52-3.42 (m, 2H), 2.97 (s, 3H), 1.41 (s, 9H), 1.35 (s, 3H), 0.75-0.68 (m, 2H), 0.61-0.56 (m, 2H).<br>$[M + H]^+$ = 448.2 |
| 25 | $^1$H NMR (400 MHz, $d_6$-DMSO) δ 8.45 (d, J = 4.5 Hz, 1H), 8.11 (s, 2H), 7.85 (dd, J = 8.3, 1.9 Hz, 1H), 7.79 (d, J = 1.8 Hz, 1H), 7.33 (s, 1H), 7.23 (s, 1H), 7.10 (d, J = 1.5 Hz, 1H), 7.04 (d, J = 8.3 Hz, 1H), 6.92-6.85 (m, 1H), 3.52 (s, 4H), 2.87-2.79 (m, 1H), 1.87 (s, 1H), 0.98-0.91 (m, 2H), 0.70 (td, J = 7.1, 4.8 Hz, 2H), 0.60 (dd, J = 5.5, 1.8 Hz, 2H), 0.56-0.50 (m, 2H).<br>$^{13}$C NMR (151 MHz, $d_6$-DMSO) δ 175.5, 168.1, 165.8, 144.0, 140.9, 138.9, 132.9, 132.6, 127.9, 127.8, 120.3, 119.5, 118.8, 118.1, 41.7, 23.1, 11.7, 7.3, 6.1<br>$[M + H]^+$ = 438.0 |
| 26 | $^1$H NMR (400 MHz, $d_6$-DMSO) δ 9.68 (s, 1H), 8.08 (s, 2H), 7.79 (dd, J = 8.4, 1.9 Hz, 1H), 7.71 (d, J = 1.9 Hz, 1H), 7.60 (s, 1H), 7.45 (d, J = 1.8 Hz, 1H), 7.19-7.05 (m, 3H), 6.75 (d, J = 8.3 Hz, 1H), 3.51 (s, 4H), 2.64-2.52 (m, 1H), 1.95 (tt, J = 8.4, 5.4 Hz, 1H), 1.08 (d, J = 6.8 Hz, 6H), 0.99-0.89 (m, 2H), 0.61-0.52 (m, 2H).<br>$^{13}$C NMR (151 MHz, $d_6$-DMSO) δ 175.6, 146.1, 144.0, 140.6, 131.1, 129.5, 127.8, 127.5, 116.0, 114.2, 112.2, 109.9, 41.9, 35.3, 19.9, 11.6, 7.6<br>$[M + H]^+$ = 406.1 |
| 27 | $^1$H NMR (400 MHz, $d_6$-DMSO) δ 8.22 (t, J = 5.7 Hz, 1H), 8.10 (s, 2H), 7.83 (s, 2H), 7.26 (s, 2H), 7.14-7.01 (m, 3H), 3.74 (s, 3H), 3.52 (s, 4H), 3.30-3.23 (m, 2H), 1.89 (ddd, J = 13.7, 8.2, 5.3 Hz, 1H), 1.66 (dp, J = 13.4, 6.7 Hz, 1H), 1.43 (q, J = 7.0 Hz, 2H), 1.03-0.95 (m, 2H), 0.92 (d, J = 6.6 Hz, 6H), 0.65-0.56 (m, 2H).<br>$[M + H]^+$ = 464.2 |
| 28 | $^1$H NMR (400 MHz, $d_6$-DMSO) δ 8.67 (d, J = 6.7 Hz, 1H), 8.11 (s, 2H), 7.84 (s, 1H), 7.80 (s, 1H), 7.34 (s, 1H), 7.29-7.20 (m, 1H), 7.13-7.08 (m, 1H), 7.05 (d, J = 8.4 Hz, 1H), 6.91 (dd, J = 7.4, 1.5 Hz, 1H), 4.42 (s, 1H), 3.87 (dd, J = 8.9, 6.2 Hz, 1H), 3.80 (t, J = 7.6 Hz, 1H), 3.71 (d, J = 5.5 Hz, 1H), 3.59 (dd, J = 8.9, 4.1 Hz, 1H), 3.52 (s, 4H), 2.15 (dd, J = 12.8, 7.6 Hz, 1H), 1.87 (s, 2H), 0.95 (dd, J = 8.3, 2.0 Hz, 2H), 0.61 (d, J = 3.6 Hz, 2H).<br>$[M + H]^+$ = 468.0 |
| 29 | $^1$H NMR (400 MHz, $d_6$-DMSO) δ 8.27 (t, J = 5.7 Hz, 1H), 8.11 (s, 2H), 7.91 (d, J = 1.9 Hz, 1H), 7.88 (dd, J = 8.4, 2.0 Hz, 1H), 7.57 (s, 1H), 7.48 (s, 1H), 7.27 (d, J = 5.1 Hz, 2H), 7.16 (d, J = 8.5 Hz, 1H), 7.14 (d, J = 3.7 Hz, 1H), 5.19 (s, 1H), 5.04 (s, 1H), 3.52 (s, 4H), 3.29-3.21 (m, 2H), 2.00 (s, 3H), 1.61 (dp, J = 13.0, 6.9 Hz, 1H), 1.40 (q, J = 7.0 Hz, 2H), 0.90 (d, J = 6.6 Hz, 6H).<br>$[M + H]^+$ = 434.3 |
| 30 | $^1$H NMR (400 MHz, $d_6$-DMSO) δ 9.32 (s, 1H), 8.11 (s, 2H), 8.05 (d, J = 1.9 Hz, 1H), 7.89 (dd, J = 8.4, 1.9 Hz, 1H), 7.53 (t, J = 7.9 Hz, 1H), 7.45 (d, J = 8.4 Hz, 1H), 7.19 (d, J = 8.4 Hz, 1H), 6.87 (d, J = 7.3 Hz, 1H), 5.96 (s, 1H), 3.70-3.46 (m, 10H), 3.28-3.19 (m, 1H), 3.14 (dq, J = 10.1, 3.4 |

TABLE II-continued

| No | Characterizations |
| --- | --- |
| | Hz, 1H), 1.56 (d, J = 11.9 Hz, 6H). [M + H]$^+$ = 520.0 |
| 31 | $^1$H NMR (400 MHz, $_d$6-DMSO) δ 8.48 (s, 1H), 8.09 (s, 2H), 7.83-7.73 (m, 2H), 7.71 (d, J = 1.8 Hz, 1H), 7.54-7.48 (m, 1H), 7.33-7.24 (m, 2H), 7.20-7.14 (m, 1H), 7.10 (d, J = 8.4 Hz, 1H), 3.51 (s, 4H), 1.99-1.89 (m, 1H), 1.59 (q, J = 7.5 Hz, 2H), 0.97-0.91 (m, 2H), 0.89 (t, J = 7.4 Hz, 3H), 0.72-0.65 (m, 2H), 0.63-0.53 (m, 4H). [M + H]$^+$ = 432.2 |
| 32 | $^1$H NMR (400 MHz, $d_6$-DMSO) δ 8.19 (d, J = 7.7 Hz, 1H), 8.15-8.07 (m, 3H), 7.83 (dd, J = 2.0, 8.4 Hz, 1H), 7.71 (d, J = 2.0 Hz, 1H), 7.33 (t, J = 1.7 Hz, 1H), 7.19 (d, J = 8.4 Hz, 1H), 7.09-7.01 (m, 1H), 6.84 (td, J = 2.2, 11.3 Hz, 1H), 4.12-3.96 (m, 1H), 3.52 (s, 4H), 2.00-1.89 (m, 1H), 1.15 (d, J = 6.6 Hz, 6H), 1.00-0.89 (m, 2H), 0.62-0.56 (m, 2H). [M + H]$^+$ = 424.1 |
| 33 | $^1$H NMR (400 MHz, $d_6$-DMSO) δ 8.26 (t, J = 5.7 Hz, 1H), 8.21 (d, J = 1.7 Hz, 1H), 8.13 (s, 2H), 7.88 (dd, J = 8.1, 1.6 Hz, 1H), 7.19 (dd, J = 14.4, 6.0 Hz, 3H), 7.11 (dd, J = 7.9, 4.2 Hz, 2H), 6.81 (d, J = 7.6 Hz, 1H), 3.75 (t, J = 11.7 Hz, 2H), 3.53 (s, 4H), 3.30-3.17 (m, 3H), 2.98 (t, J = 10.4 Hz, 1H), 1.83 (d, J = 12.6 Hz, 1H), 1.58-1.45 (m, 3H), 1.39 (s, 9H), 1.38-1.28 (m, 2H), 1.12 (qd, J = 11.2, 4.4 Hz, 1H). [M + H]$^+$ = 492.1 |
| 34 | $^1$H NMR (400 MHz, $d_6$-DMSO) δ 10.04-9.95 (m, 1H), 8.08 (s, 2H), 7.86-7.76 (m, 2H), 7.71 (d, J = 1.9 Hz, 1H), 7.42 (t, J = 1.9 Hz, 1H), 7.30-7.21 (m, 1H), 7.17-7.06 (m, 3H), 4.76-4.58 (m, 1H), 3.51 (s, 4H), 2.01-1.91 (m, 1H), 1.24 (d, J = 6.6 Hz, 6H), 1.00-0.91 (m, 2H), 0.64-0.52 (m, 2H). [M + H]$^+$ = 422.1 |
| 35 | $^1$H NMR (400 MHz, $d_6$-DMSO) δ 8.21 (d, J = 1.8 Hz, 2H), 8.13 (s, 2H), 7.88 (dd, J = 8.1, 1.8 Hz, 1H), 7.24-7.13 (m, 3H), 7.10 (d, J = 8.2 Hz, 2H), 6.82 (d, J = 9.5 Hz, 1H), 3.83 (d, J = 10.7 Hz, 1H), 3.53 (s, 4H), 3.25 (td, J = 13.1, 12.4, 5.5 Hz, 4H), 1.74 (s, 1H), 1.59 (p, J = 8.9, 7.9 Hz, 3H), 1.39 (s, 12H), 1.16 (d, J = 11.3 Hz, 1H). [M + H]$^+$ = 492.3 |
| 36 | $^1$H NMR (400 MHz, $d_6$-DMSO) δ 8.62 (s, 1H), 8.13 (d, J = 7.8 Hz, 1H), 7.88 (d, J = 8.5 Hz, 1H), 7.81 (s, 1H), 7.76 (s, 1H), 7.55 (s, 1H), 7.31 (q, J = 7.9 Hz, 2H), 7.20 (d, J = 7.2 Hz, 1H), 7.12 (d, J = 8.4 Hz, 1H), 4.08 (dq, J = 13.4, 6.8 Hz, 1H), 3.59-3.50 (m, 2H), 3.48-3.39 (m, 2H), 2.95 (s, 3H), 1.96 (ddd, J = 13.6, 8.3, 5.5 Hz, 1H), 1.15 (d, J = 6.6 Hz, 6H), 1.01-0.91 (m, 2H), 0.60 (d, J = 5.0 Hz, 2H). [M + H]$^+$ = 420.1 |
| 37 | $^1$H NMR (400 MHz, $d_6$-DMSO) δ 9.56 (s, 1H), 8.21-8.06 (m, 3H), 7.87 (dd, J = 8.2, 1.9 Hz, 1H), 7.11 (d, J = 8.2 Hz, 1H), 7.06-6.96 (m, 4H), 6.46 (dt, J = 7.6, 1.6 Hz, 1H), 3.54 (s, 4H), 2.56-2.52 (m, 1H), 1.39 (s, 9H), 1.04 (d, J = 6.8 Hz, 6H). [M + H]$^+$ = 422.3 |
| 38 | $^1$H NMR (400 MHz, $d_6$-DMSO) δ 8.20 (d, J = 1.9 Hz, 1H), 8.13 (s, 2H), 7.88 (dd, J = 8.1, 1.9 Hz, 1H), 7.26-7.10 (m, 3H), 6.89-6.45 (m, 3H), 4.77-3.79 (m, 1H), 3.53 (s, 4H), 2.73 (s, 3H), 1.39 (s, 9H), 1.10-1.01 (m, 6H). [M + H]$^+$ = 436.1 |
| 39 | $^1$H NMR (400 MHz, $d_6$-DMSO) δ 8.28-8.18 (m, 2H), 8.13 (s, 2H), 7.88 (dd, J = 8.2, 1.8 Hz, 1H), 7.24-7.15 (m, 3H), 7.11 (dd, J = 7.9, 4.8 Hz, 2H), 6.85-6.78 (m, 1H), 3.82 (dd, J = 11.2, 3.1 Hz, 2H), 3.54 (s, 4H), 3.30-3.20 (m, 4H), 1.64-1.41 (m, 5H), 1.39 (s, 9H), 1.15 (qd, J = 12.4, 4.3 Hz, 2H). [M + H]$^+$ = 492.1 |
| 40 | $^1$H NMR (400 MHz, $d_6$-DMSO) δ 8.39 (t, J = 5.6 Hz, 1H), 8.12 (s, 2H), 8.08-8.02 (m, 2H), 7.91-7.83 (m, 2H), 7.62 (s, 1H), 6.71 (d, J = 5.1 Hz, 1H), 3.52 (s, 4H), 3.26 (q, J = 6.7 Hz, 2H), 2.27 (s, 3H), 1.95 (ddd, J = 13.8, 8.4, 5.5 Hz, 1H), 1.65 (dp, J = 13.3, 6.6 Hz, 1H), 1.42 (q, J = 7.0 Hz, 2H), 1.01-0.95 (m, 2H), 0.92 (d, J = 6.6 Hz, 6H), 0.64-0.56 (m, 2H). [M + H]$^+$ = 449.2 |
| 41 | $^1$H NMR (400 MHz, $d_6$-DMSO) δ 11.24 (s, 1H), 9.35 (s, 1H), 7.81 (d, J = 9.6 Hz, 1H), 7.75 (s, 2H), 7.16 (t, J = 8.2 Hz, 2H), 6.78-6.64 (m, 2H), 6.50 (d, J = 8.5 Hz, 1H), 4.06 (s, 2H), 3.91 (t, J = 6.5 Hz, 2H), 1.93 (d, J = 13.8 Hz, 1H), 1.67 (d, J = 14.8 Hz, 7H), 1.30-1.16 (m, 6H), 0.98 (d, J = 8.6 Hz, 2H), 0.86 (s, 2H), 0.61 (s, 2H). [M + H]$^+$ = 475.1 |
| 42 | $^1$H NMR (400 MHz, $d_6$-DMSO) δ 8.33 (d, J = 1.9 Hz, 1H), 8.15 (s, 2H), 8.06 (dd, J = 8.7, 1.7 Hz, 1H), 7.40 (s, 1H), 7.36-7.24 (m, 2H), 6.98 (dd, J = 7.0, 1.8 Hz, 1H), 6.94 (d, J = 8.7 Hz, 1H), 3.74-3.49 (m, 10H), 3.29-3.17 (m, 2H), 1.70 (ddd, J = 14.2, 8.4, 5.7 Hz, 1H), 0.75 (ddd, J = 17.3, 8.8, 4.7 Hz, 2H), 0.61 (td, J = 9.2, 8.8, 5.3 Hz, 1H), 0.31-0.22 (m, 1H). [M + H]$^+$ = 502.2 |
| 43 | $^1$H NMR (400 MHz, $d_6$-DMSO) δ 8.67 (s, 1H), 8.13 (d, J = 7.8 Hz, 1H), 7.87 (d, J = 8.4 Hz, 1H), 7.82 (s, 2H), 7.55 (s, 1H), 7.31 (q, J = 7.7 Hz, 2H), 7.20 (d, J = 7.2 Hz, 1H), 7.12 (d, J = 8.4 Hz, 1H), 4.08 (dq, J = 13.4, 6.7 Hz, 1H), 3.55-3.46 (m, 2H), 3.44-3.35 (m, 2H), 2.71 (ddt, J = 10.9, 7.1, 3.5 Hz, 1H), 1.97 (ddd, J = 13.7, 8.4, 5.0 Hz, 1H), 1.15 (d, J = 6.6 Hz, 6H), 1.01-0.91 (m, 2H), 0.75 (d, J = 6.7 Hz, 4H), 0.61 (q, J = 5.7 Hz, 2H). [M + H]$^+$ = 446.1 |
| 44 | $^1$H NMR (500 MHz, $d_6$-DMSO) δ 8.92 (s, 1H), 8.37 (t, J = 5.6 Hz, 1H), 8.08 (s, 2H), 8.03 (d, J = 1.8 Hz, 1H), 7.87 (dd, J = 8.4, 1.8 Hz, 1H), 7.51 (s, 1H), 7.37-7.30 (m, 2H), 7.25-7.20 (m, 2H), 5.91 (s, 1H), 3.51 (s, 4H), 3.29-3.23 (m, 2H), 1.61 (dt, J = 13.6, 6.8 Hz, 1H), 1.57 (s, 6H), 1.41 (q, J = 7.0 Hz, 2H), 0.90 (d, J = 6.6 Hz, 6H). [M + H]$^+$ = 452.3 |
| 45 | $^1$H NMR (400 MHz, $d_6$-DMSO) δ 9.33 (s, 1H), 8.13 (s, 2H), 8.05 (s, 1H), 7.92 (d, J = 8.2 Hz, 1H), 7.42 (d, J = 7.4 Hz, 1H), 7.29 (dd, J = 8.1, 3.9 Hz, 2H), 6.85 (d, J = 7.7 Hz, 1H), 6.04 (s, 1H), 3.67 (s, 4H), 3.59-3.50 (m, 6H), 3.21 (d, J = 5.1 Hz, 2H), 1.56 (d, J = 10.1 Hz, 6H). |

TABLE II-continued

| No | Characterizations |
|---|---|
| | $^{13}C$ NMR (151 MHz, $d_6$-DMSO) δ 166.3, 140.3, 137.3, 135.5, 128.8, 128.6, 127.1, 118.9, 118.2, 117.9, 116.9, 72.8, 66.6, 66.4, 47.1, 41.9, 41.7, 29.9<br>$[M + H]^+$ = 486.2 |
| 46 | $^1H$ NMR (400 MHz, $d_6$-DMSO) δ 9.70 (s, 1H), 7.81 (d, J = 8.4 Hz, 1H), 7.73 (d, J = 10.6 Hz, 2H), 7.16 (dd, J = 14.6, 8.2 Hz, 2H), 6.71 (d, J = 8.1 Hz, 1H), 6.67 (s, 1H), 6.48 (d, J = 8.4 Hz, 1H), 3.91 (t, J = 6.5 Hz, 2H), 3.87-3.78 (m, 2H), 3.59 (t, J = 8.5 Hz, 2H), 2.72 (s, 3H), 1.96 (t, J = 5.3 Hz, 1H), 1.68 (t, J = 14.8 Hz, 7H), 1.33-1.09 (m, 6H), 0.98 (q, J = 5.1, 4.5 Hz, 2H), 0.88 (q, J = 10.2, 9.2 Hz, 2H), 0.58 (q, J = 5.1 Hz, 2H).<br>$^{13}C$ NMR (151 MHz, $d_6$-DMSO) δ 176.3, 170.0, 160.0, 158.4, 146.5, 144.8, 131.1, 130.2, 129.6, 128.1, 127.8, 115.8, 111.5, 107.6, 105.5, 68.1, 42.5, 37.2, 33.7, 33.3, 26.6, 26.5, 26.3, 25.9, 11.4, 7.7<br>$[M + H]^+$ = 503.1 |
| 47 | $^1H$ NMR (400 MHz, $d_6$-DMSO) δ 8.59 (s, 1H), 8.11 (s, 2H), 8.07 (s, 1H), 7.84 (dd, J = 8.3, 2.0 Hz, 1H), 7.71 (d, J = 1.9 Hz, 1H), 7.29 (t, J = 1.7 Hz, 1H), 7.18 (d, J = 8.4 Hz, 1H), 7.03-6.97 (m, 1H), 6.83 (dt, J = 11.2, 2.2 Hz, 1H), 3.52 (s, 4H), 2.00-1.88 (m, 1H), 1.34 (s, 3H), 0.99-0.89 (m, 2H), 0.75-0.68 (m, 2H), 0.63-0.54 (m, 4H).<br>$[M + H]^+$ = 436.2 |
| 48 | $^1H$ NMR (400 MHz, $d_6$-DMSO) δ 8.29 (t, J = 5.7 Hz, 1H), 8.21 (d, J = 1.8 Hz, 1H), 8.13 (s, 2H), 7.88 (dd, J = 8.2, 1.8 Hz, 1H), 7.23-7.15 (m, 3H), 7.14-7.07 (m, 2H), 6.81 (dd, J = 1.6, 1.8 Hz, 1H), 3.81 (t, J = 7.6 Hz, 1H), 3.71 (td, J = 8.2, 4.7 Hz, 1H), 3.61 (q, J = 7.7 Hz, 1H), 3.53 (s, 4H), 3.27-3.17 (m, 3H), 2.13 (dq, J = 14.7, 7.4 Hz, 1H), 2.06-1.96 (m, 1H), 1.56 (q, J = 6.9 Hz, 2H), 1.39 (s, 10H).<br>$[M + H]^+$ = 478.3 |
| 49 | $^1H$ NMR (400 MHz, $d_6$-DMSO) δ 11.33 (s, 1H), 9.43 (s, 1H), 8.22 (s, 1H), 8.05 (d, J = 8.0 Hz, 1H), 7.90 (d, J = 8.2 Hz, 1H), 7.31 (s, 1H), 7.20 (s, 3H), 7.15 (d, J = 8.2 Hz, 1H), 6.89 (s, 1H), 4.17-3.99 (m, 3H), 1.42 (s, 9H), 1.14 (d, J = 6.6 Hz, 6H).<br>$[M + H]^+$ = 436.1 |
| 50 | $^1H$ NMR (400 MHz, $d_6$-DMSO) δ 8.43 (d, J = 7.8 Hz, 1H), 8.12 (s, 2H), 7.85 (dd, J = 8.3, 1.9 Hz, 1H), 7.80 (d, J = 1.8 Hz, 1H), 7.34 (s, 1H), 7.28-7.21 (m, 1H), 7.10 (dd, J = 8.2, 1.5 Hz, 1H), 7.05 (d, J = 8.4 Hz, 1H), 6.90 (dd, J = 7.4, 1.5 Hz, 1H), 3.97 (d, J = 7.6 Hz, 1H), 3.90-3.81 (m, 2H), 3.52 (s, 4H), 3.44-3.35 (m, 2H), 1.93-1.83 (m, 1H), 1.79 (d, J = 12.5 Hz, 2H), 1.58-1.45 (m, 2H), 1.00-0.90 (m, 2H), 0.64-0.57 (m, 2H).<br>$[M + H]^+$ = 482.0 |
| 51 | $^1H$ NMR (400 MHz, $d_6$-DMSO) δ 8.11 (s, 2H), 8.03 (d, J = 1.8 Hz, 1H), 7.80 (dd, J = 8.4, 1.9 Hz, 1H), 7.51 (s, 1H), 7.15 (d, J = 8.4 Hz, 1H), 7.08 (t, J = 8.1 Hz, 1H), 6.55 (d, J = 8.1 Hz, 1H), 6.49 (d, J = 2.1 Hz, 1H), 6.37 (dd, J = 8.1, 2.1 Hz, 1H), 3.93-3.72 (m, 5H), 3.69-3.58 (m, 2H), 3.52 (s, 4H), 3.50-3.34 (m, 2H), 3.28 (t, J = 8.6 Hz, 1H), 2.01 (s, 2H), 1.79 (d, J = 8.2 Hz, 2H), 1.64 (dd, J = 7.1, 4.7 Hz, 2H), 1.48 (s, 2H).<br>$[M + H]^+$ = 465.1 |
| 52 | $^1H$ NMR (400 MHz, $d_6$-DMSO) δ 8.19 (d, J = 1.9 Hz, 1H), 8.12 (s, 2H), 7.87 (dd, J = 8.2, 1.9 Hz, 1H), 7.12 (d, J = 8.2 Hz, 1H), 7.06-6.96 (m, 2H), 6.33 (d, J = 8.2 Hz, 1H), 6.29-6.22 (m, 2H), 3.85-3.71 (m, 5H), 3.67-3.57 (m, 2H), 3.53 (s, 4H), 3.49-3.43 (m, 1H), 3.39-3.36 (m, 1H), 1.38 (s, 9H).<br>$[M + H]^+$ = 453.1 |
| 53 | $^1H$ NMR (400 MHz, $d_6$-DMSO) δ 9.11-9.01 (m, 1 H), 8.13-8.05 (m, 2 H), 7.87-7.77 (m, 2 H), 7.74-7.70 (m, 1 H), 7.56-7.49 (m, 1 H), 7.36-7.27 (m, 2 H), 7.26-7.19 (m, 1 H), 7.15-7.06 (m, 1 H), 3.51 (s, 4 H), 1.99-1.87 (m, 1 H), 1.34-1.25 (m, 2 H), 1.16-1.08 (m, 2 H), 1.00-0.89 (m, 2 H), 0.62-0.52 (m, 2 H).<br>$[M + H]^+$ = 472.1 |
| 54 | $^1H$ NMR (400 MHz, $d_6$-DMSO) δ 9.66 (s, 1H), 8.33 (d, J = 8.0 Hz, 1H), 8.19 (s, 1H), 8.12 (s, 2H), 7.87 (d, J = 6.3 Hz, 1H), 7.66 (d, J = 6.6 Hz, 1H), 7.23 (d, J = 8.3 Hz, 2H), 6.92 (d, J = 8.3 Hz, 1H), 6.75 (t, J = 7.3 Hz, 1H), 4.18-4.05 (m, 1H), 3.54 (s, 4H), 1.41 (s, 9H), 1.18 (d, J = 6.6 Hz, 6H).<br>$^{13}C$ NMR (151 MHz, $d_6$-DMSO) δ 168.6, 146.0, 142.4, 141.9, 132.2, 129.2, 128.2, 127.7, 124.1, 118.6, 117.5, 114.7, 41.8, 41.2, 34.9, 30.4, 22.7<br>$[M + H]^+$ = 422.0 |
| 55 | $^1H$ NMR (400 MHz, $d_6$-DMSO) δ 8.46 (s, 1H), 8.22 (s, 1H), 8.15 (s, 2H), 8.08 (d, J = 5.2 Hz, 1H), 8.03 (s, 1H), 7.90 (d, J = 8.1 Hz, 1H), 7.17 (d, J = 7.9 Hz, 1H), 6.95 (d, J = 5.8 Hz, 1H), 6.90 (s, 1H), 3.54 (s, 4H), 3.23 (d, J = 8.1 Hz, 2H), 1.58 (d, J = 6.7 Hz, 1H), 1.37 (s, 11H), 0.89 (d, J = 6.6 Hz, 6H).<br>$[M + H]^+$ = 451.1 |
| 56 | $^1H$ NMR (400 MHz, $d_6$-DMSO) δ 9.64 (s, 1H), 8.57 (s, 1H), 8.17 (s, 3H), 7.84 (s, 1H), 7.67 (d, J = 7.8 Hz, 1H), 7.26 (s, 2H), 6.78 (s, 2H), 3.56 (s, 4H), 3.12-3.07 (m, 2H), 1.90-1.81 (m, 1H), 1.41 (s, 9H), 0.91 (d, J = 6.7 Hz, 6H).<br>$[M + H]^+$ = 436.0 |
| 57 | $[M + H]^+$ = 435.3 |
| 58 | $^1H$ NMR (500 MHz, $d_6$-DMSO) δ 8.32 (t, J = 5.6 Hz, 1H), 8.08 (s, 2H), 7.78 (s, 2H), 7.72 (d, J = 1.9 Hz, 1H), 7.53 (s, 1H), 7.30 (d, J = 5.0 Hz, 2H), 7.22-7.15 (m, 1H), 7.11 (d, J = 8.4 Hz, 1H), 3.82 (dd, J = 11.4, 2.8 Hz, 2H), 3.51 (s, 4H), 3.30-3.21 (m, 4H), 1.94 (ddd, J = 13.7, 8.4, 5.4 Hz, 1H), 1.60 (d, J = 13.0 Hz, 2H), 1.45 (q, J = 6.9 Hz, 3H), 1.15 (qd, J = 12.0, 4.4 Hz, 2H), 0.98-0.90 (m, 2H), 0.61-0.54 (m, 2H).<br>$[M + H]^+$ = 476.1 |
| 59 | $^1H$ NMR (400 MHz, $d_6$-DMSO) δ 8.11 (d, J = 11.1 Hz, 3H), 8.05 (s, 1H), 7.84 (d, J = 9.8 Hz, 1H), 7.81 (s, 1H), 7.43 (s, 1H), 7.28 (s, 2H), 7.14 (d, J = 8.4 Hz, 1H), 7.07 (s, 1H), 4.11-3.99 (m, 2H), 3.96 (d, J = 4.6 Hz, 1H), 3.80-3.65 (m, 2H), 3.59-3.54 (m, 1H), 3.53 (s, 4H), 2.33 (s, 1H), 1.89 (d, J = 7.4 Hz, 1H), 1.15 (d, J = 6.6 Hz, 6H).<br>$[M + H]^+$ = 436.1 |

TABLE II-continued

| No | Characterizations |
|---|---|
| 60 | $[M + H]^+$ = 457.3 |
| 61 | $^1$H NMR (400 MHz, $d_6$-DMSO) δ 9.45 (s, 1H), 8.16 (d, J = 7.8 Hz, 1H), 7.92 (s, 2H), 7.81 (s, 1H), 7.62 (s, 1H), 7.39 (d, J = 7.8 Hz, 1H), 7.34 (t, J = 7.8 Hz, 1H), 7.27 (d, J = 8.1 Hz, 1H), 7.15 (d, J = 8.5 Hz, 1H), 4.12 (s, 2H), 4.11-4.04 (m, 1H), 3.06 (s, 3H), 1.98 (s, 1H), 1.16 (d, J = 6.6 Hz, 6H), 1.02-0.94 (m, 2H), 0.62 (q, J = 5.6 Hz, 2H). $[M + H]^+$ = 434.0 |
| 62 | $^1$H NMR (400 MHz, $d_6$-DMSO) δ 9.91 (s, 1H), 8.52 (s, 1H), 8.10 (s, 2H), 7.83 (d, J = 10.4 Hz, 2H), 7.63 (d, J = 7.5 Hz, 1H), 7.41-7.32 (m, 2H), 7.29 (d, J = 8.3 Hz, 1H), 6.93-6.86 (m, 1H), 3.52 (s, 4H), 3.28 (d, J = 6.7 Hz, 2H), 1.81 (s, 1H), 1.67-1.59 (m, 1H), 1.43 (q, J = 7.0 Hz, 2H), 1.01 (d, J = 8.3 Hz, 2H), 0.90 (d, J = 6.6 Hz, 6H), 0.57 (d, J = 3.7 Hz, 2H). $[M + H]^+$ = 434.0 |
| 63 | $^1$H NMR (400 MHz, $d_6$-DMSO) δ 9.66 (s, 1H), 8.13 (s, 2H), 8.03 (s, 1H), 7.84 (d, J = 9.8 Hz, 1H), 7.66 (s, 1H), 7.33 (s, 1H), 7.15 (d, J = 8.4 Hz, 1H), 7.10 (t, J = 8.1 Hz, 1H), 7.03 (d, J = 8.0 Hz, 1H), 6.62 (d, J = 7.2 Hz, 1H), 4.02 (s, 1H), 3.94 (dd, J = 8.4, 4.5 Hz, 1H), 3.76 (q, J = 7.8 Hz, 1H), 3.72-3.65 (m, 1H), 3.58-3.54 (m, 1H), 3.52 (s, 4H), 2.59-2.52 (m, 1H), 2.31 (dd, J = 11.8, 4.5 Hz, 1H), 1.86 (dd, J = 12.2, 7.9 Hz, 1H), 1.07 (d, J = 6.8 Hz, 6H). $[M + H]^+$ = 436.0 |
| 64 | $^1$H NMR (300 MHz, $d_6$-DMSO) δ 9.22 (s, 1H), 8.12 (s, 2H), 7.77-7.71 (m, 2H), 7.27-7.15 (m, 3H), 7.05 (d, J = 7.0 Hz, 1H), 6.56 (d, J = 9.0 Hz, 1H), 3.52 (s, 4H), 2.17 (s, 3H), 1.94-1.82 (m, 1H), 1.56 (dd, J = 8.2, 5.4 Hz, 2H), 1.28 (dd, J = 8.2, 5.4 Hz, 2H), 1.01-0.91 (q, J = 5.7 Hz, 2H), 0.59 (q, J = 5.7 Hz, 2H). $[M + H]^+$ = 443.3 |
| 65 | $^1$H NMR (400 MHz, $d_6$-DMSO) δ 8.40 (d, J = 7.8 Hz, 1H), 8.31 (s, 1H), 8.13 (s, 2H), 7.86 (dd, J = 8.3, 2.0 Hz, 1H), 7.77-7.66 (m, 2H), 7.58 (s, 1H), 7.32 (t, J = 1.9 Hz, 1H), 7.20 (d, J = 8.4 Hz, 1H), 4.10 (dq, J = 13.5, 6.7 Hz, 1H), 3.54 (s, 4H), 1.93 (m, 1H), 1.18 (d, J = 6.6 Hz, 6H), 1.00-0.88 (m, 2H), 0.66-0.58 (m, 2H). $[M + H]^+$ = 474.2 |
| 66 | $^1$H NMR (400 MHz, $d_6$-DMSO) δ 8.13-8.03 (m, 3H), 7.82-7.68 (m, 3H), 7.26-7.21 (m, 1H), 7.20-7.11 (m, 2H), 7.05 (d, J = 8.4 Hz, 1H), 4.09-3.99 (m, 1H), 3.51 (s, 4H), 1.96-1.87 (m, 1H), 1.14 (d, J = 6.6 Hz, 6H), 0.99-0.91 (m, 2H), 0.62-0.54 (m, 2H). $[M + H]^+$ = 424.1 |
| 67 | $^1$H NMR (400 MHz, $d_6$-DMSO) δ 8.79 (s, 1H), 8.08 (s, 2H), 8.02 (d, J = 1.9 Hz, 1H), 7.87 (dd, J = 8.5, 1.8 Hz, 1H), 7.24 (d, J = 8.4 Hz, 1H), 7.15 (t, J = 8.1 Hz, 1H), 6.63 (d, J = 8.1 Hz, 1H), 6.59 (d, J = 2.2 Hz, 1H), 6.47 (dd, J = 8.2, 2.0 Hz, 1H), 5.86 (s, 1H), 3.92 (d, J = 6.5 Hz, 2H), 3.83 (dd, J = 10.8, 3.0 Hz, 2H), 3.52 (s, 4H), 3.30-3.22 (m, 2H), 1.71 (dt, J = 14.5, 6.6 Hz, 2H), 1.60 (s, 1H), 1.56 (s, 7H), 1.50 (s, 1H), 1.37-1.31 (m, 2H), 1.20-1.07 (m, 2H). $[M + H]^+$ = 481.1 |
| 68 | $^1$H NMR (300 MHz, $CDCl_3$) δ 8.01 (s, 1H), 7.93 (d, J = 9.5 Hz, 1H), 7.67 (s, 1H), 7.53 (d, J = 8.4 Hz, 1H), 7.23 (d, J = 8.0 Hz, 1H), 7.18 (d, J = 7.5 Hz, 1H), 6.67 (d, J = 8.5 Hz, 1H), 6.31 (s, 1H), 5.00 (d, J = 6.0 Hz, 2H), 4.61 (d, J = 6.1 Hz, 2H), 3.72 (s, 4H), 2.14 (s, 3H), 1.82-1.73 (m, 1H), 1.71 (s, 3H), 1.04-0.95 (m, 2H), 0.81-0.74 (m, 2H). $[M + H]^+$ = 448.3 |
| 69 | $^1$H NMR (400 MHz, $d_6$-DMSO) δ 8.79 (s, 1H), 8.08 (s, 2H), 8.02 (d, J = 1.9 Hz, 1H), 7.87 (dd, J = 8.5, 1.8 Hz, 1H), 7.24 (d, J = 8.4 Hz, 1H), 7.15 (t, J = 8.1 Hz, 1H), 6.63 (d, J = 8.1 Hz, 1H), 6.59 (d, J = 2.2 Hz, 1H), 6.47 (dd, J = 8.2, 2.0 Hz, 1H), 5.86 (s, 1H), 3.92 (d, J = 6.5 Hz, 2H), 3.83 (dd, J = 10.8, 3.0 Hz, 2H), 3.52 (s, 4H), 3.30-3.22 (m, 2H), 1.71 (dt, J = 14.5, 6.6 Hz, 2H), 1.60 (s, 1H), 1.56 (s, 7H), 1.50 (s, 1H), 1.37-1.31 (m, 2H), 1.20-1.07 (m, 2H). $[M + H]^+$ = 450.0 |
| 70 | $^1$H NMR (400 MHz, $d_6$-DMSO) δ 9.89 (s, 1H), 8.35 (d, J = 7.7 Hz, 1H), 8.10 (s, 2H), 7.84 (d, J = 8.7 Hz, 2H), 7.64 (d, J = 7.4 Hz, 1H), 7.42-7.33 (m, 2H), 7.29 (d, J = 8.2 Hz, 1H), 6.93-6.86 (m, 1H), 4.14-4.04 (m, 1H), 3.52 (s, 4H), 1.84-1.76 (m, 1H), 1.17 (d, J = 6.6 Hz, 6H), 1.02 (dd, J = 8.3, 1.9 Hz, 2H), 0.57 (d, J = 3.8 Hz, 2H). $[M + H]^+$ = 406.0 |
| 71 | $^1$H NMR (400 MHz, $d_6$-DMSO) δ 8.17 (d, J = 2.0 Hz, 1H), 8.03 (d, J = 7.8 Hz, 1H), 7.84 (dd, J = 8.1, 1.9 Hz, 1H), 7.25-7.06 (m, 5H), 6.84-6.74 (m, 1H), 4.14-3.99 (m, 1H), 3.58 (s, 4H), 2.81 (s, 6H), 1.40 (s, 9H), 1.16 (d, J = 6.6 Hz, 6H). $[M + H]^+$ = 450.3 |
| 72 | $^1$H NMR (400 MHz, $d_6$-DMSO) δ 9.76 (s, 1H), 8.11 (s, 2H), 8.07 (s, 1H), 7.87 (s, 1H), 7.84 (d, J = 8.9 Hz, 1H), 7.54 (s, 1H), 7.21 (d, J = 4.4 Hz, 3H), 6.84 (s, 1H), 3.53 (s, 4H), 2.62-2.53 (m, 1H), 1.08 (d, J = 6.8 Hz, 6H). $[M + H]^+$ = 400.0 |
| 73 | $^1$H NMR (400 MHz, $d_6$-DMSO) δ 8.18-8.06 (m, 3H), 7.84 (dd, J = 8.3, 2.0 Hz, 1H), 7.70 (d, J = 1.9 Hz, 1H), 7.20 (d, J = 8.3 Hz, 1H), 6.83-6.72 (m, 2H), 6.65-6.53 (m, 1H), 3.70-3.33 (m, 12H), 2.01-1.86 (m, 1H), 1.02-0.91 (m, 2H), 0.66-0.55 (m, 2H). $[M + H]^+$ = 452.2 |
| 74 | $^1$H NMR (400 MHz, $d_6$-DMSO) δ 8.48 (t, J = 5.7 Hz, 1H), 8.22 (d, J = 1.9 Hz, 1H), 8.15 (s, 2H), 8.08 (d, J = 5.2 Hz, 1H), 8.04 (s, 1H), 7.90 (dd, J = 8.1, 1.8 Hz, 1H), 7.17 (d, J = 8.1 Hz, 1H), 6.95 (d, J = 5.3 Hz, 1H), 6.89 (s, 1H), 3.82 (dd, J = 11.1, 3.0 Hz, 2H), 3.54 (s, 4H), 3.29-3.20 (m, 4H), 1.59 (d, J = 13.2 Hz, 2H), 1.54-1.40 (m, 3H), 1.37 (s, 8H), 1.15 (qd, J = 12.4, 4.3 Hz, 2H). $[M + H]^+$ = 493.1 |
| 75 | $^1$H NMR (400 MHz, $d_6$-DMSO) δ 8.10 (s, 2H), 7.86 (s, 1H), 7.79 (d, J = 8.4 Hz, 1H), 7.70 (s, 1H), 7.31 (t, J = 7.9 Hz, 1H), 7.16 (d, J = 8.4 Hz, 1H), 7.05 (d, J = 8.5 Hz, 1H), 6.90 (s, 1H), 6.76 (d, J = 8.1 Hz, 1H), 3.52 (s, 4H), 3.12 (s, 3H), 2.58 (s, 1H), 2.02-1.90 (m, 1H), 0.94 (d, J = 6.6 Hz, 8H), 0.58 (q, J = 5.0, 4.5 Hz, 2H). $[M + H]^+$ = 420.0 |
| 76 | $^1$H NMR (400 MHz, $d_6$-DMSO) δ 8.08 (s, 2H), 7.89 (d, J = 7.5 Hz, 1H), 7.76 (dd, J = 1.9, 8.4 Hz, 1H), 7.70 (d, J = 1.8 Hz, 1H), 7.59 (s, 1H), 7.21-7.13 (m, 1H), 7.09 (d, J = 8.5 Hz, 1H), 7.04-6.99 (m, 1H), 6.97-6.90 (m, 1H), 6.76 (d, J = 7.4 Hz, 1H), 3.86-3.74 (m, 1H), 3.50 (s, 4H), 3.28 |

TABLE II-continued

| No | Characterizations |
|---|---|
| | (s, 2H), 2.00-1.87 (m, 1H), 1.04 (d, J = 6.6 Hz, 6H), 0.97-0.90 (m, 2H), 0.60-0.51 (m, 2H). $[M + H]^+$ = 420.2 |
| 77 | $^1$H NMR (400 MHz, $d_6$-DMSO) δ 8.19 (d, J = 7.7 Hz, 1H), 8.15-8.07 (m, 3H), 7.83 (dd, J = 2.0, 8.4 Hz, 1H), 7.71 (d, J = 2.0 Hz, 1H), 7.33 (t, J = 1.7 Hz, 1H), 7.19 (d, J = 8.4 Hz, 1H), 7.09-7.01 (m, 1H), 6.84 (td, J = 2.2, 11.3 Hz, 1H), 4.12-3.96 (m, 1H), 3.52 (s, 4H), 2.00-1.89 (m, 1H), 1.15 (d, J = 6.6 Hz, 6H), 1.00-0.89 (m, 2H), 0.62-0.56 (m, 2H). $[M + H]^+$ = 424.1 |
| 78 | $^1$H NMR (400 MHz, $d_6$-DMSO) δ 9.11 (s, 1H), 8.09 (s, 2H), 8.05 (d, J = 1.9 Hz, 1H), 7.87 (dd, J = 8.5, 1.9 Hz, 1H), 7.30 (dd, J = 8.2, 1.1 Hz, 1H), 7.25 (d, J = 8.5 Hz, 1H), 7.17 (t, J = 7.8 Hz, 1H), 6.67 (dd, J = 7.5, 1.1 Hz, 1H), 5.82 (s, 1H), 3.76-3.48 (m, 10H), 3.24 (t, J = 5.5 Hz, 2H), 1.59 (d, J = 9.9 Hz, 7H), 1.00-0.88 (m, 2H), 0.69-0.61 (m, 1H), 0.36-0.29 (m, 1H). $[M + H]^+$ = 492.3 |
| 79 | $^1$H NMR (400 MHz, $d_6$-DMSO) δ 8.29 (t, J = 5.7 Hz, 1H), 8.13 (d, J = 2.3 Hz, 3H), 7.92 (dd, J = 10.4, 1.4 Hz, 2H), 7.73 (t, J = 1.7 Hz, 1H), 7.66 (s, 1H), 7.44 (s, 1H), 7.29-7.22 (m, 3H), 7.11-7.03 (m, 1H), 6.73 (d, J = 1.1 Hz, 1H), 3.82 (dd, J = 10.9, 3.5 Hz, 2H), 3.53 (s, 4H), 3.29-3.20 (m, 4H), 1.60 (d, J = 13.5 Hz, 2H), 1.53 (s, 1H), 1.44 (q, J = 6.8 Hz, 2H), 1.15 (qd, J = 12.4, 4.5 Hz, 2H). $[M + H]^+$ = 502.2 |
| 80 | $^1$H NMR (400 MHz, $d_6$-DMSO) δ 9.86 (s, 1H), 8.58 (t, J = 5.8 Hz, 1H), 8.11 (s, 2H), 7.83 (dd, J = 10.8, 2.4 Hz, 2H), 7.68-7.63 (m, 1H), 7.38 (d, J = 6.6 Hz, 2H), 7.30 (d, J = 8.3 Hz, 1H), 6.91 (t, J = 6.3 Hz, 1H), 3.53 (s, 4H), 3.12-3.06 (m, 2H), 1.90-1.83 (m, 1H), 1.83-1.77 (m, 1H), 1.05-0.98 (m, 2H), 0.90 (d, J = 6.7 Hz, 6H), 0.56 (d, J = 3.8 Hz, 2H). $[M + H]^+$ = 420.0 |
| 81 | $^1$H NMR (400 MHz, $d_6$-DMSO) δ 11.17 (s, 1H), 8.16 (d, J = 7.8 Hz, 1H), 7.91 (d, J = 8.7 Hz, 2H), 7.77 (s, 1H), 7.62 (s, 1H), 7.43-7.30 (m, 2H), 7.27 (d, J = 7.7 Hz, 1H), 7.14 (d, J = 8.4 Hz, 1H), 4.16-4.01 (m, 3H), 3.09 (s, 3H), 1.97 (ddd, J = 13.7, 8.3, 5.4 Hz, 1H), 1.16 (d, J = 6.6 Hz, 6H), 1.03-0.94 (m, 2H), 0.61 (q, J = 5.3 Hz, 2H). $[M + H]^+$ = 434.3 |
| 82 | $^1$H NMR (400 MHz, $d_6$-DMSO) δ 8.09 (s, 2H), 7.78 (dd, J = 8.4, 2.0 Hz, 1H), 7.73 (d, J = 2.0 Hz, 1H), 7.66 (s, 1H), 7.30 (t, J = 7.8 Hz, 1H), 7.23 (s, 1H), 7.11 (d, J = 8.4 Hz, 1H), 7.04 (td, J = 7.6, 1.9 Hz, 2H), 4.76 (d, J = 5.9 Hz, 2H), 4.66 (d, J = 5.9 Hz, 2H), 3.52 (s, 4H), 2.83-2.65 (m, 1H), 2.44 (t, J = 6.2 Hz, 1H), 1.98 (m, 1H), 1.02-0.93 (m, 2H), 0.86 (d, J = 6.3 Hz, 6H), 0.65-0.55 (m, 2H). $[M + H]^+$ = 434.2 |
| 83 | $^1$H NMR (400 MHz, $d_6$-DMSO) δ 8.26-8.17 (m, 1H), 8.08 (s, 2H), 7.76 (dd, J = 1.9, 8.5 Hz, 1H), 7.71 (d, J = 1.7 Hz, 1H), 7.62 (s, 1H), 7.19 (t, J = 7.8 Hz, 1H), 7.10 (d, J = 8.4 Hz, 1H), 6.99-6.93 (m, 2H), 6.78-6.72 (m, 1H), 4.20 (d, J = 5.8 Hz, 2H), 3.51 (s, 4H), 2.45-2.37 (m, 1H), 2.00-1.89 (m, 1H), 1.02 (d, J = 6.8 Hz, 6H), 0.98-0.92 (m, 2H), 0.60-0.52 (m, 2H). $[M + H]^+$ = 420.2 |
| 84 | $^1$H NMR (400 MHz, $d_6$-DMSO) δ 9.02 (s, 1H), 8.10 (s, 3H), 7.92 (d, J = 8.5 Hz, 1H), 7.50 (d, J = 12.5 Hz, 2H), 7.38 (d, J = 8.0 Hz, 1H), 7.33 (d, J = 7.0 Hz, 1H), 7.28 (d, J = 8.2 Hz, 1H), 5.93 (s, 1H), 3.78 (d, J = 11.6 Hz, 2H), 3.53 (s, 4H), 3.29-3.19 (m, 4H), 1.56 (s, 9H), 1.46 (d, J = 12.2 Hz, 2H), 1.24 (s, 2H), 1.06 (d, J = 10.5 Hz, 2H). $[M + H]^+$ = 529.0 |
| 85 | $^1$H NMR (400 MHz, $d_6$-DMSO) δ 8.79 (s, 1H), 8.08 (s, 2H), 8.02 (d, J = 1.9 Hz, 1H), 7.87 (dd, J = 8.4, 1.9 Hz, 1H), 7.25 (d, J = 8.5 Hz, 1H), 7.15 (t, J = 8.1 Hz, 1H), 6.67-6.58 (m, 2H), 6.48 (dd, J = 8.1, 2.1 Hz, 1H), 5.85 (s, 1H), 3.98 (t, J = 6.3 Hz, 2H), 3.83 (dd, J = 11.1, 3.0 Hz, 2H), 3.52 (s, 4H), 3.30-3.23 (m, 2H), 1.69 (s, 1H), 1.67-1.62 (m, 3H), 1.60 (s, 1H), 1.56 (s, 6H), 1.26-1.16 (m, 2H). $[M + H]^+$ = 467.1 |
| 86 | $^1$H NMR (400 MHz, $d_6$-DMSO) δ 8.81 (s, 1H), 8.29 (s, 1H), 8.13 (s, 2H), 7.86 (dd, J = 8.3, 2.0 Hz, 1H), 7.73 (d, J = 2.0 Hz, 1H), 7.68 (t, J = 1.8 Hz, 1H), 7.54 (s, 1H), 7.31 (t, J = 2.0 Hz, 1H), 7.19 (d, J = 8.3 Hz, 1H), 3.54 (s, 4H), 1.99-1.86 (m, 1H), 1.37 (s, 3H), 0.99-0.88 (m, 2H), 0.74 (q, J = 4.6, 4.1 Hz, 2H), 0.62 (m, 4H). $[M + H]^+$ = 486.2 |
| 87 | $^1$H NMR (400 MHz, $d_6$-DMSO) δ 8.15 (t, J = 5.5 Hz, 3H), 7.82 (d, J = 7.8 Hz, 1H), 7.68 (s, 1H), 7.65 (dd, J = 7.6, 1.7 Hz, 1H), 7.43 (t, J = 7.1 Hz, 1H), 7.21 (t, J = 7.3 Hz, 1H), 6.84 (d, J = 7.1 Hz, 1H), 6.81 (d, J = 8.5 Hz, 1H), 3.55 (br s, 4H), 3.22 (q, J = 6.7 Hz, 2H), 2.15 (br s, 1H), 1.52 (dp, J = 13.3, 6.7 Hz, 1H), 1.31 (q, J = 7.0 Hz, 2H), 0.97-0.86 (m, 2H), 0.82 (d, J = 6.6 Hz, 6H), 0.72-0.61 (m, 2H). $[M + H]^+$ = 435.2 |
| 88 | $^1$H NMR (400 MHz, $d_6$-DMSO) δ 8.81 (s, 1H), 8.10 (s, 2H), 8.02 (d, J = 1.9 Hz, 1H), 7.87 (dd, J = 8.5, 1.9 Hz, 1H), 7.25 (d, J = 8.5 Hz, 1H), 7.16 (t, J = 8.1 Hz, 1H), 6.65 (dd, J = 7.9, 1.6 Hz, 1H), 6.61 (s, 1H), 6.48 (dd, J = 8.1, 2.0 Hz, 1H), 5.86 (s, 1H), 4.00 (t, J = 6.4 Hz, 2H), 3.72 (td, J = 11.7, 2.5 Hz, 2H), 3.68-3.61 (m, 2H), 3.60-3.55 (m, 1H), 3.52 (s, 4H), 3.45 (td, J = 11.0, 2.6 Hz, 1H), 3.22 (dd, J = 11.3, 9.9 Hz, 1H), 1.75 (pt, J = 13.9, 6.4 Hz, 2H), 1.56 (s, 6H). $[M + H]^+$ = 469.1 |
| 89 | $^1$H NMR (300 MHz, $CDCl_3$) δ 8.00 (s, 1H), 7.93 (dd, J = 8.6, 1.8 Hz, 1H), 7.16 (d, J = 5.3 Hz, 2H), 7.13-7.07 (m, 1H), 6.86 (d, J = 8.5 Hz, 1H), 6.29 (s, 1H), 4.31-4.18 (m, 4H), 3.71 (s, 4H), 2.22 (s, 3H), 1.81-1.72 (m, 1H), 1.38 (td, J = 7.1, 0.9 Hz, 7H), 1.04-0.94 (m, 2H), 0.81-0.74 (m, 2H). $[M + H]^+$ = 487.3 |
| 90 | $^1$H NMR (300 MHz, $CDCl_3$) δ 7.96 (d, J = 8.4 Hz, 3H), 7.78 (d, J = 7.7 Hz, 1H), 7.43 (t, J = 7.9 Hz, 1H), 7.33-7.26 (m, 2H), 6.50 (s, 1H), 5.55 (t, J = 7.2 Hz, 1H), 5.23 (d, J = 7.2 Hz, 2H), 3.65 (s, 4H), 1.86 (s, 3H), 1.81 (s, 3H), 1.81-1.74 (m, 1H), 1.00 (q, J = 5.5 Hz, 2H), 0.77 (q, J = 5.5 Hz, 2H). $[M + H]^+$ = 457.3 |

TABLE II-continued

| No | Characterizations |
|---|---|
| 91 | $^1H$ NMR (400 MHz, $d_6$-DMSO) δ 8.15 (s, 2H), 8.05 (d, J = 7.8 Hz, 1H), 7.87 (s, 1H), 7.62 (dd, J = 11.4, 1.8 Hz, 1H), 7.49 (d, J = 1.8 Hz, 1H), 7.22-7.12 (m, 3H), 6.73 (d, J = 7.1 Hz, 1H), 4.11-4.00 (m, 1H), 3.54 (s, 4H), 2.03-1.93 (m, 1H), 1.14 (d, J = 6.6 Hz, 6H), 0.95-0.88 (m, 2H), 0.65-0.58 (m, 2H).<br>$[M + H]^+$ = 424.2 |
| 92 | $^1H$ NMR (400 MHz, $d_6$-DMSO) δ 8.06 (s, 2H), 7.85 (d, J = 8.0 Hz, 1H), 7.82-7.75 (m, 2H), 7.73 (t, J = 1.7 Hz, 1H), 7.67 (dd, J = 1.6, 0.8 Hz, 1H), 7.42-7.30 (m, 2H), 7.03 (d, J = 8.3 Hz, 1H), 6.98 (dd, J = 7.3, 1.4 Hz, 1H), 6.75 (s, 1H), 6.52 (dd, J = 1.8, 0.8 Hz, 1H), 3.91-3.78 (m, 1H), 3.50 (s, 4H), 1.67-1.58 (m, 1H), 0.94 (d, J = 6.6 Hz, 6H), 0.80-0.70 (m, 2H), 0.42-0.32 (m, 2H).<br>$[M + H]^+$ = 472.2 |
| 93 | $^1H$ NMR (400 MHz, $d_6$-DMSO) 8 9.36 (s, 1H), 8.18 (d, J = 2.1 Hz, 1H), 8.13 (s, 2H), 7.88 (dd, J = 8.4, 2.0 Hz, 1H), 7.80 (s, 1H), 7.14-7.04 (m, 2H), 6.77 (d, J = 9.6 Hz, 1H), 6.72 (d, J = 8.4 Hz, 1H), 3.53 (s, 4H), 2.32 (t, J = 7.5 Hz, 2H), 1.50 (dd, J = 12.9, 6.5 Hz, 1H), 1.47-1.42 (m, 2H), 1.41 (s, 9H), 0.84 (d, J = 6.4 Hz, 6H).<br>$[M + H]^+$ = 451.1 |
| 94 | $^1H$ NMR (400 MHz, $d_6$-DMSO) δ 8.59 (d, J = 7.8 Hz, 1H), 8.11 (s, 2H), 7.85 (dd, J = 8.3, 1.9 Hz, 1H), 7.79 (d, J = 1.8 Hz, 1H), 7.35 (s, 1H), 7.30-7.21 (m, 1H), 7.10 (dd, J = 8.2, 1.5 Hz, 1H), 7.05 (d, J = 8.3 Hz, 1H), 6.92 (dd, J = 7.4, 1.5 Hz, 1H), 4.27-4.04 (m, 1H), 3.52 (s, 4H), 3.30-3.22 (m, 2H), 3.14 (d, J = 14.5 Hz, 2H), 2.16 (s, 2H), 2.03 (d, J = 10.3 Hz, 2H), 1.88 (ddd, J = 13.7, 8.2, 5.4 Hz, 1H), 0.99-0.90 (m, 2H), 0.65-0.56 (m, 2H).<br>$[M + H]^+$ = 529.9 |
| 95 | $^1H$ NMR (400 MHz, $d_6$-DMSO) δ 8.41 (d, J = 6.5 Hz, 1H), 8.10 (s, 2H), 8.05 (d, J = 1.9 Hz, 1H), 7.80 (dd, J = 8.4, 1.9 Hz, 1H), 7.68 (s, 1H), 7.47-7.42 (m, 1H), 7.31-7.21 (m, 2H), 7.12 (d, J = 8.4 Hz, 1H), 7.10-7.04 (m, 1H), 4.41 (dd, J = 11.7, 7.1 Hz, 1H), 3.89-3.78 (m, 2H), 3.70 (td, J = 8.0, 5.9 Hz, 1H), 3.56 (dd, J = 8.8, 4.5 Hz, 1H), 3.52 (s, 4H), 3.30-3.22 (m, 1H), 2.18-2.08 (m, 1H), 2.02 (s, 2H), 1.96-1.85 (m, 1H), 1.79 (d, J = 8.1 Hz, 2H), 1.63 (dd, J = 7.1, 4.6 Hz, 2H), 1.55-1.43 (m, 2H).<br>$[M + H]^+$ = 462.2 |
| 96 | $^1H$ NMR (400 MHz, $d_6$-DMSO) δ 8.20 (d, J = 7.7 Hz, 1H), 8.10 (s, 2H), 8.05 (d, J = 1.9 Hz, 1H), 7.80 (dd, J = 8.3, 1.9 Hz, 1H), 7.69 (s, 1H), 7.44 (s, 1H), 7.26 (d, J = 5.0 Hz, 2H), 7.12 (d, J = 8.4 Hz, 1H), 7.07 (d, J = 2.4 Hz, 1H), 3.97 (dd, J = 11.4, 3.8 Hz, 1H), 3.87 (d, J = 11.7 Hz, 2H), 3.52 (s, 4H), 3.43-3.33 (m, 2H), 3.31-3.22 (m, 1H), 2.02 (s, 2H), 1.83-1.69 (m, 4H), 1.67-1.41 (m, 6H).<br>$[M + H]^+$ = 476.0 |
| 97 | $^1H$ NMR (400 MHz, $d_6$-DMSO) δ 8.13 (s, 2H), 8.07 (dd, J = 6.0, 1.9 Hz, 1H), 7.95 (dd, J = 8.4, 1.9 Hz, 1H), 7.88 (d, J = 26.3 Hz, 1H), 7.28 (td, J = 7.9, 2.4 Hz, 1H), 7.24-7.14 (m, 2H), 6.85 (dd, J = 7.3, 1.5 Hz, 1H), 4.94-4.83 (m, 1H), 4.09 (td, J = 12.8, 12.1, 5.8 Hz, 1H), 3.82 (q, J = 7.9 Hz, 1H), 3.66 (s, 4H), 3.55 (d, J = 11.9 Hz, 6H), 3.24-3.14 (m, 2H), 2.24 (td, J = 11.9, 7.5 Hz, 1H), 1.97 (tt, J = 14.7, 7.7 Hz, 2H), 1.85-1.69 (m, 1H).<br>$[M + H]^+$ = 497.9 |
| 98 | $^1H$ NMR (400 MHz, $d_6$-DMSO) δ 8.16 (d, J = 7.7 Hz, 1H), 8.09 (s, 2H), 7.80 (dd, J = 2.0, 8.4 Hz, 1H), 7.73 (d, J = 2.0 Hz, 1H), 7.44 (s, 1H), 7.20-7.14 (m, 1H), 7.12 (t, J = 7.7 Hz, 1H), 7.08-7.03 (m, 1H), 6.88 (d, J = 8.4 Hz, 1H), 4.05 (qd, J = 6.7, 13.9 Hz, 1H), 3.51 (s, 4H), 1.97-1.88 (m, 1H), 1.15 (d, J = 6.6 Hz, 6H), 0.97-0.91 (m, 2H), 0.61-0.55 (m, 2H).<br>$[M + H]^+$ = 424.1 |
| 99 | $^1H$ NMR (400 MHz, $d_6$-DMSO) δ 8.63 (s, 1H), 8.61 (s, 1H), 8.19 (s, 2H), 7.91 (d, J = 5.4 Hz, 1H), 7.67 (dd, J = 10.8, 1.7 Hz, 1H), 7.52 (s, 1H), 6.36 (t, J = 5.1 Hz, 1H), 3.55 (s, 4H), 2.05-1.96 (m, 1H), 1.37 (s, 3H), 0.98-0.88 (m, 2H), 0.79-0.71 (m, 2H), 0.66-0.59 (m, 4H).<br>$[M + H]^+$ = 455.1 |
| 100 | $^1H$ NMR (400 MHz, $d_6$-DMSO) δ 9.37 (s, 1H), 8.13 (s, 2H), 7.91 (s, 1H), 7.83 (dd, J = 8.4, 2.1 Hz, 1H), 7.71 (d, J = 2.0 Hz, 1H), 7.14-7.02 (m, 2H), 6.76 (dd, J = 9.0, 5.9 Hz, 2H), 3.53 (s, 4H), 2.39-2.31 (m, 2H), 2.15 (ddd, J = 13.9, 8.6, 5.4 Hz, 1H), 1.50 (dt, J = 13.0, 6.5 Hz, 1H), 1.42 (q, J = 7.1, 6.6 Hz, 2H), 0.94-0.87 (m, 2H), 0.84 (d, J = 6.4 Hz, 6H), 0.70-0.62 (m, 2H).<br>$[M + H]^+$ = 435.1 |
| 101 | $^1H$ NMR (400 MHz, $d_6$-DMSO) δ 8.64 (s, 1H), 8.60 (s, 1H), 8.31 (d, J = 2.0 Hz, 1H), 8.17 (s, 2H), 8.08 (dd, J = 8.5, 2.0 Hz, 1H), 7.29 (d, J = 4.5 Hz, 2H), 7.11 (d, J = 8.6 Hz, 1H), 6.99 (t, J = 4.5 Hz, 1H), 3.54 (s, 4H), 2.86 (s, 3H), 1.39 (s, 3H), 0.73 (s, 2H), 0.62-0.56 (m, 2H).<br>$[M + H]^+$ = 474.0 |
| 102 | $^1H$ NMR (400 MHz, $d_6$-DMSO) δ 8.63 (s, 1H), 8.58 (d, J = 2.0 Hz, 1H), 8.29 (s, 1H), 8.20 (s, 2H), 8.17 (d, J = 2.1 Hz, 1H), 7.57 (d, J = 6.6 Hz, 1H), 7.38 (t, J = 7.8 Hz, 1H), 7.18 (d, J = 8.7 Hz, 1H), 7.14-7.09 (m, 1H), 3.54 (s, 4H), 3.26 (s, 3H), 1.40 (s, 3H), 0.74 (s, 2H), 0.63-0.57 (m, 2H).<br>$[M + H]^+$ = 489.9 |
| 103 | $^1H$ NMR (400 MHz, $d_6$-DMSO) δ 8.11 (s, 2H), 7.85 (dd, J = 8.4, 1.8 Hz, 1H), 7.79 (d, J = 1.7 Hz, 1H), 7.43 (s, 1H), 7.31 (t, J = 7.9 Hz, 1H), 7.10 (d, J = 6.8 Hz, 1H), 7.06 (dd, J = 5.2, 2.2 Hz, 2H), 4.36 (s, 1H), 3.79 (s, 1H), 3.62 (s, 2H), 3.52 (s, 4H), 3.37 (d, J = 7.6 Hz, 1H), 3.27 (s, 2H), 3.09 (s, 1H), 1.89 (s, 1H), 0.94 (d, J = 8.4 Hz, 2H), 0.61 (s, 2H).<br>$[M + H]^+$ = 515.9 |
| 104 | $^1H$ NMR (400 MHz, $d_6$-DMSO) δ 8.11 (s, 2H), 7.85 (d, J = 8.6 Hz, 1H), 7.79 (s, 1H), 7.44-7.37 (m, 1H), 7.29 (t, J = 7.7 Hz, 1H), 7.12-6.73 (m, 3H), 4.38-3.65 (m, 3H), 3.52 (s, 4H), 3.40 (s, 2H), 3.29 (s, 1H), 3.11-2.99 (m, 1H), 2.34-2.24 (m, 1H), 1.88 (s, 1H), 1.05-0.57 (m, 10H).<br>$[M + H]^+$ = 510.0 |
| 105 | $^1H$ NMR (400 MHz, $d_6$-DMSO) δ 8.11 (s, 2H), 7.87-7.80 (m, 1H), 7.79 (d, J = 1.9 Hz, 1H), 7.48-7.37 (m, 1H), 7.29 (td, J = 7.8, 3.5 Hz, 1H), 7.13-6.80 (m, 3H), 4.52-3.73 (m, 2H), 3.52 (s, 4H), 3.44 (d, J = 19.8 Hz, 1H), 3.25-2.66 (m, 4H), 1.93-1.81 (m, 1H), 1.81-1.51 (m, 1H), 0.97-0.56 (m, 10H).<br>$[M + H]^+$ = 510.0 |

TABLE II-continued

| No | Characterizations |
| --- | --- |
| 106 | $^1$H NMR (400 MHz, $d_6$-DMSO) δ 8.13 (s, 2H), 8.00 (d, J = 7.9 Hz, 1H), 7.82-7.76 (m, 1H), 7.61 (s, 1H), 7.48 (d, J = 2.0 Hz, 1H), 7.12 (t, J = 7.7 Hz, 1H), 7.08-7.02 (m, 2H), 6.53-6.47 (m, 1H), 4.10-3.98 (m, 1H), 3.52 (s, 4H), 2.14 (s, 3H), 2.00-1.90 (m, 1H), 1.13 (d, J = 6.6 Hz, 6H), 0.85-0.76 (m, 2H), 0.56-0.48 (m, 2H). [M + H]$^+$ = 420.2 |
| 107 | $^1$H NMR (400 MHz, $d_6$-DMSO) δ 8.42 (s, 1H), 8.08 (s, 2H), 7.81-7.73 (m, 2H), 7.72 (d, J = 1.9 Hz, 1H), 7.50 (d, J = 1.7 Hz, 1H), 7.32-7.24 (m, 2H), 7.21-7.14 (m, 1H), 7.10 (d, J = 8.4 Hz, 1H), 3.51 (s, 4H), 1.99-1.89 (m, 1H), 1.79-1.65 (m, 1H), 1.49 (d, J = 7.0 Hz, 2H), 0.99-0.87 (m, 8H), 0.76-0.69 (m, 2H), 0.61-0.53 (m, 4H). [M + H]$^+$ = 460.2 |
| 108 | $^1$H NMR (400 MHz, $d_6$-DMSO) δ 9.54 (s, 1H), 8.08 (s, 2H), 7.79 (dd, J = 8.4, 2.0 Hz, 1H), 7.71 (d, J = 1.9 Hz, 1H), 7.62 (s, 1H), 7.53 (s, 1H), 7.18-7.11 (m, 3H), 6.82-6.76 (m, 1H), 4.36 (dd, J = 8.1, 5.5 Hz, 1H), 4.01-3.93 (m, 1H), 3.86-3.77 (m, 1H), 3.51 (s, 4H), 2.17 (dq, J = 12.1, 7.8 Hz, 1H), 2.01-1.91 (m, 2H), 1.89-1.80 (m, 2H), 0.97-0.91 (m, 2H), 0.60-0.53 (m, 2H). [M + H]$^+$ = 434.3 |
| 109 | $^1$H NMR (400 MHz, $d_6$-DMSO) δ 8.48 (t, J = 5.9 Hz, 1H), 8.11 (s, 2H), 7.85 (dd, J = 8.3, 1.9 Hz, 1H), 7.80 (d, J = 1.8 Hz, 1H), 7.34 (s, 1H), 7.25 (t, J = 7.8 Hz, 1H), 7.11 (dd, J = 8.2, 1.4 Hz, 1H), 7.04 (d, J = 8.3 Hz, 1H), 6.90 (dd, J = 7.4, 1.4 Hz, 1H), 3.97 (p, J = 6.3 Hz, 1H), 3.84-3.74 (m, 1H), 3.64 (q, J = 7.4 Hz, 1H), 3.52 (s, 4H), 3.37-3.32 (m, 1H), 3.29-3.22 (m, 1H), 2.00-1.76 (m, 4H), 1.70-1.60 (m, 1H), 0.99-0.91 (m, 2H), 0.64-0.57 (m, 2H). [M + H]$^+$ = 482.1 |
| 110 | $^1$H NMR (400 MHz, $d_6$-DMSO) δ 9.72 (d, J = 3.5 Hz, 2H), 7.81 (dd, J = 8.4, 2.0 Hz, 1H), 7.78-7.70 (m, 2H), 7.50 (s, 1H), 7.20-7.12 (m, 3H), 6.80 (dt, J = 7.0, 2.1 Hz, 1H), 3.83 (dd, J = 10.0, 7.2 Hz, 2H), 3.64-3.55 (m, 2H), 2.73 (s, 3H), 2.63-2.53 (m, 1H), 1.98 (ddd, J = 13.7, 8.4, 5.4 Hz, 1H), 1.09 (d, J = 6.8 Hz, 6H), 1.02-0.92 (m, 2H), 0.62-0.53 (m, 2H). [M + H]$^+$ = 448.3 |
| 111 | $^1$H NMR (400 MHz, $d_6$-DMSO) δ 8.30 (s, 1H), 8.08 (s, 2H), 7.78 (dd, J = 8.3, 1.9 Hz, 1H), 7.76-7.69 (m, 2H), 7.48 (d, J = 2.0 Hz, 1H), 7.27 (d, J = 5.3 Hz, 2H), 7.20-7.13 (m, 1H), 7.11 (d, J = 8.4 Hz, 1H), 3.51 (s, 4H), 1.98-1.88 (m, 1H), 0.98-0.85 (m, 11H), 0.85-0.79 (m, 2H), 0.69-0.62 (m, 2H), 0.61-0.53 (m, 2H). [M + H]$^+$ = 460.2 |
| 112 | $^1$H NMR (400 MHz, $d_6$-DMSO) δ 8.31 (d, J = 11.5 Hz, 2H), 8.11 (s, 2H), 7.85 (dd, J = 8.3, 2.0 Hz, 1H), 7.73-7.69 (m, 2H), 7.64 (t, J = 1.4 Hz, 1H), 7.33 (dd, J = 2.4, 1.4 Hz, 1H), 7.19 (d, J = 8.3 Hz, 1H), 4.06 (dq, J = 13.5, 6.8 Hz, 1H), 3.52 (s, 4H), 1.97-1.86 (m, 1H), 1.15 (d, J = 6.6 Hz, 6H), 0.97-0.87 (m, 2H), 0.64-0.54 (m, 2H). [M + H]$^+$ = 431.2 |
| 113 | $^1$H NMR (400 MHz, $d_6$-DMSO) δ 9.69 (s, 1H), 8.79 (s, 1H), 7.86 (dd, J = 8.4, 1.9 Hz, 1H), 7.73 (d, J = 1.9 Hz, 1H), 7.65 (s, 1H), 7.46 (s, 1H), 7.19-7.08 (m, 3H), 6.77 (dt, J = 7.5, 1.8 Hz, 1H), 6.28 (s, 1H), 3.86 (td, J = 15.9, 3.7 Hz, 2H), 3.66-3.49 (m, J = 5.1 Hz, 4H), 2.57 (p, J = 6.8 Hz, 1H), 2.02-1.91 (m, 1H), 1.08 (d, J = 6.8 Hz, 6H), 1.00-0.90 (m, 2H), 0.62-0.53 (m, 2H). [M + H]$^+$ = 470.3 |
| 114 | $^1$H NMR (400 MHz, $d_6$-DMSO) δ 9.19 (s, 1H), 8.10 (s, 2H), 7.84 (dd, J = 8.4, 1.9 Hz, 1H), 7.78 (d, J = 1.9 Hz, 1H), 7.36 (s, 1H), 7.24 (t, J = 7.8 Hz, 1H), 7.08 (dd, J = 8.2, 1.5 Hz, 1H), 7.04 (d, J = 8.3 Hz, 1H), 6.88 (dd, J = 7.4, 1.5 Hz, 1H), 3.51 (s, 4H), 1.91-1.81 (m, 1H), 1.35-1.28 (m, 2H), 1.14 (s, 2H), 0.97-0.88 (m, 2H), 0.64-0.54 (m, 2H). [M + H]$^+$ = 506.2 |
| 115 | $^1$H NMR (400 MHz, $d_6$-DMSO) δ 8.12 (s, 2H), 7.89-7.79 (m, 2H), 7.55 (t, J = 7.9 Hz, 1H), 7.25 (s, 1H), 7.18 (d, J = 8.3 Hz, 1H), 7.01 (d, J = 8.3 Hz, 1H), 6.93 (d, J = 7.4 Hz, 1H), 3.73-3.45 (m, 10H), 3.21 (ddd, J = 13.1, 6.1, 3.2 Hz, 1H), 3.11 (ddd, J = 13.3, 6.5, 3.3 Hz, 1H), 1.84 (ddd, J = 13.7, 8.3, 5.4 Hz, 1H), 0.95-0.87 (m, 2H), 0.61-0.52 (m, 2H). [M + H]$^+$ = 502.4 |
| 116 | $^1$H NMR (400 MHz, $d_6$-DMSO) δ 8.49 (d, J = 4.1 Hz, 1H), 8.13 (s, 2H), 7.81 (s, 2H), 7.52 (t, J = 7.9 Hz, 1H), 7.21 (d, J = 8.0 Hz, 2H), 6.94 (t, J = 6.8 Hz, 2H), 3.53 (s, 4H), 2.76 (tq, J = 7.5, 3.8 Hz, 1H), 1.83 (ddd, J = 13.6, 8.5, 5.5 Hz, 1H), 0.97-0.87 (m, 2H), 0.68 (td, J = 7.0, 4.8 Hz, 2H), 0.59-0.53 (m, 2H), 0.49 (dd, J = 3.9, 2.3 Hz, 2H). [M + H]$^+$ = 472.4 |
| 117 | $^1$H NMR (400 MHz, $d_6$-DMSO) δ 8.47 (s, 1H), 8.15 (s, 2H), 7.86 (s, 1H), 7.62 (dd, J = 11.3, 1.8 Hz, 1H), 7.49 (d, J = 1.7 Hz, 1H), 7.20-7.08 (m, 3H), 6.73 (d, J = 7.7 Hz, 1H), 3.54 (s, 4H), 2.04-1.90 (m, 1H), 1.33 (s, 3H), 0.96-0.86 (m, 2H), 0.73-0.66 (m, 2H), 0.66-0.53 (m, 4H). [M + H]$^+$ = 436.2 |
| 118 | $^1$H NMR (400 MHz, $d_6$-DMSO) δ 8.13 (s, 2H), 7.88 (dd, J = 8.3, 2.0 Hz, 1H), 7.76 (d, J = 1.9 Hz, 1H), 7.69 (s, 1H), 7.16 (d, J = 8.3 Hz, 1H), 6.72 (dd, J = 7.9, 2.9 Hz, 1H), 6.57 (dd, J = 11.0, 2.9 Hz, 1H), 3.73-3.47 (m, 10H), 3.24-3.17 (m, 2H), 1.94-1.82 (m, 1H), 0.98-0.86 (m, 2H), 0.65-0.54 (m, 2H). [M + H]$^+$ = 486.2 |
| 119 | $^1$H NMR (400 MHz, $d_6$-DMSO) δ 8.15 (s, 2H), 7.94 (s, 1H), 7.62 (dd, J = 11.4, 1.5 Hz, 1H), 7.47 (s, 1H), 7.20 (t, J = 7.9 Hz, 1H), 6.82-6.65 (m, 2H), 6.59 (s, 1H), 3.80-3.34 (m, 12H), 2.05-1.92 (m, 1H), 0.98-0.89 (m, 2H), 0.65-0.57 (m, 2H). [M + H]$^+$ = 452.2 |
| 120 | $^1$H NMR (400 MHz, $d_6$-DMSO) δ 8.11 (s, 2H), 7.85 (dt, J = 8.3, 1.8 Hz, 1H), 7.79 (d, J = 1.9 Hz, 1H), 7.40 (d, J = 4.4 Hz, 1H), 7.34-7.25 (m, 1H), 7.15-7.07 (m, 1H), 7.03 (dd, J = 13.0, 8.3 Hz, 1H), 6.98-6.86 (m, 1H), 4.96-3.99 (m, 2H), 3.88-3.58 (m, 2H), 3.56-3.33 (m, 5H), 3.19-2.99 (m, 1H), 1.95-1.73 (m, 3H), 0.99-0.89 (m, 2H), 0.64-0.55 (m, 2H). [M + H]$^+$ = 480.2 |

TABLE II-continued

| No | Characterizations |
|---|---|
| 121 | $^1H$ NMR (400 MHz, $d_6$-DMSO) δ 8.15 (s, 2H), 7.84 (d, J = 8.2 Hz, 1H), 7.78 (s, 1H), 7.45 (s, 1H), 7.31 (s, 1H), 7.11 (s, 1H), 7.04 (d, J = 7.3 Hz, 1H), 6.92 (d, J = 30.9 Hz, 1H), 4.54-4.18 (m, 2H), 4.11-3.88 (m, 1H), 3.66 (dd, J = 36.7, 10.9 Hz, 1H), 3.54 (s, 4H), 3.29 (s, 2H), 3.19-3.02 (m, 1H), 1.88 (d, J = 7.7 Hz, 1H), 0.94 (d, J = 8.6 Hz, 2H), 0.60 (s, 2H). $[M + H]^+$ = 536.0 |
| 122 | $^1H$ NMR (400 MHz, $d_6$-DMSO) δ 8.20 (s, 2H), 7.82 (d, J = 8.4 Hz, 1H), 7.76 (s, 1H), 7.56 (s, 1H), 7.36 (s, 1H), 7.17 (s, 1H), 7.02 (s, 2H), 5.20 (s, 1H), 4.20 (dd, J = 13.2, 7.5 Hz, 1H), 4.09-3.86 (m, 1H), 3.81-3.45 (m, 7H), 3.26-3.14 (m, 1H), 1.89 (s, 1H), 0.96 (d, J = 8.1 Hz, 2H), 0.62 (s, 2H). $[M + H]^+$ = 536.0 |
| 123 | $^1H$ NMR (400 MHz, $d_6$-DMSO) δ 8.79 (s, 1H), 8.30 (s, 1H), 8.15 (dd, J = 9.0, 4.2 Hz, 4H), 7.92 (dd, J = 8.4, 1.9 Hz, 1H), 7.90-7.87 (m, 1H), 6.80 (d, J = 4.9 Hz, 1H), 3.53 (s, 4H), 1.91 (ddd, J = 13.6, 8.4, 5.4 Hz, 1H), 1.40 (s, 3H), 1.05-1.00 (m, 2H), 0.77-0.73 (m, 2H), 0.64-0.59 (m, 4H). $[M + H]^+$ = 453.2 |
| 124 | $^1H$ NMR (400 MHz, $d_6$-DMSO) δ 9.91 (s, 1H), 8.08 (s, 2H), 7.79 (dd, J = 8.4, 1.9 Hz, 1H), 7.71 (d, J = 1.8 Hz, 1H), 7.64 (s, 1H), 7.42 (s, 1H), 7.18-7.11 (m, 2H), 7.08 (d, J = 8.5 Hz, 1H), 6.76 (d, J = 8.2 Hz, 1H), 3.51 (s, 4H), 3.17 (d, J = 13.7 Hz, 4H), 2.70-2.61 (m, 1H), 2.22-2.02 (m, 4H), 1.99-1.89 (m, 1H), 0.97-0.90 (m, 2H), 0.61-0.52 (m, 2H). $[M + H]^+$ = 496.1 |
| 125 | $^1H$ NMR (400 MHz, $d_6$-DMSO) δ 8.49 (s, 1H), 8.20 (s, 2H), 8.05 (s, 1H), 7.71 (dd, J = 11.6, 1.7 Hz, 1H), 7.63 (s, 1H), 7.21-7.10 (m, 2H), 7.08 (s, 1H), 6.68 (d, J = 6.6 Hz, 1H), 4.99 (t, J = 7.3 Hz, 1H), 4.01 (q, J = 6.7 Hz, 1H), 3.77 (q, J = 7.2 Hz, 1H), 3.55 (s, 4H), 2.24 (dq, J = 13.0, 6.7 Hz, 1H), 1.87 (p, J = 6.9 Hz, 2H), 1.45 (dq, J = 12.2, 8.2 Hz, 1H), 1.33 (s, 3H), 0.70 (s, 2H), 0.61-0.53 (m, 2H). $[M + H]^+$ = 466.1 |
| 126 | $^1H$ NMR (400 MHz, $d_6$-DMSO) δ 8.13 (s, 2H), 7.87 (dd, J = 8.3, 1.9 Hz, 1H), 7.79 (d, J = 1.8 Hz, 1H), 7.65 (s, 1H), 7.46 (dd, J = 7.8, 1.5 Hz, 1H), 7.39 (t, J = 8.0 Hz, 1H), 7.20 (dd, J = 8.2, 1.5 Hz, 1H), 7.08 (d, J = 8.3 Hz, 1H), 3.68-3.58 (m, 4H), 3.53 (s, 4H), 3.25-3.15 (m, 4H), 1.87 (t, J = 5.3 Hz, 1H), 0.95-0.86 (m, 2H), 0.64-0.55 (m, 2H). $[M + H]^+$ = 504.1 |
| 127 | $^1H$ NMR (400 MHz, $d_6$-DMSO) δ 9.17 (s, 1H), 8.15 (s, 2H), 7.95 (s, 1H), 7.63 (dd, J = 11.3, 1.8 Hz, 1H), 7.52-7.45 (m, 1H), 7.22 (t, J = 7.9 Hz, 1H), 7.18-7.12 (m, 2H), 6.80 (d, J = 8.0 Hz, 1H), 3.54 (s, 4H), 2.03-1.91 (m, 1H), 1.56-1.48 (m, 2H), 1.28-1.20 (m, 2H), 0.96-0.86 (m, 2H), 0.66-0.57 (m, 2H). $[M + H]^+$ = 447.3 |
| 128 | $^1H$ NMR (400 MHz, $d_6$-DMSO) δ 8.21-8.10 (m, 4H), 7.64 (dd, J = 11.2, 1.8 Hz, 1H), 7.49 (d, J = 1.7 Hz, 1H), 7.03-6.98 (m, 1H), 6.98-6.92 (m, 1H), 6.42 (d, J = 11.1 Hz, 1H), 4.10-3.98 (m, 1H), 3.54 (s, 4H), 2.03-1.91 (m, 1H), 1.13 (d, J = 6.6 Hz, 6H), 0.98-0.89 (m, 2H), 0.67-0.58 (m, 2H). $[M + H]^+$ = 442.2 |
| 129 | $^1H$ NMR (400 MHz, $d_6$-DMSO) δ 8.57 (s, 1H), 8.17 (s, 2H), 7.65 (dd, J = 10.8, 1.8 Hz, 1H), 7.52 (d, J = 1.8 Hz, 1H), 7.27 (s, 1H), 7.07 (t, J = 7.8 Hz, 1H), 6.66 (dd, J = 7.4, 1.5 Hz, 1H), 6.31 (dt, J = 8.1, 1.7 Hz, 1H), 3.55 (s, 4H), 1.99 (ddd, J = 13.7, 8.5, 5.2 Hz, 1H), 1.40 (s, 3H), 0.97-0.88 (m, 2H), 0.79-0.70 (m, 2H), 0.67-0.54 (m, 4H). $[M + H]^+$ = 470.2 |
| 130 | $^1H$ NMR (400 MHz, $d_6$-DMSO) δ 8.16 (d, J = 6.5 Hz, 3H), 7.63 (dd, J = 11.2, 1.7 Hz, 1H), 7.57 (d, J = 1.8 Hz, 1H), 7.50 (t, J = 1.2 Hz, 1H), 6.94 (t, J = 7.8 Hz, 1H), 6.84-6.75 (m, 1H), 6.49-6.41 (m, 1H), 4.11-4.00 (m, 1H), 3.54 (s, 4H), 2.09-1.97 (m, 1H), 1.15 (d, J = 6.5 Hz, 6H), 0.95-0.87 (m, 2H), 0.65-0.57 (m, 2H). $[M + H]^+$ = 442.2 |
| 131 | $^1H$ NMR (400 MHz, $d_6$-DMSO) δ 8.17 (d, J = 7.8 Hz, 1H), 8.07 (s, 2H), 7.88 (s, 1H), 7.62 (d, J = 2.1 Hz, 1H), 7.57 (d, J = 8.6 Hz, 1H), 7.46-7.40 (m, 1H), 7.36 (t, J = 7.7 Hz, 1H), 7.31-7.25 (m, 1H), 6.69 (d, J = 13.4 Hz, 1H), 4.15-4.02 (m, 1H), 3.50 (s, 4H), 1.87 (ddd, J = 13.6, 8.4, 5.3 Hz, 1H), 1.15 (d, J = 6.6 Hz, 6H), 0.97-0.89 (m, 2H), 0.57-0.49 (m, 2H). $[M + H]^+$ = 424.3 |
| 132 | $^1H$ NMR (400 MHz, $d_6$-DMSO) δ 8.57 (s, 1H), 8.23 (d, J = 2.0 Hz, 1H), 8.13 (s, 2H), 7.92 (dd, J = 8.2, 1.9 Hz, 1H), 7.13-7.04 (m, 2H), 6.81 (s, 1H), 6.67 (dd, J = 7.5, 1.5 Hz, 1H), 6.56 (dd, J = 8.2, 1.5 Hz, 1H), 3.53 (s, 4H), 1.38 (d, J = 5.6 Hz, 12H), 0.76-0.70 (m, 2H), 0.61-0.55 (m, 2H). $[M + H]^+$ = 468.3 |
| 133 | $^1H$ NMR (400 MHz, $d_6$-DMSO) δ 8.65 (d, J = 2.1 Hz, 1H), 8.39 (s, 1H), 8.13 (d, J = 7.8 Hz, 1H), 8.10-8.05 (m, 3H), 8.01-7.96 (m, 1H), 7.87 (dd, J = 2.1, 0.8 Hz, 1H), 7.45-7.40 (m, 1H), 7.35 (t, J = 7.8 Hz, 1H), 4.10 (dq, J = 13.5, 6.6 Hz, 1H), 3.51 (s, 4H), 1.99 (td, J = 8.4, 4.3 Hz, 1H), 1.17 (d, J = 6.6 Hz, 6H), 1.08-0.99 (m, 2H), 0.63-0.55 (m, 2H). $[M + H]^+$ = 407.3 |
| 134 | $^1H$ NMR (400 MHz, $d_6$-DMSO) δ 8.22 (s, 2H), 7.96 (s, 1H), 7.72 (dd, J = 10.9, 1.7 Hz, 1H), 7.44 (s, 1H), 7.12 (t, J = 7.8 Hz, 1H), 6.71-6.63 (m, 1H), 6.26 (d, J = 8.3 Hz, 1H), 3.92 (dd, J = 12.4, 7.3 Hz, 2H), 3.77-3.68 (m, 2H), 3.67 (s, 4H), 3.63-3.57 (m, 3H), 3.56 (s, 4H), 3.19 (t, J = 4.7 Hz, 2H), 2.23 (dd, J = 8.5, 3.7 Hz, 1H), 1.93-1.79 (m, 1H). $[M + H]^+$ = 516.0 |
| 135 | $^1H$ NMR (400 MHz, $d_6$-DMSO) δ 8.59 (s, 1H), 8.20 (s, 2H), 8.02 (s, 1H), 7.76 (dd, J = 11.4, 1.7 Hz, 1H), 7.42 (s, 1H), 7.09 (t, J = 7.8 Hz, 1H), 6.69 (dd, J = 7.4, 1.4 Hz, 1H), 6.36 (dd, J = 8.2, 2.2 Hz, 1H), 4.94 (t, J = 7.5 Hz, 1H), 4.04 (q, J = 7.5 Hz, 1H), 3.78 (q, J = 7.6 Hz, 1H), 3.55 (s, 4H), 2.19 (td, J = 12.3, 7.3 Hz, 1H), 1.97-1.83 (m, 2H), 1.55 (dq, J = 12.2, 8.2 Hz, 1H), 1.40 (s, 3H), 0.74 (d, J = 11.2 Hz, 2H), 0.63-0.55 (m, 2H). $[M + H]^+$ = 500.0 |

TABLE II-continued

| No | Characterizations |
|---|---|
| 136 | $^1$H NMR (400 MHz, $d_6$-DMSO) δ 8.76 (s, 1H), 8.26 (s, 1H), 8.17 (s, 2H), 7.89 (d, J = 4.9 Hz, 1H), 7.59 (dd, J = 10.6, 1.7 Hz, 1H), 7.49 (d, J = 1.2 Hz, 1H), 6.62 (d, J = 4.9 Hz, 1H), 3.54 (s, 4H), 2.00 (ddd, J = 13.8, 8.4, 5.3 Hz, 1H), 1.40 (s, 3H), 0.94-0.84 (m, 2H), 0.78-0.70 (m, 2H), 0.64-0.54 (m, 4H).<br>$^{13}$C NMR (151 MHz, $d_6$-DMSO) δ 174.1, 166.1, 159.3, 157.7, 153.6, 146.3, 145.4, 143.2, 138.2, 129.6 (d, J = 13.2 Hz), 120.6, 113.0, 112.8, 111.2, 41.8, 29.2, 22.8, 14.0, 11.7, 8.9<br>$[M + H]^+$ = 471.1 |
| 137 | $^1$H NMR (400 MHz, $d_6$-DMSO) δ 8.59 (s, 1H), 8.13 (s, 2H), 8.06 (d, J = 1.9 Hz, 1H), 7.95 (dd, J = 8.4, 1.9 Hz, 1H), 7.87 (s, 1H), 7.26-7.15 (m, 3H), 6.82 (dd, J = 6.0, 2.9 Hz, 1H), 4.86 (dd, J = 8.9, 6.5 Hz, 1H), 4.14-4.04 (m, 1H), 3.87-3.77 (m, 1H), 3.53 (s, 4H), 2.23 (td, J = 11.7, 7.2 Hz, 1H), 1.97 (dt, J = 14.8. 7.4 Hz, 2H), 1.85-1.71 (m, 1H), 1.40 (s, 3H), 0.78-0.70 (m, 2H), 0.63-0.55 (m, 2H).<br>$[M + H]^+$ = 482.2 |
| 138 | $^1$H NMR (400 MHz, $d_6$-DMSO) δ 8.26 (d, J = 7.8 Hz, 1H), 8.11 (s, 2H), 7.84 (dd, J = 8.3, 1.9 Hz, 1H), 7.80 (s, 1H), 7.72 (d, J = 1.9 Hz, 1H), 7.04 (d, J = 8.3 Hz, 1H), 6.76-6.64 (m, 2H), 4.10-3.97 (m, 1H), 3.52 (s, 4H), 1.98-1.87 (m, 1H), 1.15 (d, J = 6.6 Hz, 6H), 0.97-0.88 (m, 2H), 0.64-0.55 (m, 2H).<br>$[M + H]^+$ = 442.3 |
| 139 | $^1$H NMR (400 MHz, $d_6$-DMSO) δ 8.59 (s, 1H), 8.11 (s, 2H), 7.84 (dd, J = 8.3, 2.0 Hz, 1H), 7.78 (s, 1H), 7.71 (d, J = 1.9 Hz, 1H), 7.02 (d, J = 8.3 Hz, 1H), 6.74-6.64 (m, 2H), 3.52 (s, 4H), 1.97-1.85 (m, 1H), 1.37 (s, 3H), 0.97-0.88 (m, 2H), 0.76-0.68 (m, 2H), 0.63-0.54 (m, 4H).<br>$[M + H]^+$ = 454.3 |
| 140 | $^1$H NMR (400 MHz, $d_6$-DMSO) δ 8.53 (s, 1H), 8.13 (d, J = 2.5 Hz, 3H), 7.87 (dd, J = 8.4, 2.0 Hz, 1H), 7.60 (s, 1H), 7.44 (s, 1H), 7.26 (d, J = 5.0 Hz, 2H), 7.18-7.07 (m, 2H), 5.01 (t, J = 7.3 Hz, 1H), 4.10-4.00 (m, 1H), 3.81 (q, J = 7.2 Hz, 1H), 3.52 (s, 4H), 2.34 (dq, J = 12.8, 6.5 Hz, 1H), 1.94 (p, J = 6.9 Hz, 2H), 1.60 (dq, J = 12.1, 8.2 Hz, 1H), 1.35 (s, 3H), 0.71 (d, J = 11.1 Hz, 2H), 0.62-0.55 (m, 2H).<br>$[M + H]^+$ = 448.3 |
| 141 | $^1$H NMR (400 MHz, $d_6$-DMSO) δ 9.89 (s, 1H), 8.08 (s, 2H), 7.79 (d, J = 8.4 Hz, 1H), 7.72 (s, 1H), 7.66 (s, 1H), 7.38 (s, 1H), 7.18 (t, J = 8.0 Hz, 1H), 7.13 (d, J = 8.4 Hz, 1H), 7.09 (d, J = 7.6 Hz, 1H), 6.82 (d, J = 7.3 Hz, 1H), 3.51 (s, 4H), 1.95 (s, 1H), 1.64 (s, 4H), 0.97-0.92 (m, 2H), 0.56 (d, J = 3.8 Hz, 2H).<br>$[M + H]^+$ = 429.1 |
| 142 | $^1$H NMR (400 MHz, $d_6$-DMSO) δ 8.15 (s, 2H), 8.01 (s, 1H), 7.63 (d, J = 11.3 Hz, 1H), 7.48 (s, 1H), 7.24 (t, J = 7.9 Hz, 1H), 6.83-6.59 (m, 3H), 5.17 (s, 1H), 4.13 (s, 1H), 3.81 (s, 1H), 3.74 (s, 1H), 3.54 (s, 4H), 3.53-3.38 (m, 3H), 1.99 (s, 1H), 0.94 (d, J = 8.8 Hz, 2H), 0.63 (s, 2H).<br>$[M + H]^+$ = 520.1 |
| 143 | $^1$H NMR (400 MHz, $d_6$-DMSO) δ 8.50 (s, 1H), 8.16 (s, 2H), 7.66-7.60 (m, 1H), 7.56 (s, 1H), 7.50 (s, 1H), 6.93 (t, J = 7.8 Hz, 1H), 6.78 (t, J = 6.0 Hz, 1H), 6.45 (t, J = 8.3 Hz, 1H), 3.54 (s, 4H), 2.03 (s, 1H), 1.38 (s, 3H), 0.91 (dd, J = 8.4, 2.1 Hz, 2H), 0.76-0.70 (m, 2H), 0.65-0.56 (m, 4H).<br>$[M + H]^+$ = 454.1 |
| 144 | $^1$H NMR (400 MHz, $d_6$-DMSO) δ 8.15 (s, 2H), 7.96 (s, 1H), 7.63 (dd, J = 11.4, 1.6 Hz, 1H), 7.49 (s, 1H), 7.23 (t, J = 7.8 Hz, 1H), 6.77 (dd, J = 15.0, 7.8 Hz, 2H), 6.63 (s, 1H), 4.67-3.56 (m, 5H), 3.54 (s, 4H), 3.20 (s, 2H), 2.07-1.93 (m, 1H), 0.96-0.90 (m, 2H), 0.65-0.58 (m, 2H).<br>$[M + H]^+$ = 520.0 |
| 145 | $^1$H NMR (400 MHz, $d_6$-DMSO) δ 8.19 (s, 2H), 8.05 (d, J = 1.6 Hz, 1H), 7.72 (d, J = 12.7 Hz, 2H), 7.21 (t, J = 7.8 Hz, 1H), 6.71 (t, J = 7.9 Hz, 2H), 6.54 (s, 1H), 4.99 (t, J = 7.4 Hz, 1H), 4.07-3.97 (m, 1H), 3.77 (q, J = 7.1 Hz, 1H), 3.55 (s, 12H), 2.25 (dq, J = 13.4, 6.7 Hz, 1H), 1.88 (p, J = 6.8 Hz, 2H), 1.46 (dq, J = 12.4, 8.1 Hz, 1H).<br>$[M + H]^+$ = 482.3 |
| 146 | $^1$H NMR (400 MHz, $d_6$-DMSO) δ 8.71 (d, J = 2.1 Hz, 1H), 8.62 (s, 1H), 8.57 (dd, J = 8.3, 1.6 Hz, 1H), 8.13 (d, J = 14.3 Hz, 3H), 8.02 (dd, J = 2.2, 1.0 Hz, 1H), 7.39-7.31 (m, 1H), 6.99 (dd, J = 7.5, 1.6 Hz, 1H), 3.52 (s, 4H), 1.96-1.85 (m, 1H), 1.45 (s, 3H), 1.14-1.04 (m, 2H), 0.74 (q, J = 4.6 Hz, 2H), 0.65 (td, J = 5.8, 4.0 Hz, 2H), 0.62-0.56 (m, 2H).<br>$[M + H]^+$ = 453.3 |
| 147 | $^1$H NMR (400 MHz, $d_6$-DMSO) δ 8.78 (s, 1H), 8.55 (s, 1H), 8.17 (s, 2H), 7.76 (d, J = 5.0 Hz, 1H), 7.59 (dd, J = 10.7, 1.5 Hz, 1H), 7.48 (s, 1H), 6.67 (t, J = 4.6 Hz, 1H), 3.54 (s, 4H), 2.04 (td, J = 8.4, 4.3 Hz, 1H), 1.38 (s, 3H), 0.94-0.84 (m, 2H), 0.74 (d, J = 11.1 Hz, 2H), 0.64-0.60 (m, 2H), 0.60-0.54 (m, 2H).<br>$[M + H]^+$ = 455.3 |
| 148 | $^1$H NMR (400 MHz, $d_6$-DMSO) δ 8.19-8.05 (m, 3H), 7.88 (dd, J = 8.3, 1.9 Hz, 1H), 7.83 (d, J = 1.9 Hz, 1H), 7.35 (s, 1H), 7.16 (d, J = 8.4 Hz, 1H), 6.81 (dd, J = 11.2, 2.7 Hz, 1H), 6.54 (dd, J = 8.6, 2.7 Hz, 1H), 4.05 (dq, J = 13.6, 6.6 Hz, 1H), 3.52 (s, 4H), 1.99-1.85 (m, 1H), 1.84-1.71 (m, 1H), 1.16 (d, J = 6.6 Hz, 6H), 1.02-0.95 (m, 2H), 0.95-0.89 (m, 2H), 0.69-0.58 (m, 2H), 0.52-0.37 (m, 2H).<br>$[M + H]^+$ = 464.3 |
| 149 | $^1$H NMR (400 MHz, $d_6$-DMSO) δ 8.53 (s, 1H), 8.38 (s, 1H), 8.18 (s, 2H), 8.16 (d, J = 1.9 Hz, 1H), 7.89 (d, J = 1.8 Hz, 1H), 7.23 (d, J = 7.4 Hz, 3H), 6.83 (dd, J = 7.2, 2.3 Hz, 1H), 3.55 (s, 4H), 1.90 (ddd, J = 13.2, 8.3, 5.2 Hz, 1H), 1.34 (s, 3H), 0.93-0.86 (m, 2H), 0.74-0.68 (m, 2H), 0.64-0.60 (m, 2H), 0.60-0.55 (m, 2H).<br>$[M + H]^+$ = 443.2 |
| 150 | $^1$H NMR (400 MHz, $d_6$-DMSO) δ 8.64 (s, 1H), 8.27 (s, 1H), 8.16 (s, 2H), 7.99 (d, J = 5.6 Hz, 1H), 7.92 (dd, J = 8.2, 1.9 Hz, 1H), 7.75 (d, J = 1.8 Hz, 1H), 7.21 (d, J = 8.2 Hz, 1H), 6.44 (d, J = 5.6 Hz, 1H), 3.54 (s, 4H), 1.91-1.79 (m, 1H), 1.39 (s, 3H), 0.89 (dd, J = 8.4, 1.9 Hz, 2H), 0.78-0.70 (m, 2H), 0.65-0.56 (m, 4H).<br>$[M + H]^+$ = 453.2 |

TABLE II-continued

| No | Characterizations |
|---|---|
| 151 | $^1$H NMR (400 MHz, $d_6$-DMSO) δ 9.23 (s, 1H), 8.89 (s, 1H), 8.51 (d, J = 3.3 Hz, 2H), 8.11 (s, 2H), 7.78 (d, J = 8.1 Hz, 2H), 6.66 (d, J = 8.1 Hz, 1H), 3.52 (s, 4H), 1.91 (s, 1H), 1.23 (s, 3H), 0.97 (d, J = 8.3 Hz, 2H), 0.65-0.55 (m, 4H), 0.55-0.48 (m, 2H).<br>$[M + H]^+$ = 453.1 |
| 152 | $^1$H NMR (400 MHz, $d_6$-DMSO) δ 9.53 (s, 1H), 8.68 (s, 1H), 8.17 (s, 2H), 7.82 (d, J = 5.1 Hz, 1H), 7.60 (dd, J = 10.7, 1.6 Hz, 1H), 7.49 (s, 1H), 6.80-6.72 (m, 1H), 3.54 (s, 4H), 2.10-1.99 (m, 1H), 1.64-1.56 (m, 2H), 1.33-1.26 (m, 2H), 0.94-0.84 (m, 2H), 0.63-0.54 (m, 2H).<br>$[M + H]^+$ = 466.4 |
| 153 | $^1$H NMR (400 MHz, $d_6$-DMSO) δ 8.35 (s, 1H), 8.18 (s, 2H), 7.96 (d, J = 4.9 Hz, 1H), 7.61 (dd, J = 10.7, 1.6 Hz, 1H), 7.49 (s, 1H), 6.69 (d, J = 4.9 Hz, 1H), 3.71-3.63 (m, 4H), 3.61-3.57 (m, 2H), 3.55 (s, 4H), 3.24-3.18 (m, 2H), 2.02 (ddd, J = 13.9, 8.5, 5.4 Hz, 1H), 0.89 (dd, J = 8.4, 2.0 Hz, 2H), 0.63-0.52 (m, 2H).<br>$^{13}$C NMR (151 MHz, $d_6$-DMSO) δ 174.1, 165.8, 164.8, 158.5 (d, J = 244.9 Hz), 153.7, 146.9, 144.0, 143.3, 138.4 (d, J = 7.1 Hz), 129.4 (d, J = 13.4 Hz), 120.6, 113.0, 112.8, 112.1, 110.6, 66.6, 66.4, 47.0, 41.9, 41.8, 11.7 (d, J = 2.8 Hz), 9.0, 8.9<br>$[M + H]^+$ = 487.1 |
| 154 | $^1$H NMR (400 MHz, $d_6$-DMSO) δ 8.36 (s, 1H), 8.18 (s, 2H), 7.97 (d, J = 4.9 Hz, 1H), 7.61 (d, J = 10.7 Hz, 1H), 7.49 (s, 1H), 6.76 (d, J = 4.9 Hz, 1H), 4.71 (s, 1H), 4.07 (s, 1H), 3.82-3.76 (m, 1H), 3.66 (d, J = 6.7 Hz, 1H), 3.55 (s, 4H), 3.50 (d, J = 11.5 Hz, 1H), 3.36 (d, J = 12.0 Hz, 1H), 2.09-1.95 (m, 1H), 1.89 (s, 1H), 1.82 (d, J = 9.4 Hz, 1H), 0.89 (ddt, J = 8.0, 5.1, 3.1 Hz, 2H), 0.61-0.55 (m, 2H).<br>$[M + H]^+$ = 499.2 |
| 155 | $^1$H NMR (400 MHz, $d_6$-DMSO) δ 8.35 (s, 1H), 8.18 (s, 2H), 7.95 (d, J = 4.9 Hz, 1H), 7.61 (d, J = 10.7 Hz, 1H), 7.49 (s, 1H), 6.68 (d, J = 4.9 Hz, 1H), 4.92 (s, 1H), 4.62 (s, 1H), 3.84 (d, J = 7.4 Hz, 1H), 3.81-3.76 (m, 1H), 3.55 (s, 4H), 3.20 (dd, J = 9.8, 1.2 Hz, 1H), 3.06 (d, J = 9.8 Hz, 1H), 2.07-1.97 (m, 1H), 1.92 (s, 1H), 1.89 (s, 1H), 0.89 (ddt, J = 8.1, 5.1, 3.1 Hz, 2H), 0.61-0.55 (m, 2H).<br>$[M + H]^+$ = 499.2 |
| 156 | $^1$H NMR (400 MHz, $d_6$-DMSO) δ 8.64 (s, 1H), 8.17 (s, 2H), 7.82 (d, J = 5.0 Hz, 1H), 7.60 (dd, J = 10.8, 1.7 Hz, 1H), 7.48 (d, J = 1.3 Hz, 1H), 6.67 (dd, J = 4.9, 4.1 Hz, 1H), 3.67 (s, 4H), 3.59 (q, J = 5.3 Hz, 2H), 3.54 (s, 4H), 3.30 (s, 2H), 2.07 (ddd, J = 13.7, 8.5, 5.3 Hz, 1H), 0.93-0.87 (m, 2H), 0.63-0.54 (m, 2H).<br>$[M + H]^+$ = 471.4 |
| 157 | $^1$H NMR (400 MHz, $d_6$-DMSO) δ 8.66 (s, 1H), 8.27 (s, 1H), 8.19 (s, 2H), 7.97 (d, J = 5.6 Hz, 1H), 7.70-7.65 (m, 1H), 7.53 (s, 1H), 6.18 (dd, J = 5.6, 1.6 Hz, 1H), 3.55 (s, 4H), 1.95 (s, 1H), 1.39 (s, 3H), 0.96-0.90 (m, 2H), 0.76-0.71 (m, 2H), 0.64 (d, J = 5.1 Hz, 2H), 0.62-0.58 (m, 2H).<br>$[M + H]^+$ = 471.0 |
| 158 | $^1$H NMR (400 MHz, $d_6$-DMSO) δ 8.16 (s, 2H), 7.68 (s, 1H), 7.62 (dd, J = 11.4, 1.6 Hz, 1H), 7.50 (s, 1H), 7.01 (t, J = 7.9 Hz, 1H), 6.69 (t, J = 5.9 Hz, 1H), 6.54 (t, J = 8.2 Hz, 1H), 3.66 (s, 4H), 3.56 (s, 2H), 3.54 (s, 4H), 3.29 (s, 2H), 2.04 (d, J = 5.3 Hz, 1H), 0.97-0.87 (m, 2H), 0.61 (q, J = 5.2, 4.6 Hz, 2H).<br>$[M + H]^+$ = 470.1 |
| 159 | $^1$H NMR (400 MHz, $d_6$-DMSO) δ 8.64 (d, J = 16.5 Hz, 1H), 8.17 (s, 2H), 7.83 (dd, J = 8.3, 4.9 Hz, 1H), 7.62-7.57 (m, 1H), 7.48 (s, 1H), 6.70 (dt, J = 17.6, 4.2 Hz, 1H), 4.92 (s, 2H), 3.83-3.68 (m, 2H), 3.54 (s, 4H), 3.44 (dd, J = 58.9, 12.3 Hz, 2H), 2.07 (d, J = 8.5 Hz, 1H), 1.95-1.80 (m, 2H), 0.89 (dt, J = 6.0, 3.0 Hz, 2H), 0.59 (d, J = 3.7 Hz, 2H).<br>$[M + H]^+$ = 483.1 |
| 160 | $^1$H NMR (300 MHz, $CDCl_3$) δ 8.75 (s, 1H), 8.09 (d, J = 8.5 Hz, 1H), 8.06 (s, 1H), 7.92 (s, 1H), 7.77 (d, J = 7.6 Hz, 1H), 7.42 (t, J = 7.8 Hz, 1H), 7.33 (br s, 1H), 7.30 (d, J = 8.4 Hz, 1H), 6.47 (s, 1H), 5.55 (t, J = 7.2 Hz, 1H), 5.23 (d, J = 7.2 Hz, 2H), 3.68 (t, J = 8.6 Hz, 2H), 3.48 (t, J = 8.5 Hz, 2H), 3.07 (s, 4H), 1.86 (s, 3H), 1.81 (s, 3H), 1.78-1.74 (m, 1H), 0.99 (q, J = 5.6 Hz, 2H), 0.75 (q, J = 5.6 Hz, 2H).<br>$[M + H]^+$ = 471.3 |
| 161 | $^1$H NMR (300 MHz, $CDCl_3$) δ 7.32-7.20 (m, 3H), 7.54 (s, 1H), 7.32-7.20 (m, 4H), 6.95 (d, J = 7.7 Hz, 1H), 6.50 (s, 1H), 4.98 (d, J = 6.1 Hz, 2H), 4.56 (d, J = 6.1 Hz, 2H), 3.75 (s, 4H), 1.76-1.72 (m, 1H), 1.68 (s, 3H), 0.99 (q, J = 5.4 Hz, 2H), 0.75 (q, J = 5.4 Hz, 2H).<br>$[M + H]^+$ = 434.4 |
| 162 | $^1$H NMR (300 MHz, $d_6$-DMSO) δ 8.56 (s, 1H), 8.10 (br s, 2H), 7.79 (d, J = 8.5 Hz, 1H), 7.75 (d, J = 12.3 Hz, 1H), 7.55 (s, 1H), 7.34 (d, J = 7.7 Hz, 1H), 7.29 (t, J = 7.6 Hz, 1H), 7.19 (d, J = 7.5 Hz, 1H), 7.11 (d, J = 8.5 Hz, 1H), 4.73 (t, J = 5.8 Hz, 1H), 3.52 (br s, 6H), 1.97-1.90 (m, 1H), 0.95 (q, J = 5.5 Hz, 2H), 0.78 (d, J = 8.0 Hz, 2H), 0.67 (d, J = 8.0 Hz, 2H), 0.58 (q, J = 5.5 Hz, 2H).<br>$[M + H]^+$ = 434.4 |
| 163 | $^1$H NMR (300 MHz, $CDCl_3$) δ 7.75 (d, J = 11.3 Hz, 1H), 7.63 (s, 1H), 7.49 (s, 1H), 7.18 (t, J = 8.0 Hz, 1H), 7.06 (d, J = 7.7 Hz, 2H), 6.57 (d, J = 7.4 Hz, 1H), 5.83 (s, 1H), 4.94 (d, J = 6.0 Hz, 2H), 4.53 (d, J = 6.0 Hz, 2H), 3.72 (s, 4H), 1.91-1.78 (m, 1H), 1.65 (s, 3H), 0.91 (q, J = 5.3 Hz, 2H), 0.75 (q, J = 5.3 Hz, 2H).<br>$^{13}$C NMR (75 MHz, $CDCl_3$) δ 176.1, 172.7, 165.6, 157.5, 154.2, 145.2, 138.6, 133.9, 133.8, 131.9, 131.7, 129.6, 122.5, 114.5, 114.2, 112.4, 111.9, 107.6, 80.1, 46.4, 41.9, 22.0, 12.0, 7.9<br>$[M + H]^+$ = 452.5 |
| 164 | $^1$H NMR (300 MHz, $CDCl_3$) δ 8.03 (d, J = 4.9 Hz, 1H), 7.89 (br s, 1H), 7.73 (dd, J = 10.6, 1.4 Hz, 1H), 7.62 (s, 1H), 6.80 (d, J = 5.0 Hz, 1H), 6.78 (s, 1H), 6.38 (s, 1H), 3.64 (s, 4H), 2.53 (s, 1H), 2.21 (s, 6H), 1.92-1.83 (m, 1H), 0.91 (q, J = 5.3 Hz, 2H), 0.76 (q, J = 5.3 Hz, 2H).<br>$^{13}$C NMR (75 MHz, $CDCl_3$) δ 176.3, 166.0, 165.3, 158.9, 155.6, 152.5, 146.6, 143.3, 140.7, 136.8, 136.7, 129.1, 128.9, 122.2, 114.3, 114.0, 113.8, 112.2, 53.1, 48.8, 41.9, 25.1, 12.1, 7.7<br>$[M + H]^+$ = 483.4 |

TABLE II-continued

| No | Characterizations |
| --- | --- |
| 165 | $^1$H NMR (300 MHz, $CDCl_3$) δ 7.77 (d, J = 11.3 Hz, 1H), 7.65 (s, 1H), 7.47 (d, J = 7.7 Hz, 1H), 7.40 (s, 1H), 7.38-7.30 (m, 1H), 6.89 (d, J = 7.7 Hz, 1H), 5.88 (s, 1H), 4.40 (t, J = 9.5 Hz, 2H), 4.03 (t, J = 9.5 Hz, 2H), 3.72 (s, 4H), 1.89-1.76 (m, 1H), 0.90 (q, J = 5.4 Hz, 2H), 0.77 (q, J = 5.4 Hz, 2H).<br>$[M + H]^+$ = 408.3 |
| 166 | $^1$H NMR (300 MHz, $CDCl_3$) δ 8.08 (d, J = 4.9 Hz, 1H), 7.79 (d, J = 10.6 Hz, 1H), 7.68 (s, 1H), 6.82 (d, J = 4.9 Hz, 1H), 6.79 (s, 1H), 6.32 (s, 1H), 3.72 (s, 4H), 2.55 (s, 6H), 1.92-1.83 (m, 1H), 0.98-0.86 (m, 2H), 0.82-0.73 (m, 2H).<br>$[M + H]^+$ = 501.3 |
| 167 | $^1$H NMR (400 MHz, $d_6$-DMSO) δ 8.58 (s, 1H), 8.11 (s, 2H), 7.85 (dd, J = 8.3, 1.9 Hz, 1H), 7.80 (s, 1H), 7.31 (s, 1H), 7.22 (t, J = 7.8 Hz, 1H), 7.09 (dd, J = 8.2, 1.4 Hz, 1H), 7.04 (d, J = 8.3 Hz, 1H), 6.85 (dd, J = 7.4, 1.4 Hz, 1H), 3.52 (s, 4H), 1.87 (s, 1H), 1.40 (s, 3H), 0.99-0.90 (m, 2H), 0.77-0.71 (m, 2H), 0.63-0.54 (m, 4H).<br>$^{13}$C NMR (151 MHz, $d_6$-DMSO) δ 175.5, 167.5, 165.8, 144.0, 140.9, 139.2, 132.9, 132.5, 128.0, 127.9, 127.8, 120.2, 119.5, 118.7, 118.0, 41.7, 29.2, 22.9, 14.1, 11.7, 7.2<br>$[M + H]^+$ = 452.1 |
| 168 | $^1$H NMR (300 MHz, $CDCl_3$) δ 8.06 (d, J = 5.0 Hz, 1H), 7.77 (dd, J = 10.6, 1.5 Hz, 1H), 7.66 (s, 1H), 7.46 (s, 2H), 6.75 (d, J = 5.0 Hz, 1H), 6.71 (s, 1H), 4.09-3.96 (m, 4H), 3.69 (s, 4H), 1.93-1.84 (m, 1H), 1.22 (s, 9H), 0.98-0.86 (m, 2H), 0.82-0.73 (m, 2H).<br>$[M + H]^+$ = 542.3 |
| 169 | $^1$H NMR (300 MHz, $d_6$-DMSO) δ 8.16 (s, 2H), 7.84 (s, 1H), 7.61 (d, J = 11.5 Hz, 1H), 7.48 (s, 1H), 7.22-7.08 (m, 3H), 6.75 (d, J = 7.7 Hz, 1H), 3.53 (s, 4H), 3.33 (s, 4H), 2.04-1.94 (m, 1H), 0.90 (q, J = 5.3 Hz, 2H), 0.60 (q, J = 5.3 Hz, 2H).<br>$^{13}$C NMR (75 MHz, $d_6$-DMSO) δ 173.8, 165.3, 164.2, 156.6 (d, J = 242.4 Hz), 145.6, 140.3, 135.6 (d, J = 6.8 Hz), 131.3, 130.5 (d, J = 12.8 Hz), 128.5, 120.6, 117.0, 116.2, 113.1 (d, J = 21.0 Hz), 112.8, 41.3, 11.3, 8.8<br>$[M + H]^+$ = 407.3 |
| 170 | $^1$H NMR (300 MHz, $d_6$-DMSO) δ 8.16 (s, 2H), 7.87 (s, 1H), 7.61 (d, J = 11.3 Hz, 1H), 7.46 (s, 1H), 7.12 (t, J = 8.1 Hz, 1H), 7.04 (s, 1H), 6.84 (d, J = 8.2 Hz, 1H), 6.38 (d, J = 8.0 Hz, 1H), 4.43-4.35 (m, 2H), 3.97 (t, J = 7.9 Hz, 2H), 3.54 (s, 4H), 2.07-1.93 (m, 1H), 0.93 (q, J = 6.1 Hz, 2H), 0.61 (q, J = 5.7 Hz, 2H).<br>$[M + H]^+$ = 424.3 |
| 171 | $^1$H NMR (300 MHz, $CDCl_3$) δ 7.76 (dd, J = 11.5, 1.6 Hz, 1H), 7.64 (s, 1H), 7.41 (br s, 2H), 7.25 (t, J = 7.7 Hz, 2H), 6.90-6.81 (m, 2H), 6.76 (s, 1H), 5.88 (s, 1H), 3.99 (br s, 2H), 3.80-3.59 (m, 6H), 2.79-2.45 (m, 4H), 1.91-1.78 (m, 1H), 0.99-0.87 (m, 2H), 0.76 (q, J = 5.3 Hz, 2H).<br>$[M + H]^+$ = 468.4 |
| 172 | $^1$H NMR (300 MHz, $CDCl_3$) δ 8.04 (d, J = 4.9 Hz, 1H), 7.77 (dd, J = 10.6, 1.6 Hz, 1H), 7.71 (s, 1H), 6.80 (s, 2H), 5.56 (s, 1H), 3.72 (s, 4H), 2.14 (s, 9H), 1.93-1.84 (m, 1H), 1.73 (s, 6H), 0.93 (q, J = 5.2 Hz, 2H), 0.81 (q, J = 5.2 Hz, 2H).<br>$[M + H]^+$ = 551.4 |
| 173 | $^1$H NMR (300 MHz, $d_6$-DMSO) δ 8.16 (s, 2H), 7.87 (s, 1H), 7.61 (dd, J = 11.4, 1.5 Hz, 1H), 7.47 (s, 1H), 7.42 (s, 1H), 7.19-7.04 (m, 3H), 6.70 (d, J = 7.6 Hz, 1H), 3.53 (s, 4H), 2.03 (s, 9H), 2.00-1.92 (m, 1H), 1.64 (s, 6H), 0.91 (q, J = 5.2 Hz, 2H), 0.61 (q, J = 5.2 Hz, 2H).<br>$[M + H]^+$ = 516.5 |
| 174 | $^1$H NMR (300 MHz, $CDCl_3$) δ 8.69 (s, 1H), 7.87 (d, J = 11.3 Hz, 1H), 7.67 (s, 1H), 7.25-7.12 (m, 3H), 6.84 (d, J = 8.0 Hz, 1H), 5.88 (s, 1H), 5.75 (s, 1H), 3.70 (t, J = 8.7 Hz, 2H), 3.51 (t, J = 8.7 Hz, 2H), 3.07 (s, 3H), 2.10 (s, 9H), 1.91-1.78 (m, 1H), 1.71 (s, 6H), 0.91 (q, J = 5.2 Hz, 2H), 0.76 (q, J = 5.2 Hz, 2H).<br>$[M + H]^+$ = 530.5 |
| 175 | $^1$H NMR (300 MHz, $d_6$-DMSO) δ 9.74 (s, 1H), 8.15 (s, 2H), 7.74 (s, 1H), 7.61 (d, J = 11.5 Hz, 1H), 7.47 (s, 1H), 7.08 (s, 1H), 7.04 (t, J = 8.2 Hz, 1H), 6.91 (d, J = 8.2 Hz, 1H), 6.37 (d, J = 7.9 Hz, 1H), 3.61 (dd, J = 8.8, 5.5 Hz, 1H), 3.54 (s, 4H), 2.86 (t, J = 6.5 Hz, 2H), 2.07-1.94 (m, 2H), 1.78-1.69 (m, 1H), 1.67-1.57 (m, 2H), 0.91 (q, J = 5.1 Hz, 2H), 0.61 (q, J = 5.1 Hz, 2H).<br>$[M + H]^+$ = 451.4 |
| 176 | $^1$H NMR (300 MHz, $d_6$-DMSO) δ 8.96 (d, J = 6.3 Hz, 1H), 8.61 (s, 1H), 7.95 (s, 1H), 7.71 (dd, J = 11.4, 1.5 Hz, 1H), 7.52 (s, 1H), 7.22 (d, J = 4.8 Hz, 2H), 7.16 (s, 1H), 6.79 (br s, 1H), 5.05-4.88 (m, 1H), 4.73 (t, J = 6.8 Hz, 2H), 4.56 (t, J = 6.8 Hz, 2H), 3.62-3.51 (m, 2H), 3.50-3.41 (m, 2H), 2.95 (s, 3H), 2.05-1.92 (m, 1H), 0.92 (q, J = 5.2 Hz, 2H), 0.63 (q, J = 5.2 Hz, 2H).<br>$[M + H]^+$ = 452.3 |
| 177 | $^1$H NMR (300 MHz, $CDCl_3$) δ 7.74 (dd, J = 11.3, 1.6 Hz, 1H), 7.61 (s, 1H), 7.50 (br s, 1H), 7.32-7.18 (m, 4H), 6.90 (d, J = 7.0 Hz, 1H), 6.66 (d, J = 7.0 Hz, 1H), 5.90 (s, 1H), 5.26-5.15 (m, 1H), 5.00 (t, J = 7.1 Hz, 2H), 4.59 (t, J = 7.1 Hz, 2H), 3.69 (s, 4H), 1.87-1.78 (m, 1H), 0.91 (q, J = 5.3 Hz, 2H), 0.76 (q, J = 5.3 Hz, 2H).<br>$[M + H]^+$ = 438.4 |
| 178 | $^1$H NMR (300 MHz, $d_6$-DMSO) δ 11.33 (s, 1H), 8.18 (s, 2H), 8.03 (s, 1H), 7.93 (s, 1H), 7.63 (d, J = 11.4 Hz, 1H), 7.49 (s, 1H), 7.37-7.21 (m, 3H), 7.17 (s, 1H), 6.87 (d, J = 7.3 Hz, 1H), 3.54 (s, 4H), 2.04-1.94 (m, 1H), 0.92 (q, J = 5.2 Hz, 2H), 0.62 (q, J = 5.2 Hz, 2H).<br>$[M + H]^+$ = 449.4 |
| 179 | $^1$H NMR (300 MHz, $d_6$-DMSO) δ 9.81 (s, 1H), 8.16 (s, 1H), 7.84 (s, 1H), 7.76 (s, 1H), 7.62 (d, J = 11.6 Hz, 1H), 7.47 (s, 1H), 7.06-6.93 (m, 2H), 6.93 (s, 1H), 6.43 (d, J = 6.7 Hz, 1H), 4.15-4.10 (m, 1H), 3.54 (s, 4H), 2.34-2.08 (m, 3H), 2.07-1.89 (m, 2H), 0.91 (q, J = 5.3 Hz, 2H), 0.61 (q, J = 5.3 Hz, 2H).<br>$[M + H]^+$ = 465.4 |
| 180 | $^1$H NMR (300 MHz, $d_6$-DMSO) δ 9.41 (s, 1H), 8.16 (s, 2H), 7.71 (s, 1H), 7.61 (dd, J = 11.4, 1.5 Hz, 1H), 7.47 (s, 1H), 7.11 (s, 1H), 7.03 (d, J = 5.0 Hz, 2H), 6.43 (br s, 1H), 3.82 (s, 2H), 3.53 (s, 4H), 2.93 (t, J = 3.1 Hz, 1H), 2.09 (br s, 2H), 2.06-1.93 (m, 1H), 1.67-1.55 (m, 2H), 0.90 (q, J = 5.3 Hz, 2H), 0.59 (q, J = 5.3 Hz, 2H).<br>$[M + H]^+$ = 464.4 |

TABLE II-continued

| No | Characterizations |
|---|---|
| 181 | $^1$H NMR (400 MHz, $d_6$-DMSO) δ 9.35 (s, 1H), 8.17 (s, 2H), 7.65 (dd, J = 10.8, 1.6 Hz, 1H), 7.53 (s, 1H), 7.39 (s, 1H), 7.12 (t, J = 7.9 Hz, 1H), 6.75 (dd, J = 7.4, 1.4 Hz, 1H), 6.39-6.35 (m, 1H), 3.55 (s, 4H), 1.99 (ddd, J = 13.8, 8.4, 5.3 Hz, 1H), 1.60-1.55 (m, 2H), 1.29-1.24 (m, 2H), 0.94-0.89 (m, 2H), 0.66-0.60 (m, 2H).<br>$[M + H]^+$ = 481.0 |

The following examples are provided as illustrations and in no way limit the scope of this invention.

The following examples illustrate in detail the preparation of some compounds according to the invention. The structures of the products obtained have been confirmed by NMR spectra.

EXAMPLES

Example 1: Compound (7) in Table I

According to procedure (E), a solution of methyl 2-bromo-3-chlorobenzoate (500 mg, 2.0 mmoles, 1 eq) and potassium cyclopropyltrifluoroborate (445 mg, 3.0 mmoles, 1.5 eq.) in toluene (10 mL) and water (2 mL) was degassed with argon during 5 minutes then tripotassium phosphate (1.08 g, 5.0 mmoles, 2.5 eq.), RuPhos (37.4 mg, 80 moles, 0.04 eq.) and palladium(II) acetate (9.1 mg, 40 moles, 0.02 eq.) were added. The reaction mixture was heated at 110° C. and stirred for 2 h 30 under inert atmosphere. Upon cooling down to room temperature, it was filtered over a pad of celite and the pad was washed with EtOAc. A saturated aqueous solution of brine was then added to the filtrate and the mixture was extracted with EtOAc. The combined organic layers were dried over $MgSO_4$, filtered and concentrated under reduced pressure. The resulting residue was purified by column chromatography on silica gel to give methyl 3-chloro-2-cyclopropylbenzoate (201 mg, 47%).

$^1$H NMR (400 MHz, $d_6$-DMSO) δ 7.59 (dd, J=8.0, 1.3 Hz, 1H), 7.46 (dd, J=7.7, 1.3 Hz, 1H), 7.35 (t, J=7.8 Hz, 1H), 3.86 (s, 3H), 1.94 (tt, J=8.5, 5.8 Hz, 1H), 1.08-0.93 (m, 2H), 0.47-0.34 (m, 2H).

According to procedure (B), methyl 3-chloro-2-cyclopropylbenzoate (200 mg, 949 moles, 1 eq.) was placed in methanol (2 mL) and a 4M aqueous solution of NaOH (1.2 mL, 4.75 mmoles, 5 eq.) was added. The reaction mixture was heated at 80° C. and stirred for 3 hours. It was then concentrated under reduced pressure and, after addition of an aqueous solution of 2M HCl (10 eq.), extracted with dichloromethane. The combined organic phases were dried over magnesium sulphate, filtered and concentrated under reduced pressure to give 3-chloro-2-cyclopropylbenzoic acid (176 mg, 71%).

$^1$H NMR (400 MHz, $d_6$-DMSO) δ 13.16 (s, 1H), 7.54 (dd, J=7.9, 1.3 Hz, 1H), 7.43 (dd, J=7.6, 1.3 Hz, 1H), 7.36-7.27 (m, 1H), 1.94 (tt, J=8.5, 5.7 Hz, 1H), 1.08-0.93 (m, 2H), 0.55-0.40 (m, 2H).

3-chloro-2-cyclopropylbenzoic acid (170 mg, 865 moles, 1 eq.) and 3-methylbutan-1-amine (110 μL, 951 moles, 1.1 eq.) were placed in anhydrous N,N-dimethylformamide (2 mL). HATU (329 mg, 865 moles, 1 eq.) and DIPEA (226 μL, 1.30 mmole, 1.5 eq.) were added and the resulting reaction mixture was stirred at room temperature for 16 hours. The reaction was quenched with 1M aqueous hydrochloric acid and extracted with ethyl acetate. The combined organic phases were dried over magnesium sulphate, filtered and concentrated under reduced pressure. The resulting residue was purified by column chromatography on silica gel to give 3-chloro-2-cyclopropyl-N-(3-methylbutyl)benzamide (168 mg, 73%).

$^1$H NMR (400 MHz, $d_6$-DMSO) δ 8.23 (t, J=5.4 Hz, 1H), 7.46 (dd, J=7.9, 1.3 Hz, 1H), 7.27 (t, J=7.8 Hz, 1H), 7.18 (dd, J=7.6, 1.2 Hz, 1H), 3.28-3.19 (m, 2H), 1.92 (tt, J=8.6, 5.7 Hz, 1H), 1.65 (tq, J=13.3, 6.7 Hz, 1H), 1.42 (q, J=7.0 Hz, 2H), 0.98-0.88 (m, 8H), 0.58-0.44 (m, 2H).

According to route (A1), a mixture of 3-chloro-2-cyclopropyl-N-(3-methylbutyl)benzamide (99.4 mg, 374 moles, 1.1 eq.), methyl 4-amino-3-cyclopropyl-benzoate (65 mg, 340 moles, 1 eq.), $Pd(OAc)_2$ (2.3 mg, 10.2 moles, 3 mol %), rac-BINAP (4.2 mg, 6.8 moles, 2 mol %) and $K_2CO_3$ (141 mg, 1.02 mmole, 3 eq.) in anhydrous toluene (1 mL) was degassed with $N_2$ and heated at 130° C. for 75 minutes under inert atmosphere.

The reaction mixture was cooled down to room temperature, filtered over a pad of celite and the pad was washed with EtOAc. A saturated aqueous solution of brine was then added to the filtrate and the mixture was extracted with EtOAc. The combined organic phases were dried over $MgSO_4$, filtered and concentrated under reduced pressure. The resulting residue was purified by column chromatography on silica gel to give methyl 3-cyclopropyl-4-({2-cyclopropyl-3-[(3-methylbutyl)carbamoyl]phenyl}amino)benzoate (95 mg, 63%).

$^1$H NMR (400 MHz, $d_6$-DMSO) δ 8.17 (t, J=5.6 Hz, 1H), 7.67 (dd, J=8.5, 2.0 Hz, 1H), 7.63 (d, J=1.7 Hz, 1H), 7.49 (s, 1H), 7.35-7.22 (m, 2H), 6.98 (dd, J=7.2, 1.4 Hz, 1H), 6.91 (d, J=8.5 Hz, 1H), 3.78 (s, 3H), 3.29-3.21 (m, 2H), 1.98-1.78 (m, 2H), 1.66 (dq, J=13.3, 6.7 Hz, 1H), 1.43 (q, J=7.0 Hz, 2H), 1.07-0.99 (m, 2H), 0.92 (d, J=6.6 Hz, 6H), 0.83-0.75 (m, 2H), 0.70-0.61 (m, 2H), 0.42 (q, J=5.7 Hz, 2H).

According to procedure (B), methyl 3-cyclopropyl-4-({2-cyclopropyl-3-[(3-methylbutyl)carbamoyl]phenyl}amino)benzoate (86.0 mg, 205 moles, 1 eq.) was placed in methanol (2 mL) and a 2M aqueous solution of NaOH (1.03 mL, 2.05 mmoles, 10 eq.) was added. The reaction mixture was heated at 80° C. and stirred for 3 hours. It was then concentrated under reduced pressure and, after addition of an aqueous solution of 2M HCl (10 eq.), extracted with dichloromethane. The combined organic phases were dried over magnesium sulphate, filtered and concentrated under reduced pressure to give 3-cyclopropyl-4-({2-cyclopropyl-3-[(3-methylbutyl)carbamoyl]phenyl}amino)benzoic acid (73.0 mg, 83%).

$^1$H NMR (400 MHz, $d_6$-DMSO) δ 12.32 (s, 1H), 8.16 (t, J=5.6 Hz, 1H), 7.70-7.60 (m, 2H), 7.41 (s, 1H), 7.27 (dt, J=15.3, 7.3 Hz, 2H), 6.99-6.91 (m, 2H), 3.29-3.22 (m, 2H), 1.98-1.78 (m, 2H), 1.67 (dp, J=13.0, 6.5 Hz, 1H), 1.43 (q, J=7.0 Hz, 2H), 1.05-0.97 (m, 2H), 0.92 (d, J=6.6 Hz, 6H), 0.86-0.78 (m, 2H), 0.70-0.61 (m, 2H), 0.43 (q, J=5.8 Hz, 2H).

According to procedure (C), a reaction mixture of 3-cyclopropyl-4-({2-cyclopropyl-3-[(3-methylbutyl)carbamoyl]phenyl}amino)benzoic acid (66 mg, 154 moles, 1.0 eq.) and CDI (30.0 mg, 185 moles, 1.2 eq.) in anhydrous DMF (1.0 mL) was stirred at room temperature for 1 hour. The mixture was then added to a solution of imidazolidin-2-imine hydrobromide (53.9 mg, 309 moles, 2 eq.) and DIPEA (80.6 μL, 463 moles, 3 eq.) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was triturated in acetonitrile to afford 2-cyclopropyl-3-({2-cyclopropyl-4-[(imidazolidin-2-ylidene)carbamoyl] phenyl}amino)-N-(3-methylbutyl)benzamide (7) (20.0 mg, 26%).

$^1$H NMR (400 MHz, $d_6$-DMSO) δ 8.14 (t, J=5.5 Hz, 1H), 8.08 (s, 2H), 7.82 (d, J=8.5 Hz, 2H), 7.26-7.15 (m, 3H), 7.03 (d, J=8.2 Hz, 1H), 6.84 (d, J=6.2 Hz, 1H), 3.51 (s, 4H), 3.25 (q, J=6.5 Hz, 2H), 1.96-1.78 (m, 2H), 1.67 (dp, J=13.3, 6.7 Hz, 1H), 1.43 (q, J=7.0 Hz, 2H), 1.04-0.95 (m, 2H), 0.92 (d, J=6.6 Hz, 6H), 0.87 (d, J=8.6 Hz, 2H), 0.62 (q, J=5.4 Hz, 2H), 0.45 (q, J=5.4 Hz, 2H).

$^{13}$C NMR (151 MHz, $d_6$-DMSO) δ 175.7, 169.6, 165.7, 145.6, 143.1, 141.8, 130.6, 129.6, 129.0, 128.7, 128.2, 127.1, 120.5, 119.0, 114.2, 41.7, 38.4, 37.7, 25.8, 22.9, 11.9, 11.0, 7.3, 6.5

$[M+H]^+$=474.2

Example 2: Compound (25) in Table I 3-bromo-2-chlorobenzoic acid (500 mg, 2.1 mmoles, 1 eq.) and cyclopropanamine (173 μL, 2.5 mmoles, 1.2 eq.) were placed in anhydrous N,N-dimethylformamide (5 mL). HATU (1.24 g, 3.1 mmoles, 1.5 eq.) and DIPEA (1.1 mL, 6.2 mmoles, 3 eq.) were added and the resulting reaction mixture was stirred at room temperature for 16 hours. The reaction was quenched with 1M aqueous hydrochloric acid and extracted with ethyl acetate. The combined organic phases were dried over magnesium sulphate, filtered and concentrated under reduced pressure. The resulting residue was purified by column chromatography on silica gel to give 3-bromo-2-chloro-N-cyclopropylbenzamide (375 mg, 60%).

$^1$H NMR (400 MHz, $d_6$-DMSO) δ 8.54 (d, J=4.0 Hz, 1H), 7.82 (dd, J=8.0, 1.6 Hz, 1H), 7.40 (dd, J=7.6, 1.6 Hz, 1H), 7.32 (t, J=7.8 Hz, 1H), 2.81 (td, J=7.3, 4.0 Hz, 1H), 0.70 (td, J=7.0, 4.8 Hz, 2H), 0.54-0.49 (m, 2H).

According to route (A1), a reaction mixture of 3-bromo-2-chloro-N-cyclopropylbenzamide (108 mg, 0.392 mmole, 1.0 eq.), methyl 4-amino-3-cyclopropyl-benzoate (75 mg, 0.392 mmole, 1.0 eq.), BrettPhos Pd G3 (26.7 mg, 29.4 moles, 7.5 mol %) and $Cs_2CO_3$ (153 mg, 0.471 mmole, 1.2 eq.) in anhydrous DMF (2 mL) was degassed with $N_2$ and heated at 80° C. for 75 minutes under inert atmosphere. The reaction mixture was cooled down to room temperature, filtered over a pad of celite and the pad was washed with EtOAc. A saturated aqueous solution of brine was then added to the filtrate and the mixture was extracted with EtOAc. The combined organic phases were dried over $MgSO_4$, filtered and concentrated under reduced pressure. The resulting residue was purified by column chromatography on silica gel to give methyl 4-{[2-chloro-3-(cyclopropylcarbamoyl)phenyl]amino}-3-cyclopropylbenzoate (75 mg, 41%).

$^1$H NMR (500 MHz, $d_6$-DMSO) δ 8.47 (d, J=4.4 Hz, 1H), 7.69 (dd, J=8.5, 2.0 Hz, 1H), 7.63-7.58 (m, 2H), 7.36-7.29 (m, 2H), 7.08 (s, 1H), 6.89 (d, J=8.5 Hz, 1H), 3.79 (s, 3H), 2.82 (td, J=7.3, 3.8 Hz, 1H), 1.88 (s, 1H), 1.01-0.96 (m, 2H), 0.69 (dd, J=7.1, 2.2 Hz, 2H), 0.64 (dd, J=5.4, 1.7 Hz, 2H), 0.53 (dd, J=3.9, 2.4 Hz, 2H).

According to procedure (B), methyl 4-{[2-chloro-3-(cyclopropylcarbamoyl)phenyl]amino}-3-cyclopropylbenzoate (75 mg, 0.195 mmole, 1 eq.) was placed in methanol (3 mL) and an aqueous solution of 2M NaOH (0.808 mL, 1.62 mmole, 10 eq.) was added. The reaction mixture was heated at 80° C. and stirred for 3 hours.

It was then concentrated under reduced pressure and, after addition of an aqueous solution of 2M HCl (10 eq.), extracted with dichloromethane. The combined organic phases were dried over magnesium sulphate, filtered and concentrated under reduced pressure to give 4-{[2-chloro-3-(cyclopropylcarbamoyl)phenyl]amino}-3-cyclopropylbenzoic acid (70 mg, 97%).

$^1$H NMR (400 MHz, $d_6$-DMSO) δ 12.46 (s, 1H), 8.48 (d, J=4.4 Hz, 1H), 7.69 (dd, J=8.4, 2.0 Hz, 1H), 7.60 (d, J=1.8 Hz, 1H), 7.54 (s, 1H), 7.35-7.29 (m, 1H), 7.27 (dd, J=8.1, 1.8 Hz, 1H), 7.04 (dd, J=7.2, 1.8 Hz, 1H), 6.93 (d, J=8.4 Hz, 1H), 2.83 (td, J=7.3, 4.0 Hz, 1H), 1.93-1.84 (m, 1H), 1.01-0.95 (m, 2H), 0.69 (dt, J=7.0, 3.4 Hz, 2H), 0.64 (dd, J=5.4, 1.8 Hz, 2H), 0.53 (dd, J=4.0, 2.3 Hz, 2H).

According to procedure (C), a reaction mixture of 4-{[2-chloro-3-(cyclopropylcarbamoyl)phenyl]amino}-3-cyclopropylbenzoic acid (70 mg, 188 moles, 1.0 eq.) and CDI (36.5 mg, 225 moles, 1.2 eq.) in anhydrous DMF (1.0 mL) was stirred at room temperature for 1 hour. The mixture was then added to a solution of imidazolidin-2-imine hydrobromide (39.4 mg, 225 moles, 1.2 eq.) and DIPEA (98 μL, 563 moles, 3 eq.) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was purified by column chromatography on silica gel to give 4-{[2-chloro-3-(cyclopropylcarbamoyl)phenyl]amino}-3-cyclopropyl-N-(imidazolidin-2-ylidene)benzamide (25) (18.2 mg, 22%).

$^1$H NMR (400 MHz, $d_6$-DMSO) δ 8.45 (d, J=4.5 Hz, 1H), 8.11 (s, 2H), 7.85 (dd, J=8.3, 1.9 Hz, 1H), 7.79 (d, J=1.8 Hz, 1H), 7.33 (s, 1H), 7.23 (s, 1H), 7.10 (d, J=1.5 Hz, 1H), 7.04 (d, J=8.3 Hz, 1H), 6.92-6.85 (m, 1H), 3.52 (s, 4H), 2.87-2.79 (m, 1H), 1.87 (s, 1H), 0.98-0.91 (m, 2H), 0.70 (td, J=7.1, 4.8 Hz, 2H), 0.60 (dd, J=5.5, 1.8 Hz, 2H), 0.56-0.50 (m, 2H).

$^{13}$C NMR (151 MHz, $d_6$-DMSO) δ 175.5, 168.1, 165.8, 144.0, 140.9, 138.9, 132.9, 132.6, 127.9, 127.8, 120.3, 119.5, 118.8, 118.1, 41.7, 23.1, 11.7, 7.3, 6.1 $[M+H]^+$=438.0

Example 3: Compound (26) in Table I 2-methylpropanoic acid (461 mg, 5.23 mmoles, 1.2 eq.) and 3-bromoaniline (475 L, 4.36 mmoles, 1.0 eq.) were placed in anhydrous N,N-dimethylformamide (10 mL). HATU (2.59 g, 6.54 mmoles, 1.5 eq.) and DIPEA (2.30 mL, 13.1 mmoles, 3.0 eq.) were added and the resulting reaction mixture was stirred at room temperature for 16 hours. The reaction was quenched with 1M aqueous hydrochloric acid and extracted with ethyl acetate.

The combined organic phases were dried over magnesium sulphate, filtered and concentrated under reduced pressure. The resulting residue was purified by column chromatography on silica gel to give N-(3-bromophenyl)-2-methylpropanamide (979 mg, 88%).

$^{1}$H NMR (400 MHz, $d_6$-DMSO) δ 9.98 (s, 1H), 7.98 (d, J=1.8 Hz, 1H), 7.51 (d, J=7.9 Hz, 1H), 7.26 (t, J=7.9 Hz, 1H), 7.21 (d, J=8.1 Hz, 1H), 2.58 (p, J=6.8 Hz, 1H), 1.10 (d, J=6.8 Hz, 6H).

According to route (A1), a reaction mixture of N-(3-bromophenyl)-2-methylpropanamide (279 mg, 1.15 mmole, 1.1 eq.), methyl 4-amino-3-cyclopropyl-benzoate (200 mg, 1.05 mmole, 1.0 eq.), BrettPhos Pd G3 (47.4 mg, 52.3 moles, 5 mol %) and $Cs_2CO_3$ (409 mg, 1.26 mmole, 1.2 eq.) in anhydrous DMF (3 mL) was degassed with $N_2$ and heated at 80° C. for 75 minutes under inert atmosphere. The reaction mixture was cooled down to room temperature, filtered over a pad of celite and the pad was washed with EtOAc. A saturated aqueous solution of brine was then added to the filtrate and the mixture was extracted with EtOAc. The combined organic phases were dried over $MgSO_4$, filtered and concentrated under reduced pressure. The resulting residue was purified by column chromatography on silica gel to give methyl 3-cyclopropyl-4-{[3-(2-methylpropanamido)phenyl]amino}benzoate (368 mg, 99%).

$^{1}$H NMR (400 MHz, $d_6$-DMSO) δ 9.77 (s, 1H), 7.86 (s, 1H), 7.66 (dd, J=8.5, 2.1 Hz, 1H), 7.59 (d, J=1.9 Hz, 1H), 7.54 (d, J=2.0 Hz, 1H), 7.25-7.17 (m, 2H), 7.14 (d, J=8.5 Hz, 1H), 6.85 (d, J=7.3 Hz, 1H), 3.78 (s, 3H), 2.63-2.53 (m, 1H), 1.95 (s, 1H), 1.09 (d, J=6.8 Hz, 6H), 0.98 (dd, J=8.3, 2.0 Hz, 2H), 0.60 (d, J=3.6 Hz, 2H).

According to procedure (B), methyl 3-cyclopropyl-4-{[3-(2-methylpropanamido)phenyl]amino}benzoate (368 mg, 1.04 mmole, 1 eq.) was placed in methanol (3 mL) and an aqueous solution of 2M NaOH (2.61 mL, 5.21 mmoles, 5 eq.) was added. The reaction mixture was heated at 80° C. and stirred for 3 hours. It was then concentrated under reduced pressure and, after addition of an aqueous solution of 2M HCl (10 eq.), extracted with dichloromethane. The combined organic phases were dried over magnesium sulphate, filtered and concentrated under reduced pressure to give 3-cyclopropyl-4-{[3-(2-methylpropanamido)phenyl]amino}benzoic acid (278 mg, 79%).

$^{1}$H NMR (400 MHz, $d_6$-DMSO) δ 12.34 (s, 1H), 9.75 (s, 1H), 7.80 (s, 1H), 7.64 (dd, J=8.5, 2.0 Hz, 1H), 7.54 (dd, J=12.8, 1.9 Hz, 2H), 7.24-7.10 (m, 3H), 6.84 (dt, J=7.3, 1.9 Hz, 1H), 2.58 (p, J=6.8 Hz, 1H), 1.95 (tt, J=8.4, 5.4 Hz, 1H), 1.09 (d, J=6.8 Hz, 6H), 0.97 (dd, J=8.3, 2.0 Hz, 2H), 0.63-0.56 (m, 2H).

According to procedure (C), a reaction mixture of 3-cyclopropyl-4-{[3-(2-methylpropanamido)phenyl]amino}benzoic acid (178 mg, 526 moles, 1.0 eq.) and CDI (102 mg, 631 moles, 1.2 eq.) in anhydrous DMF (1.0 mL) was stirred at room temperature for 1 hour. The mixture was then added to a solution of imidazolidin-2-imine hydrobromide (110 mg, 631 moles, 1.2 eq.) and DIPEA (276 μL, 1.58 mmole, 3 eq.) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was purified by column chromatography on silica gel followed by preparative TLC to give 3-cyclopropyl-N-(imidazolidin-2-ylidene)-4-{[3-(2-methylpropanamido)phenyl]amino}benzamide (26) (25.7 mg, 12%).

$^{1}$H NMR (400 MHz, $d_6$-DMSO) δ 9.71 (s, 1H), 8.21 (s, 2H), 7.82-7.73 (m, 1H), 7.69 (s, 2H), 7.51 (s, 1H), 7.13 (dt, J=13.7, 7.3 Hz, 3H), 6.78 (d, J=7.7 Hz, 1H), 3.56 (s, 4H), 2.61-2.54 (m, 1H), 1.98 (d, J=14.4 Hz, 1H), 1.08 (d, J=6.8 Hz, 6H), 0.95 (d, J=8.4 Hz, 2H), 0.58 (d, J=4.0 Hz, 2H).

$^{13}$C NMR (151 MHz, $d_6$-DMSO) δ 175.6, 146.1, 144.0, 140.6, 131.1, 129.5, 127.8, 127.5, 116.0, 114.2, 112.2, 109.9, 41.9, 35.3, 19.9, 11.6, 7.6 $[M+H]^+$=406.0

Example 4: Compound (41) in Table I

According to procedure (E), a solution of methyl 4-amino-3-bromobenzoate (3.00 g, 12.8 mmoles, 1 eq.) and potassium cyclopropyltrifluoroborate (2.84 g, 19.2 mmoles, 1.5 eq.) in toluene (52.5 mL) and water (13.5 mL) was degassed with argon during 5 minutes then tripotassium phosphate (6.88 g, 31.9 mmoles, 2.5 eq.), RuPhos (239 mg, 511 moles, 0.04 eq.) andpalladium(II) acetate (57.9 mg, 256 moles, 0.02 eq.) were added. The reaction mixture was heated at 110° C. and stirred for 2h30 under inert atmosphere. Upon cooling down to room temperature, it was filtered over a pad of celite and the pad was washed with EtOAc. A saturated aqueous solution of brine was then added to the filtrate and the mixture was extracted with EtOAc. The combined organic layers were dried over $MgSO_4$, filtered and concentrated under reduced pressure. The resulting residue was purified by column chromatography on silica gel to give methyl 4-amino-3-cyclopropylbenzoate (2.02 g, 81%).

$^{1}$H NMR (400 MHz, $d_6$-DMSO) δ 7.53 (dd, J=8.4, 2.0 Hz, 1H), 7.42 (d, J=1.9 Hz, 1H), 6.63 (d, J=8.4 Hz, 1H), 5.87 (s, 2H), 3.73 (s, 3H), 1.65 (tt, J=8.3, 5.4 Hz, 1H), 0.95-0.82 (m, 2H), 0.54-0.40 (m, 2H).

3-Bromophenol (701 mg, 3.97 mmoles, 1.2 eq.) was placed in N,N-dimethylformamide (4 mL) with $Cs_2CO_3$ (1.3 g, 3.97 mmoles, 1.2 eq.). Upon addition of (3-bromopropyl)cyclohexane (715 mg, 3.31 mmoles, 1 eq.), the reaction mixture was stirred at room temperature for 16 hours under an inert atmosphere of argon. To the reaction mixture was added a saturated aqueous solution of $NaHCO_3$ and it was extracted with ethyl acetate. The combined organic phases were dried over magnesium sulphate, filtered and concentrated under reduced pressure. The resulting residue was purified by column chromatography on silica gel to give 1-bromo-3-(3-cyclohexylpropoxy)benzene (882 mg, 90%).

$^{1}$H NMR (500 MHz, $d_6$-DMSO) δ 7.22 (t, J=8.1 Hz, 1H), 7.14-7.08 (m, 2H), 6.93 (dd, J=8.3, 2.3 Hz, 1H), 3.95 (t, J=6.5 Hz, 2H), 1.68 (tt, J=15.1, 9.2 Hz, 7H), 1.32-1.06 (m, 6H), 0.92-0.82 (m, 2H).

According to procedure (A1), a reaction mixture of 1-bromo-3-(3-cyclohexylpropoxy)benzene (547 mg, 1.84 mmole, 1.1 eq.), methyl 4-amino-3-cyclopropyl-benzoate (320 mg, 1.67 mmole, 1 eq.), BrettPhos Pd G3 (31.9 mg, 33.5 moles, 2 mol %) and $Cs_2CO_3$ (818 mg, 2.51 mmoles, 1.5 eq.) in anhydrous DMF (8 mL) was degassed with $N_2$ and heated at 80° C. for 75 minutes under inert atmosphere. The reaction mixture was cooled down to room temperature, filtered over a pad of celite and the pad was washed with EtOAc. A saturated aqueous solution of brine was then added to the filtrate and the mixture was extracted with EtOAc. The combined organic phases were dried over $MgSO_4$, filtered and concentrated under reduced pressure. The resulting residue was purified by column chromatography on silica gel to give methyl 4-{[3-(3-cyclohexylpropoxy)phenyl]amino}-3-cyclopropylbenzoate (1.35 g, 80%).

$^{1}$H NMR (400 MHz, $d_6$-DMSO) δ 7.82 (s, 1H), 7.66 (dd, J=8.5, 2.0 Hz, 1H), 7.54 (d, J=2.0 Hz, 1H), 7.24-7.14 (m, 2H), 6.76 (d, J=7.9 Hz, 1H), 6.73 (t, J=2.1 Hz, 1H), 6.56 (dd, J=8.1, 2.2 Hz, 1H), 3.92 (t, J=6.5 Hz, 2H), 3.78 (s, 3H), 1.94

(ddd, J=13.8, 8.3, 5.4 Hz, 1H), 1.75-1.58 (m, 7H), 1.35-1.08 (m, 6H), 1.04-0.94 (m, 2H), 0.88 (q, J=10.0, 9.3 Hz, 2H), 0.65-0.56 (m, 2H).

According to procedure (B), methyl 4-{[3-(3-cyclohexylpropoxy)phenyl]amino}-3-cyclopropylbenzoate (575 mg, 1.34 mmole, 1 eq.) was placed in methanol (10 mL) and an aqueous solution of 2M NaOH (4.7 mL, 9.4 mmoles, 7 eq.) was added. The reaction mixture was heated at 80° C. and stirred for 3 hours. It was then concentrated under reduced pressure and, after addition of an aqueous solution of 2M HCl (7 mL, 14 mmoles, 10.5 eq.), extracted with dichloromethane. The combined organic phases were dried over magnesium sulphate, filtered and concentrated under reduced pressure to give 4-{[3-(3-cyclohexylpropoxy)phenyl]amino}-3-cyclopropylbenzoic acid (540 mg, 97%).

$^1$H NMR (400 MHz, $d_6$-DMSO) δ 12.37 (s, 1H), 7.76 (s, 1H), 7.64 (dd, J=8.5, 2.0 Hz, 1H), 7.52 (d, J=1.9 Hz, 1H), 7.18 (t, J=8.6 Hz, 2H), 6.74 (d, J=7.9 Hz, 1H), 6.71 (d, J=2.1 Hz, 1H), 6.53 (dd, J=8.1, 2.1 Hz, 1H), 3.91 (t, J=6.5 Hz, 2H), 1.94 (ddd, J=13.6, 8.4, 5.4 Hz, 1H), 1.75-1.58 (m, 7H), 1.35-1.09 (m, 6H), 0.98 (dd, J=4.0, 2.0 Hz, 2H), 0.88 (q, J=10.1, 9.3 Hz, 2H), 0.65-0.56 (m, 2H).

According to procedure (C), a reaction mixture of 4-{[3-(3-cyclohexylpropoxy)phenyl]amino}-3-cyclopropylbenzoic acid (150 mg, 362 moles, 1 eq.) and CDI (70.5 mg, 435 moles, 1.2 eq.) in anhydrous DMF (3.0 mL) was stirred at room temperature for 1 hour. The mixture was then added to a solution of guanidinium carbonate (2:1 salt) (130 mg, 724 moles, 2 eq.) and DIPEA (158 µL, 905 moles, 2.5 eq) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was purified by column chromatography on silica gel to give 4-{[3-(3-cyclohexylpropoxy)phenyl]amino}-3-cyclopropyl-N-(diaminomethylidene)benzamide (135 mg, 82%).

$^1$H NMR (400 MHz, $d_6$-DMSO) δ 7.79 (d, J=8.4 Hz, 1H), 7.70 (s, 1H), 7.57 (s, 1H), 7.12 (dd, J=11.2, 8.5 Hz, 2H), 6.64 (d, J=8.0 Hz, 1H), 6.60 (s, 1H), 6.41 (d, J=8.2 Hz, 1H), 3.89 (t, J=6.4 Hz, 2H), 2.00-1.88 (m, 1H), 1.68 (t, J=13.7 Hz, 7H), 1.34-1.09 (m, 6H), 0.91 (dd, J=28.4, 9.6 Hz, 4H), 0.58 (d, J=5.0 Hz, 2H).

To a solution of 4-{[3-(3-cyclohexylpropoxy)phenyl]amino}-3-cyclopropyl-N-(diaminomethylidene)benzamide (69.0 mg, 151 moles, 1 eq.) and DIPEA (131 µL, 754 moles, 5 eq.) in anhydrous DMF (1.5 mL) was added 2-chloroacetyl chloride (23.7 µL, 226 moles, 1.5 eq.). The resulting reaction mixture was stirred at room temperature for 2 hours and then heated at 90° C. and stirred for 2 hours. The reaction mixture was then cooled down to room temperature, quenched with a saturated aqueous solution of sodium bicarbonate and extracted with DCM. The combined organic layers were then washed with a saturated aqueous solution of brine, dried over $MgSO_4$, filtered and concentrated under reduced pressure. The resulting residue was purified by column chromatography on silica gel to give 4-{[3-(3-cyclohexylpropoxy)phenyl]amino}-3-cyclopropyl-N-[(2E)-4-oxoimidazolidin-2-ylidene]benzamide (41) (4.0 mg, 5%).

$^1$H NMR (400 MHz, $d_6$-DMSO) δ 11.24 (s, 1H), 9.35 (s, 1H), 7.81 (d, J=9.6 Hz, 1H), 7.75 (s, 2H), 7.16 (t, J=8.2 Hz, 2H), 6.78-6.64 (m, 2H), 6.50 (d, J=8.5 Hz, 1H), 4.06 (s, 2H), 3.91 (t, J=6.5 Hz, 2H), 1.93 (d, J=13.8 Hz, 1H), 1.67 (d, J=14.8 Hz, 7H), 1.30-1.16 (m, 6H), 0.98 (d, J=8.6 Hz, 2H), 0.86 (s, 2H), 0.61 (s, 2H). $[M+H]^+$=475.1

Example 5: Compound (45) in Table I 3-bromo-2-chlorobenzoic acid (200 mg, 832 moles, 1 eq.) and morpholine (87.0 mg, 999 moles, 1.2 eq.) were placed in anhydrous N,N-dimethylformamide (4 mL). HATU (495 mg, 1.25 mmole, 1.5 eq.) and DIPEA (438 µL, 2.50 mmoles, 3 eq.) were added and the resulting reaction mixture was stirred at room temperature for 16 hours. The reaction was quenched with 1M aqueous hydrochloric acid and extracted with ethyl acetate. The combined organic phases were dried over magnesium sulphate, filtered and concentrated under reduced pressure. The resulting residue was purified by column chromatography on silica gel to give 4-(3-bromo-2-chlorobenzoyl)morpholine (216 mg, 85%).

$^1$H NMR (400 MHz, $d_6$-DMSO) δ 7.84 (dd, J=7.8, 1.7 Hz, 1H), 7.46-7.33 (m, 2H), 3.66 (qd, J=8.3, 7.2, 3.8 Hz, 4H), 3.56-3.51 (m, 2H), 3.15-3.10 (m, 2H).

The experimental set-up was dried with a heat gun under a nitrogen stream, kept under inert atmosphere and then cooled down to room temperature. Methyl 3-acetyl-4-aminobenzoate (1.10 g, 5.41 mmoles, 1 eq.) and anhydrous THF (40 mL) were then added and the reaction mixture was cooled down to −10° C. A 3M methylmagnesium bromide solution in diethyl ether (3.79 mL, 11.4 mmoles, 2.1 eq.) was added dropwise and the reaction mixture was stirred at −10° C. during 30 minutes, then additional 3M methylmagnesium bromide solution in diethyl ether (1.80 mL, 5.43 mmoles, 1 eq.) was added and the reaction mixture was further stirred at −10° C. during 30 minutes. The reaction mixture was quenched with a saturated aqueous solution of ammonium chloride at −10° C. then warmed up to room temperature and extracted with DCM. The combined organic phases were dried over magnesium sulphate, filtered and concentrated under reduced pressure. The resulting residue was purified by column chromatography on silica gel to give methyl 4-amino-3-(2-hydroxypropan-2-yl)benzoate (986 mg, 87%).

$^1$H NMR (400 MHz, $d_6$-DMSO) δ 7.64 (s, 1H), 7.55 (d, J=8.4 Hz, 1H), 6.64 (d, J=8.4 Hz, 1H), 6.22 (s, 2H), 5.37 (s, 1H), 3.74 (s, 3H), 1.51 (s, 6H).

According to route (A1), a mixture of 4-(3-bromo-2-chlorobenzoyl)morpholine (218 mg, 717 moles, 1.5 eq.), methyl 4-amino-3-(2-hydroxypropan-2-yl)benzoate (100 mg, 478 moles, 1 eq.), $Pd(OAc)_2$ (3.2 mg, 14.3 moles, 3 mol %), rac-BINAP (6.0 mg, 9.6 µmoles, 2 mol %) and $K_2CO_3$ (198 mg, 1.43 mmole, 3 eq.) in anhydrous toluene (3 mL) was degassed with $N_2$ and heated at 110° C. for 75 minutes under inert atmosphere. The reaction mixture was cooled down to room temperature, filtered over a pad of celite and the pad was washed with EtOAc. A saturated aqueous solution of brine was then added to the filtrate and the mixture was extracted with EtOAc. The combined organic phases were dried over $MgSO_4$, filtered and concentrated under reduced pressure. The resulting residue was purified by column chromatography on silica gel to give methyl 4-{[2-chloro-3-(morpholine-4-carbonyl)phenyl]amino}-3-(2-hydroxypropan-2-yl)benzoate (278 mg, 99%).

$^1$H NMR (400 MHz, $d_6$-DMSO) δ 9.53 (s, 1H), 7.86 (d, J=2.0 Hz, 1H), 7.79 (dd, J=8.5, 2.0 Hz, 1H), 7.47 (dd, J=8.2, 1.4 Hz, 1H), 7.33 (dd, J=8.3, 4.5 Hz, 2H), 6.95 (dd, J=7.4, 1.4 Hz, 1H), 6.18 (s, 1H), 3.82 (s, 3H), 3.67 (s, 4H), 3.58-3.54 (m, 2H), 3.22-3.18 (m, 2H), 1.58 (d, J=5.8 Hz, 6H).

According to procedure (B), methyl 4-{[2-chloro-3-(morpholine-4-carbonyl)phenyl]amino}-3-(2-hydroxypropan-2- yl)benzoate (278 mg, 642 moles, 1 eq.) was placed in methanol (5 mL) and a 2M aqueous solution of NaOH (1.61 mL, 3.21 mmoles, 5 eq.) was added. The reaction mixture was heated at 80° C. and stirred for 3 hours. It was then concentrated under reduced pressure and, after addition of an aqueous solution of 2M HCl (10 eq.), extracted with dichloromethane. The combined organic phases were dried over magnesium sulphate, filtered and concentrated under reduced pressure to give 4-{[2-chloro-3-(morpholine-4-carbonyl)phenyl]amino}-3-(2-hydroxypropan-2-yl)benzoic acid (240 mg, 55%).

$^1$H NMR (400 MHz, $d_6$-DMSO) δ 12.56 (s, 1H), 9.48 (s, 1H), 7.86 (d, J=1.9 Hz, 1H), 7.77 (dd, J=8.5, 1.9 Hz, 1H), 7.46 (d, J=8.2 Hz, 1H), 7.33 (d, J=1.9 Hz, 2H), 6.92 (dd, J=7.4, 1.3 Hz, 1H), 6.14 (s, 1H), 3.67 (s, 4H), 3.58-3.54 (m, 2H), 3.22-3.18 (m, 2H), 1.58 (d, J=6.5 Hz, 6H).

According to procedure (C), a reaction mixture of 4-{[2-chloro-3-(morpholine-4-carbonyl)phenyl]amino}-3-(2-hydroxypropan-2-yl)benzoic acid (80 mg, 191 moles, 1.0 eq.) and CDI (37.2 mg, 229 moles, 1.2 eq.) in anhydrous DMF (1.0 mL) was stirred at room temperature for 1 hour. The mixture was then added to a solution of imidazolidin-2-imine hydrobromide (63.4 mg, 382 moles, 2 eq.) and DIPEA (100 μL, 573 moles, 3 eq.) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was purified by column chromatography on silica gel to give 4-{[2-chloro-3-(morpholine-4-carbonyl)phenyl]amino}-3-(2-hydroxypropan-2-yl)-N-(imidazolidin-2-ylidene)benzamide (45) (9.9 mg, 11%).

$^1$H NMR (400 MHz, $d_6$-DMSO) δ 9.33 (s, 1H), 8.13 (s, 2H), 8.05 (s, 1H), 7.92 (d, J=8.2 Hz, 1H), 7.42 (d, J=7.4 Hz, 1H), 7.29 (dd, J=8.1, 3.9 Hz, 2H), 6.85 (d, J=7.7 Hz, 1H), 6.04 (s, 1H), 3.67 (s, 4H), 3.59-3.50 (m, 6H), 3.21 (d, J=5.1 Hz, 2H), 1.56 (d, J=10.1 Hz, 6H).

$^{13}$C NMR (151 MHz, $d_6$-DMSO) δ 166.3, 140.3, 137.3, 135.5, 128.8, 128.6, 127.1, 118.9, 118.2, 117.9, 116.9, 72.8, 66.6, 66.4, 47.1, 41.9, 41.7, 29.9 $[M+H]^+$=486.2

Example 6: Compound (46) in Table I

According to procedure (C), a reaction mixture of 4-{[3-(3-cyclohexylpropoxy)phenyl]amino}-3-cyclopropylbenzoic acid (100 mg, 241 moles, 1 eq.) and CDI (47.0 mg, 290 moles, 1.2 eq.) in anhydrous DMF (1.0 mL) was stirred at room temperature for 1 hour. The mixture was then added to a solution of imidazolidin-2-imine hydrobromide (84.4 mg, 483 moles, 2 eq.) and DIPEA (126 μL, 724 moles, 3 eq.) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was purified by column chromatography on silica gel to give 4-{[3-(3-cyclohexylpropoxy)phenyl]amino}-3-cyclopropyl-N-(imidazolidin-2-ylidene)benzamide (27.0 mg, 23%).

$^1$H NMR (400 MHz, $d_6$-DMSO) δ 8.08 (s, 2H), 7.79 (dd, J=8.4, 1.9 Hz, 1H), 7.70 (d, J=1.8 Hz, 1H), 7.58 (s, 1H), 7.18-7.07 (m, 2H), 6.65 (d, J=8.0 Hz, 1H), 6.61 (t, J=2.1 Hz, 1H), 6.43 (dd, J=8.1, 2.2 Hz, 1H), 3.89 (t, J=6.5 Hz, 2H), 3.51 (s, 4H), 1.94 (ddd, J=13.7, 8.4, 5.5 Hz, 1H), 1.74-1.58 (m, 7H), 1.21 (ddt, J=36.1, 21.2, 10.0 Hz, 6H), 0.98-0.83 (m, 4H), 0.61-0.52 (m, 2H). $[M+H]^+$=431.3

To a solution of 4-{[3-(3-cyclohexylpropoxy)phenyl]amino}-3-cyclopropyl-N-(imidazolidin-2-ylidene)benzamide (84.0 mg, 109 moles, 1 eq.) and DIPEA (95 μL, 547 moles, 5 eq.) in DCM (2.0 mL) was added acetyl chloride (16 μL, 219 moles, 2.0 eq.).

The resulting reaction mixture was stirred at room temperature for 20 minutes and then quenched with a saturated aqueous solution of brine and extracted with DCM. The combined organic layers were then dried over $MgSO_4$, filtered and concentrated under reduced pressure. The resulting residue was purified by column chromatography on silica gel to give N-[(2E)-1-acetylimidazolidin-2-ylidene]-4-{[3-(3-cyclohexylpropoxy)phenyl]amino}-3-cyclopropylbenzamide (46) (12.0 mg, 20%).

$^1$H NMR (400 MHz, $d_6$-DMSO) δ 9.70 (s, 1H), 7.81 (d, J=8.4 Hz, 1H), 7.73 (d, J=10.6 Hz, 2H), 7.16 (dd, J=14.6, 8.2 Hz, 2H), 6.71 (d, J=8.1 Hz, 1H), 6.67 (s, 1H), 6.48 (d, J=8.4 Hz, 1H), 3.91 (t, J=6.5 Hz, 2H), 3.87-3.78 (m, 2H), 3.59 (t, J=8.5 Hz, 2H), 2.72 (s, 3H), 1.96 (t, J=5.3 Hz, 1H), 1.68 (t, J=14.8 Hz, 7H), 1.33-1.09 (m, 6H), 0.98 (q, J=5.1, 4.5 Hz, 2H), 0.88 (q, J=10.2, 9.2 Hz, 2H), 0.58 (q, J=5.1 Hz, 2H).

$^{13}$C NMR (151 MHz, $d_6$-DMSO) δ 176.3, 170.0, 160.0, 158.4, 146.5, 144.8, 131.1, 130.2, 129.6, 128.1, 127.8, 115.8, 111.5, 107.6, 105.5, 68.1, 42.5, 37.2, 33.7, 33.3, 26.6, 26.5, 26.3, 25.9, 11.4, 7.7 $[M+H]^+$=503.1

Example 7: Compound (123) in Table I 2,3-dichloropyridine-4-carboxylic acid (288 mg, 1.5 mmole, 1 eq.) and 1-methylcyclopropan-1-amine hydrochloride (178 mg, 1.58 mmole, 1.05 eq.) were placed in anhydrous N,N-dimethylformamide (4 mL). HATU (570 mg, 1.5 mmole, 1.0 eq.) and DIPEA (523 μL, 3.75 mmoles, 2.5 eq.) were added and the resulting reaction mixture was stirred at room temperature for 16 hours. The reaction was quenched with 1M aqueous hydrochloric acid and extracted with ethyl acetate. The combined organic phases were dried over magnesium sulphate, filtered and concentrated under reduced pressure. The resulting residue was purified by column chromatography on silica gel to give 2,3-dichloro-N-(1-methylcyclopropyl)pyridine-4-carboxamide (213 mg, 58%).

$^1$H NMR (400 MHz, $d_6$-DMSO) δ 8.88 (s, 1H), 8.43 (d, J=4.8 Hz, 1H), 7.46 (d, J=4.8 Hz, 1H), 1.39 (s, 3H), 0.77-0.72 (m, 2H), 0.65-0.60 (m, 2H).

According to route (A1), a reaction mixture of 2,3-dichloro-N-(1-methylcyclopropyl)pyridine-4-carboxamide (100 mg, 0.408 mmole, 1.0 eq.), methyl 4-amino-3-cyclopropyl-benzoate (78 mg, 0.408 mmole, 1.0 eq.), BrettPhos Pd G3 (18.5 mg, 20.4 moles, 5 mol %) and $Cs_2CO_3$ (199 mg, 0.612 mmole, 1.5 eq.) in anhydrous DMF (2 mL) was degassed with $N_2$ and heated at 80° C. for 75 minutes under inert atmosphere. The reaction mixture was cooled down to room temperature, filtered over a pad of celite and the pad was washed with EtOAc. A saturated aqueous solution of brine was then added to the filtrate and the mixture was extracted with EtOAc. The combined organic phases were dried over $MgSO_4$, filtered and concentrated under reduced pressure. The resulting residue was purified by column chromatography on silica gel to give methyl 4-({3-chloro-4-[(1-methylcyclopropyl)carbamoyl]pyridin-2-yl}amino)-3-cyclopropylbenzoate (56 mg, 34%).

According to procedure (B), methyl 4-({3-chloro-4-[(1-methylcyclopropyl)carbamoyl]pyridin-2-yl}amino)-3-cyclopropylbenzoate (56 mg, 0.140 mmole, 1 eq.) was placed in methanol (2 mL) and an aqueous solution of 1M NaOH (0.700 mL, 0.700 mmole, 5 eq.) was added. The reaction mixture was heated at 80° C. and stirred for 3 hours. It was then concentrated under reduced pressure and, after addition of an aqueous solution of 1M HCl (5 eq.), extracted with dichloromethane. The combined organic phases were dried over magnesium sulphate, filtered and concentrated under reduced pressure to give 4-({3-chloro-4-[(1-methylcyclopropyl)carbamoyl]pyridin-2-yl}amino)-3-cyclopropylbenzoic acid (51 mg, 94%).

According to procedure (C), a reaction mixture of 4-({3-chloro-4-[(1-methylcyclopropyl)carbamoyl]pyridin-2-yl}amino)-3-cyclopropylbenzoic acid (51 mg, 132 μmoles, 1.0 eq.) and CDI (32.1 mg, 198 moles, 1.5 eq.) in anhydrous DMF (1.0 mL) was stirred at room temperature for 1 hour. The mixture was then added to a solution of imidazolidin-2-imine hydrobromide (46.2 mg, 264 moles, 2.0 eq.) and DIPEA (69.3 μL, 397 moles, 3 eq.) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was purified by preparative HPLC to give 3-chloro-2-[(2-cyclopropyl-4-{[imidazolidin-2-ylidene]carbamoyl}phenyl)amino]-N-(1-methylcyclopropyl)pyridine-4-carboxamide (123) (9.0 mg, 14%).

$^1$H NMR (400 MHz, $d_6$-DMSO) δ 8.79 (s, 1H), 8.30 (s, 1H), 8.15 (dd, J=9.0, 4.2 Hz, 4H), 7.92 (dd, J=8.4, 1.9 Hz, 1H), 7.90-7.87 (m, 1H), 6.80 (d, J=4.9 Hz, 1H), 3.53 (s, 4H), 1.91 (ddd, J=13.6, 8.4, 5.4 Hz, 1H), 1.40 (s, 3H), 1.05-1.00 (m, 2H), 0.77-0.73 (m, 2H), 0.64-0.59 (m, 4H). $[M+H]^+$ =453.2

Example 8: Compound (136) in Table I

According to procedure (E), a solution of methyl 4-amino-3-bromo-5-fluorobenzoate (1.00 g, 4.03 mmoles, 1 eq) and potassium cyclopropyltrifluoroborate (895 mg, 6.04 mmoles, 1.5 eq.) in toluene (16 mL) and water (4 mL) was degassed with argon during 5 minutes then tripotassium phosphate (2.17 g, 10.1 mmoles, 2.5 eq.), RuPhos (75.2 mg, 161 moles, 0.04 eq.) and palladium(II) acetate (18.3 mg, 80.6 moles, 0.02 eq.) were added. The reaction mixture was heated at 110° C. and stirred for 2h30 under inert atmosphere. Upon cooling down to room temperature, it was filtered over a pad of celite and the pad was washed with EtOAc. A saturated aqueous solution of brine was then added to the filtrate and the mixture was extracted with EtOAc. The combined organic layers were dried over $MgSO_4$, filtered and concentrated under reduced pressure. The resulting residue was purified by column chromatography on silica gel to give methyl 4-amino-3-cyclopropyl-5-fluorobenzoate (847 mg, 100%).

$^1$H NMR (400 MHz, $d_6$-DMSO) δ 7.39 (dd, J=11.8, 1.9 Hz, 1H), 7.28 (d, J=1.7 Hz, 1H), 5.91 (s, 2H), 3.75 (s, 3H), 1.77 (tt, J=8.3, 5.4 Hz, 1H), 1.00-0.90 (m, 2H), 0.59-0.45 (m, 2H).

According to route (A1), a reaction mixture of 2,3-dichloro-N-(1-methylcyclopropyl)pyridine-4-carboxamide (100 mg, 0.408 mmole, 1.0 eq.), methyl 4-amino-3-cyclopropyl-5-fluorobenzoate (85 mg, 0.408 mmole, 1.0 eq.), BrettPhos Pd G3 (39.0 mg, 40.8 μmoles, 10 mol %) and $Cs_2CO_3$ (199 mg, 0.612 mmole, 1.5 eq.) in anhydrous DMF (2 mL) was degassed with $N_2$ and heated at 80° C. for 75 minutes under inert atmosphere. The reaction mixture was cooled down to room temperature, filtered over a pad of celite and the pad was washed with EtOAc. A saturated aqueous solution of brine was then added to the filtrate and the mixture was extracted with EtOAc. The combined organic phases were dried over $MgSO_4$, filtered and concentrated under reduced pressure. The resulting residue was purified by column chromatography on silica gel to give methyl 4-({3-chloro-4-[(1-methylcyclopropyl)carbamoyl]pyridin-2-yl}amino)-3-cyclopropyl-5-fluorobenzoate (40 mg, 24%).

$^1$H NMR (400 MHz, $d_6$-DMSO) δ 8.78 (s, 1H), 8.42 (s, 1H), 7.91 (d, J=4.9 Hz, 1H), 7.55 (dd, J=9.9, 1.8 Hz, 1H), 7.33 (s, 1H), 6.67 (d, J=4.9 Hz, 1H), 3.86 (s, 3H), 2.08-2.00 (m, 1H), 1.40 (s, 3H), 0.95-0.88 (m, 2H), 0.77-0.72 (m, 2H), 0.65 (q, J=5.1, 4.5 Hz, 2H), 0.63-0.59 (m, 2H).

According to procedure (B), methyl 4-({3-chloro-4-[(1-methylcyclopropyl)carbamoyl]pyridin-2-yl}amino)-3-cyclopropyl-5-fluorobenzoate (40 mg, 0.096 mmole, 1 eq.) was placed in methanol (2 mL) and an aqueous solution of 1M NaOH (0.479 mL, 0.479 mmole, 5 eq.) was added. The reaction mixture was heated at 80° C. and stirred for 3 hours. It was then concentrated under reduced pressure and, after addition of an aqueous solution of 1M HCl (5 eq.), extracted with dichloromethane. The combined organic phases were dried over magnesium sulphate, filtered and concentrated under reduced pressure to give 4-({3-chloro-4-[(1-methylcyclopropyl)carbamoyl]pyridin-2-yl}amino)-3-cyclopropyl-5-fluorobenzoic acid (38.6 mg, 100%).

According to procedure (C), a reaction mixture of 4-({3-chloro-4-[(1-methylcyclopropyl)carbamoyl]pyridin-2-yl}amino)-3-cyclopropyl-5-fluorobenzoic acid (38.6 mg, 96 μmoles, 1.0 eq.) and CDI (23.3 mg, 144 moles, 1.5 eq.) in anhydrous DMF (1.0 mL) was stirred at room temperature for 1 hour. The mixture was then added to a solution of imidazolidin-2-imine hydrobromide (33.4 mg, 191 moles, 2.0 eq.) and DIPEA (50.1 μL, 287 moles, 3 eq.) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was purified by preparative HPLC to give 3-chloro-2-[(2-cyclopropyl-6-fluoro-4-{[imidazolidin-2-ylidene]carbamoyl}phenyl)amino]-N-(1-methylcyclopropyl)pyridine-4-carboxamide (136) (14.1 mg, 30%).

$^1$H NMR (400 MHz, $d_6$-DMSO) δ 8.76 (s, 1H), 8.26 (s, 1H), 8.17 (s, 2H), 7.89 (d, J=4.9 Hz, 1H), 7.59 (dd, J=10.6, 1.7 Hz, 1H), 7.49 (d, J=1.2 Hz, 1H), 6.62 (d, J=4.9 Hz, 1H), 3.54 (s, 4H), 2.00 (ddd, J=13.8, 8.4, 5.3 Hz, 1H), 1.40 (s, 3H), 0.94-0.84 (m, 2H), 0.78-0.70 (m, 2H), 0.64-0.54 (m, 4H).

$^{13}$C NMR (151 MHz, $d_6$-DMSO) δ 174.1, 166.1, 159.3, 157.7, 153.6, 146.3, 145.4, 143.2, 138.2, 129.6 (d, J=13.2 Hz), 120.6, 113.0, 112.8, 111.2, 41.8, 29.2, 22.8, 14.0, 11.7, 8.9 $[M+H]^+$=471.1

Example 9: Compound (153) in Table I

To a solution of 2,3-dichloropyridine-4-carboxylic acid (288 mg, 1.5 mmole, 1 eq.) and anhydrous DMF (2 drops) in anhydrous DCM (10 mL) was added oxalyl dichloride (193 μL, 2.25 mmoles, 1.5 eq.) dropwise. The resulting reaction mixture was stirred at room temperature for 1 hour and concentrated under reduced pressure. The resulting residue was taken up in anhydrous DCM (8 mL). To the resulting solution was added a solution of morpholine (182 μL, 1.50 mmol, 1 eq) and triethylamine (523 μL, 3.75 mmoles, 2.5 eq) in anhydrous DCM (2 mL) dropwise. The resulting reaction mixture was stirred at room temperature for 2h30. The reaction was quenched with water and extracted with dichloromethane. The combined organic phases were dried over magnesium sulphate, filtered and concentrated under reduced pressure. The resulting residue was purified by column chromatography on silica gel to give 4-(2,3-dichloropyridine-4-carbonyl)morpholine (364 mg, 93%).

$^1$H NMR (400 MHz, $d_6$-DMSO) δ 8.48 (d, J=4.8 Hz, 1H), 7.54 (d, J=4.8 Hz, 1H), 3.74-3.67 (m, 2H), 3.67-3.58 (m, 2H), 3.53 (ddd, J=16.4, 10.5, 4.8 Hz, 2H), 3.18 (t, J=4.9 Hz, 2H).

According to route (A1), a reaction mixture of 4-(2,3-dichloropyridine-4-carbonyl)morpholine (75 mg, 0.287 mmole, 1.0 eq.), methyl 4-amino-3-cyclopropyl-5-fluorobenzoate (60 mg, 0.287 mmole, 1.0 eq.), $Pd(OAc)_2$ (7.8 mg, 34.5 moles, 12 mol %), rac-BINAP (14.3 mg, 23 moles, 8 mol %) and $Cs_2CO_3$ (187 mg, 575 moles, 2 eq.) in anhydrous toluene (2 mL) was degassed with $N_2$ and heated at 110° C. for 75 minutes under inert atmosphere. The reaction mixture was cooled down to room temperature, filtered over a pad of celite and the pad was washed with EtOAc. A saturated aqueous solution of brine was then added to the filtrate and the mixture was extracted with EtOAc. The combined organic phases were dried over $MgSO_4$, filtered and concentrated under reduced pressure.

The resulting residue was purified by column chromatography on silica gel to give methyl 4-{[3-chloro-4-(morpholine-4-carbonyl)pyridin-2-yl]amino}-3-cyclopropyl-5-fluorobenzoate (64.0 mg, 51%).

$^1$H NMR (400 MHz, $d_6$-DMSO) δ 8.51 (s, 1H), 7.98 (d, J=4.9 Hz, 1H), 7.56 (dd, J=10.0, 1.8 Hz, 1H), 7.33 (s, 1H), 6.74 (d, J=4.9 Hz, 1H), 3.87 (s, 3H), 3.72-3.62 (m, 4H), 3.62-3.54 (m, 2H), 3.25-3.18 (m, 2H), 2.06 (ddd, J=13.7, 8.4, 5.2 Hz, 1H), 0.92 (dd, J=8.4, 2.0 Hz, 2H), 0.65 (td, J=5.1, 2.4 Hz, 2H).

According to procedure (B), methyl 4-{[3-chloro-4-(morpholine-4-carbonyl)pyridin-2-yl]amino}-3-cyclopropyl-5-fluorobenzoate (64.0 mg, 0.148 mmole, 1 eq.) was placed in methanol (2 mL) and an aqueous solution of 1M NaOH (0.738 mL, 0.738 mmole, 5 eq.) was added. The reaction mixture was heated at 80° C. and stirred for 3 hours. It was then concentrated under reduced pressure and, after addition of an aqueous solution of 1M HCl (5 eq.), extracted with dichloromethane. The combined organic phases were dried over magnesium sulphate, filtered and concentrated under reduced pressure to give 4-{[3-chloro-4-(morpholine-4-carbonyl)pyridin-2-yl]amino}-3-cyclopropyl-5-fluorobenzoic acid (62.0 mg, 100%).

According to procedure (C), a reaction mixture of 4-{[3-chloro-4-(morpholine-4-carbonyl)pyridin-2-yl]amino}-3-cyclopropyl-5-fluorobenzoic acid (62.0 mg, 148 moles, 1.0 eq.) and CDI (35.9 mg, 222 moles, 1.5 eq.) in anhydrous DMF (1.0 mL) was stirred at room temperature for 1 hour. The mixture was then added to a solution of imidazolidin-2-imine hydrobromide (51.6 mg, 295 moles, 2.0 eq.) and DIPEA (77.4 μL, 443 moles, 3 eq.) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was purified by preparative HPLC to give 4-{[3-chloro-4-(morpholine-4-carbonyl)pyridin-2-yl]amino}-3-cyclopropyl-5-fluoro-N-[imidazolidin-2-ylidene]benzamide (153) (36.6 mg, 48%).

$^1$H NMR (400 MHz, $d_6$-DMSO) δ 8.35 (s, 1H), 8.18 (s, 2H), 7.96 (d, J=4.9 Hz, 1H), 7.61 (dd, J=10.7, 1.6 Hz, 1H), 7.49 (s, 1H), 6.69 (d, J=4.9 Hz, 1H), 3.71-3.63 (m, 4H), 3.61-3.57 (m, 2H), 3.55 (s, 4H), 3.24-3.18 (m, 2H), 2.02 (ddd, J=13.9, 8.5, 5.4 Hz, 1H), 0.89 (dd, J=8.4, 2.0 Hz, 2H), 0.63-0.52 (m, 2H).

$^{13}$C NMR (151 MHz, $d_6$-DMSO) δ 174.1, 165.8, 164.8, 158.5 (d, J=244.9 Hz), 153.7, 146.9, 144.0, 143.3, 138.4 (d, J=7.1 Hz), 129.4 (d, J=13.4 Hz), 120.6, 113.0, 112.8, 112.1, 110.6, 66.6, 66.4, 47.0, 41.9, 41.8, 11.7 (d, J=2.8 Hz), 9.0, 8.9 $[M+H]^+$=487.1

Example 10: Compound (163) in Table I

According to procedure (E), methyl 4-amino-3-bromo-5-fluorobenzoate (4.0 g, 16.13 mmoles, 1 eq) was placed in anhydrous 1,4-dioxane (60 mL) with $Pd(dppf)C_{12}\cdot CH_2Cl_2$ (1.3 g, 1.61 mmole, 0.1 eq.). Upon addition of $K_3PO_4$ (12.0 g, 56.44 mmoles, 3.5 eq.) and cyclopropylboronic acid (1.8 g, 20.96 mmoles, 1.3 eq.), the reaction mixture was heated at 100° C. and stirred for 3 hours under an inert atmosphere of argon. Upon filtration over a pad of celite, the reaction mixture was then concentrated under reduced pressure and the resulting residue was purified by column chromatography on silica gel to afford methyl 4-amino-3-cyclopropyl-5-fluorobenzoate (2.8 g, 83%).

$^1$H NMR (300 MHz, $CDCl_3$) δ 7.57-7.54 (m, J=4.8 Hz, 2H), 4.40 (br s, 2H), 3.85 (s, 3H), 1.76-1.60 (m, 1H), 1.03-0.88 (m, 2H), 0.69-0.60 (m, 2H).

3-methyloxetane-3-carboxylic acid (1 g, 8.61 mmoles, 1 eq.) was placed in anhydrous dichloromethane (34.5 mL). PyBOP (6.7 g, 12.92 mmoles, 1.5 eq.), DIPEA (5.7 mL, 34.45 mmoles, 4 eq.) and 3-bromoaniline (940 μL, 8.61 mmoles, 1 eq.) were added and the resulting reaction mixture was stirred at room temperature for 16 hours. The reaction mixture was then concentrated under reduced pressure and the resulting residue was diluted with ethyl acetate. The organic phase was washed with a saturated aqueous solution of brine, dried over $MgSO_4$, filtered and concentrated under reduced pressure. The resulting residue was purified by column chromatography on silica gel to afford N-(3-bromophenyl)-3-methyloxetane-3-carboxamide (1.3 g, 56%).

$^1$H NMR (300 MHz, $CDCl_3$) δ 7.83 (t, J=1.9 Hz, 1H), 7.71 (br s, 1H), 7.50-7.44 (m, 1H), 7.30-7.17 (m, 3H), 4.92 (d, J=6.2 Hz, 1H), 4.58 (d, J=6.3 Hz, 2H), 1.65 (s, 3H).

According to route (A1), a reaction mixture of methyl 4-amino-3-cyclopropyl-5-fluorobenzoate (542 mg, 2.59 mmoles, 1 eq.), N-(3-bromophenyl)-3-methyloxetane-3-carboxamide (700 mg, 2.59 mmoles, 1 eq.), $Pd_2(dba)_3$ (237 mg, 0.26 mmoles, 0.1 eq.), XPhos (247 mg, 0.52 mmoles, 0.2 eq.) and $K_2CO_3$ (1.4 g, 10.37 mmoles, 4 eq.) in t-BuOH (10.5 mL) was heated at 90° C. and stirred for 16 hours under an inert atmosphere of argon.

The reaction mixture was then concentrated under reduced pressure and the resulting residue was diluted with dichloromethane. The organic phase was washed with a saturated aqueous solution of brine, dried over $MgSO_4$, filtered and concentrated under reduced pressure. The resulting residue was purified by column chromatography on silica gel to afford methyl 3-cyclopropyl-5-fluoro-4-{[3-(3-methyloxetane-3-amido)phenyl]amino}benzoate (694 mg, 67%).

$^1$H NMR (300 MHz, $CDCl_3$) δ 7.63 (dd, J=11.1, 1.8 Hz, 1H), 7.52 (s, 2H), 7.19 (t, J=8.0 Hz, 1H), 6.99 (d, J=7.9 Hz, 1H), 6.59 (d, J=8.0 Hz, 1H), 5.94 (s, 1H), 4.93 (d, J=6.0 Hz, 2H), 4.56 (d, J=6.1 Hz, 2H), 3.90 (s, 3H), 1.88-1.79 (m, 1H), 1.65 (s, 3H), 0.96 (q, J=6.0 Hz, 2H), 0.72 (q, J=6.0 Hz, 2H).

According to procedure (B), methyl 3-cyclopropyl-5-fluoro-4-{[3-(3-methyloxetane-3-amido)phenyl]amino}benzoate (694 mg, 1.74 mmole, 1 eq.) was placed in a mixture of THF (10 mL), methanol (1.9 mL) and water (1.9 mL), and $LiOH{\cdot}H_2O$ (365 mg, 8.71 mmoles, 5 eq.) was added. The reaction mixture was stirred for 16 hours at room temperature. It was then concentrated under reduced pressure and, after addition of an aqueous solution of 6M HCl (5 eq.), the aqueous phase was extracted with dichloromethane. The combined organic phases were washed with a saturated aqueous solution of brine, dried over magnesium sulphate, filtered and concentrated under reduced pressure to give 3-cyclopropyl-5-fluoro-4-{[3-(3-methyloxetane-3-amido)phenyl]amino}benzoic acid (537 mg, 80%).

$^1$H NMR (300 MHz, $CDCl_3$) δ 7.71 (s, 1H), 7.67 (dd, J=11.0, 1.7 Hz, 1H), 7.60 (br s, 1H), 7.31 (br s, 1H), 7.21 (t, J=8.1 Hz, 1H), 7.04 (d, J=7.9 Hz, 1H), 6.63 (d, J=8.2 Hz, 1H), 6.05 (s, 1H), 4.97 (d, J=6.1 Hz, 2H), 4.57 (d, J=6.1 Hz, 2H), 1.88-1.78 (m, 1H), 1.66 (s, 3H), 0.96 (q, J=5.4 Hz, 2H)), 0.73 (q, J=5.4 Hz, 2H).

According to procedure (C), a reaction mixture of 3-cyclopropyl-5-fluoro-4-{[3-(3-methyloxetane-3-amido)phenyl]amino}benzoic acid (200 mg, 520 moles, 1.0 eq.) and CDI (101 mg, 620 moles, 1.2 eq.) in anhydrous DMF (2.6 mL) was stirred at room temperature for 3 hours. The mixture was then added to a solution of 4,5-dihydro-1H-imidazol-2-amine (66.5 mg, 780 moles, 1.5 eq.) and DIPEA (430 μL, 2.60 mmoles, 5 eq.) in anhydrous DMF (2.7 mL) and the resulting mixture was heated at 60° C. and stirred for 16 hours. The reaction mixture was then cooled down to room temperature and concentrated under reduced pressure. The resulting residue was taken up in EtOAc and this organic phase was then washed with a saturated aqueous solution of $NH_4Cl$, dried over $MgSO_4$, filtered and concentrated under reduced pressure. The resulting residue was purified by column chromatography on silica gel to give a fraction which, after trituration in diethyl ether, afforded N-{3-[(2-cyclopropyl-6-fluoro-4-{[imidazolidin-2-ylidene]carbamoyl}phenyl)amino]phenyl}-3-methyloxetane-3-carboxamide (163) (109 mg, 46%).

$^1$H NMR (300 MHz, $CDCl_3$) δ 7.75 (d, J=11.3 Hz, 1H), 7.63 (s, 1H), 7.49 (s, 1H), 7.18 (t, J=8.0 Hz, 1H), 7.06 (d, J=7.7 Hz, 2H), 6.57 (d, J=7.4 Hz, 1H), 5.83 (s, 1H), 4.94 (d, J=6.0 Hz, 2H), 4.53 (d, J=6.0 Hz, 2H), 3.72 (s, 4H), 1.91-1.78 (m, 1H), 1.65 (s, 3H), 0.91 (q, J=5.3 Hz, 2H), 0.75 (q, J=5.3 Hz, 2H).

$^{13}$C NMR (75 MHz, $CDCl_3$) δ 176.1, 172.7, 165.6, 157.5, 154.2, 145.2, 138.6, 133.9, 133.8, 131.9, 131.7, 129.6, 122.5, 114.5, 114.2, 112.4, 111.9, 107.6, 80.1, 46.4, 41.9, 22.0, 12.0, 7.9 $[M+H]^+$=452.5

Example 11: Compound (164) in Table I

According to procedure (E), methyl 4-amino-3-bromo-5-fluorobenzoate (4.0 g, 16.13 mmoles, 1 eq) was placed in anhydrous 1,4-dioxane (60 mL) with $Pd(dppf)C_{12}{\cdot}CH_2Cl_2$ (1.3 g, 1.61 mmole, 0.1 eq.). Upon addition of $K_3PO_4$ (12.0 g, 56.44 mmoles, 3.5 eq.) and cyclopropylboronic acid (1.8 g, 20.96 mmoles, 1.3 eq.), the reaction mixture was heated at 100° C. and stirred for 3 hours under an inert atmosphere of argon. Upon filtration over a pad of celite, the reaction mixture was then concentrated under reduced pressure and the resulting residue was purified by column chromatography on silica gel to afford methyl 4-amino-3-cyclopropyl-5-fluorobenzoate (2.8 g, 83%).

$^1$H NMR (300 MHz, $CDCl_3$) δ 7.57-7.54 (m, J=4.8 Hz, 2H), 4.40 (br s, 2H), 3.85 (s, 3H), 1.76-1.60 (m, 1H), 1.03-0.88 (m, 2H), 0.69-0.60 (m, 2H).

2,3-dichloropyridine-4-carboxylic acid (730 mg, 3.80 mmoles, 1 eq.) was placed in anhydrous dichloromethane (15.5 mL). PyBOP (3.0 g, 5.70 mmoles, 1.5 eq.), DIPEA (2.5 mL, 15.20 mmoles, 4 eq.) and bicyclo[1.1.1]pentan-1-amine hydrochloride (500 mg, 4.18 mmoles, 1.1 eq.) were added and the resulting reaction mixture was stirred at room temperature for 16 hours. The reaction mixture was then concentrated under reduced pressure and the resulting residue was diluted with ethyl acetate. The organic phase was washed with a saturated aqueous solution of brine, dried over $MgSO_4$, filtered and concentrated under reduced pressure. The resulting residue was purified by column chromatography on silica gel to afford N-{bicyclo[1.1.1]pentan-1-yl}-2,3-dichloropyridine-4-carboxamide (728 mg, 74%).

$^1$H NMR (300 MHz, $CDCl_3$) δ 8.34 (d, J=4.8 Hz, 1H), 7.40 (d, J=4.8 Hz, 1H), 7.26 (s, 1H), 6.42 (s, 1H), 2.55 (s, 1H), 2.21 (s, 6H).

According to route (A1), a reaction mixture of N-{bicyclo[1.1.1]pentan-1-yl}-2,3-dichloropyridine-4-carboxamide (386 mg, 1.5 mmole, 1.0 eq.), methyl 4-amino-3-cyclopropyl-5-fluorobenzoate (314 mg, 1.5 mmole, 1.0 eq.), $Pd(OAc)_2$ (41 mg, 180 moles, 12 mol %), rac-BINAP (75 mg, 120 moles, 8 mol %) and $Cs_2CO_3$ (977 mg, 3.0 mmoles, 2 eq.) in anhydrous toluene (9.5 mL) was degassed with argon and heated at 110° C. for 16 hours under inert atmosphere. The reaction mixture was cooled down to room temperature and concentrated under reduced pressure. The resulting residue was taken up in dichloromethane and this organic phase was then washed with a saturated aqueous solution of brine, dried over $MgSO_4$, filtered and concentrated under reduced pressure. The resulting residue was purified by column chromatography on silica gel to give methyl 4-{[4-({bicyclo[1.1.1]pentan-1-yl}carbamoyl)-3-chloropyridin-2-yl]amino}-3-cyclopropyl-5-fluorobenzoate (220 mg, 34%).

$^1$H NMR (300 MHz, $CDCl_3$) δ 8.07 (d, J=5.0 Hz, 1H), 7.65 (dd, J=10.2, 1.7 Hz, 1H), 7.55 (s, 1H), 6.86 (d, J=5.0 Hz, 1H), 6.83 (s, 1H), 6.29 (s, 1H), 3.91 (s, 3H), 2.54 (s, 1H), 2.22 (s, 6H), 1.93-1.84 (m, 1H), 0.96 (q, J=5.3 Hz, 2H), 0.74 (q, J=5.3 Hz, 2H).

According to procedure (B), methyl 4-{[4-({bicyclo[1.1.1]pentan-1-yl}carbamoyl)-3-chloropyridin-2-yl]amino}-3-cyclopropyl-5-fluorobenzoate (220 mg, 0.51 mmole, 1 eq.) was placed in a mixture of THF (3 mL), methanol (560 μL) and water (560 μL), and $LiOH{\cdot}H_2O$ (107 mg, 2.56 mmoles, 5 eq.) was added. The reaction mixture was stirred for 16 hours at room temperature. It was then concentrated under reduced pressure and, after addition of an aqueous solution of 6M HCl (5 eq.), the aqueous phase was extracted with dichloromethane. The combined organic phases were washed with a saturated aqueous solution of brine, dried over magnesium sulphate, filtered and concentrated under reduced pressure to give 4-{[4-({bicyclo[1.1.1]pentan-1-yl}carbamoyl)-3-chloropyridin-2-yl]amino}-3-cyclopropyl-5-fluorobenzoic acid (130 mg, 61%).

$^1$H NMR (300 MHz, $d_6$-DMSO) δ 9.12 (s, 1H), 8.44 (s, 1H), 7.92 (d, J=4.9 Hz, 1H), 7.51 (dd, J=10.0, 1.6 Hz, 1H), 7.32 (s, 1H), 6.69 (d, J=4.9 Hz, 1H), 2.47 (s, 1H), 2.08 (s, 6H), 2.06-1.99 (m, 1H), 0.91 (q, J=5.3 Hz, 2H), 0.64 (q, J=5.3 Hz, 2H).

According to procedure (C), a reaction mixture of 4-{[4-({bicyclo[1.1.1]pentan-1-yl}carbamoyl)-3-chloropyridin-2-yl]amino}-3-cyclopropyl-5-fluorobenzoic acid (130 mg, 310 moles, 1.0 eq.) and CDI (61 mg, 370 moles, 1.2 eq.) in anhydrous DMF (1.6 mL) was stirred at room temperature for 3 hours. The mixture was then added to a solution of 4,5-dihydro-1H-imidazol-2-amine (40 mg, 470 moles, 1.5 eq.) and DIPEA (260 μL, 1.56 mmole, 5 eq.) in anhydrous DMF (1.6 mL) and the resulting mixture was heated at 60° C. and stirred for 16 hours. The reaction mixture was then cooled down to room temperature and concentrated under reduced pressure. The resulting residue was taken up in EtOAc and this organic phase was then washed with a saturated aqueous solution of $NH_4Cl$, dried over $MgSO_4$, filtered and concentrated under reduced pressure. The resulting residue was purified by column chromatography on silica gel to give N-{bicyclo[1.1.1]pentan-2-yl}-3-chloro-2-[(2-cyclopropyl-6-fluoro-4-{[imidazolidin-2-ylidene]carbamoyl}phenyl)amino]pyridine-4-carboxamide (164) (66 mg, 44%).

$^1H$ NMR (300 MHz, $CDCl_3$) δ 8.03 (d, J=4.9 Hz, 1H), 7.89 (br s, 1H), 7.73 (dd, J=10.6, 1.4 Hz, 1H), 7.62 (s, 1H), 6.80 (d, J=5.0 Hz, 1H), 6.78 (s, 1H), 6.38 (s, 1H), 3.64 (s, 4H), 2.53 (s, 1H), 2.21 (s, 6H), 1.92-1.83 (m, 1H), 0.91 (q, J=5.3 Hz, 2H), 0.76 (q, J=5.3 Hz, 2H).

$^{13}C$ NMR (75 MHz, $CDCl_3$) δ 176.3, 166.0, 165.3, 158.9, 155.6, 152.5, 146.6, 143.3, 140.7, 136.8, 136.7, 129.1, 128.9, 122.2, 114.3, 114.0, 113.8, 112.2, 53.1, 48.8, 41.9, 25.1, 12.1, 7.7 $[M+H]^+$=483.4

Example 12: Compound (167) in Table I 3-bromo-2-chlorobenzoic acid (500 mg, 2.1 mmoles, 1 eq.) and 1-methylcyclopropan-1-amine hydrochloride (247 mg, 2.2 mmoles, 1.05 eq.) were placed in anhydrous N,N-dimethylformamide (5 mL). HATU (907 mg, 2.3 mmoles, 1.1 eq.) and DIPEA (544 μL, 3.1 mmoles, 1.5 eq.) were added and the resulting reaction mixture was stirred at room temperature for 16 hours. The reaction was quenched with 1M aqueous hydrochloric acid and extracted with ethyl acetate. The combined organic phases were dried over magnesium sulphate, filtered and concentrated under reduced pressure. The resulting residue was purified by column chromatography on silica gel to give 3-bromo-2-chloro-N-(1-methylcyclopropyl)benzamide (370 mg, 62%).

$^1H$ NMR (400 MHz, $d_6$-DMSO) δ 8.67 (s, 1H), 7.80 (dd, J=7.8, 1.7 Hz, 1H), 7.35 (dd, J=7.5, 1.7 Hz, 1H), 7.30 (t, J=7.7 Hz, 1H), 1.39 (s, 3H), 0.76-0.68 (m, 2H), 0.64-0.56 (m, 2H).

According to route (A1), a reaction mixture of 3-bromo-2-chloro-N-(1-methylcyclopropyl)benzamide (226 mg, 0.784 mmole, 1.0 eq.), methyl 4-amino-3-cyclopropyl-benzoate (150 mg, 0.784 mmole, 1.0 eq.), BrettPhos Pd G3 (35.6 mg, 39.2 moles, 5 mol %) and $Cs_2CO_3$ (383 mg, 1.18 mmole, 1.5 eq.) in anhydrous DMF (4 mL) was degassed with $N_2$ and heated at 80° C. for 75 minutes under inert atmosphere. The reaction mixture was cooled down to room temperature, filtered over a pad of celite and the pad was washed with EtOAc. A saturated aqueous solution of brine was then added to the filtrate and the mixture was extracted with EtOAc. The combined organic phases were dried over $MgSO_4$, filtered and concentrated under reduced pressure. The resulting residue was purified by column chromatography on silica gel to give methyl 4-({2-chloro-3-[(1-methylcyclopropyl)carbamoyl]phenyl}amino)-3-cyclopropylbenzoate (77 mg, 25%).

$^1H$ NMR (400 MHz, $d_6$-DMSO) δ 8.61 (s, 1H), 7.70 (dd, J=8.5, 2.1 Hz, 1H), 7.63-7.59 (m, 2H), 7.35-7.29 (m, 2H), 7.04 (dd, J=6.3, 2.7 Hz, 1H), 6.90 (d, J=8.5 Hz, 1H), 3.80 (s, 3H), 1.89 (ddd, J=13.5, 8.3, 5.4 Hz, 1H), 1.40 (s, 3H), 1.02-0.95 (m, 2H), 0.78-0.70 (m, 2H), 0.67-0.62 (m, 2H), 0.62-0.57 (m, 2H).

According to procedure (B), methyl 4-({2-chloro-3-[(1-methylcyclopropyl)carbamoyl]phenyl}amino)-3-cyclopropylbenzoate (77 mg, 0.193 mmole, 1 eq.) was placed in methanol (3 mL) and an aqueous solution of 1M NaOH (0.965 mL, 0.965 mmole, 5 eq.) was added. The reaction mixture was heated at 80° C. and stirred for 3 hours. It was then concentrated under reduced pressure and, after addition of an aqueous solution of 1M HCl (5 eq.), extracted with dichloromethane. The combined organic phases were dried over magnesium sulphate, filtered and concentrated under reduced pressure to give 4-({2-chloro-3-[(1-methylcyclopropyl)carbamoyl]phenyl}amino)-3-cyclopropylbenzoic acid (71 mg, 96%).

$^1H$ NMR (400 MHz, $d_6$-DMSO) δ 12.47 (s, 1H), 8.61 (s, 1H), 7.69 (dd, J=8.4, 2.0 Hz, 1H), 7.60 (d, J=1.9 Hz, 1H), 7.52 (s, 1H), 7.35-7.22 (m, 2H), 6.99 (dd, J=7.2, 1.8 Hz, 1H), 6.93 (d, J=8.4 Hz, 1H), 1.88 (s, 1H), 1.40 (s, 3H), 1.03-0.93 (m, 2H), 0.78-0.70 (m, 2H), 0.66-0.62 (m, 2H), 0.61-0.58 (m, 2H).

According to procedure (C), a reaction mixture of 4-({2-chloro-3-[(1-methylcyclopropyl)carbamoyl]phenyl}amino)-3-cyclopropylbenzoic acid (35 mg, 91 moles, 1.0 eq.) and CDI (22.1 mg, 136 moles, 1.5 eq.) in anhydrous DMF (1.0 mL) was stirred at room temperature for 1 hour. The mixture was then added to a solution of imidazolidin-2-imine hydrobromide (31.8 mg, 182 moles, 2 eq.) and DIPEA (47.6 μL, 273 moles, 3 eq.) in anhydrous DMF (1.0 mL) and the resulting mixture was heated at 75° C. and stirred for 16 hours. The reaction mixture was then cooled down to room temperature, quenched with a saturated aqueous solution of sodium bicarbonate and extracted with EtOAc. The combined organic layers were then washed with a saturated aqueous solution of brine, dried over $MgSO_4$, filtered and concentrated under reduced pressure. The resulting residue was purified by column chromatography on silica gel to give 4-({2-chloro-3-[(1-methylcyclopropyl)carbamoyl]phenyl}amino)-3-cyclopropyl-N-[imidazolidin-2-ylidene]benzamide (167) (7.7 mg, 18%).

$^1H$ NMR (400 MHz, $d_6$-DMSO) δ 8.58 (s, 1H), 8.11 (s, 2H), 7.85 (dd, J=8.3, 1.9 Hz, 1H), 7.80 (s, 1H), 7.31 (s, 1H), 7.22 (t, J=7.8 Hz, 1H), 7.09 (dd, J=8.2, 1.4 Hz, 1H), 7.04 (d, J=8.3 Hz, 1H), 6.85 (dd, J=7.4, 1.4 Hz, 1H), 3.52 (s, 4H), 1.87 (s, 1H), 1.40 (s, 3H), 0.99-0.90 (m, 2H), 0.77-0.71 (m, 2H), 0.63-0.54 (m, 4H). $^{13}C$ NMR (151 MHz, $d_6$-DMSO) δ 175.5, 167.5, 165.8, 144.0, 140.9, 139.2, 132.9, 132.5, 128.0, 127.9, 127.8, 120.2, 119.5, 118.7, 118.0, 41.7, 29.2, 22.9, 14.1, 11.7, 7.2 $[M+H]^+$=452.1

Example 13: Compound (169) in Table I

According to procedure (E), methyl 4-amino-3-bromo-5-fluorobenzoate (4.0 g, 16.13 mmoles, 1 eq) was placed in anhydrous 1,4-dioxane (60 mL) with $Pd(dppf)C_{12}\cdot CH_2Cl_2$ (1.3 g, 1.61 mmole, 0.1 eq.). Upon addition of $K_3PO_4$ (12.0 g, 56.44 mmoles, 3.5 eq.) and cyclopropylboronic acid (1.8 g, 20.96 mmoles, 1.3 eq.), the reaction mixture was heated at 100° C. and stirred for 3 hours under an inert atmosphere of argon. Upon filtration over a pad of celite, the reaction mixture was then concentrated under reduced pressure and the resulting residue was purified by column chromatography on silica gel to afford methyl 4-amino-3-cyclopropyl-5-fluorobenzoate (2.8 g, 83%).

$^1$H NMR (300 MHz, $CDCl_3$) δ 7.57-7.54 (m, J=4.8 Hz, 2H), 4.40 (br s, 2H), 3.85 (s, 3H), 1.76-1.60 (m, 1H), 1.03-0.88 (m, 2H), 0.69-0.60 (m, 2H).

3-bromobenzaldehyde (1.2 mL, 10 mmoles, 1 eq.) was placed in water (240 mL). Ethylenediamine (4.0 mL, 60 mmoles, 6 eq.) and pyridinium bromide perbromide (6.4 g, 20 mmoles, 2 eq.) were added and the resulting reaction mixture was stirred at room temperature for 24 hours. The reaction mixture was then treated with an aqueous solution of 3M NaOH and the resulting aqueous phase was extracted with dichloromethane. The combined organic layers were then dried over $MgSO_4$, filtered and concentrated under reduced pressure to give 2-(3-bromophenyl)-4,5-dihydro-1H-imidazole (1.1 g, 49%).

$^1$H NMR (300 MHz, $CDCl_3$) δ 7.96-7.94 (m, 1H), 7.70 (d, J=7.7 Hz, 1H), 7.57 (d, J=7.7 Hz, 1H), 7.28 (t, J=7.7 Hz, 1H), 3.80 (s, 4H). 2-(3-bromophenyl)-4,5-dihydro-1H-imidazole (1.1 g, 4.88 mmoles, 1 eq.) was placed at 0° C. in a 1/1 mixture of water/dichloromethane (30 mL). $NaHCO_3$ (1.6 g, 19.55 mmoles, 4 eq.) and $Boc_2O$ (1.6 g, 7.33 mmoles, 1.5 eq.) were added and the resulting reaction mixture was stirred at room temperature for 21 hours. Upon decantation, the aqueous layer was extracted with dichloromethane. The combined organic layers were then washed with a saturated aqueous solution of brine, dried over $MgSO_4$, filtered and concentrated under reduced pressure to afford tert-butyl 2-(3-bromophenyl)-4,5-dihydro-1H-imidazole-1-carboxylate (1.5 g, 94%).

$^1$H NMR (300 MHz, $CDCl_3$) δ 7.65 (s, 1H), 7.53 (d, J=7.8 Hz, 1H), 7.45 (d, J=7.8 Hz, 1H), 7.25 (t, J=7.8 Hz, 1H), 3.97 (s, 4H), 1.27 (s, 9H).

According to route (A1), a reaction mixture of methyl 4-amino-3-cyclopropyl-5-fluorobenzoate (418 mg, 2 mmoles, 1 eq.), tert-butyl 2-(3-bromophenyl)-4,5-dihydro-1H-imidazole-1-carboxylate (650 mg, 2 mmoles, 1 eq.), $Pd_2(dba)_3$ (183 mg, 0.2 mmole, 0.1 eq.), XPhos (191 mg, 0.4 mmole, 0.2 eq.) and $K_2CO_3$ (1.1 g, 8 mmoles, 4 eq.) in t-BuOH (10.5 mL) was heated at 90° C. and stirred for 20 hours under an inert atmosphere of argon. The reaction mixture was then concentrated under reduced pressure and the resulting residue was diluted with ethyl acetate. The organic phase was washed with a saturated aqueous solution of brine, dried over $MgSO_4$, filtered and concentrated under reduced pressure. The resulting residue was purified by column chromatography on silica gel to afford tert-butyl 2-(3-{[2-cyclopropyl-6-fluoro-4-(methoxycarbonyl)phenyl]amino}phenyl)-4,5-dihydro-1H-imidazole-1-carboxylate (320 mg, 35%).

$^1$H NMR (300 MHz, $CDCl_3$) δ 7.62 (dd, J=11.0, 1.7 Hz, 1H), 7.52 (s, 1H), 7.23 (t, J=7.9 Hz, 1H), 7.04 (d, J=7.8 Hz, 1H), 7.01 (s, 1H), 6.85 (d, J=7.8 Hz, 1H), 5.97 (s, 1H), 3.95 (dd, J=6.2, 4.6 Hz, 4H), 3.90 (s, 3H), 1.84-1.75 (m, 1H), 1.25 (s, 9H), 0.93 (q, J=5.3 Hz, 2H), 0.71 (q, J=5.3 Hz, 2H).

According to procedure (B), tert-butyl 2-(3-{[2-cyclopropyl-6-fluoro-4-(methoxycarbonyl)phenyl]amino}phenyl)-4,5-dihydro-1H-imidazole-1-carboxylate (320 mg, 0.70 mmole, 1 eq.) was placed in a mixture of THF (4.2 mL), methanol (0.8 mL) and water (0.8 mL), and $LiOH \cdot H_2O$ (148 mg, 3.53 mmoles, 5 eq.) was added. The reaction mixture was stirred for 16 hours at room temperature. It was then concentrated under reduced pressure and, after addition of an aqueous solution of 6M HCl (5 eq.), the aqueous phase was extracted with dichloromethane. The combined organic phases were washed with a saturated aqueous solution of brine, dried over magnesium sulphate, filtered and concentrated under reduced pressure to give 4-[(3-{1-[(tert-butoxy)carbonyl]-4,5-dihydro-1H-imidazol-2-yl}phenyl)amino]-3-cyclopropyl-5-fluorobenzoic acid (294 mg, 95%).

$^1$H NMR (300 MHz, $CDCl_3$) δ 7.54 (d, J=6.9 Hz, 2H), 7.28 (t, J=7.8 Hz, 1H), 7.04 (d, J=8.0 Hz, 2H), 6.99 (d, J=7.8 Hz, 1H), 6.01 (s, 1H), 4.04 (s, 4H), 1.84-1.79 (m, 1H), 1.29 (s, 9H), 0.93 (q, J=5.3 Hz, 2H), 0.72 (q, J=5.3 Hz, 2H).

According to procedure (C), a reaction mixture of 4-[(3-{1-[(tert-butoxy)carbonyl]-4,5-dihydro-1H-imidazol-2-yl}phenyl)amino]-3-cyclopropyl-5-fluorobenzoic acid (250 mg, 0.57 mmole, 1 eq.) and CDI (111 mg, 0.68 mmole, 1.2 eq.) in anhydrous DMF (2.9 mL) was stirred at room temperature for 5 hours. The mixture was then added to a solution of 4,5-dihydro-1H-imidazol-2-amine (73 mg, 0.85 mmole, 1.5 eq.) and DIPEA (470 μL, 2.84 mmoles, 5 eq.) in anhydrous DMF (2.9 mL) and the resulting mixture was heated at 60° C. and stirred for 16 hours. The reaction mixture was then cooled down to room temperature and concentrated under reduced pressure. The resulting residue was purified by column chromatography on silica gel to give tert-butyl-2-[3-({2-cyclopropyl-6-fluoro-4-[(imidazolidin-2-ylidene)carbamoyl]phenyl}amino)phenyl]-4,5-dihydro-1H-imidazole-1-carboxylate (127 mg, 44%).

$^1$H NMR (300 MHz, $CDCl_3$) δ 7.72 (dd, J=11.2, 1.6 Hz, 1H), 7.66 (br s, 1H), 7.60 (s, 1H), 7.19 (t, J=7.8 Hz, 1H), 6.98 (d, J=7.8 Hz, 1H), 6.95 (s, 1H), 6.80 (d, J=7.8 Hz, 1H), 5.83 (s, 1H), 3.93 (dd, J=6.6, 4.8 Hz, 4H), 3.67 (s, 4H), 1.88-1.76 (m, 1H), 1.23 (s, 9H), 0.89 (q, J=5.3 Hz, 2H), 0.74 (q, J=5.3 Hz, 2H).

To a solution of tert-butyl-2-[3-({2-cyclopropyl-6-fluoro-4-[(imidazolidin-2-ylidene)carbamoyl]phenyl}amino)phenyl]-4,5-dihydro-1H-imidazole-1-carboxylate (100 mg, 0.20 mmole, 1 eq.) in anhydrous DCM (600 μL) was added a 4N HCl solution in dioxane (250 μL, 0.99 mmole, 5 eq.) and the reaction mixture was stirred at room temperature for 6 hours. After filtering the resulting precipitate and washing it with dichloromethane, 20 mg were loaded onto a SCX cartridge, eluting with MeOH and then with a 2N ammonia solution in MeOH to afford 3-cyclopropyl-4-{[3-(4,5-dihydro-1H-imidazol-2-yl)phenyl]amino}-5-fluoro-N-(imidazolidin-2-ylidene)benzamide (169) (15 mg, 59% extrapolated).

$^1$H NMR (300 MHz, $d_6$-DMSO) δ 8.16 (s, 2H), 7.84 (s, 1H), 7.61 (d, J=11.5 Hz, 1H), 7.48 (s, 1H), 7.22-7.08 (m, 3H), 6.75 (d, J=7.7 Hz, 1H), 3.53 (s, 4H), 3.33 (s, 4H), 2.04-1.94 (m, 1H), 0.90 (q, J=5.3 Hz, 2H), 0.60 (q, J=5.3 Hz, 2H).

$^{13}$C NMR (75 MHz, $d_6$-DMSO) δ 173.8, 165.3, 164.2, 156.6 (d, J=242.4 Hz), 145.6, 140.3, 135.6 (d, J=6.8 Hz), 131.3, 130.5 (d, J=12.8 Hz), 128.5, 120.6, 117.0, 116.2, 113.1 (d, J=21.0 Hz), 112.8, 41.3, 11.3, 8.8 $[M+H]^+$=407.3

Pharmacological Data

Example 14: RSV Virus

The compounds of the invention have been the subject of pharmacological tests which have demonstrated their relevance as active substances in therapy and in particular for preventing, inhibiting or treating RSV virus infection.

Material and Methods

Protocol for Screening Antiviral Compounds for RSV Inhibition and Cytotoxicity Using Viral ToxGlo Assay HEp-2 cells were maintained in Eagle's minimum essential medium (EMEM) with Earle's BSS adjusted to contain 2 mM L-glutamine, 10% fetal bovine serum, 100 U/ml penicillin and 100 g/ml streptomycin. For the purposes of the screening assay they were grown to 90% confluency, trypsinized and recovered. The trypsin was neutralised with cell culture media and cells were centrifuged at 150×g for 5 minutes before discarding the supernatant and resuspending cell pellet in assay media (EMEM with Earle's BSS adjusted to contain 2 mM L-glutamine, 2% fetal bovine serum and 100 U/ml penicillin and 100 g/ml streptomycin). The cells were seeded into white clear-bottomed cell culture plates at a density of $1.5 \times 10^4$ cells/well in 50 μl and $4 \times 10^3$ cells/well in 25 μl for 96 well plates and 384 well plates respectively. For the media/background control column assay media only was added. Cell plates were placed in a humid chamber and incubated overnight at 37° C./5% $CO_2$. After overnight incubation cells were checked for confluency and healthy appearance.

Test articles were made up at 10× test concentration in a maximum DMSO concentration of 10% (final assay concentration maximal 1% DMSO) and added to the cell plates in volumes of 101 for 96 well plates and 5 μl for 384 well plates. For cell control and virus control wells the test article solvent only was added. Virus or assay media for cytotoxicity test wells and media/cell control wells was added immediately after test articles at an MOI of 0.5, 40 or 201 for 96 and 384 well plates respectively. Virus suspension was prepared by thawing RSV A2 frozen stocks and diluting to the required concentration of plaque forming units in assay media on ice.

Cell plates were further incubated inside a humid chamber for 72h p.i at 37° C./5% $CO_2$. After the incubation period cells were observed under the microscope to check for characteristic cytopathic effect in virus control wells and healthy cells in the cell control wells. After plates were adjusted to room temperature 20/40 μl Viral ToxGlo (Promega) was added to each well of the 384/96 well cell plates. Plates were incubated at room temperature, protected from light on a plate rocker for 20 minutes before measuring the luminescence on a spectrophotometer (Biotek Synergy HTX).

RSV inhibition was calculated as percentage of cytopathic effect inhibition relative to the virus control and cytotoxicity as percentage of cell survival relative to cell control wells. This allowed $EC_{50}$ values to be calculated for each test article where a virus inhibition or cytotoxic dose response was identified. $EC_{50}$ values ranging between 0.001 μM and 2.5 μM were found, and more particularly for compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 69, 70, 71, 72, 73, 74, 91, 92, 94, 95, 96, 97, 98, 99, 100, 102, 103, 104, 105, 106, 107, 109, 110, 111, 112, 113, 114, 115, 116, 117, 118, 119, 120, 121, 122, 123, 125, 127, 128, 129, 130, 131, 132, 134, 135, 136, 137, 138, 139, 140, 141, 142, 143, 144, 145, 146, 147, 148, 149, 150, 152, 153, 154, 155, 156, 157, 158, 159, 160, 161, 163, 164 and 167.

TABLE III

| Ex | $EC_{50}$ (nM) |
|---|---|
| 1 | 1.6 |
| 2 | 1.9 |
| 3 | 2.2 |
| 4 | 5.7 |
| 5 | 6.1 |
| 6 | 6.5 |
| 7 | 7.0 |
| 8 | 10.3 |
| 9 | 10.8 |
| 10 | 11.5 |
| 11 | 11.8 |
| 12 | 12.2 |
| 13 | 13.6 |
| 14 | 14.4 |
| 15 | 14.9 |
| 16 | 15.6 |
| 17 | 19.8 |
| 18 | 21.2 |
| 19 | 22.8 |
| 20 | 23.5 |
| 21 | 25.8 |
| 22 | 26.0 |
| 23 | 30.3 |
| 24 | 31.7 |
| 25 | 32.2 |
| 26 | 34.4 |
| 27 | 41.4 |
| 28 | 42.1 |
| 29 | 42.3 |
| 30 | 42.7 |
| 31 | 47.7 |
| 32 | 49.2 |
| 33 | 50.2 |
| 34 | 50.4 |
| 35 | 51.6 |
| 36 | 55.4 |
| 37 | 55.5 |
| 38 | 63.7 |
| 39 | 66.2 |
| 40 | 69.2 |
| 41 | 77.2 |
| 42 | 78.4 |
| 43 | 79.8 |
| 44 | 90.4 |
| 45 | 91.5 |
| 46 | 103.9 |
| 47 | 113.4 |
| 48 | 117.1 |
| 49 | 118.1 |
| 50 | 135.7 |
| 51 | 140.4 |
| 52 | 141.8 |
| 53 | 152.8 |
| 54 | 165.9 |
| 55 | 168.3 |
| 56 | 174.0 |
| 57 | 199.7 |
| 58 | 206.6 |
| 59 | 237.1 |
| 60 | 241.1 |
| 61 | 515.9 |
| 62 | 640.9 |
| 63 | 726.9 |
| 64 | 950.4 |
| 69 | 1134 |
| 70 | 1148 |
| 71 | 1170 |
| 72 | 1227 |
| 73 | 1288 |
| 74 | 1307 |
| 91 | 2.0 |
| 92 | 276.7 |
| 94 | 240.0 |
| 95 | 95.9 |
| 96 | 839.4 |
| 97 | 51.0 |
| 98 | 228.4 |
| 99 | 35.3 |

TABLE III-continued

| Ex | $EC_{50}$ (nM) |
|---|---|
| 100 | 458.3 |
| 102 | 819.4 |
| 103 | 19.4 |
| 104 | 12.4 |
| 105 | 3.2 |
| 106 | 5.7 |
| 107 | 14.0 |
| 109 | 45.0 |
| 110 | 323.8 |
| 111 | 30.4 |
| 112 | 709.7 |
| 113 | 59.9 |
| 114 | 32.6 |
| 115 | 29.6 |
| 116 | 130.6 |
| 117 | 5.6 |
| 118 | 27.0 |
| 119 | 108.3 |
| 120 | 19.5 |
| 121 | 5.1 |
| 122 | 7.8 |
| 123 | 83.0 |
| 125 | 19.1 |
| 127 | 100.8 |
| 128 | 13.2 |
| 129 | 4.3 |
| 130 | 7.3 |
| 131 | 77.9 |
| 132 | 23.6 |
| 134 | 39.2 |
| 135 | 28.7 |
| 136 | 32.0 |
| 137 | 204.5 |
| 138 | 233.2 |
| 139 | 151.9 |
| 140 | 227.1 |
| 141 | 150.5 |
| 142 | 41.4 |
| 143 | 59.7 |
| 144 | 48.1 |
| 145 | 474.6 |
| 146 | 252.7 |
| 147 | 99.4 |
| 148 | 346.7 |
| 149 | 45.8 |
| 150 | 262.6 |
| 152 | 1136.6 |
| 153 | 31.6 |
| 154 | 69.8 |
| 155 | 51.8 |
| 156 | 40.7 |
| 157 | 26.6 |
| 158 | 6.8 |
| 159 | 225.2 |
| 160 | 544.7 |
| 161 | 690.2 |
| 163 | 35.0 |
| 164 | 3.8 |
| 167 | 17.8 |

CONCLUSION

Based on the previous results, it can be concluded that the compounds of formula (I) are suitable chemical compounds for treating and/or preventing RNA virus infections caused by RNA viruses of group V, more particularly, pneumovirus infections, and most particularly RSV virus infections.

The present invention further relates to a pharmaceutical composition comprising at least one new compound as defined above or any of its pharmaceutically acceptable salts, or at least any of compounds (1) to (181) as defined above or any of its pharmaceutically acceptable salts and also at least one pharmaceutically acceptable excipient.

Pharmaceutical compositions of the invention can contain one or more compound(s) of the invention in any form described herein.

Still a further object of the present invention consists of the use of at least one compound of formula (I), as defined above, and compounds (1) to (181) as defined above, or one of their pharmaceutically acceptable salts according to the present invention for preparing a drug to prevent or treat, in a subject, a RNA virus infection caused by a RNA virus from group V according to the Baltimore classification, and for example a RSV infection.

Therefore, the present invention relates to one compound of formula (I), as defined above, and compounds (1) to (181) or one of their acceptable salts as an agent for inhibiting, preventing or treating a RNA virus infection, and most preferably a RNA virus infection from group V, and for example a RSV infection.

According to a particular embodiment, the treatment is continuous or non-continuous.

A "continuous treatment" means a long-term treatment which can be implemented with various administration frequencies, such as once every day, every three days, once a week, or once every two weeks or once every month.

According to one embodiment, the compound of formula (I), or anyone of its pharmaceutically acceptable salts, is administered at a dose varying from 0.1 to 1000 mg, in particular varying from 0.1 to 10 mg, or for example varying from 10 to 200 mg, or for example varying from 200 to 1000 mg.

Another object of the invention relates to a therapeutic method for treating and/or preventing a subject from a RNA virus infection, and most preferably a RNA virus infection caused by a virus belonging to group V of the Baltimore classification comprising the administration of a therapeutically effective quantity of a compound of formula (I), compounds (1) to (181), as defined above, or one of their acceptable salts.

In a specific embodiment, the invention provides a use of a compound of formula (I) according to the invention or a pharmaceutically acceptable salt thereof or a pharmaceutically active derivative thereof or a method according to the invention wherein the compound of formula (I) is to be administered in combination with a co-agent useful in the treatment of said RNA virus infection, and most preferably said RNA virus infection from group V, and for example RSV infection.

The compounds can be administered through any mode of administration such as, for example, intramuscular, intravenous, intranasal or oral route, etc.

Compounds of the present invention may, in appropriate cases, be administered as prodrugs, such as esters, of compounds with which the invention is concerned. "Prodrug" means a compound which is convertible in vivo by metabolic means (e.g. by hydrolysis, reduction or oxidation) to a compound of the present invention. For example, an ester prodrug of a compound of the present invention may be convertible by hydrolysis in vivo to the parent molecule. Suitable esters of compounds of the present invention are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulfamates and quinates. Examples of ester prodrugs are those described by F. J. Leinweber, Drug Metab. Res., 1987, 18, 379. As used herein, references to the compounds of the present invention are meant to also include any prodrug or metabolite forms.

The inventive composition can further include one or more additives such as diluents, excipients, stabilizers and preservatives. Such additives are well known to those skilled in the art and are described notably in "*Ullmann's Encyclopedia of Industrial Chemistry, 6th Ed.*" (various editors, 1989-1998, Marcel Dekker) and in "*Pharmaceutical Dosage Forms and Drug Delivery Systems*" (ANSEL et al., 1994, WILLIAMS & WILKINS).

The aforementioned excipients are selected according to the dosage form and the desired mode of administration.

According to another embodiment, pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Compositions of this invention may be administered in any manner, including, but not limited to, orally, parenterally, sublingually, transdermally, vaginally, rectally, transmucosally, topically, intranasally via inhalation, via buccal or intranasal administration, or combinations thereof. Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v. infusion.

For example, a compound of formula (I) can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

In a particular embodiment, a compound of formula (I) according to the invention is administered orally.

Oral route of administration is in particular preferred in the prophylaxis or treatment aspect of the invention.

The invention claimed is:

1. A compound of formula (I):

(I)

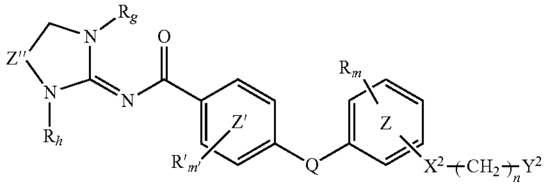

or a pharmaceutically acceptable salt thereof, wherein:

ring Z is phenylene or pyridinylene;

ring Z' is phenylene or pyridinylene;

Z" is —$CH_2$— or —C(O)—;

$R_g$ is H, $C_1$-$C_4$ alkyl, $C_3$-$C_6$cycloalkyl, —$CH_2CHF_2$, or —C(O)$CH_3$;

$R_h$ is H, $C_1$-$C_4$ alkyl, $C_3$-$C_6$cycloalkyl, —$CH_2CHF_2$, or —C(O)$CH_3$;

Q is —NH— or —O—;

$X^2$ is —C(O)—$NR_k$—, —$NR'_k$—C(O)—, —O—, —C(O)—, —$S(O)_2$—, —C(S)—NH—, —$CH_2$—NH—, -oxetan-3-ylene-NH, or 5- or 6-membered heterocyclyl;

wherein the heterocyclyl comprises 1, 2, 3, or 4 heteroatoms independently selected from the group consisting of O, S, and N; and wherein the heterocyclyl is optionally substituted by one or more substituents selected from the group consisting of $C_1$-$C_4$ alkyl, halogen, —C(O)$OR_p$, and ═O;

$R_k$ is H or $CH_3$;

$R'_k$ is H or $CH_3$;

each $R_p$ is independently $C_1$-$C_4$ alkyl;

$Y^2$ is H, halogen, OH, morpholinyl, bridged morpholinyl, $C_5$-$C_{11}$ bicycloalkyl, adamantly, piperidinyl, $C_2$-$C_4$ alkenyl, —P(O)($OR_a$)(OR), 5-membered heteroaryl, or —$CR^1R^2R^3$, wherein the heteroaryl comprises 1 or 2 heteroatom(s) independently selected from the group consisting of O and N;

wherein the morpholinyl is optionally substituted by one or more substituents independently selected from the group consisting of $C_1$-$C_4$ alkyl and —$CF_3$;

wherein the bridged morpholinyl is optionally substituted by one or more independently selected halogen substituents; and wherein one —$CH_2$— group of the piperidinyl is optionally replaced by one $S(O)_2$ group;

one of (i) and (ii) is satisfied:

(i) $R^1$ is H, $F_z$ or $C_1$-$C_4$ alkyl; and $R^2$ is H, $F_z$ or $C_1$-$C_4$ alkyl; or (ii) $R^1$ and $R^2$, together with the carbon atom to which they are attached, form a $C_3$-$C_8$ cycloalkyl;

wherein the $C_3$-$C_8$ cycloalkyl is optionally substituted by one or two independently selected $C_1$-$C_4$ alkyl substituents;

wherein each $C_1$-$C_4$ alkyl substituent is optionally and independently substituted by one or more substituents independently selected from the group consisting of OH, halogen, $CF_3$, CN, P(O)($OR_a$)(OR), ═O, and $OC_1$-$C_4$ alkyl; and wherein one or two —$CH_2$— groups of the $C_3$-$C_8$ cycloalkyl are optionally and independently replaced by one or two groups independently selected from the group consisting of —O—, —NH—, —S—, and —$S(O)_2$—; and $R^3$ is H, $F_z$ or $C_1$-$C_4$ alkyl, wherein one —$CH_2$— group of the $C_1$-$C_4$ alkyl is optionally replaced by one —NH—;

each R is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

each R' is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

each $R_a$ is independently H or $C_1$-$C_4$ alkyl;

each $R_b$ is independently H or $C_1$-$C_4$ alkyl;

n is 0, 1, 2, or 3;

m is 0, 12 or 2; and m' is 0, 1, or 2;

with the proviso that no more than one of $R^1$, $R^2$, and $R^3$ is H.

2. The compound according to claim 1, or a pharmaceutically acceptable salt thereof, wherein:

$R_g$ is H; and $R_h$ is H.

3. The compound according to claim 1, or a pharmaceutically acceptable salt thereof, wherein Q is —NH—.

4. The compound according to claim 1, or a pharmaceutically acceptable salt thereof, wherein:

(i) ring Z' is phenylene; and ring Z is phenylene; or (ii) ring Z' is phenylene; and ring Z is pyridinylene.

5. The compound according to claim 1, or a pharmaceutically acceptable salt thereof, wherein:

each R is independently $C_1$-$C_4$ alkyl, $C_3$-$C_6$ cycloalkyl, tetrahydrofuranyl, tetrahydropyranyl, $CF_3$, furanyl, Cl, F, CN, or $OC_1$-$C_5$ alkyl;

wherein each $C_1$-$C_4$ alkyl is optionally and independently substituted by one or more OH substituents; and wherein one —$CH_2$— group of each $C_1$-$C_4$ alkyl is optionally and independently replaced by one group independently selected from the group consisting of —S(O)— and —$S(O)_2$—; and each R' is independently $C_1$-$C_4$ alkyl, $C_3$-$C_6$ cycloalkyl, tetrahydrofuranyl, tetrahydropyranyl, —$CF_3$, furanyl, Cl, F, CN, or $OC_1$-$C_5$ alkyl, wherein each $C_1$-$C_4$ alkyl is optionally and independently substituted by one or more OH substituents; and wherein one —$CH_2$— group of each $C_1$-$C_4$ alkyl is optionally and independently replaced by one group independently selected from the group consisting of —S(O)— and —$S(O)_2$—.

6. The compound according to claim 1, or a pharmaceutically acceptable salt thereof, wherein $X^2$ is —C(O)—, —C(O)NH—, —NHC(O)—, —O—, or 5- or 6-membered heterocyclyl;

wherein the heterocyclyl comprises 1, 2, 3, or 4 heteroatoms independently selected from the group consisting of N, O, and S; and wherein the heterocyclyl is optionally substituted by one or more substituents independently selected from the group consisting of halogen, $C_1$-$C_4$ alkyl, —$C(O)OR_p$, and ═O.

7. The compound according to claim 1, or a pharmaceutically acceptable salt thereof, wherein $Y^2$ is H, halogen, morpholinyl, bridged morpholinyl, $C_5$-$C_{11}$ bicycloalkyl, adamantyl, $C_2$-$C_4$ alkenyl, —$PO(OR_a)(OR_b)$, oxazolyl, isoxazolyl, pyrazolyl, imidazolyl, or —$CR^1R^2R^3$;

wherein the morpholinyl is optionally substituted by one or more substituents independently selected from the group consisting of $C_1$-$C_4$ alkyl and —$CF_3$; and wherein the bridged morpholinyl is optionally substituted by one or more independently selected halogen substituents;

one of (i) and (ii) is satisfied:

(i) $R^1$ is H, $F_z$ or $C_1$-$C_4$ alkyl; and $R^2$ is H, $F_z$ or $C_1$-$C_4$ alkyl; or (ii) $R^1$ and $R^2$, together with the carbon atom to which they are attached, form a $C_3$-$C_8$ cycloalkyl;

wherein the $C_3$-$C_8$ cycloalkyl is optionally substituted by one or two independently selected $C_1$-$C_4$ alkyl substituents;

wherein each $C_1$-$C_4$ alkyl is optionally substituted by one or more substituents independently selected from the group consisting of halogen, $CF_3$, OH, CN, $P(O)(OR_a)(OR_b)$, and ═O; and wherein one or two $CH_2$— groups of the $C_3$-$C_8$ cycloalkyl are optionally and independently replaced by one or two groups independently selected from the group consisting of —O—, —S—, —NH—, and —$S(O)_2$—; and $R^3$ is H, $F_z$ or $C_1$-$C_4$ alkyl, wherein one —$CH_2$— group of the $C_1$-$C_4$ alkyl is optionally replaced by one —NH—.

8. The compound according to claim 1, wherein the compound is selected from the group consisting of:
| N° | Structure |
|---|---|
| 1 | 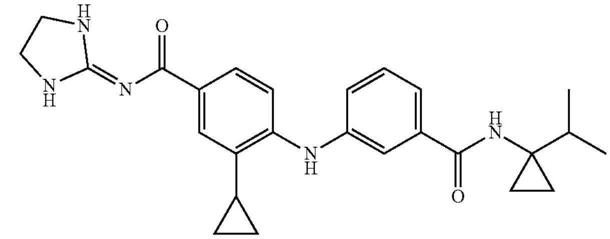 [SMILES: CC(C)C1(NC(=O)c2cccc(Nc3ccc(C(=O)N=C4NCCN4)cc3C3CC3)c2)CC1] |
| 2 | 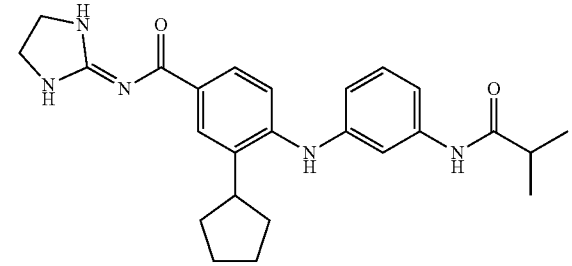 [SMILES: CC(C)C(=O)Nc1cccc(Nc2ccc(C(=O)N=C3NCCN3)cc2C2CCCC2)c1] |
| 3 | 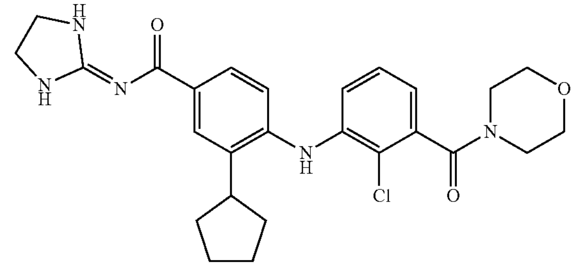 |
| 4 | 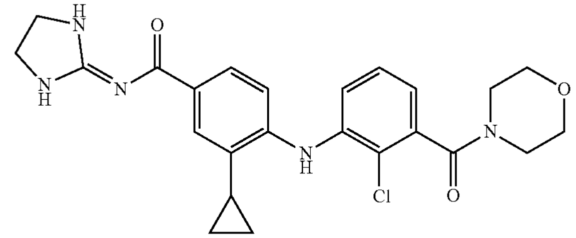 [SMILES: O=C(N=C1NCCN1)c1ccc(Nc2cccc(C(=O)N3CCOCC3)c2Cl)c(C2CC2)c1] |
| 5 | 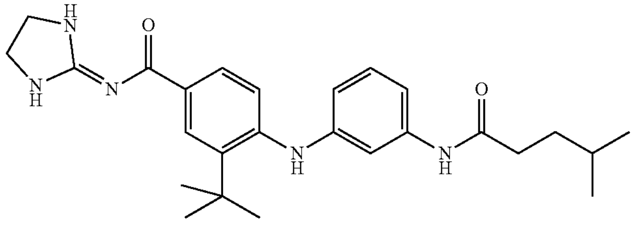 [SMILES: CC(C)CCC(=O)Nc1cccc(Nc2ccc(C(=O)N=C3NCCN3)cc2C(C)(C)C)c1] |
| 6 | 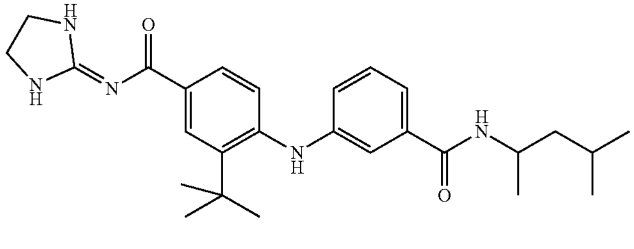 [SMILES: CC(C)CC(C)NC(=O)c1cccc(Nc2ccc(C(=O)N=C3NCCN3)cc2C(C)(C)C)c1] |

-continued
| N° | Structure |
| --- | --- |
| 7 | 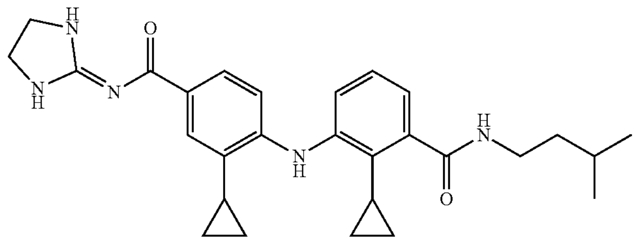 [SMILES: CC(C)CCNC(=O)c1cccc(Nc2ccc(C(=O)N=C3NCCN3)cc2C2CC2)c1C1CC1] |
| 8 | 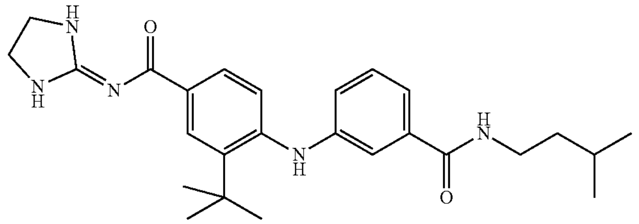 [SMILES: CC(C)CCNC(=O)c1cccc(Nc2ccc(C(=O)N=C3NCCN3)cc2C(C)(C)C)c1] |
| 9 | 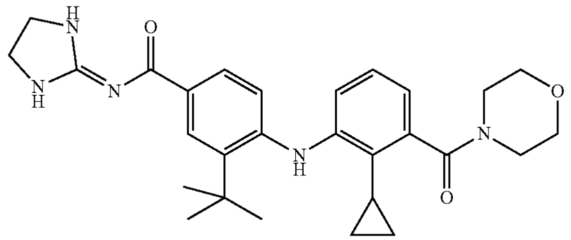 [SMILES: CC(C)(C)c1cc(C(=O)N=C2NCCN2)ccc1Nc1cccc(C(=O)N2CCOCC2)c1C1CC1] |
| 10 | 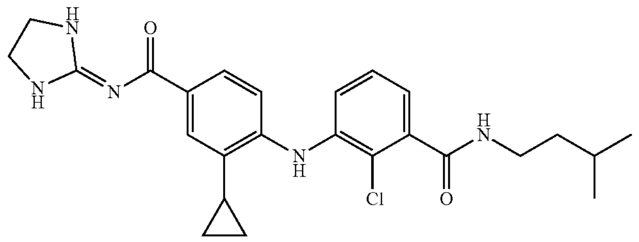 [SMILES: CC(C)CCNC(=O)c1cccc(Nc2ccc(C(=O)N=C3NCCN3)cc2C2CC2)c1Cl] |
| 11 | 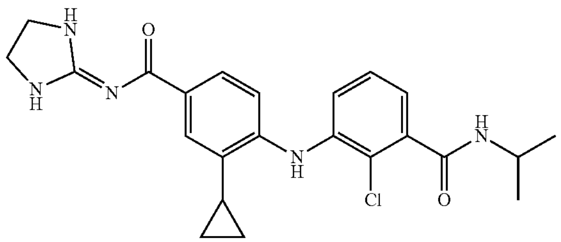 [SMILES: CC(C)NC(=O)c1cccc(Nc2ccc(C(=O)N=C3NCCN3)cc2C2CC2)c1Cl] |
| 12 | 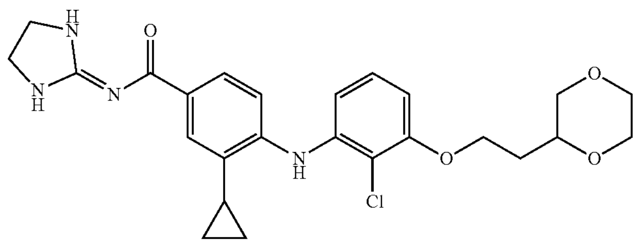 [SMILES: O=C(N=C1NCCN1)c1ccc(Nc2cccc(OCCC3COCCO3)c2Cl)c(C2CC2)c1] |

-continued
| N° | Structure |
| --- | --- |
| 13 | 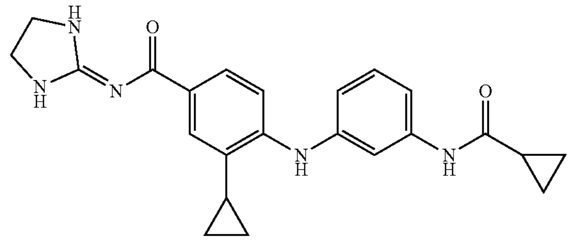 [SMILES: O=C(N=C1NCCN1)c1ccc(Nc2cccc(NC(=O)C3CC3)c2)c(C2CC2)c1] |
| 14 | 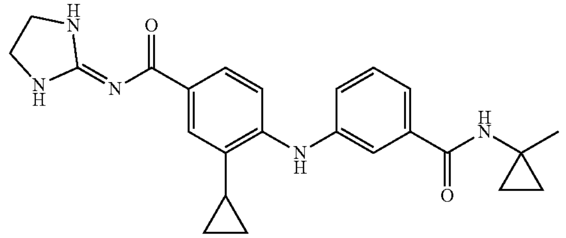 [SMILES: CC1(NC(=O)c2cccc(Nc3ccc(C(=O)N=C4NCCN4)cc3C3CC3)c2)CC1] |
| 15 | 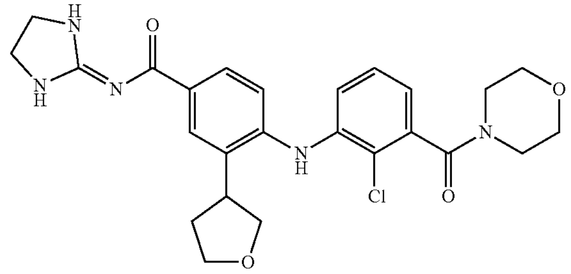 [SMILES: O=C(N=C1NCCN1)c1ccc(Nc2cccc(C(=O)N3CCOCC3)c2Cl)c(C2CCOC2)c1] |
| 16 | 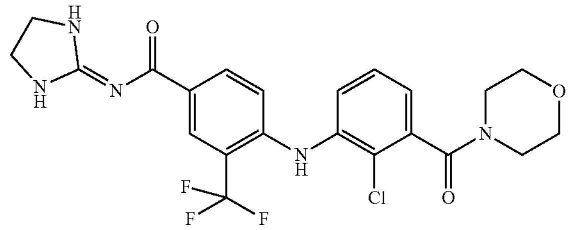 [SMILES: O=C(N=C1NCCN1)c1ccc(Nc2cccc(C(=O)N3CCOCC3)c2Cl)c(C(F)(F)F)c1] |
| 17 | 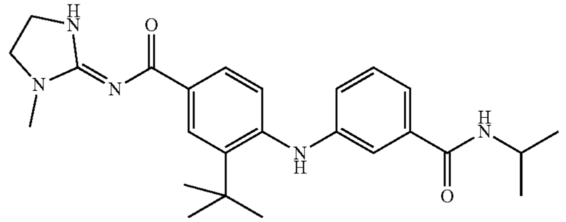 [SMILES: CC(C)NC(=O)c1cccc(Nc2ccc(C(=O)/N=C3\NCCN3C)cc2C(C)(C)C)c1] |
| 18 | 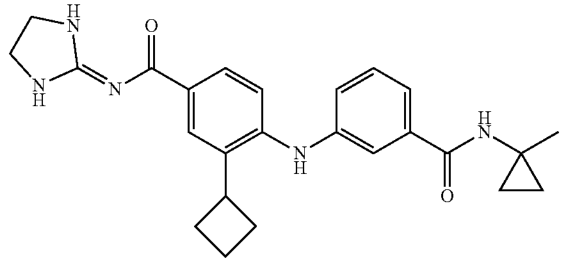 [SMILES: CC1(NC(=O)c2cccc(Nc3ccc(C(=O)N=C4NCCN4)cc3C3CCC3)c2)CC1] |

-continued
| N° | Structure |
| --- | --- |
| 19 | 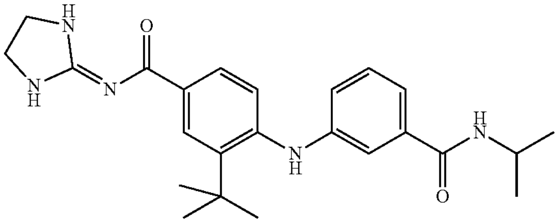 [SMILES: CC(C)NC(=O)c1cccc(Nc2ccc(C(=O)N=C3NCCN3)cc2C(C)(C)C)c1] |
| 20 | 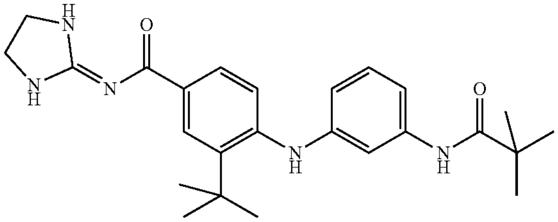 [SMILES: CC(C)(C)C(=O)Nc1cccc(Nc2ccc(C(=O)N=C3NCCN3)cc2C(C)(C)C)c1] |
| 21 | 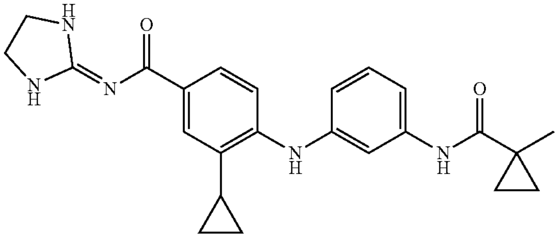 [SMILES: CC1(C(=O)Nc2cccc(Nc3ccc(C(=O)N=C4NCCN4)cc3C3CC3)c2)CC1] |
| 22 | 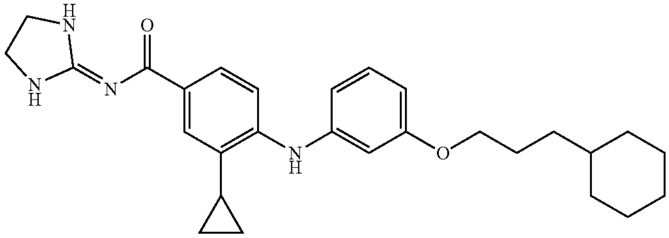 [SMILES: O=C(N=C1NCCN1)c1ccc(Nc2cccc(OCCCC3CCCCC3)c2)c(C2CC2)c1] |
| 23 | 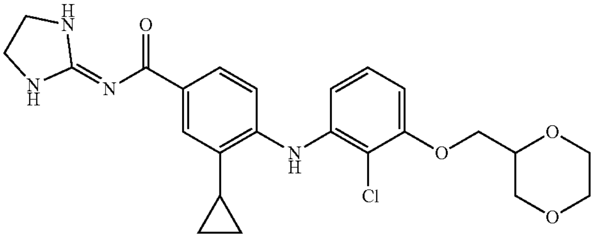 [SMILES: O=C(N=C1NCCN1)c1ccc(Nc2cccc(OCC3COCCO3)c2Cl)c(C2CC2)c1] |
| 24 | 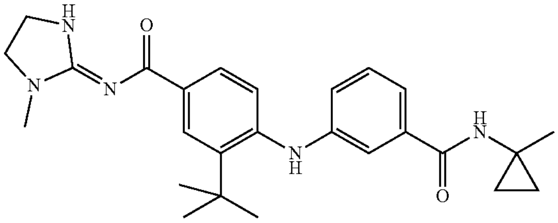 [SMILES: CN1CCN/C1=N\C(=O)c1ccc(Nc2cccc(C(=O)NC3(C)CC3)c2)c(C(C)(C)C)c1] |

-continued
| N° | Structure |
| --- | --- |
| 25 | 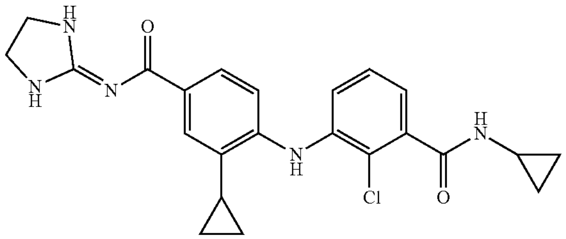 [SMILES: O=C(N=C1NCCN1)c1ccc(Nc2cccc(C(=O)NC3CC3)c2Cl)c(C2CC2)c1] |
| 26 | 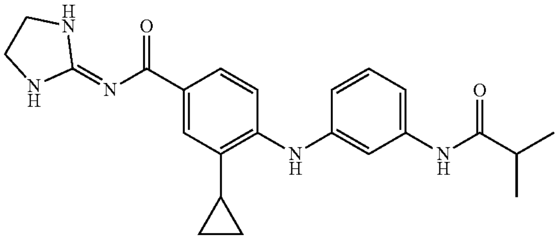 [SMILES: CC(C)C(=O)Nc1cccc(Nc2ccc(C(=O)N=C3NCCN3)cc2C2CC2)c1] |
| 27 | 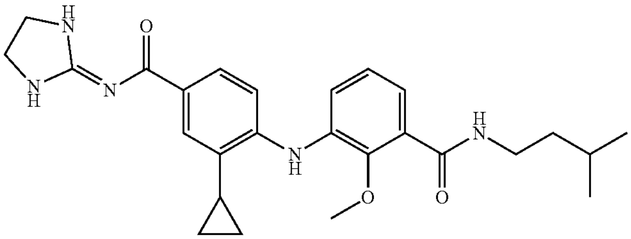 [SMILES: COc1c(Nc2ccc(C(=O)N=C3NCCN3)cc2C2CC2)cccc1C(=O)NCCC(C)C] |
| 28 | 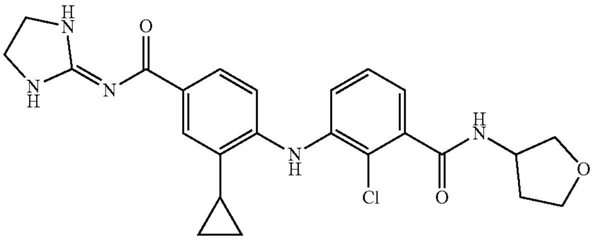 [SMILES: O=C(N=C1NCCN1)c1ccc(Nc2cccc(C(=O)NC3CCOC3)c2Cl)c(C2CC2)c1] |
| 29 | 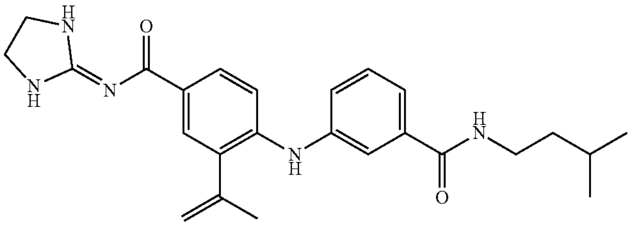 [SMILES: C=C(C)c1cc(C(=O)N=C2NCCN2)ccc1Nc1cccc(C(=O)NCCC(C)C)c1] |
| 30 | 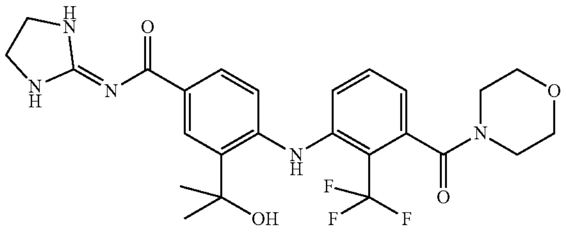 [SMILES: CC(C)(O)c1cc(C(=O)N=C2NCCN2)ccc1Nc1cccc(C(=O)N2CCOCC2)c1C(F)(F)F] |

-continued
| N° | Structure |
| --- | --- |
| 31 | 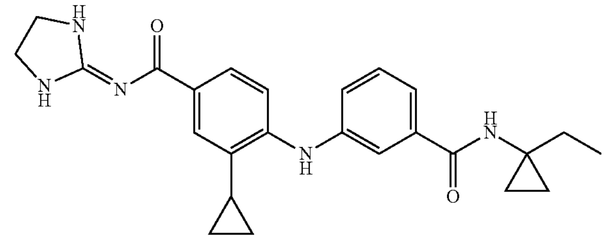 |
| 32 | 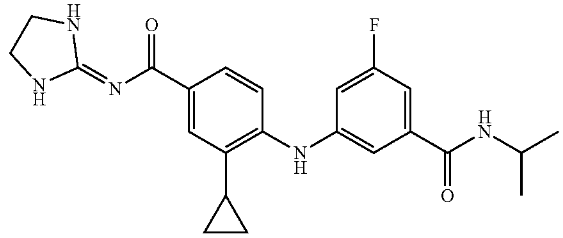 [SMILES: CC(C)NC(=O)c1cc(F)cc(Nc2ccc(C(=O)N=C3NCCN3)cc2C2CC2)c1] |
| 33 | 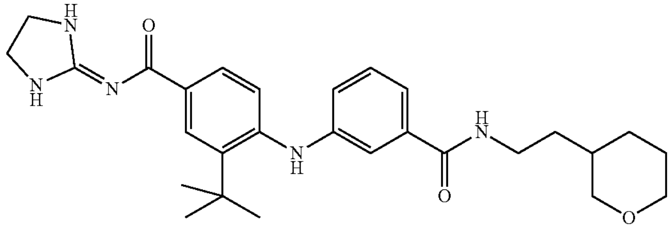 [SMILES: CC(C)(C)c1cc(C(=O)N=C2NCCN2)ccc1Nc1cccc(C(=O)NCCC2CCCOC2)c1] |
| 34 | 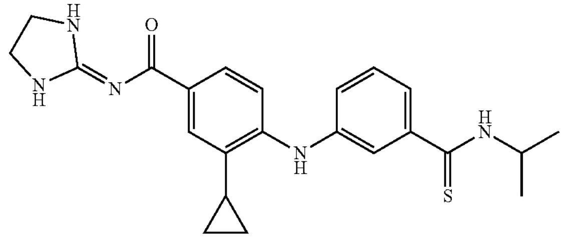 [SMILES: CC(C)NC(=S)c1cccc(Nc2ccc(C(=O)N=C3NCCN3)cc2C2CC2)c1] |
| 35 | 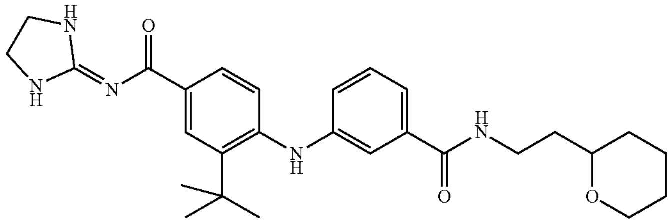 [SMILES: CC(C)(C)c1cc(C(=O)N=C2NCCN2)ccc1Nc1cccc(C(=O)NCCC2CCCCO2)c1] |
| 36 | 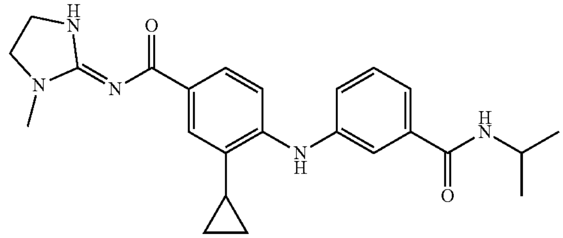 [SMILES: CC(C)NC(=O)c1cccc(Nc2ccc(C(=O)/N=C3\NCCN3C)cc2C2CC2)c1] |

-continued
| N° | Structure |
|---|---|
| 37 | 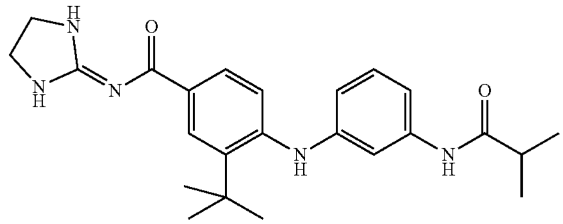 [SMILES: CC(C)C(=O)Nc1cccc(Nc2ccc(C(=O)N=C3NCCN3)cc2C(C)(C)C)c1] |
| 38 | 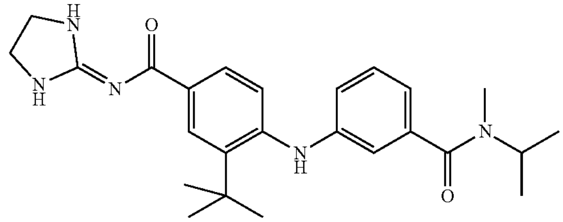 [SMILES: CC(C)N(C)C(=O)c1cccc(Nc2ccc(C(=O)N=C3NCCN3)cc2C(C)(C)C)c1] |
| 39 | 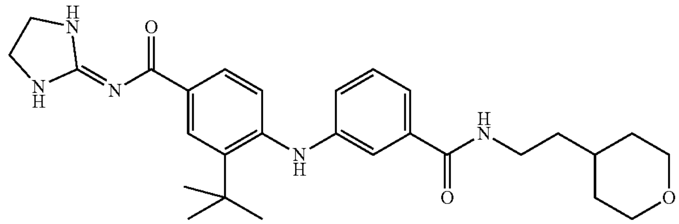 [SMILES: CC(C)(C)c1cc(C(=O)N=C2NCCN2)ccc1Nc1cccc(C(=O)NCCC2CCOCC2)c1] |
| 40 | 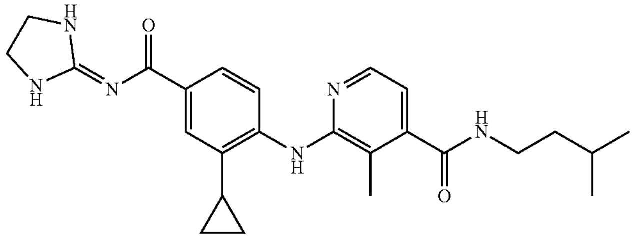 [SMILES: Cc1c(C(=O)NCCC(C)C)ccnc1Nc1ccc(C(=O)N=C2NCCN2)cc1C1CC1] |
| 41 | 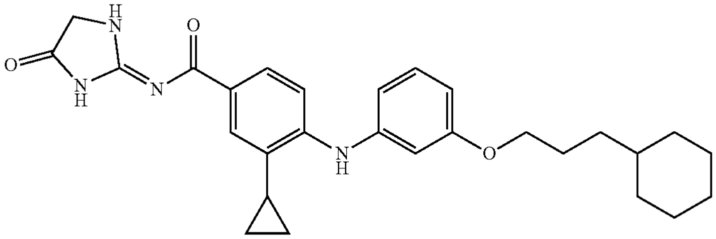 [SMILES: O=C1CN/C(=N\C(=O)c2ccc(Nc3cccc(OCCCC4CCCCC4)c3)c(C3CC3)c2)N1] |
| 42 | 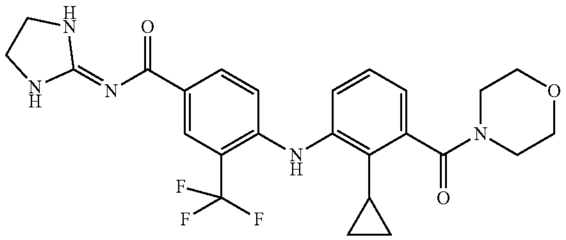 [SMILES: O=C(N=C1NCCN1)c1ccc(Nc2cccc(C(=O)N3CCOCC3)c2C2CC2)c(C(F)(F)F)c1] |

-continued
| N° | Structure |
| --- | --- |
| 43 | 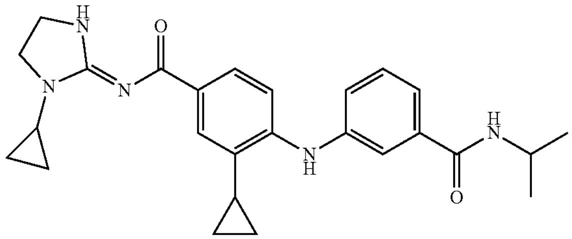 [SMILES: CC(C)NC(=O)c1cccc(Nc2ccc(C(=O)/N=C3\NCCN3C3CC3)cc2C2CC2)c1] |
| 44 | 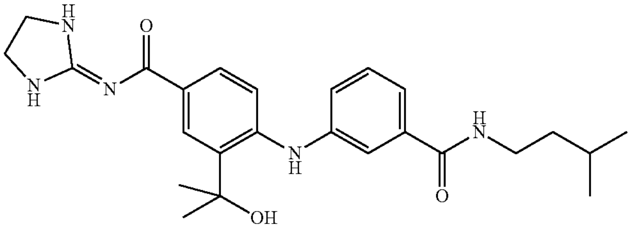 [SMILES: CC(C)CCNC(=O)c1cccc(Nc2ccc(C(=O)N=C3NCCN3)cc2C(C)(C)O)c1] |
| 45 | 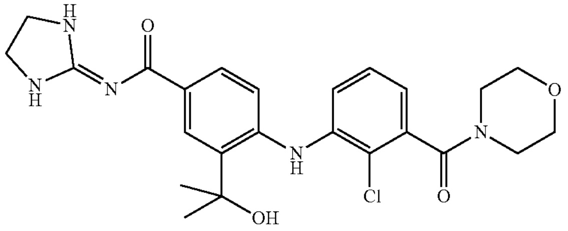 [SMILES: CC(C)(O)c1cc(C(=O)N=C2NCCN2)ccc1Nc1cccc(C(=O)N2CCOCC2)c1Cl] |
| 46 | 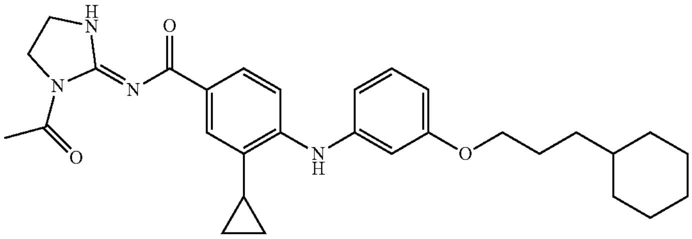 [SMILES: CC(=O)N1CCN/C1=N\C(=O)c1ccc(Nc2cccc(OCCCC3CCCCC3)c2)c(C2CC2)c1] |
| 47 | 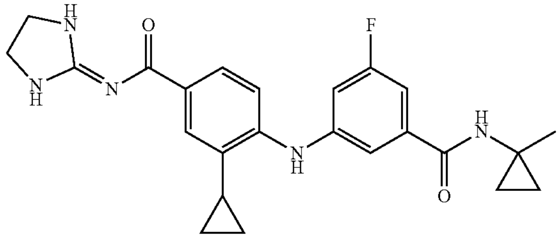 [SMILES: CC1(NC(=O)c2cc(F)cc(Nc3ccc(C(=O)N=C4NCCN4)cc3C3CC3)c2)CC1] |
| 48 | 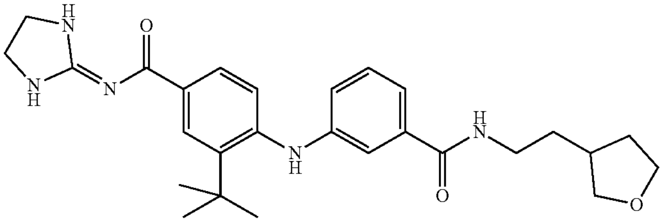 [SMILES: CC(C)(C)c1cc(C(=O)N=C2NCCN2)ccc1Nc1cccc(C(=O)NCCC2CCOC2)c1] |

-continued
| Nº | Structure |
|---|---|
| 49 | 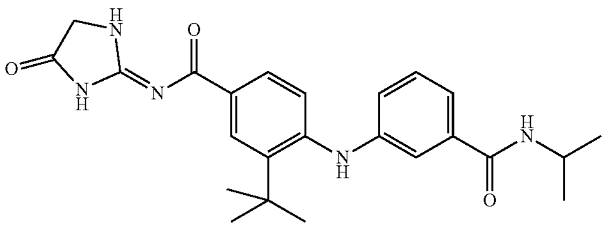 [SMILES: CC(C)NC(=O)c1cccc(Nc2ccc(C(=O)/N=C3\NCC(=O)N3)cc2C(C)(C)C)c1] |
| 50 | 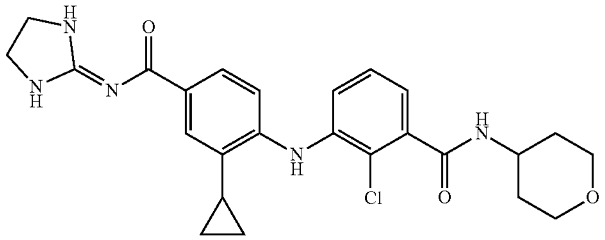 [SMILES: O=C(N=C1NCCN1)c1ccc(Nc2cccc(C(=O)NC3CCOCC3)c2Cl)c(C2CC2)c1] |
| 51 | 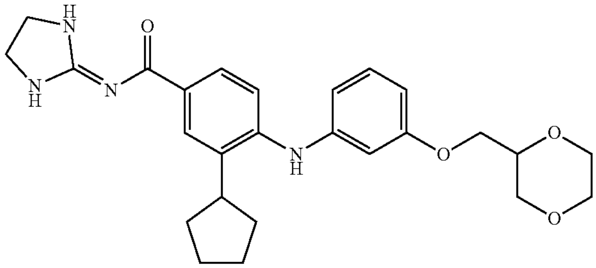 [SMILES: O=C(N=C1NCCN1)c1ccc(Nc2cccc(OCC3COCCO3)c2)c(C2CCCC2)c1] |
| 52 | 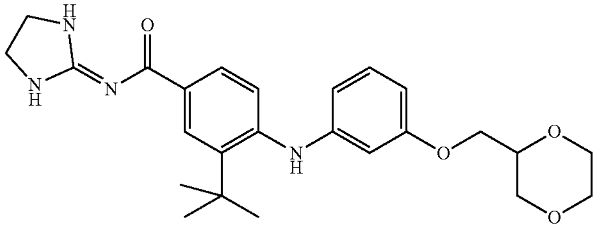 [SMILES: CC(C)(C)c1cc(C(=O)N=C2NCCN2)ccc1Nc1cccc(OCC2COCCO2)c1] |
| 53 | 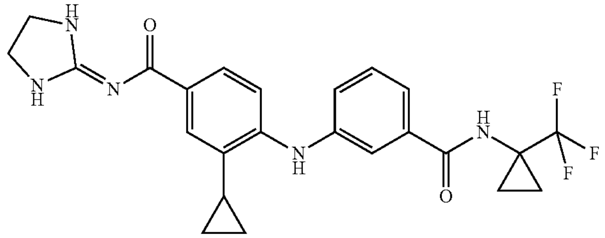 [SMILES: O=C(N=C1NCCN1)c1ccc(Nc2cccc(C(=O)NC3(C(F)(F)F)CC3)c2)c(C2CC2)c1] |
| 54 | 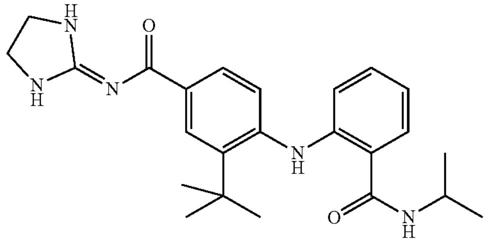 [SMILES: CC(C)NC(=O)c1ccccc1Nc1ccc(C(=O)N=C2NCCN2)cc1C(C)(C)C] |

-continued
| N° | Structure |
| --- | --- |
| 55 | 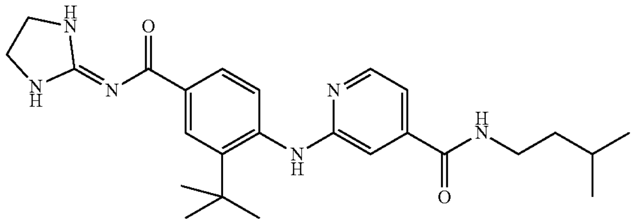 [SMILES: CC(C)CCNC(=O)c1ccnc(Nc2ccc(C(=O)N=C3NCCN3)cc2C(C)(C)C)c1] |
| 56 | 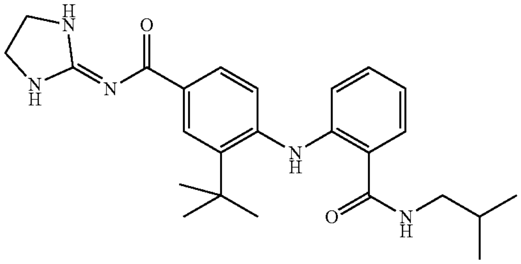 [SMILES: CC(C)CNC(=O)c1ccccc1Nc1ccc(C(=O)N=C2NCCN2)cc1C(C)(C)C] |
| 57 | 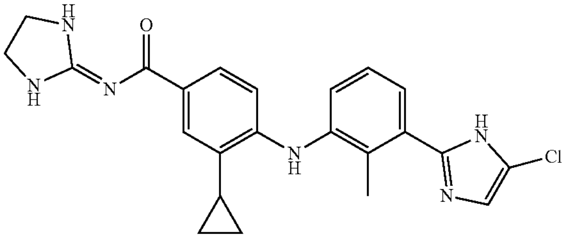 [SMILES: Cc1c(Nc2ccc(C(=O)N=C3NCCN3)cc2C2CC2)cccc1-c1ncc(Cl)[nH]1] |
| 58 | 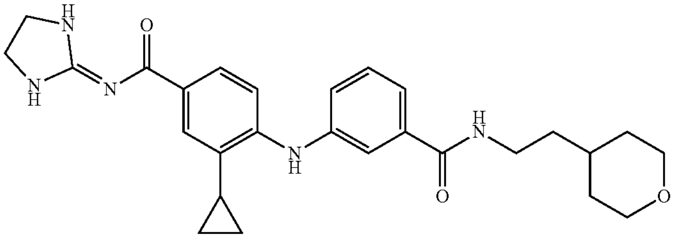 [SMILES: O=C(N=C1NCCN1)c1ccc(Nc2cccc(C(=O)NCCC3CCOCC3)c2)c(C2CC2)c1] |
| 59 | 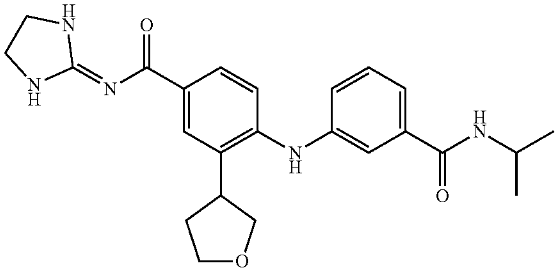 [SMILES: CC(C)NC(=O)c1cccc(Nc2ccc(C(=O)N=C3NCCN3)cc2C2CCOC2)c1] |
| 60 | 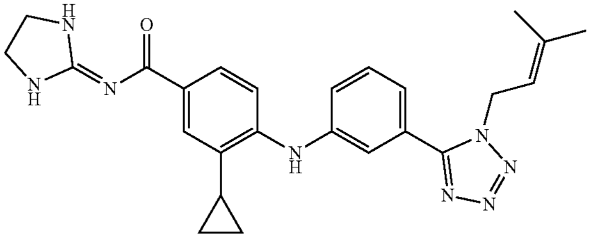 [SMILES: CC(C)=CCn1nnnc1-c1cccc(Nc2ccc(C(=O)N=C3NCCN3)cc2C2CC2)c1] |

-continued
| N° | Structure |
| --- | --- |
| 61 | 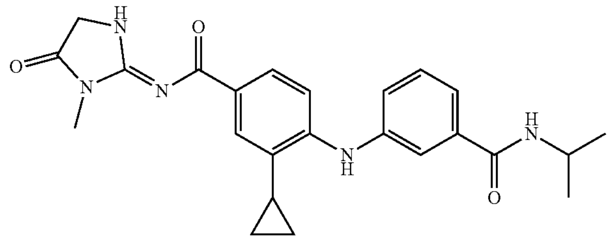 [SMILES: CC(C)NC(=O)c1cccc(Nc2ccc(C(=O)/N=C3\NCC(=O)N3C)cc2C2CC2)c1] |
| 62 | 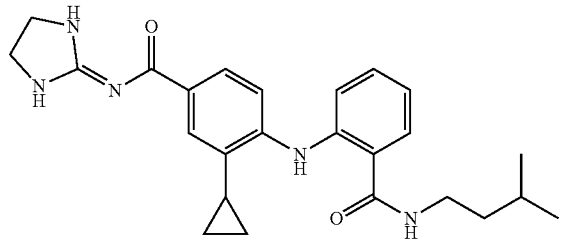 |
| 63 | 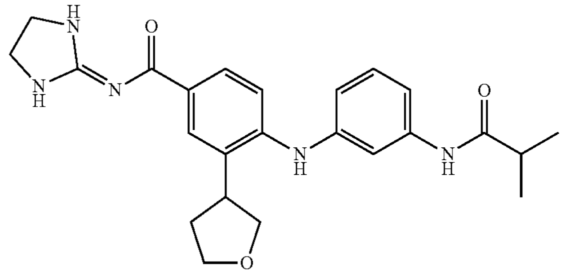 [SMILES: CC(C)C(=O)Nc1cccc(Nc2ccc(C(=O)N=C3NCCN3)cc2C2CCOC2)c1] |
| 64 | 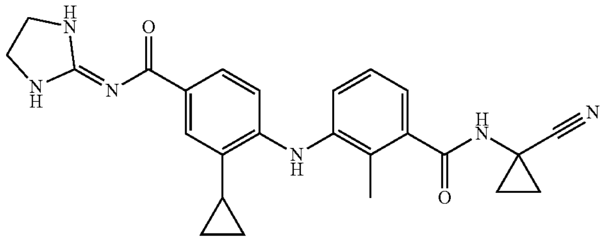 [SMILES: Cc1c(Nc2ccc(C(=O)N=C3NCCN3)cc2C2CC2)cccc1C(=O)NC1(C#N)CC1] |
| 65 | 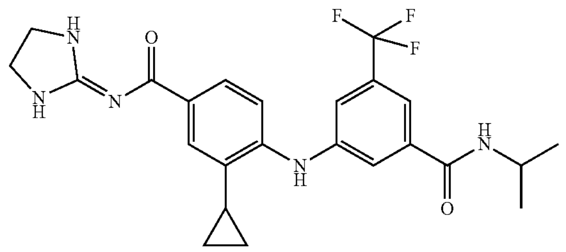 [SMILES: CC(C)NC(=O)c1cc(Nc2ccc(C(=O)N=C3NCCN3)cc2C2CC2)cc(C(F)(F)F)c1] |
| 66 | 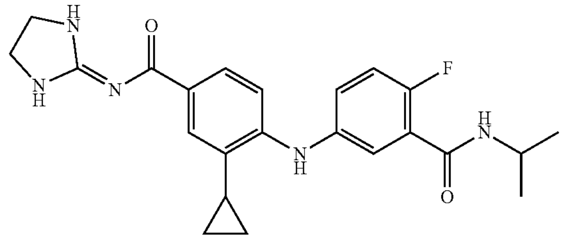 [SMILES: CC(C)NC(=O)c1cc(Nc2ccc(C(=O)N=C3NCCN3)cc2C2CC2)ccc1F] |

-continued
| N° | Structure |
|---|---|
| 67 | 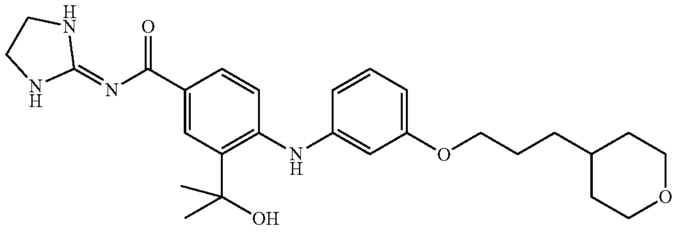 [SMILES: CC(C)(O)c1cc(C(=O)N=C2NCCN2)ccc1Nc1cccc(OCCCC2CCOCC2)c1] |
| 68 | 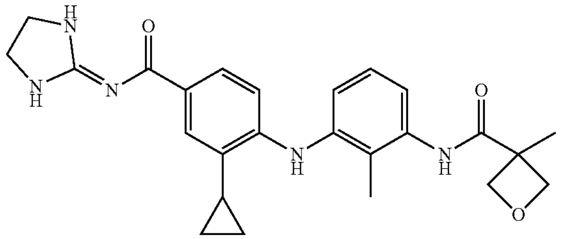 [SMILES: Cc1c(NC(=O)C2(C)COC2)cccc1Nc1ccc(C(=O)N=C2NCCN2)cc1C1CC1] |
| 69 | 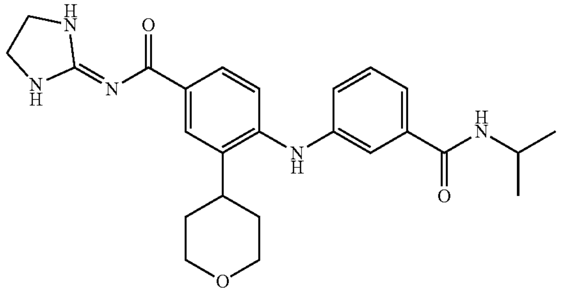 [SMILES: CC(C)NC(=O)c1cccc(Nc2ccc(C(=O)N=C3NCCN3)cc2C2CCOCC2)c1] |
| 70 | 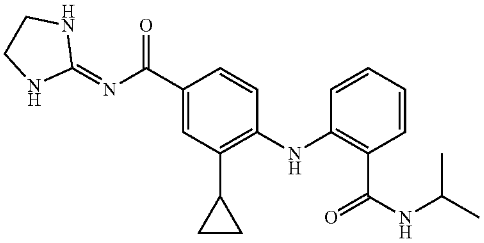 [SMILES: CC(C)NC(=O)c1ccccc1Nc1ccc(C(=O)N=C2NCCN2)cc1C1CC1] |
| 71 | 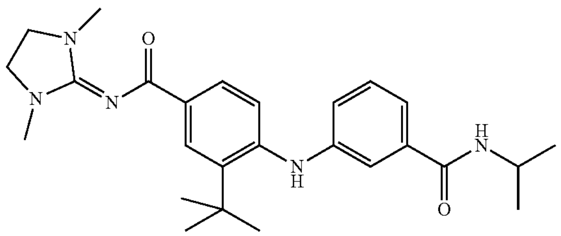 [SMILES: CC(C)NC(=O)c1cccc(Nc2ccc(C(=O)N=C3N(C)CCN3C)cc2C(C)(C)C)c1] |
| 72 | 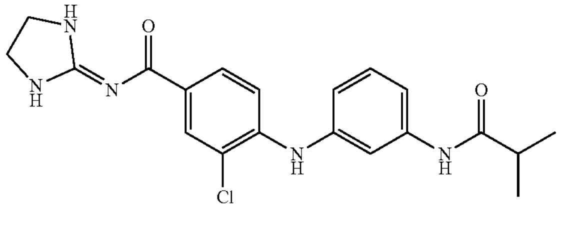 [SMILES: CC(C)C(=O)Nc1cccc(Nc2ccc(C(=O)N=C3NCCN3)cc2Cl)c1] |

-continued
| N° | Structure |
|---|---|
| 73 | 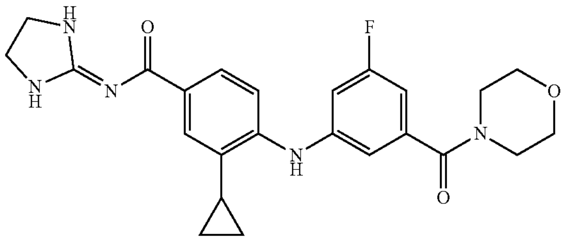 [SMILES: O=C(N=C1NCCN1)c1ccc(Nc2cc(F)cc(C(=O)N3CCOCC3)c2)c(C2CC2)c1] |
| 74 | 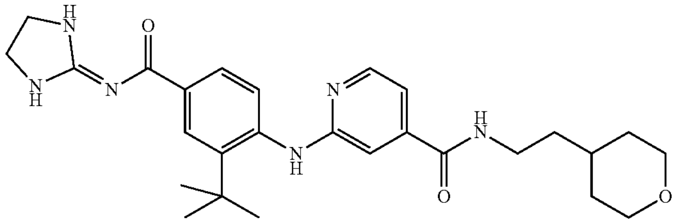 |
| 75 | 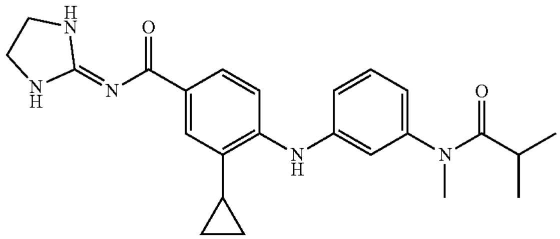 [SMILES: CC(C)C(=O)N(C)c1cccc(Nc2ccc(C(=O)N=C3NCCN3)cc2C2CC2)c1] |
| 76 | 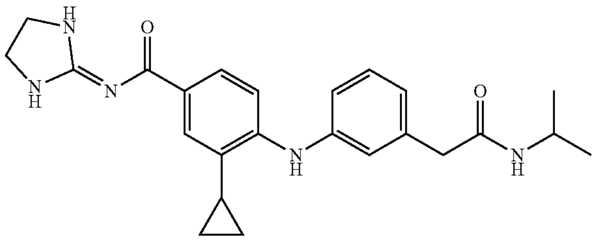 [SMILES: CC(C)NC(=O)Cc1cccc(Nc2ccc(C(=O)N=C3NCCN3)cc2C2CC2)c1] |
| 77 | 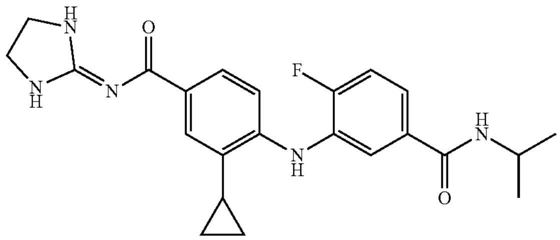 [SMILES: CC(C)NC(=O)c1ccc(F)c(Nc2ccc(C(=O)N=C3NCCN3)cc2C2CC2)c1] |
| 78 | 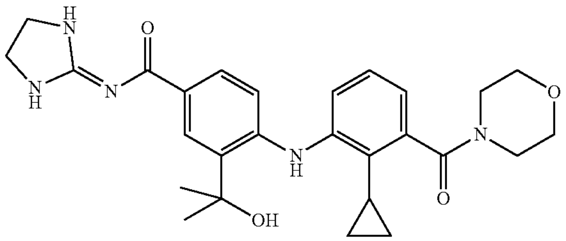 [SMILES: CC(C)(O)c1cc(C(=O)N=C2NCCN2)ccc1Nc1cccc(C(=O)N2CCOCC2)c1C1CC1] |

-continued
| Nº | Structure |
| --- | --- |
| 79 | 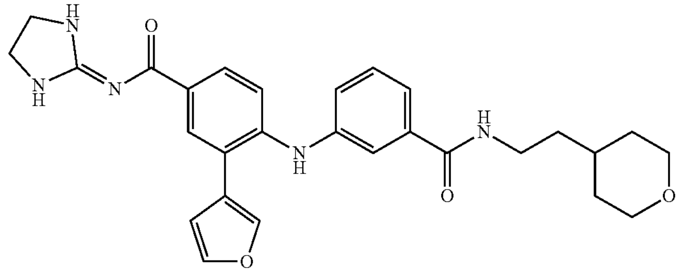 [SMILES: O=C(N=C1NCCN1)c1ccc(Nc2cccc(C(=O)NCCC3CCOCC3)c2)c(-c2ccoc2)c1] |
| 80 | 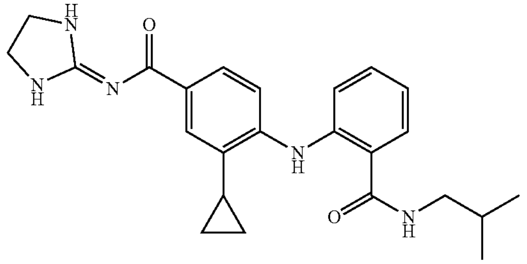 [SMILES: CC(C)CNC(=O)c1ccccc1Nc1ccc(C(=O)N=C2NCCN2)cc1C1CC1] |
| 81 | 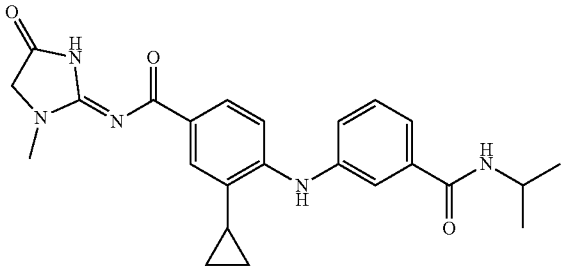 [SMILES: CC(C)NC(=O)c1cccc(Nc2ccc(C(=O)/N=C3\NC(=O)CN3C)cc2C2CC2)c1] |
| 82 | 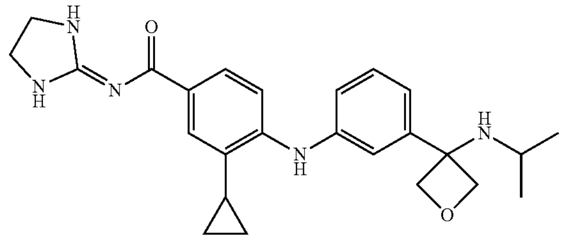 [SMILES: CC(C)NC1(c2cccc(Nc3ccc(C(=O)N=C4NCCN4)cc3C3CC3)c2)COC1] |
| 83 | 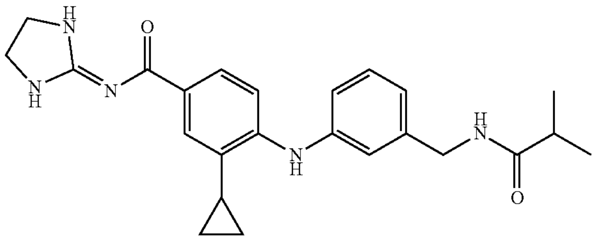 [SMILES: CC(C)C(=O)NCc1cccc(Nc2ccc(C(=O)N=C3NCCN3)cc2C2CC2)c1] |
| 84 | 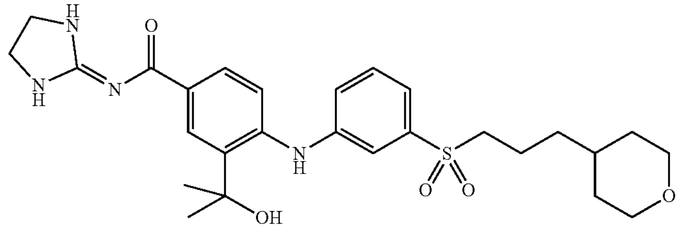 [SMILES: CC(C)(O)c1cc(C(=O)N=C2NCCN2)ccc1Nc1cccc(S(=O)(=O)CCCC2CCOCC2)c1] |

-continued
| N° | Structure |
|---|---|
| 85 | 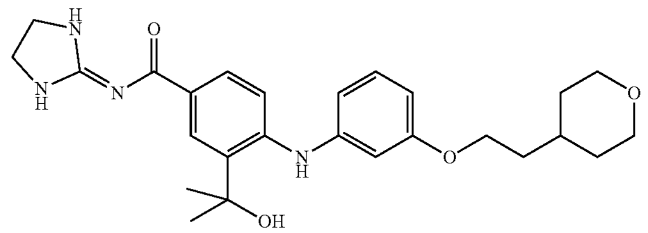 [SMILES: CC(C)(O)c1cc(C(=O)N=C2NCCN2)ccc1Nc1cccc(OCCC2CCOCC2)c1] |
| 86 | 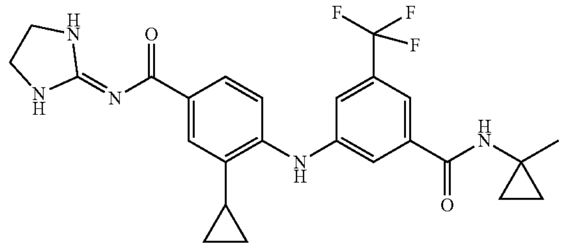 [SMILES: CC1(NC(=O)c2cc(Nc3ccc(C(=O)N=C4NCCN4)cc3C3CC3)cc(C(F)(F)F)c2)CC1] |
| 87 | 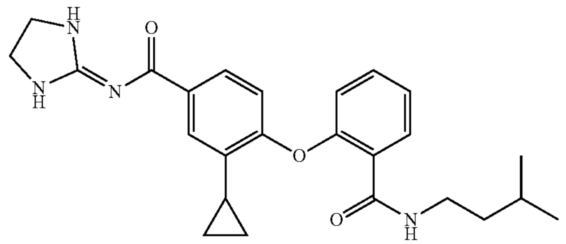 [SMILES: CC(C)CCNC(=O)c1ccccc1Oc1ccc(C(=O)N=C2NCCN2)cc1C1CC1] |
| 88 | 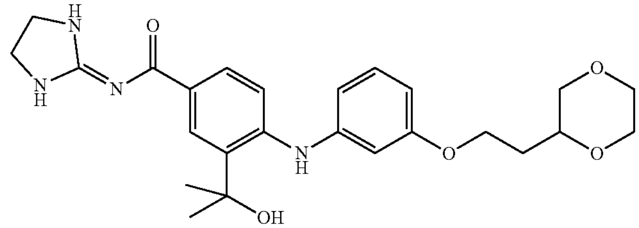 [SMILES: CC(C)(O)c1cc(C(=O)N=C2NCCN2)ccc1Nc1cccc(OCCC2COCCO2)c1] |
| 89 | 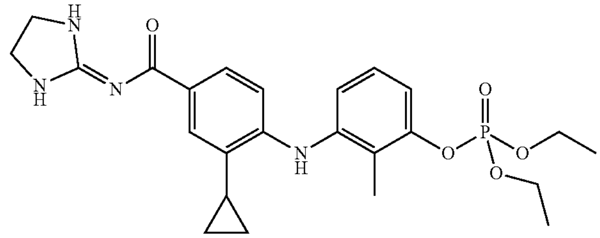 [SMILES: CCOP(=O)(OCC)Oc1cccc(Nc2ccc(C(=O)N=C3NCCN3)cc2C2CC2)c1C] |
| 90 | 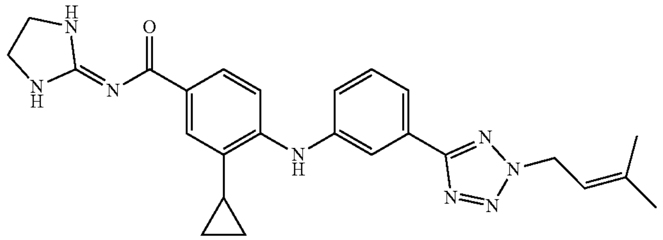 [SMILES: CC(C)=CCn1nnc(-c2cccc(Nc3ccc(C(=O)N=C4NCCN4)cc3C3CC3)c2)n1] |

-continued
| N° | Structure |
|---|---|
| 91 | 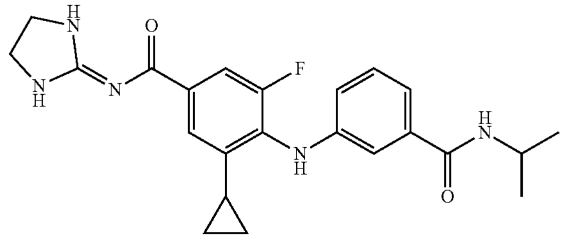 [SMILES: CC(C)NC(=O)c1cccc(Nc2c(F)cc(C(=O)N=C3NCCN3)cc2C2CC2)c1] |
| 92 | 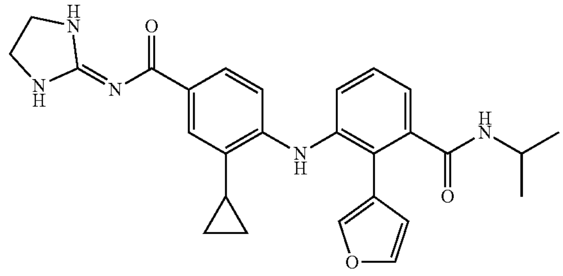 [SMILES: CC(C)NC(=O)c1cccc(Nc2ccc(C(=O)N=C3NCCN3)cc2C2CC2)c1-c1ccoc1] |
| 93 | 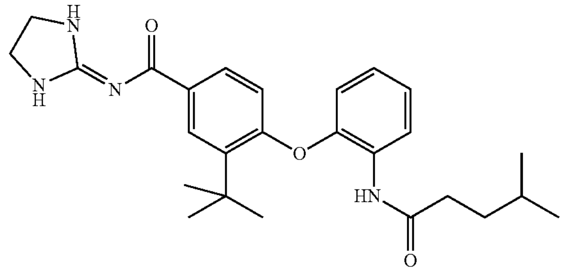 [SMILES: CC(C)CCC(=O)Nc1ccccc1Oc1ccc(C(=O)N=C2NCCN2)cc1C(C)(C)C] |
| 94 | 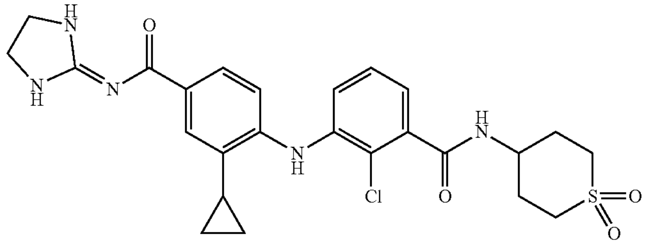 [SMILES: O=C(N=C1NCCN1)c1ccc(Nc2cccc(C(=O)NC3CCS(=O)(=O)CC3)c2Cl)c(C2CC2)c1] |
| 95 | 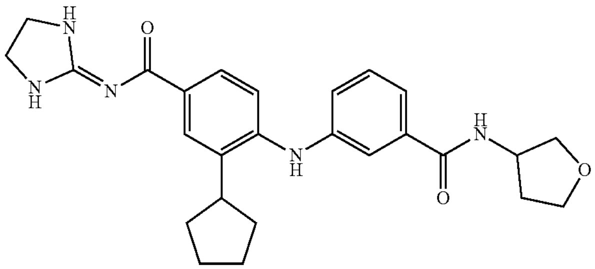 [SMILES: O=C(N=C1NCCN1)c1ccc(Nc2cccc(C(=O)NC3CCOC3)c2)c(C2CCCC2)c1] |
| 96 | 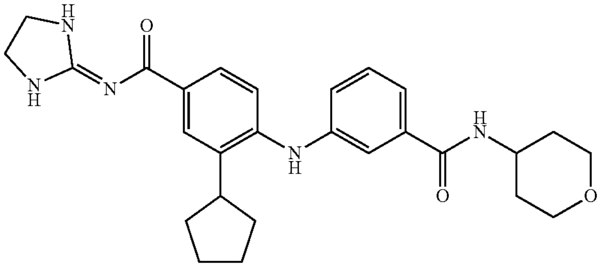 [SMILES: O=C(N=C1NCCN1)c1ccc(Nc2cccc(C(=O)NC3CCOCC3)c2)c(C2CCCC2)c1] |

-continued
| Nº | Structure |
| --- | --- |
| 97 | 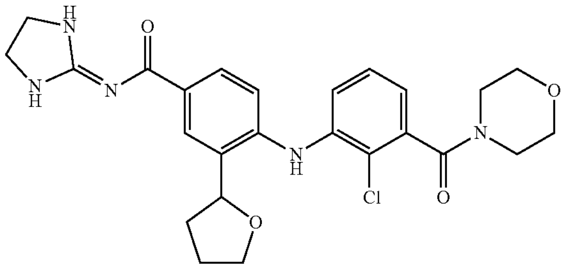 |
| 98 | 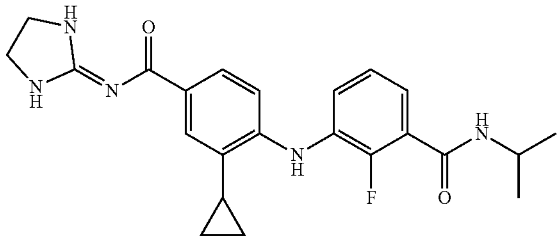 |
| 99 | 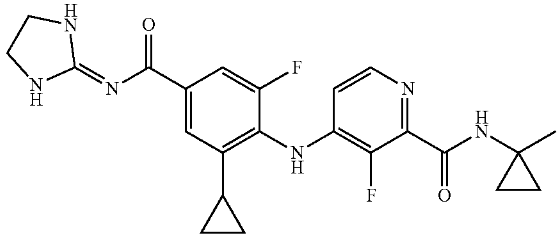 |
| 100 | 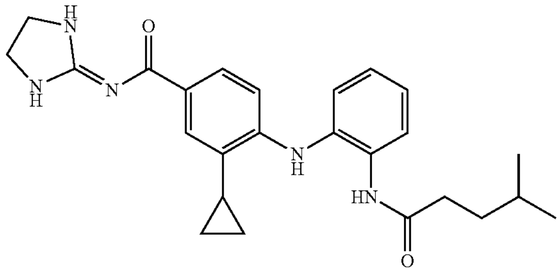 |
| 101 | 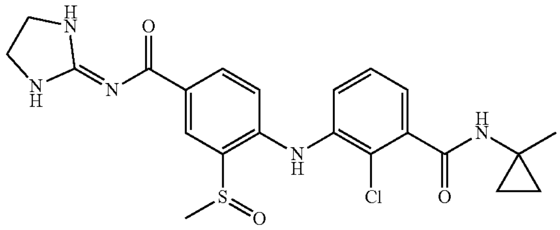 [SMILES: CS(=O)c1cc(C(=O)N=C2NCCN2)ccc1Nc1cccc(C(=O)NC2(C)CC2)c1Cl] |
| 102 | 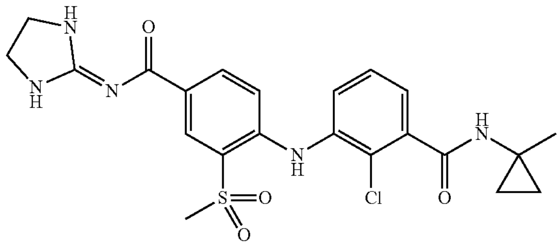 [SMILES: CC1(NC(=O)c2cccc(Nc3ccc(C(=O)N=C4NCCN4)cc3S(C)(=O)=O)c2Cl)CC1] |

-continued
| N° | Structure |
| --- | --- |
| 103 | 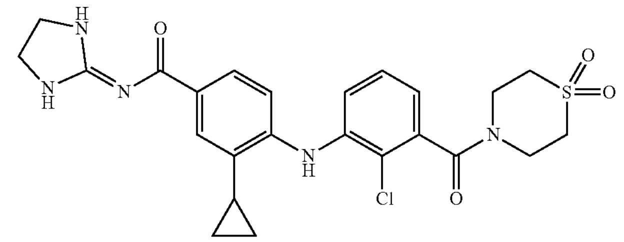 [SMILES: O=C(N=C1NCCN1)c1ccc(Nc2cccc(C(=O)N3CCS(=O)(=O)CC3)c2Cl)c(C2CC2)c1] |
| 104 | 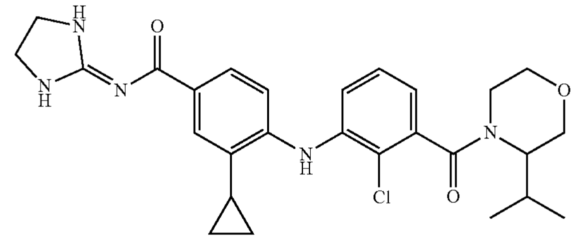 [SMILES: CC(C)C1COCCN1C(=O)c1cccc(Nc2ccc(C(=O)N=C3NCCN3)cc2C2CC2)c1Cl] |
| 105 | 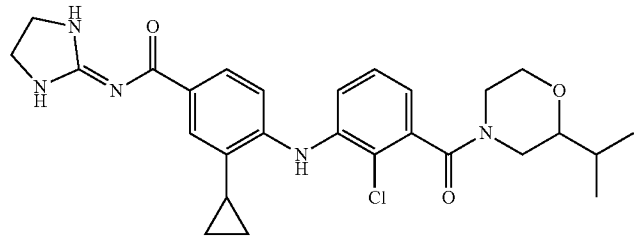 [SMILES: CC(C)C1CN(C(=O)c2cccc(Nc3ccc(C(=O)N=C4NCCN4)cc3C3CC3)c2Cl)CCO1] |
| 106 | 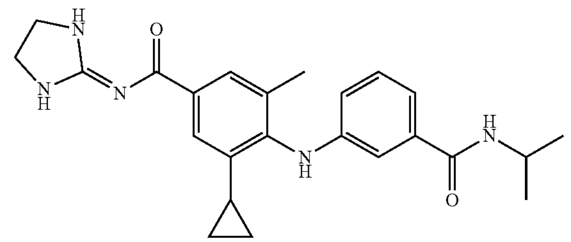 [SMILES: Cc1cc(C(=O)N=C2NCCN2)cc(C2CC2)c1Nc1cccc(C(=O)NC(C)C)c1] |
| 107 | 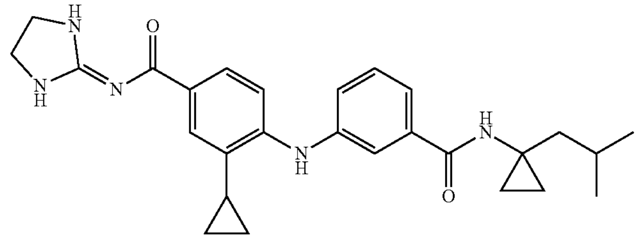 [SMILES: CC(C)CC1(NC(=O)c2cccc(Nc3ccc(C(=O)N=C4NCCN4)cc3C3CC3)c2)CC1] |
| 108 | 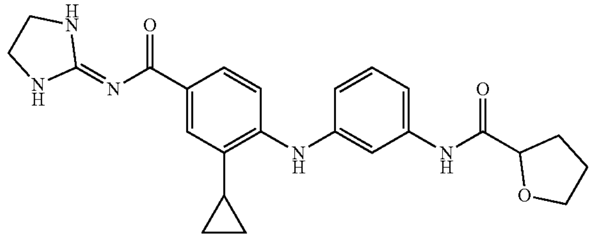 [SMILES: O=C(N=C1NCCN1)c1ccc(Nc2cccc(NC(=O)C3CCCO3)c2)c(C2CC2)c1] |

-continued
| N° | Structure |
|---|---|
| 109 | 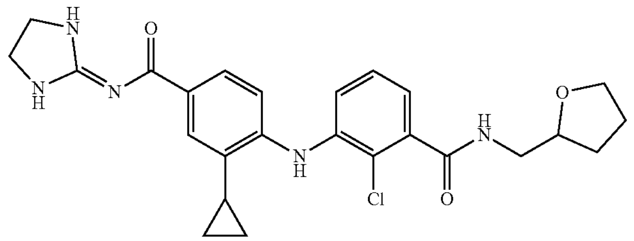 [SMILES: O=C(N=C1NCCN1)c1ccc(Nc2cccc(C(=O)NCC3CCCO3)c2Cl)c(C2CC2)c1] |
| 110 | 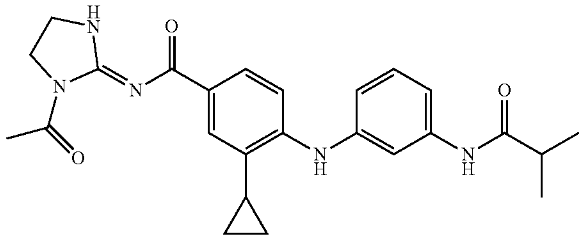 [SMILES: CC(=O)N1CCN/C1=N\C(=O)c1ccc(Nc2cccc(NC(=O)C(C)C)c2)c(C2CC2)c1] |
| 111 | 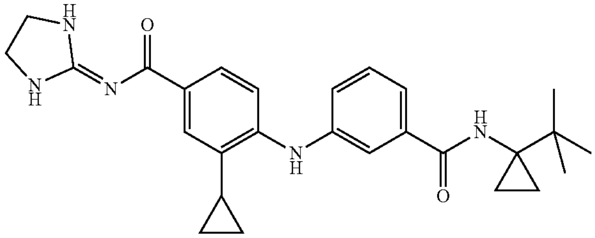 [SMILES: CC(C)(C)C1(NC(=O)c2cccc(Nc3ccc(C(=O)N=C4NCCN4)cc3C3CC3)c2)CC1] |
| 112 | 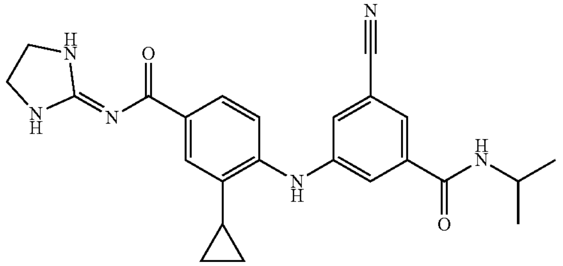 [SMILES: CC(C)NC(=O)c1cc(C#N)cc(Nc2ccc(C(=O)N=C3NCCN3)cc2C2CC2)c1] |
| 113 | 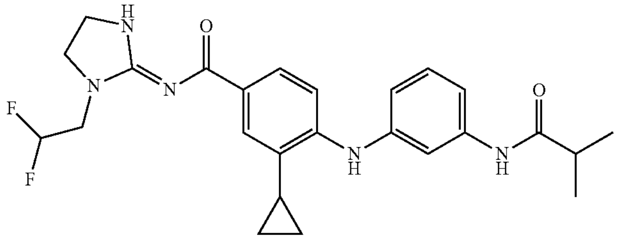 [SMILES: CC(C)C(=O)Nc1cccc(Nc2ccc(C(=O)/N=C3\NCCN3CC(F)F)cc2C2CC2)c1] |
| 114 | 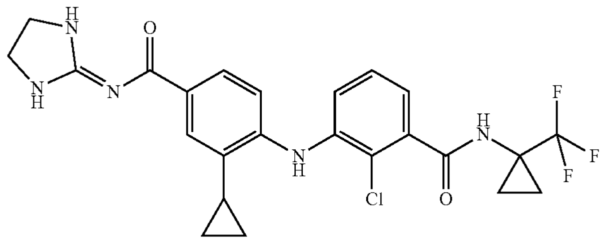 [SMILES: O=C(N=C1NCCN1)c1ccc(Nc2cccc(C(=O)NC3(C(F)(F)F)CC3)c2Cl)c(C2CC2)c1] |

-continued
| N° | Structure |
| --- | --- |
| 115 | 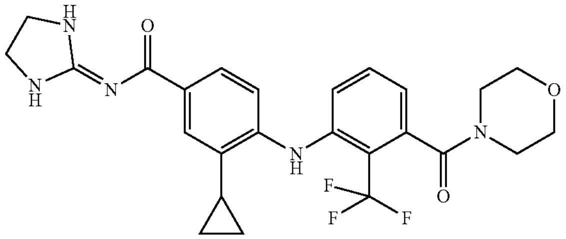 [SMILES: O=C(N=C1NCCN1)c1ccc(Nc2cccc(C(=O)N3CCOCC3)c2C(F)(F)F)c(C2CC2)c1] |
| 116 | 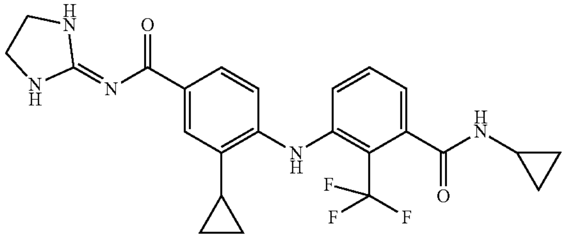 [SMILES: O=C(N=C1NCCN1)c1ccc(Nc2cccc(C(=O)NC3CC3)c2C(F)(F)F)c(C2CC2)c1] |
| 117 | 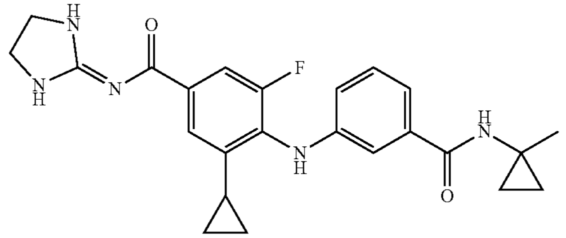 [SMILES: CC1(NC(=O)c2cccc(Nc3c(F)cc(C(=O)N=C4NCCN4)cc3C3CC3)c2)CC1] |
| 118 | 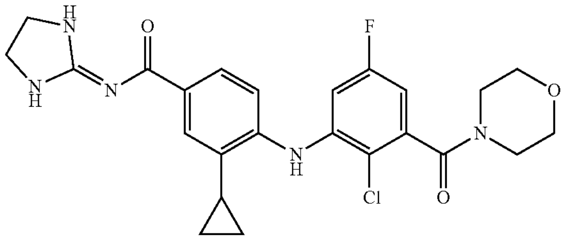 [SMILES: O=C(N=C1NCCN1)c1ccc(Nc2cc(F)cc(C(=O)N3CCOCC3)c2Cl)c(C2CC2)c1] |
| 119 | 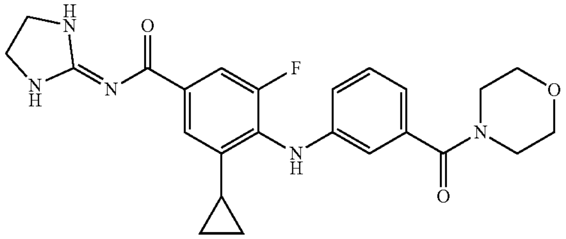 [SMILES: O=C(N=C1NCCN1)c1cc(F)c(Nc2cccc(C(=O)N3CCOCC3)c2)c(C2CC2)c1] |
| 120 | 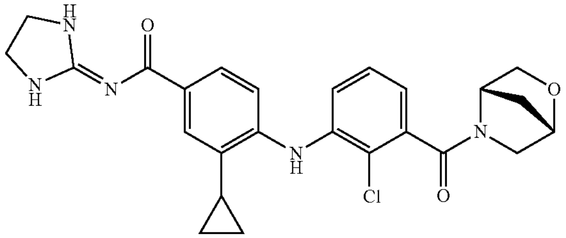 [SMILES: O=C(N=C1NCCN1)c1ccc(Nc2cccc(C(=O)N3C[C@@H]4C[C@H]3CO4)c2Cl)c(C2CC2)c1] |

-continued
| N° | Structure |
| --- | --- |
| 121 | 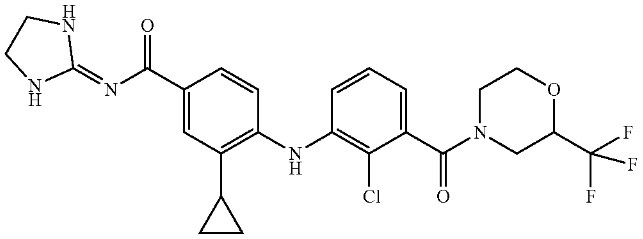 [SMILES: O=C(N=C1NCCN1)c1ccc(Nc2cccc(C(=O)N3CCOC(C(F)(F)F)C3)c2Cl)c(C2CC2)c1] |
| 122 | 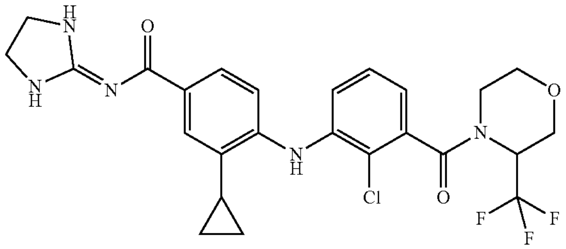 [SMILES: O=C(N=C1NCCN1)c1ccc(Nc2cccc(C(=O)N3CCOCC3C(F)(F)F)c2Cl)c(C2CC2)c1] |
| 123 | 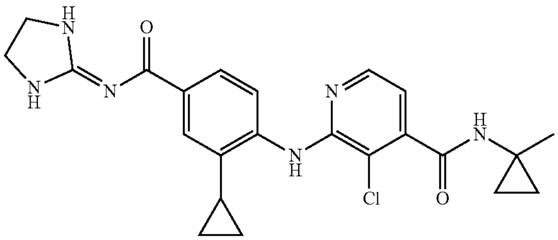 [SMILES: CC1(NC(=O)c2ccnc(Nc3ccc(C(=O)N=C4NCCN4)cc3C3CC3)c2Cl)CC1] |
| 124 | 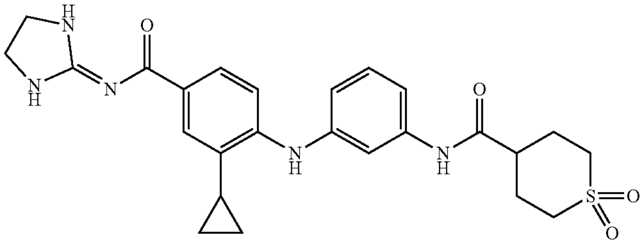 [SMILES: O=C(N=C1NCCN1)c1ccc(Nc2cccc(NC(=O)C3CCS(=O)(=O)CC3)c2)c(C2CC2)c1] |
| 125 | 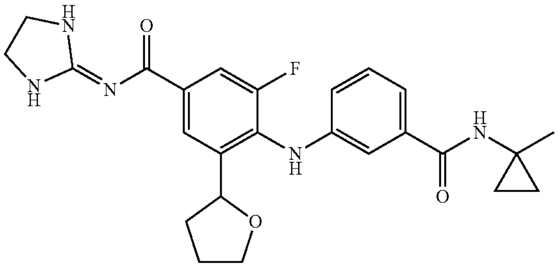 [SMILES: CC1(NC(=O)c2cccc(Nc3c(F)cc(C(=O)N=C4NCCN4)cc3C3CCCO3)c2)CC1] |
| 126 | 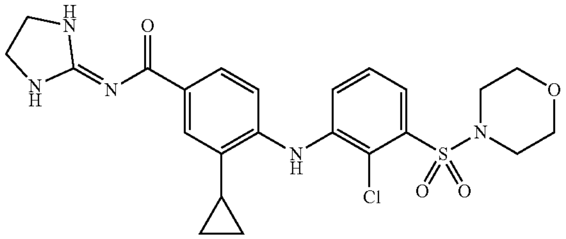 [SMILES: O=C(N=C1NCCN1)c1ccc(Nc2cccc(S(=O)(=O)N3CCOCC3)c2Cl)c(C2CC2)c1] |

-continued
| N° | Structure |
| --- | --- |
| 127 | 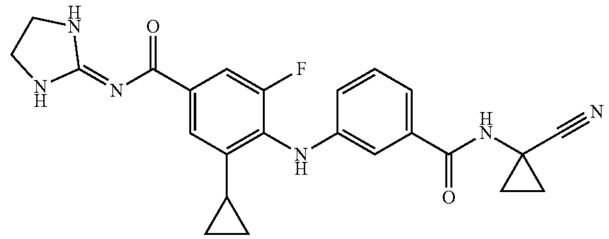 [SMILES: N#CC1(NC(=O)c2cccc(Nc3c(F)cc(C(=O)N=C4NCCN4)cc3C3CC3)c2)CC1] |
| 128 | 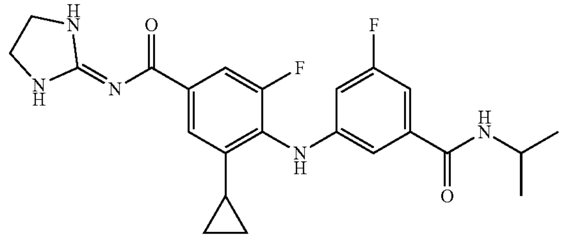 [SMILES: CC(C)NC(=O)c1cc(F)cc(Nc2c(F)cc(C(=O)N=C3NCCN3)cc2C2CC2)c1] |
| 129 | 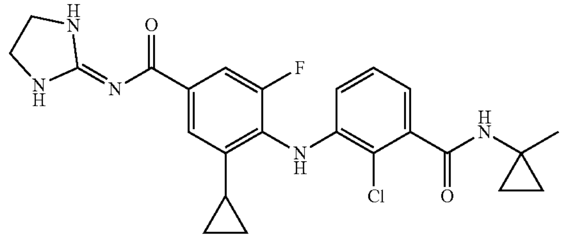 [SMILES: CC1(NC(=O)c2cccc(Nc3c(F)cc(C(=O)N=C4NCCN4)cc3C3CC3)c2Cl)CC1] |
| 130 | 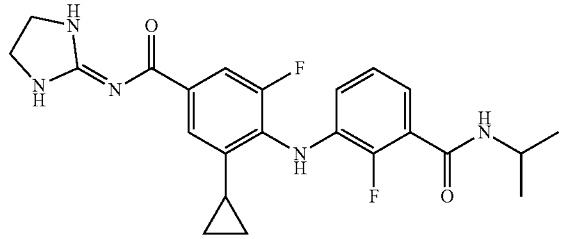 [SMILES: CC(C)NC(=O)c1cccc(Nc2c(F)cc(C(=O)N=C3NCCN3)cc2C2CC2)c1F] |
| 131 | 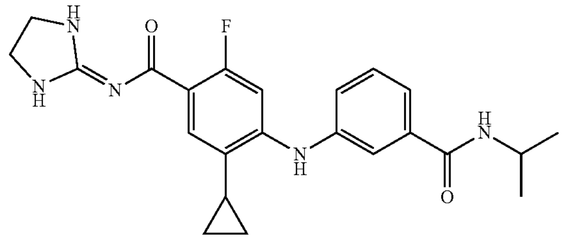 [SMILES: CC(C)NC(=O)c1cccc(Nc2cc(F)c(C(=O)N=C3NCCN3)cc2C2CC2)c1] |
| 132 | 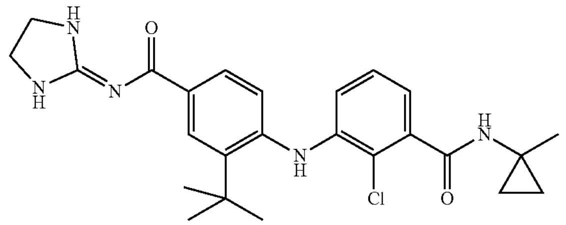 [SMILES: CC1(NC(=O)c2cccc(Nc3ccc(C(=O)N=C4NCCN4)cc3C(C)(C)C)c2Cl)CC1] |

-continued
| Nº | Structure |
| --- | --- |
| 133 | 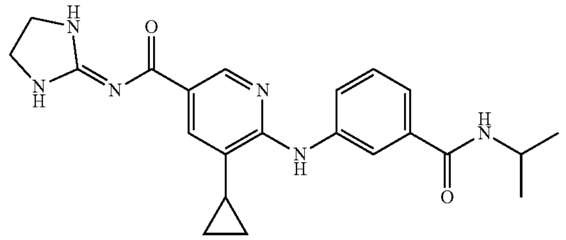 |
| 134 | 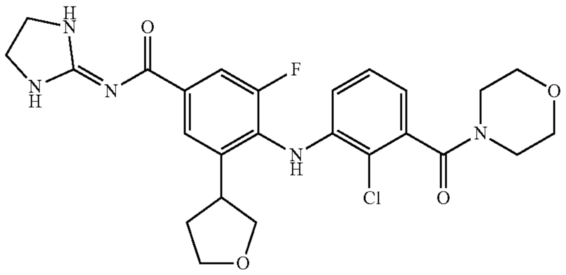 [SMILES: O=C(N=C1NCCN1)c1cc(F)c(Nc2cccc(C(=O)N3CCOCC3)c2Cl)c(C2CCOC2)c1] |
| 135 | 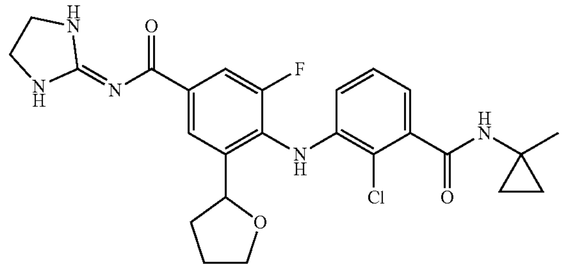 [SMILES: CC1(NC(=O)c2cccc(Nc3c(F)cc(C(=O)N=C4NCCN4)cc3C3CCCO3)c2Cl)CC1] |
| 136 | 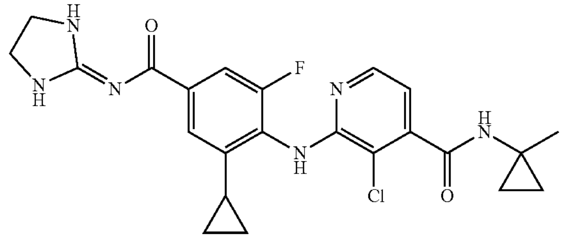 |
| 137 | 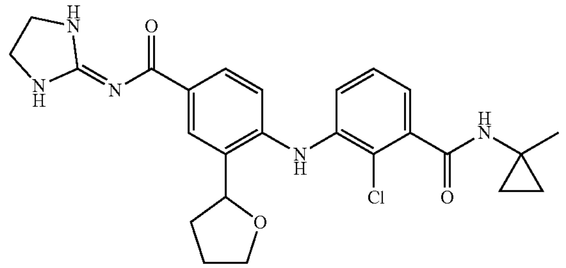 |
| 138 | 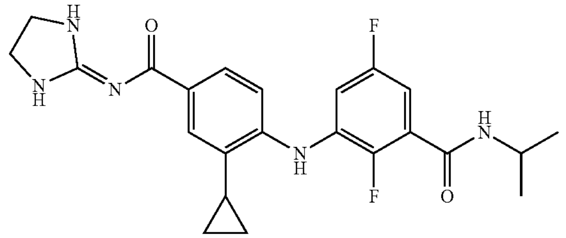 [SMILES: CC(C)NC(=O)c1cc(F)cc(Nc2ccc(C(=O)N=C3NCCN3)cc2C2CC2)c1F] |

-continued
| N° | Structure |
|---|---|
| 139 | 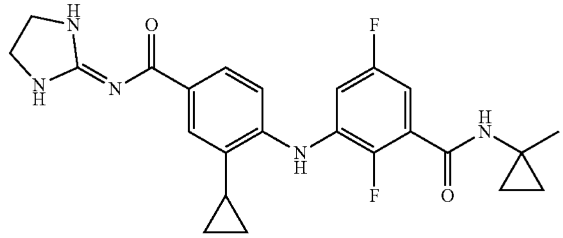 [SMILES: CC1(NC(=O)c2cc(F)cc(Nc3ccc(C(=O)N=C4NCCN4)cc3C3CC3)c2F)CC1] |
| 140 | 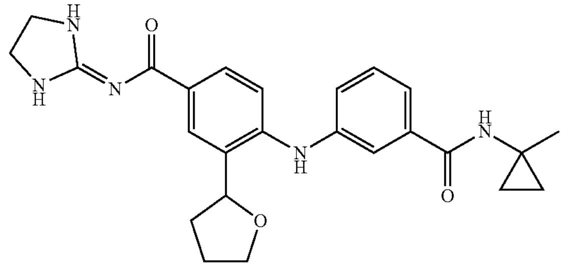 [SMILES: CC1(NC(=O)c2cccc(Nc3ccc(C(=O)N=C4NCCN4)cc3C3CCCO3)c2)CC1] |
| 141 | 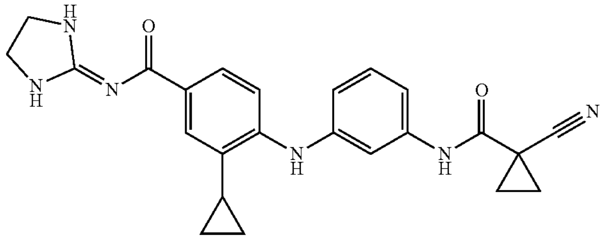 [SMILES: N#CC1(C(=O)Nc2cccc(Nc3ccc(C(=O)N=C4NCCN4)cc3C3CC3)c2)CC1] |
| 142 | 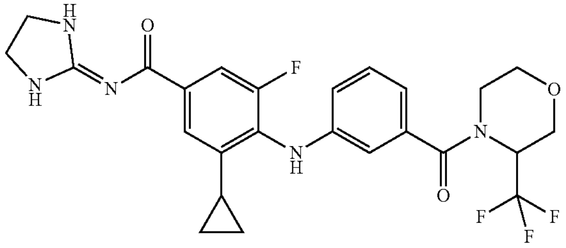 [SMILES: O=C(N=C1NCCN1)c1cc(F)c(Nc2cccc(C(=O)N3CCOCC3C(F)(F)F)c2)c(C2CC2)c1] |
| 143 | 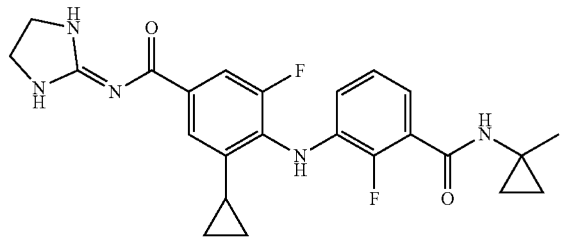 |
| 144 | 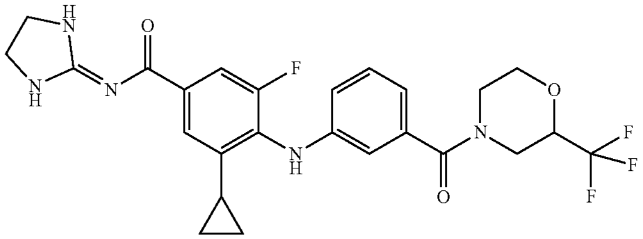 [SMILES: O=C(N=C1NCCN1)c1cc(F)c(Nc2cccc(C(=O)N3CCOC(C(F)(F)F)C3)c2)c(C2CC2)c1] |

-continued
| Nº | Structure |
|---|---|
| 145 | 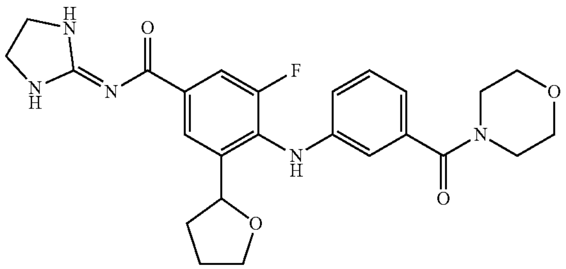 [SMILES: O=C(N=C1NCCN1)c1cc(F)c(Nc2cccc(C(=O)N3CCOCC3)c2)c(C2CCCO2)c1] |
| 146 | 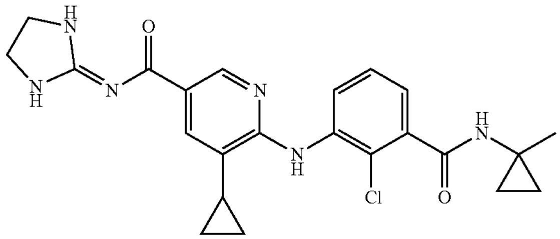 |
| 147 | 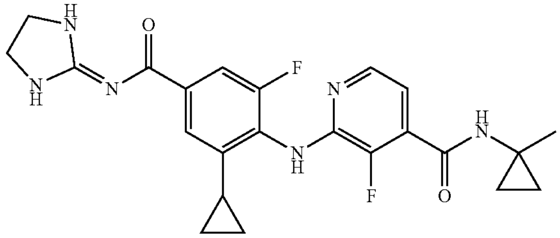 [SMILES: CC1(NC(=O)c2ccnc(Nc3c(F)cc(C(=O)N=C4NCCN4)cc3C3CC3)c2F)CC1] |
| 148 | 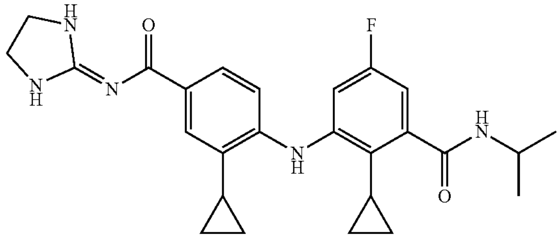 [SMILES: CC(C)NC(=O)c1cc(F)cc(Nc2ccc(C(=O)N=C3NCCN3)cc2C2CC2)c1C1CC1] |
| 149 | 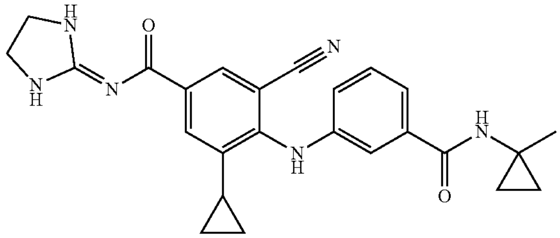 [SMILES: CC1(NC(=O)c2cccc(Nc3c(C#N)cc(C(=O)N=C4NCCN4)cc3C3CC3)c2)CC1] |
| 150 | 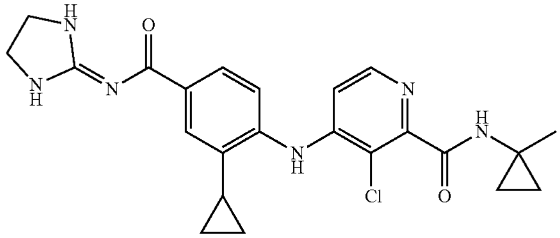 |

-continued
| N° | Structure |
| --- | --- |
| 151 | 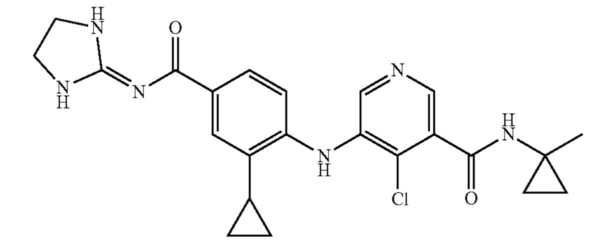 |
| 152 | 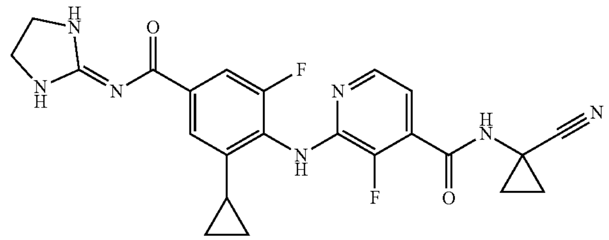 |
| 153 | 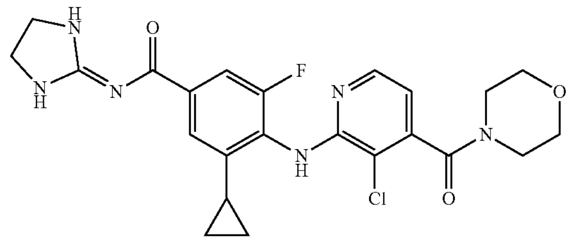 [SMILES: O=C(N=C1NCCN1)c1cc(F)c(Nc2nccc(C(=O)N3CCOCC3)c2Cl)c(C2CC2)c1] |
| 154 | 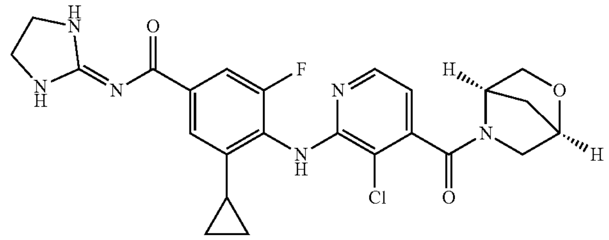 [SMILES: O=C(N=C1NCCN1)c1cc(F)c(Nc2nccc(C(=O)N3C[C@H]4C[C@@H]3CO4)c2Cl)c(C2CC2)c1] |
| 155 | 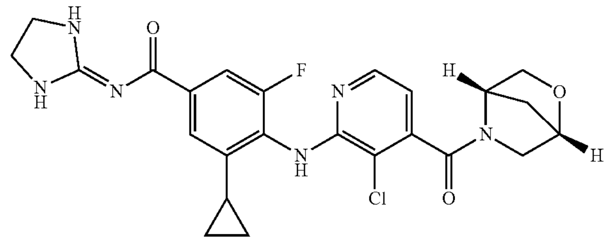 [SMILES: O=C(N=C1NCCN1)c1cc(F)c(Nc2nccc(C(=O)N3C[C@@H]4C[C@H]3CO4)c2Cl)c(C2CC2)c1] |
| 156 | 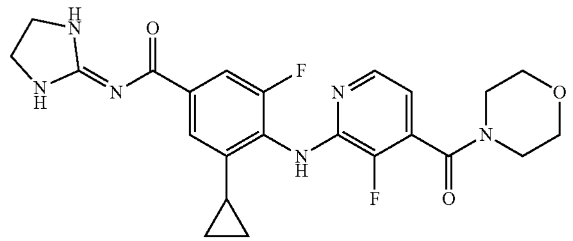 |

-continued
| N° | Structure |
| --- | --- |
| 157 | 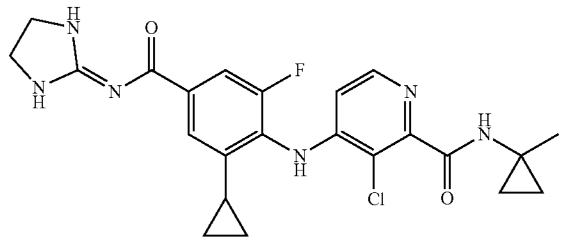 |
| 158 | 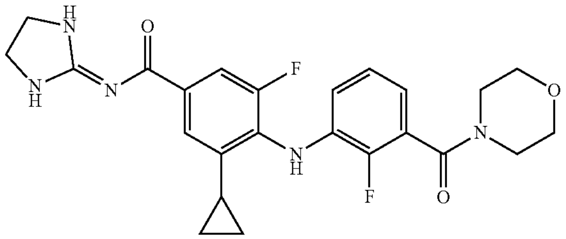 |
| 159 | 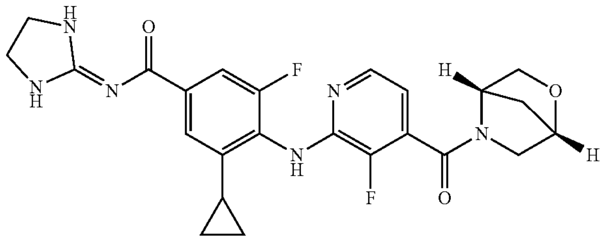 [SMILES: O=C(N=C1NCCN1)c1cc(F)c(Nc2nccc(C(=O)N3C[C@@H]4C[C@H]3CO4)c2F)c(C2CC2)c1] |
| 160 | 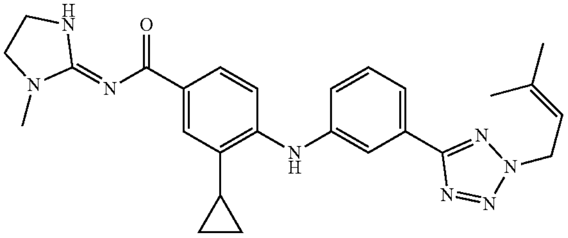 [SMILES: CC(C)=CCn1nnc(-c2cccc(Nc3ccc(C(=O)/N=C4\NCCN4C)cc3C3CC3)c2)n1] |
| 161 | 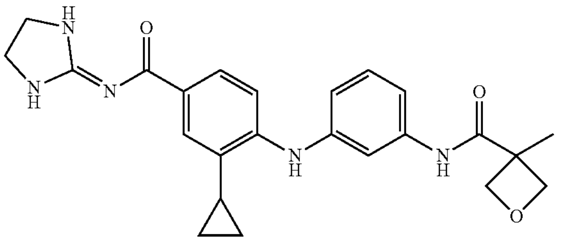 |
| 162 | 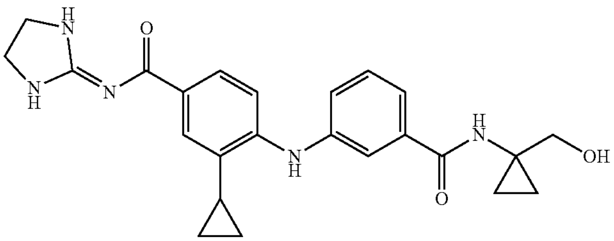 [SMILES: O=C(N=C1NCCN1)c1ccc(Nc2cccc(C(=O)NC3(CO)CC3)c2)c(C2CC2)c1] |

-continued
| N° | Structure |
|---|---|
| 163 | 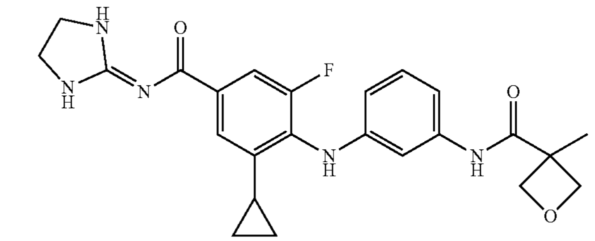 [SMILES: CC1(C(=O)Nc2cccc(Nc3c(F)cc(C(=O)N=C4NCCN4)cc3C3CC3)c2)COC1] |
| 164 | 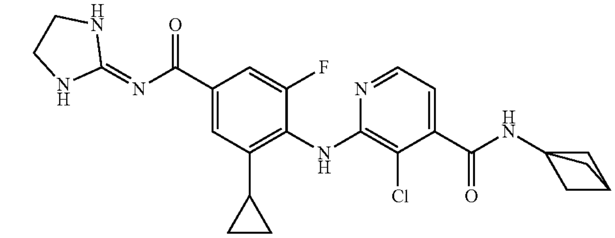 [SMILES: O=C(N=C1NCCN1)c1cc(F)c(Nc2nccc(C(=O)NC34CC(C3)C4)c2Cl)c(C2CC2)c1] |
| 165 | 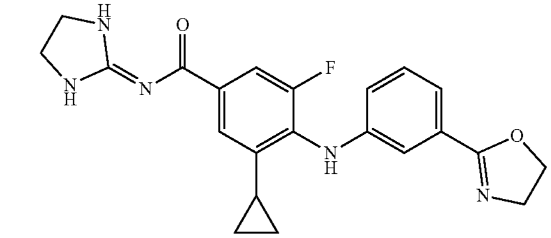 [SMILES: O=C(N=C1NCCN1)c1cc(F)c(Nc2cccc(C3=NCCO3)c2)c(C2CC2)c1] |
| 166 | 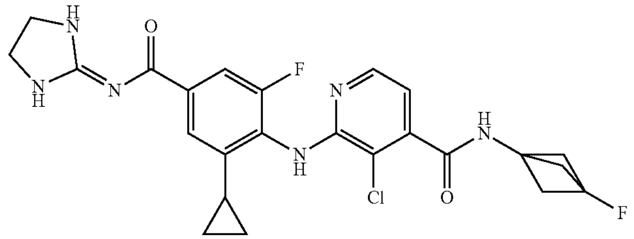 [SMILES: O=C(N=C1NCCN1)c1cc(F)c(Nc2nccc(C(=O)NC34CC(F)(C3)C4)c2Cl)c(C2CC2)c1] |
| 167 | 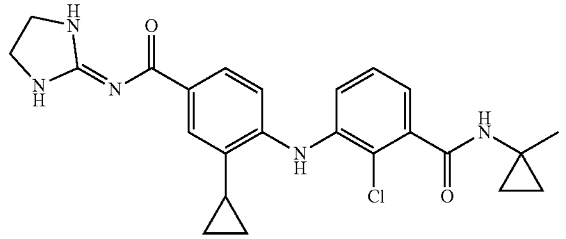 [SMILES: CC1(NC(=O)c2cccc(Nc3ccc(C(=O)N=C4NCCN4)cc3C3CC3)c2Cl)CC1] |
| 168 | 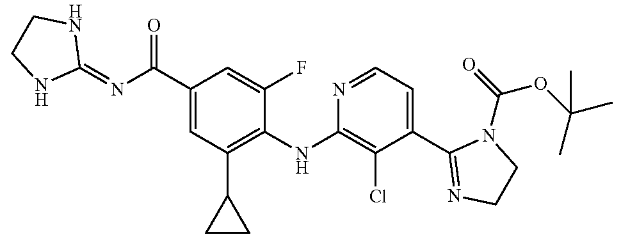 [SMILES: CC(C)(C)OC(=O)N1CCN=C1c1ccnc(Nc2c(F)cc(C(=O)N=C3NCCN3)cc2C2CC2)c1Cl] |

-continued
| N° | Structure |
| --- | --- |
| 169 | 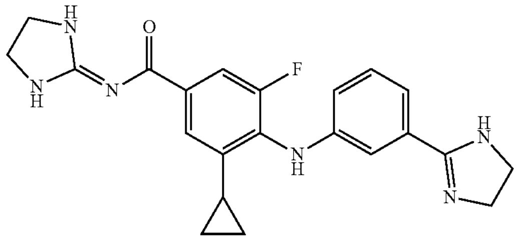 |
| 170 | 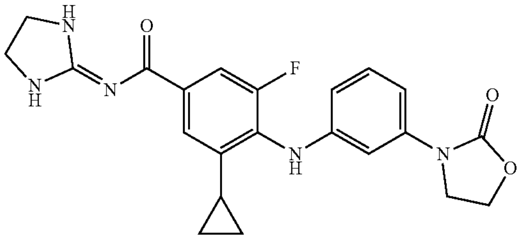 [SMILES: O=C(N=C1NCCN1)c1cc(F)c(Nc2cccc(N3CCOC3=O)c2)c(C2CC2)c1] |
| 171 | 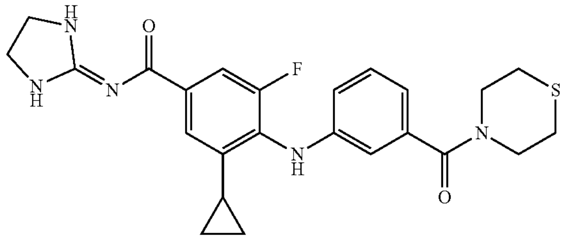 [SMILES: O=C(N=C1NCCN1)c1cc(F)c(Nc2cccc(C(=O)N3CCSCC3)c2)c(C2CC2)c1] |
| 172 | 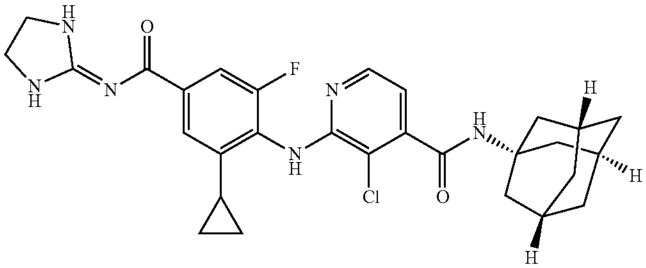 [SMILES: O=C(N=C1NCCN1)c1cc(F)c(Nc2nccc(C(=O)N[C@]34C[C@H]5C[C@H](C[C@H](C5)C3)C4)c2Cl)c(C2CC2)c1] |
| 173 | 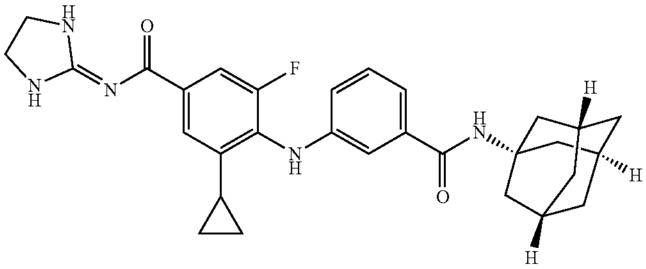 [SMILES: O=C(N=C1NCCN1)c1cc(F)c(Nc2cccc(C(=O)N[C@]34C[C@H]5C[C@H](C[C@H](C5)C3)C4)c2)c(C2CC2)c1] |
| 174 | 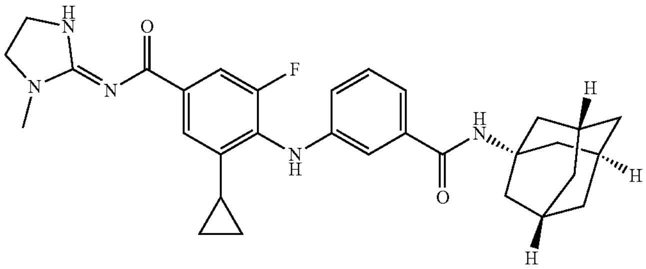 [SMILES: CN1CCN/C1=N\C(=O)c1cc(F)c(Nc2cccc(C(=O)N[C@]34C[C@H]5C[C@H](C[C@H](C5)C3)C4)c2)c(C2CC2)c1] |

-continued
| N° | Structure |
| --- | --- |
| 175 | 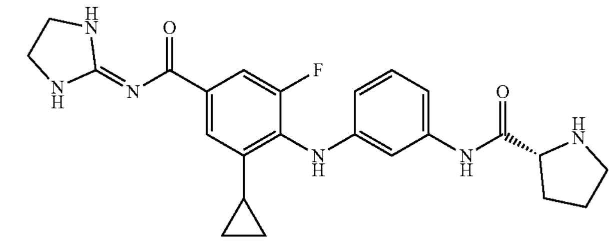 [SMILES: O=C(N=C1NCCN1)c1cc(F)c(Nc2cccc(NC(=O)[C@H]3CCCN3)c2)c(C2CC2)c1] |
| 176 | 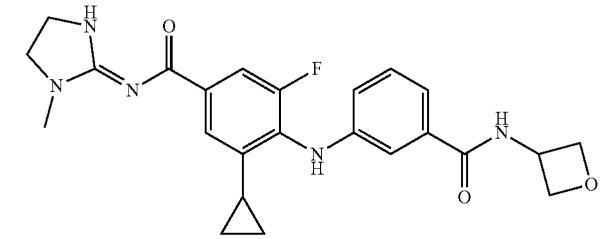 [SMILES: CN1CCN/C1=N\C(=O)c1cc(F)c(Nc2cccc(C(=O)NC3COC3)c2)c(C2CC2)c1] |
| 177 | 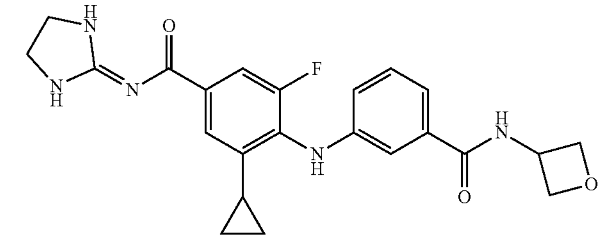 [SMILES: O=C(N=C1NCCN1)c1cc(F)c(Nc2cccc(C(=O)NC3COC3)c2)c(C2CC2)c1] |
| 178 | 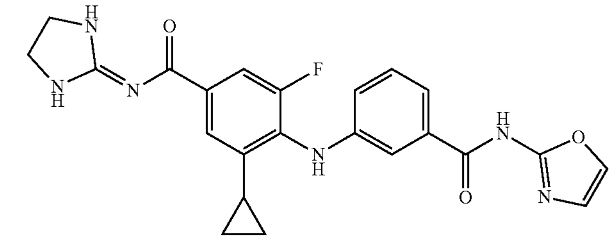 [SMILES: O=C(N=C1NCCN1)c1cc(F)c(Nc2cccc(C(=O)Nc3ncco3)c2)c(C2CC2)c1] |
| 179 | 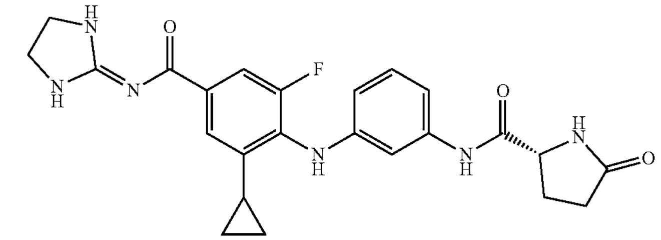 [SMILES: O=C1CC[C@H](C(=O)Nc2cccc(Nc3c(F)cc(C(=O)N=C4NCCN4)cc3C3CC3)c2)N1] |
| 180 | 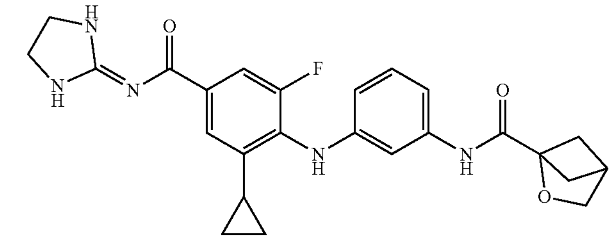 [SMILES: O=C(N=C1NCCN1)c1cc(F)c(Nc2cccc(NC(=O)C34CC(CO3)C4)c2)c(C2CC2)c1] |

-continued

| N° | Structure |
| --- | --- |
| 181 | 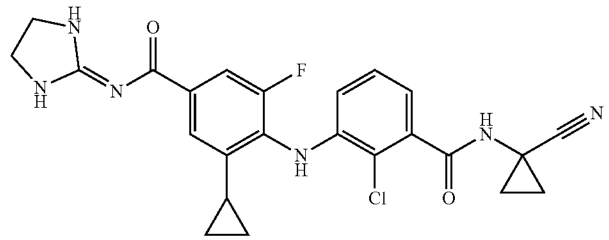 [SMILES: N#CC1(NC(=O)c2cccc(Nc3c(F)cc(C(=O)N=C4NCCN4)cc3C3CC3)c2Cl)CC1] |

or a pharmaceutically acceptable salt thereof.

9. A pharmaceutical composition comprising at least one pharmaceutically acceptable excipient and at least one compound according to claim 1, or a pharmaceutically acceptable salt thereof.

10. A method for treating a respiratory syncytial virus (RSV) in a subject, the method comprising administering to the subject in need thereof a therapeutically effective quantity of at least one compound according to claim 1, or a pharmaceutically acceptable salt thereof.

11. A method for treating respiratory syncytial virus (RSV) infection in a subject, the method comprising administering to the subject in need thereof a therapeutically effective quantity of at least one compound according to claim 8, or a pharmaceutically acceptable salt thereof.

12. A method for treating a ribonucleic acid (RNA) virus infection in a subject, the method comprising administering to the subject in need thereof a therapeutically effective quantity of at least one compound according to claim 1, or a pharmaceutically acceptable salt thereof.

13. A method for treating a ribonucleic acid (RNA) virus infection in a subject, the method comprising administering to the subject in need thereof a therapeutically effective quantity of at least one compound according to claim 8, or a pharmaceutically acceptable salt thereof.

14. A process for manufacturing a compound of formula (I) according to claim 1:

(I)

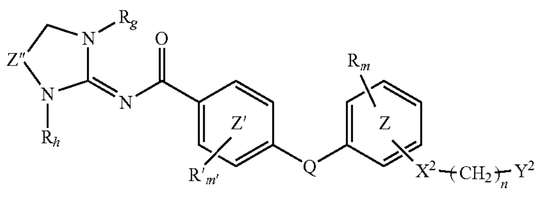

wherein ring Z is phenylene or pyridinylene;

ring Z' is phenylene or pyridinylene;

Z" is $—CH_2—$ or —C(O)—;

$R_g$ is H, $C_1$-$C_4$ alkyl, $C_3$-$C_6$ cycloalkyl, $—CH_2CHF_2$, or $—C(O)CH_3$;

$R_h$ is H, $C_1$-$C_4$ alkyl, $C_3$-$C_6$ cycloalkyl, $—CH_2CHF_2$, or $—C(O)CH_3$;

Q is —NH—;

$X^2$ is —C(O)—$NR_k$—, —$NR'_k$—C(O)—, —O—, —C(O)—, $—S(O)_2—$, —C(S)—NH—, $—CH_2—$NH—, -oxetan-3-ylene-NH, or 5- or 6-membered heterocyclyl;

wherein the heterocyclyl comprises 1, 2, 3, or 4 heteroatoms independently selected from the group consisting of O, S, and N; and wherein the heterocyclyl is optionally substituted by one or more substituents selected from the group consisting of $C_1$-$C_4$ alkyl, halogen, —C(O)$OR_p$, and =O;

$R_k$ is H or $CH_3$;

$R'_k$ is H or $CH_3$;

each $R_p$ is independently $C_1$-$C_4$ alkyl;

$Y^2$ is H, halogen, OH, morpholinyl, bridged morpholinyl, $C_5$-$C_{11}$ bicycloalkyl, adamantlyl, piperidinyl, $C_2$-$C_4$ alkenyl, —P(O)($OR_a$)($OR_b$), 5-membered heteroaryl, or $—CR^1R^2R^3$, wherein the heteroaryl comprises 1 or 2 heteroatom(s) independently selected from the group consisting of O and N;

wherein the morpholinyl is optionally substituted by one or more substituents independently selected from the group consisting of $C_1$-$C_4$ alkyl and $—CF_3$;

wherein the bridged morpholinyl is optionally substituted by one or more independently selected halogen substituents; and wherein one $—CH_2—$ group of the piperidinyl is optionally replaced by one $S(O)_2$ group;

one of (i) and (ii) is satisfied:

(i) $R^1$ is H, F, or $C_1$-$C_4$ alkyl; and $R^2$ is H, F, or $C_1$-$C_4$ alkyl; or (ii) $R^1$ and $R^2$, together with the carbon atom to which they are attached, form a $C_3$-$C_8$ cycloalkyl;

wherein the $C_3$-$C_8$ cycloalkyl is optionally substituted by one or two independently selected $C_1$-$C_4$ alkyl substituents;

wherein each $C_1$-$C_4$ alkyl substituent is optionally and independently substituted by one or more substituents independently selected from the group consisting of OH, halogen, $CF_3$, CN, P(O)($OR_a$)($OR_b$), =O, and $OC_1$-$C_4$ alkyl; and wherein one or two $—CH_2—$ groups of the $C_3$-$C_8$ cycloalkyl are optionally and independently replaced by one or two groups independently selected from the group consisting of —O—, —NH—, —S—, and $—S(O)_2—$; and $R^3$ is H, F, or $C_1$-$C_4$ alkyl, wherein one $—CH_2—$ group of the $C_1$-$C_4$ alkyl is optionally replaced by one —NH—;

each R is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one $—CH_2—$ group of each $C_1$-$C_4$ alkyl is optionally and independently replaced by one group independently selected from the group consisting of —S(O)— and $—S(O)_2—$; and wherein each $C_1$-$C_4$ alkyl is optionally and independently substituted by one or more OH substituents;

each R' is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

each $R_a$ is independently H or $C_1$-$C_4$ alkyl;

each $R_b$ is independently H or $C_1$-$C_4$ alkyl;

n is 0, 1, 2, or 3;

m is 0, 1, or 2; and m' is 0, 1, or 2;

with the proviso that no more than one of $R^1$, $R^2$, and $R^3$ is H;

the process comprising the following steps:

(i) coupling a compound of formula (II);

(II)

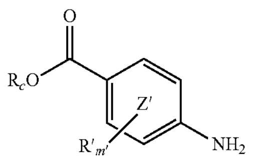

wherein:

$R_c$ is alkyl;

ring Z' is phenylene or pyridinylene;

each R' is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents; and m' is 0, 1, or 2;

with a compound of formula (III)

(III)

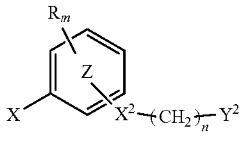

wherein:

X is Cl, Br, or I;

ring Z is phenylene or pyridinylene;

$X^2$ is —C(O)—$NR_k$—, —$NR'_k$—C(O)—, —O—, —C(O)—, —$S(O)_2$—, —C(S)—NH—, —$CH_2$—NH—, -oxetan-3-ylene-NH, or 5- or 6-membered heterocyclyl;

wherein the heterocyclyl comprises 1, 2, 3, or 4 heteroatoms independently selected from the group consisting of O, S, and N; and wherein the heterocyclyl is optionally substituted by one or more substituents selected from the group consisting of $C_1$-$C_4$ alkyl, halogen, —C(O)$OR_p$, and =O;

$R_k$ is H or $CH_3$;

$R'_k$ is H or $CH_3$;

each $R_p$ is independently $C_1$-$C_4$ alkyl;

$Y^2$ is H, halogen, OH, morpholinyl, bridged morpholinyl, $C_5$-$C_{11}$ bicycloalkyl, adamantlyl, piperidinyl, $C_2$-$C_4$ alkenyl, —P(O)($OR_a$)($OR_b$), 5-membered heteroaryl, or —$CR^1R^2R^3$, wherein the heteroaryl comprises 1 or 2 heteroatom(s) independently selected from the group consisting of O and N;

wherein the morpholinyl is optionally substituted by one or more substituents independently selected from the group consisting of $C_1$-$C_4$ alkyl and —$CF_3$;

wherein the bridged morpholinyl is optionally substituted by one or more independently selected halogen substituents; and wherein one —$CH_2$— group of the piperidinyl is optionally replaced by one $S(O)_2$ group;

one of (i) and (ii) is satisfied:

(i) $R^1$ is H, F, or $C_1$-$C_4$ alkyl; and $R^2$ is H, F, or $C_1$-$C_4$ alkyl; or (ii) $R^1$ and $R^2$, together with the carbon atom to which they are attached, form a $C_3$-$C_8$ cycloalkyl;

wherein the $C_3$-$C_8$ cycloalkyl is optionally substituted by one or two independently selected $C_1$-$C_4$ alkyl substituents;

wherein each $C_1$-$C_4$ alkyl substituent is optionally and independently substituted by one or more substituents independently selected from the group consisting of OH, halogen, $CF_3$, CN, P(O)($OR_a$)($OR_b$), =O, and $OC_1$-$C_4$ alkyl; and wherein one or two —$CH_2$— groups of the $C_3$-$C_8$ cycloalkyl are optionally and independently replaced by one or two groups independently selected from the group consisting of —O—, —NH—, —S—, and —$S(O)_2$—; and $R^3$ is H, F, or $C_1$-$C_4$ alkyl, wherein one —$CH_2$— group of the $C_1$-$C_4$ alkyl is optionally replaced by one —NH—;

each R is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

each $R_a$ is independently H or $C_1$-$C_4$ alkyl;

each $R_b$ is independently H or $C_1$-$C_4$ alkyl;

n is 0, 1, 2, or 3; and m is 0, 1, or 2;

with the proviso that no more than one of $R^1$, $R^2$, and $R^3$ is H;

in the presence of an inorganic base, a diphosphine, and an organometallic catalyst, to obtain a compound of formula (IV);

(IV)

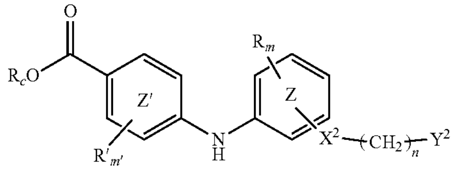

wherein:

$R_c$ is alkyl;

ring Z is phenylene or pyridinylene;

ring Z' is phenylene or pyridinylene;

$X^2$ is —C(O)—$NR_k$—, —$NR'_k$—C(O)—, —O—, —C(O)—, —$S(O)_2$—, —C(S)—NH—, —$CH_2$—NH—, -oxetan-3-ylene-NH, or 5- or 6-membered heterocyclyl;

wherein the heterocyclyl comprises 1, 2, 3, or 4 heteroatoms independently selected from the group consisting of O, S, and N; and wherein the heterocyclyl is optionally substituted by one or more substituents selected from the group consisting of $C_1$-$C_4$ alkyl, halogen, —C(O)$OR_p$, and =O;

$R_k$ is H or $CH_3$;

$R'_k$ is H or $CH_3$;

each $R_p$ is independently $C_1$-$C_4$ alkyl;

$Y^2$ is H, halogen, OH, morpholinyl, bridged morpholinyl, $C_5$-$C_{11}$ bicycloalkyl, adamantlyl, piperidinyl, $C_2$-$C_4$ alkenyl, —P(O)($OR_a$)($OR_b$), 5-membered heteroaryl, or —$CR^1R^2R^3$, wherein the heteroaryl comprises 1 or 2 heteroatom(s) independently selected from the group consisting of O and N;

wherein the morpholinyl is optionally substituted by one or more substituents independently selected from the group consisting of $C_1$-$C_4$ alkyl and —$CF_3$;

wherein the bridged morpholinyl is optionally substituted by one or more independently selected halogen substituents; and wherein one —$CH_2$— group of the piperidinyl is optionally replaced by one $S(O)_2$ group;

one of (i) and (ii) is satisfied:

(i) $R^1$ is H, F, or $C_1$-$C_4$ alkyl; and $R^2$ is H, F, or $C_1$-$C_4$ alkyl; or (ii) $R^1$ and $R^2$, together with the carbon atom to which they are attached, form a $C_3$-$C_8$ cycloalkyl;

wherein the $C_3$-$C_8$ cycloalkyl is optionally substituted by one or two independently selected $C_1$-$C_4$ alkyl substituents;

wherein each $C_1$-$C_4$ alkyl substituent is optionally and independently substituted by one or more substituents independently selected from the group consisting of OH, halogen, $CF_3$, CN, P(O)($OR_a$)($OR_b$), =O, and $OC_1$-$C_4$ alkyl; and wherein one or two —$CH_2$— groups of the $C_3$-$C_8$ cycloalkyl are optionally and independently replaced by one or two groups independently selected from the group consisting of —O—, —NH—, —S—, and —$S(O)_2$—; and $R^3$ is H, F, or $C_1$-$C_4$ alkyl, wherein one —$CH_2$— group of the $C_1$-$C_4$ alkyl is optionally replaced by one —NH—;

each $R_a$ is independently H or $C_1$-$C_4$ alkyl;

each $R_b$ is independently H or $C_1$-$C_4$ alkyl;

each R is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

each R' is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

n is 0, 1, 2, or 3;

m is 0, 1, or 2; and m' is 0, 1, or 2;

with the proviso that no more than one of $R^1$, $R^2$, and $R^3$ is H;

(ii) hydrolyzing the compound of formula (IV) above, to obtain a compound of formula (V):

(V)

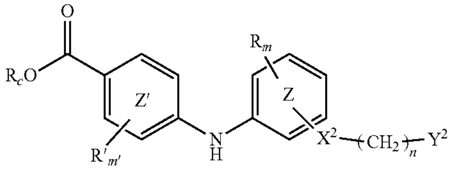

wherein:

$R_c$ is H;

ring Z' is phenylene or pyridinylene;

each R' is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

m' is 0, 1, or 2;

ring Z is phenylene or pyridinylene;

each R is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

m is 0, 1, or 2;

$X^2$ is —C(O)—$NR_k$—, —$NR'_k$—C(O)—, —O—, —C(O)—, —$S(O)_2$—, —C(S)—NH—, —$CH_2$—NH—, -oxetan-3-ylene-NH, or 5- or 6-membered heterocyclyl;

wherein the heterocyclyl comprises 1, 2, 3, or 4 heteroatoms independently selected from the group consisting of O, S, and N; and wherein the heterocyclyl is optionally substituted by one or more substituents selected from the group consisting of $C_1$-$C_4$ alkyl, halogen, —C(O)O$R_p$, and =O;

$R_k$ is H or $CH_3$;

$R'_k$ is H or $CH_3$;

each $R_p$ is independently $C_1$-$C_4$ alkyl;

n is 0, 1, 2, or 3;

$Y^2$ is H, halogen, OH, morpholinyl, bridged morpholinyl, $C_5$-$C_{11}$ bicycloalkyl, adamantlyl, piperidinyl, $C_2$-$C_4$ alkenyl, —P(O)(O$R_a$)(O$R_b$), 5-membered heteroaryl, or —C$R^1R^2R^3$, wherein the heteroaryl comprises 1 or 2 heteroatom(s) independently selected from the group consisting of O and N;

wherein the morpholinyl is optionally substituted by one or more substituents independently selected from the group consisting of $C_1$-$C_4$ alkyl and —$CF_3$;

wherein the bridged morpholinyl is optionally substituted by one or more independently selected halogen substituents; and wherein one —$CH_2$— group of the piperidinyl is optionally replaced by one $S(O)_2$ group;

one of (i) and (ii) is satisfied:

(i) $R^1$ is H, F, or $C_1$-$C_4$ alkyl; and $R^2$ is H, F, or $C_1$-$C_4$ alkyl; or (ii) $R^1$ and $R^2$, together with the carbon atom to which they are attached, form a $C_3$-$C_8$ cycloalkyl;

wherein the $C_3$-$C_8$ cycloalkyl is optionally substituted by one or two independently selected $C_1$-$C_4$ alkyl substituents;

wherein each $C_1$-$C_4$ alkyl substituent is optionally and independently substituted by one or more substituents independently selected from the group consisting of OH, halogen, $CF_3$, CN, P(O)(O$R_a$)(O$R_b$), =O, and O$C_1$-$C_4$ alkyl; and wherein one or two —$CH_2$— groups of the $C_3$-$C_8$ cycloalkyl are optionally and independently replaced by one or two groups independently selected from the group consisting of —O—, —NH—, —S—, and —$S(O)_2$—;

$R^3$ is H, F, or $C_1$-$C_4$ alkyl, wherein one —$CH_2$— group of the $C_1$-$C_4$ alkyl is optionally replaced by one —NH—;

each $R_a$ is independently H or $C_1$-$C_4$ alkyl; and each $R_b$ is independently H or $C_1$-$C_4$ alkyl;

with the proviso that no more than one of $R^1$, $R^2$, and $R^3$ is H;

(iii) reacting the compound of formula (V) above with a compound of the following formula:

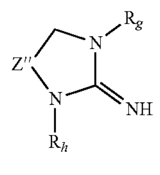

wherein:

Z" is —$CH_2$— or —C(O)—;

R, is H, $C_1$-$C_4$ alkyl, $C_3$-$C_6$ cycloalkyl, —$CH_2CHF_2$, or —C(O)$CH_3$; and $R_h$ is H, $C_1$-$C_4$ alkyl, $C_3$-$C_6$ cycloalkyl, —$CH_2CHF_2$, or —C(O)$CH_3$;

in the presence of an organic base and a coupling agent, to obtain the compound of formula (I) above, wherein Q is —NH—.

15. A process for manufacturing a compound of formula (I) according to claim 1:

(I)

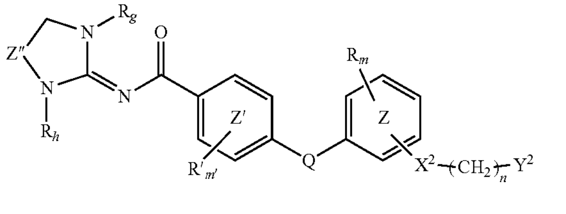

wherein:

ring Z is phenylene or pyridinylene;

ring Z' is phenylene or pyridinylene;

Z" is —$CH_2$— or —C(O)—;

R, is H, $C_1$-$C_4$ alkyl, $C_3$-$C_6$ cycloalkyl, —$CH_2CHF_2$, or —C(O)$CH_3$;

$R_h$ is H, $C_1$-$C_4$ alkyl, $C_3$-$C_6$ cycloalkyl, —$CH_2CHF_2$, or —C(O)$CH_3$;

Q is O—;

$X^2$ is —C(O)—N$R_k$—, —N$R'_k$—C(O)—, —O—, —C(O)—, —$S(O)_2$—, —C(S)—NH—, —$CH_2$—NH—, -oxetan-3-ylene-NH, or 5- or 6-membered heterocyclyl;

wherein the heterocyclyl comprises 1, 2, 3, or 4 heteroatoms independently selected from the group consisting of O, S, and N; and wherein the heterocyclyl is optionally substituted by one or more substituents selected from the group consisting of $C_1$-$C_4$ alkyl, halogen, —C(O)O$R_p$, and =O;

$R_k$ is H or $CH_3$;

$R'_k$ is H or $CH_3$;

each $R_p$ is independently $C_1$-$C_4$ alkyl;

$Y^2$ is H, halogen, OH, morpholinyl, bridged morpholinyl, $C_5$-$C_{11}$ bicycloalkyl, adamantlyl, piperidinyl, $C_2$-$C_4$ alkenyl, —P(O)(O$R_a$)(O$R_b$), 5-membered heteroaryl, or —C$R^1R^2R^3$, wherein the heteroaryl comprises 1 or 2 heteroatom(s) independently selected from the group consisting of O and N;

wherein the morpholinyl is optionally substituted by one or more substituents independently selected from the group consisting of $C_1$-$C_4$ alkyl and —$CF_3$;

wherein the bridged morpholinyl is optionally substituted by one or more independently selected halogen substituents; and wherein one —$CH_2$— group of the piperidinyl is optionally replaced by one $S(O)_2$ group;

one of (i) and (ii) is satisfied:

(i) $R^1$ is H, F, or $C_1$-$C_4$ alkyl; and $R^2$ is H, F, or $C_1$-$C_4$ alkyl; or (ii) $R^1$ and $R^2$, together with the carbon atom to which they are attached, form a $C_3$-$C_8$ cycloalkyl;

wherein the $C_3$-$C_8$ cycloalkyl is optionally substituted by one or two independently selected $C_1$-$C_4$ alkyl substituents;

wherein each $C_1$-$C_4$ alkyl substituent is optionally and independently substituted by one or more substituents independently selected from the group consisting of OH, halogen, $CF_3$, CN, P(O)$(OR_a)(OR_b)$, =O, and $OC_1$-$C_4$ alkyl; and wherein one or two —$CH_2$— groups of the $C_3$-$C_8$ cycloalkyl are optionally and independently replaced by one or two groups independently selected from the group consisting of —O—, —NH—, —S—, and —$S(O)_2$—; and $R^3$ is H, F, or $C_1$-$C_4$ alkyl, wherein one —$CH_2$— group of the $C_1$-$C_4$ alkyl is optionally replaced by one —NH—;

each R is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

each R' is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

each $R_a$ is independently H or $C_1$-$C_4$ alkyl;

each $R_b$ is independently H or $C_1$-$C_4$ alkyl;

n is 0, 1, 2, or 3;

m is 0, 1, or 2; and m' is 0, 1, or 2;

with the proviso that no more than one of $R^1$, $R^2$, and $R^3$ is H;

the process comprising-at-least the following steps:

(i) coupling a compound of formula (II'):

(II')

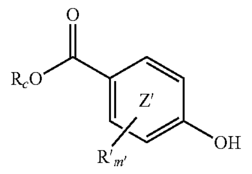

wherein:

$R_c$ is alkyl;

ring Z' is phenylene or pyridinylene;

each R' is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents; and m' is 0, 1, or 2;

with a compound of formula (III);

(III)

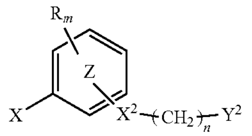

wherein:

X is F;

ring Z is phenylene or pyridinylene;

each R is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

m is 0, 1, or 2;

$X^2$ is —C(O)—$NR_k$—, —$NR'_k$—C(O)—, —O—, —C(O)—, —$S(O)_2$—, —C(S)—NH—, —$CH_2$—NH—, -oxetan-3-ylene-NH, or 5- or 6-membered heterocyclyl;

wherein the heterocyclyl comprises 1, 2, 3, or 4 heteroatoms independently selected from the group consisting of O, S, and N; and wherein the heterocyclyl is optionally substituted by one or more substituents selected from the group consisting of $C_1$-$C_4$ alkyl, halogen, —C(O)$OR_p$, and =O;

$R_k$ is H or $CH_3$;

$R'_k$ is H or $CH_3$;

each $R_p$ is independently $C_1$-$C_4$ alkyl;

n is 0, 1, 2, or 3;

$Y^2$ is H, halogen, OH, morpholinyl, bridged morpholinyl, $C_5$-$C_{11}$ bicycloalkyl, adamantlyl, piperidinyl, $C_2$-$C_4$ alkenyl, —P(O)$(OR_a)(OR_b)$, 5-membered heteroaryl, or —$CR^1R^2R^3$, wherein the heteroaryl comprises 1 or 2 heteroatom(s) independently selected from the group consisting of O and N;

wherein the morpholinyl is optionally substituted by one or more substituents independently selected from the group consisting of $C_1$-$C_4$ alkyl and —$CF_3$;

wherein the bridged morpholinyl is optionally substituted by one or more independently selected halogen substituents; and wherein one —$CH_2$— group of the piperidinyl is optionally replaced by one $S(O)_2$ group;

one of (i) and (ii) is satisfied:

(i) $R^1$ is H, F, or $C_1$-$C_4$ alkyl; and $R^2$ is H, F, or $C_1$-$C_4$ alkyl; or (ii) $R^1$ and $R^2$, together with the carbon atom to which they are attached, form a $C_3$-$C_8$ cycloalkyl;

wherein the $C_3$-$C_8$ cycloalkyl is optionally substituted by one or two independently selected $C_1$-$C_4$ alkyl substituents;

wherein each $C_1$-$C_4$ alkyl substituent is optionally and independently substituted by one or more substituents independently selected from the group consisting of OH, halogen, $CF_3$, CN, P(O)($OR_a$)($OR_b$), =O, and $OC_1$-$C_4$ alkyl; and wherein one or two —$CH_2$— groups of the $C_3$-$C_8$ cycloalkyl are optionally and independently replaced by one or two groups independently selected from the group consisting of —O—, —NH—, —S—, and —$S(O)_2$—; and $R^3$ is H, F, or $C_1$-$C_4$ alkyl, wherein one —$CH_2$— group of the $C_1$-$C_4$ alkyl is optionally replaced by one —NH—;

each $R_a$ is independently H or $C_1$-$C_4$ alkyl; and each $R_b$ is independently H or $C_1$-$C_4$ alkyl;

with the proviso that no more than one of $R^1$, $R^2$, and $R^3$ is H;

in the presence of an inorganic base, to obtain a compound of formula (IV');

(IV')

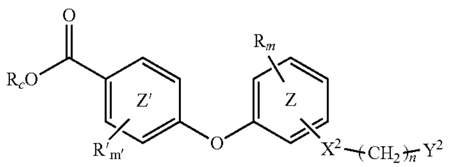

wherein:

$R_c$ is alkyl;

ring Z' is phenylene or pyridinylene;

each R' is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

m' is 0, 1, or 2;

ring Z is phenylene or pyridinylene;

each R is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

m is 0, 1, or 2;

$X^2$ is —C(O)—$NR_k$—, —$NR'_k$—C(O)—, —O—, —C(O)—, —$S(O)_2$—, —C(S)—NH—, —$CH_2$—NH—, -oxetan-3-ylene-NH, or 5- or 6-membered heterocyclyl;

wherein the heterocyclyl comprises 1, 2, 3, or 4 heteroatoms independently selected from the group consisting of O, S, and N; and wherein the heterocyclyl is optionally substituted by one or more substituents selected from the group consisting of $C_1$-$C_4$ alkyl, halogen, —C(O)$OR_p$, and =O;

$R_k$ is H or $CH_3$;

$R'_k$ is H or $CH_3$;

each $R_p$ is independently $C_1$-$C_4$ alkyl;

n is 0, 1, 2, or 3;

$Y^2$ is H, halogen, OH, morpholinyl, bridged morpholinyl, $C_5$-$C_{11}$ bicycloalkyl, adamantlyl, piperidinyl, $C_2$-$C_4$ alkenyl, —P(O)($OR_a$)($OR_b$), 5-membered heteroaryl, or —$CR^1R^2R^3$, wherein the heteroaryl comprises 1 or 2 heteroatom(s) independently selected from the group consisting of O and N;

wherein the morpholinyl is optionally substituted by one or more substituents independently selected from the group consisting of $C_1$-$C_4$ alkyl and —$CF_3$;

wherein the bridged morpholinyl is optionally substituted by one or more independently selected halogen substituents; and wherein one —$CH_2$— group of the piperidinyl is optionally replaced by one $S(O)_2$ group;

one of (i) and (ii) is satisfied:

(i) $R^1$ is H, F, or $C_1$-$C_4$ alkyl; and $R^2$ is H, F, or $C_1$-$C_4$ alkyl; or (ii) $R^1$ and $R^2$, together with the carbon atom to which they are attached, form a $C_3$-$C_8$ cycloalkyl;

wherein the $C_3$-$C_8$ cycloalkyl is optionally substituted by one or two independently selected $C_1$-$C_4$ alkyl substituents;

wherein each $C_1$-$C_4$ alkyl substituent is optionally and independently substituted by one or more substituents independently selected from the group consisting of OH, halogen, $CF_3$, CN, P(O)($OR_a$)($OR_b$), =O, and $OC_1$-$C_4$ alkyl; and wherein one or two —$CH_2$— groups of the $C_3$-$C_8$ cycloalkyl are optionally and independently replaced by one or two groups independently selected from the group consisting of —O—, —NH—, —S—, and —$S(O)_2$—; and $R^3$ is H, F, or $C_1$-$C_4$ alkyl, wherein one —$CH_2$— group of the $C_1$-$C_4$ alkyl is optionally replaced by one —NH—;

each $R_a$ is independently H or $C_1$-$C_4$ alkyl; and each $R_b$ is independently H or $C_1$-$C_4$ alkyl;

with the proviso that no more than one of $R^1$, $R^2$, and $R^3$ is H;

(ii) hydrolyzing the compound of formula (IV') above, to obtain a compound of formula (V'):

(V')

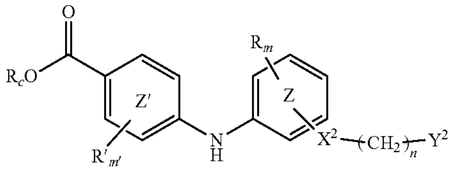

wherein:

$R_c$ is H;

ring Z' is phenylene or pyridinylene;

each R' is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

m' is 0, 1, or 2;

ring Z is phenylene or pyridinylene;

each R is independently $C_1$-$C_4$ alkyl, $C_2$-$C_4$ alkenyl, $C_3$-$C_6$ cycloalkyl, tetrahydrofuranyl, tetrahydropyranyl, $CF_3$, furanyl, halogen, CN, or $OC_1$-$C_5$ alkyl;

wherein one —$CH_2$— group of each $C_1$-$C_4$ alkyl is optionally and independently replaced by one group independently selected from the group consisting of —S(O)— and —$S(O)_2$—; and wherein each $C_1$-$C_4$ alkyl is optionally and independently substituted by one or more OH substituents;

m is 0, 1, or 2;

$X^2$ is —C(O)—$NR_k$—, —$NR'_k$—C(O)—, —O—, —C(O)—, —$S(O)_2$—, —C(S)—NH—, —$CH_2$—NH—, -oxetan-3-ylene-NH, or 5- or 6-membered heterocyclyl;

wherein the heterocyclyl comprises 1, 2, 3, or 4 heteroatoms independently selected from the group consisting of O, S, and N; and wherein the heterocyclyl is optionally substituted by one or more substituents selected from the group consisting of $C_1$-$C_4$ alkyl, halogen, —C(O)$OR_p$, and =O;

$R_k$ is H or $CH_3$;

$R'_k$ is H or $CH_3$;

each $R_p$ is independently $C_1$-$C_4$ alkyl;

n is 0, 1, 2, or 3;

$Y^2$ is H, halogen, OH, morpholinyl, bridged morpholinyl, $C_5$-$C_{11}$ bicycloalkyl, adamantlyl, piperidinyl, $C_2$-$C_4$ alkenyl, —P(O)($OR_a$)($OR_b$), 5-membered heteroaryl, or —$CR^1R^2R^3$, wherein the heteroaryl comprises 1 or 2 heteroatom(s) independently selected from the group consisting of O and N;

wherein the morpholinyl is optionally substituted by one or more substituents independently selected from the group consisting of $C_1$-$C_4$ alkyl and —$CF_3$;

wherein the bridged morpholinyl is optionally substituted by one or more independently selected halogen substituents; and wherein one —$CH_2$— group of the piperidinyl is optionally replaced by one $S(O)_2$ group;

one of (i) and (ii) is satisfied:

(i) $R^1$ is H, F, or $C_1$-$C_4$ alkyl; and $R^2$ is H, F, or $C_1$-$C_4$ alkyl; or (ii) $R^1$ and $R^2$, together with the carbon atom to which they are attached, form a $C_3$-$C_8$ cycloalkyl;

wherein the $C_3$-$C_8$ cycloalkyl is optionally substituted by one or two independently selected $C_1$-$C_4$ alkyl substituents;

wherein each $C_1$-$C_4$ alkyl substituent is optionally and independently substituted by one or more substituents independently selected from the group consisting of OH, halogen, $CF_3$, CN, P(O)($OR_a$)($OR_b$), =O, and $OC_1$-$C_4$ alkyl; and wherein one or two —$CH_2$— groups of the $C_3$-$C_8$ cycloalkyl are optionally and independently replaced by one or two groups independently selected from the group consisting of —O—, —NH—, —S—, and —$S(O)_2$—; and $R^3$ is H, F, or $C_1$-$C_4$ alkyl, wherein one —$CH_2$— group of the $C_1$-$C_4$ alkyl is optionally replaced by one —NH—;

each $R_a$ is independently H or $C_1$-$C_4$ alkyl; and each $R_b$ is independently H or $C_1$-$C_4$ alkyl;

with the proviso that no more than one of $R^1$, $R^2$, and $R^3$ is H;

(iii) reacting the compound of formula (V') above with a compound of the following formula:

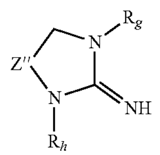

wherein:

Z" is —$CH_2$— or —C(O)—;

R, is H, $C_1$-$C_4$ alkyl, $C_3$-$C_6$ cycloalkyl, —$CH_2CHF_2$, or —C(O)$CH_3$; and $R_h$ is H, $C_1$-$C_4$ alkyl, $C_3$-$C_6$ cycloalkyl, —$CH_2CHF_2$, or —C(O)$CH_3$;

to obtain the compound of formula (I) above, wherein Q is —O—.

16. A pharmaceutical composition comprising at least one pharmaceutically acceptable excipient and a compound selected from the group consisting of:

| No | Structure |
|---|---|
| 1 | 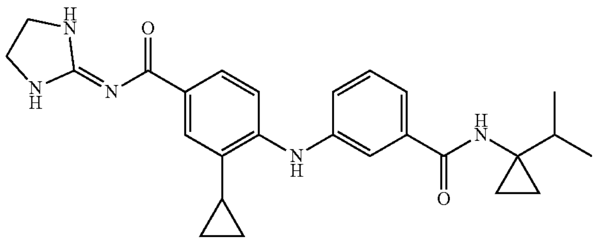 [SMILES: CC(C)C1(NC(=O)c2cccc(Nc3ccc(C(=O)N=C4NCCN4)cc3C3CC3)c2)CC1] |

-continued
| No | Structure |
| --- | --- |
| 2 | 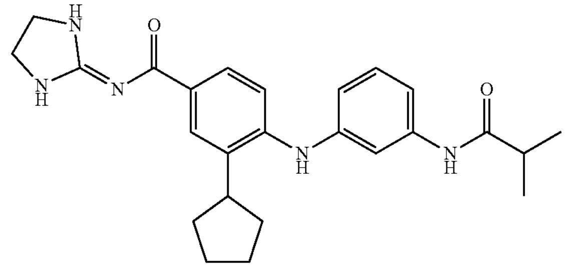 [SMILES: CC(C)C(=O)Nc1cccc(Nc2ccc(C(=O)N=C3NCCN3)cc2C2CCCC2)c1] |
| 3 | 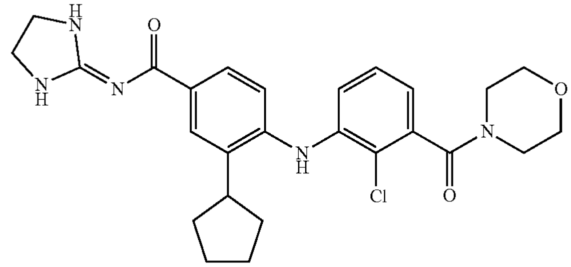 |
| 4 | 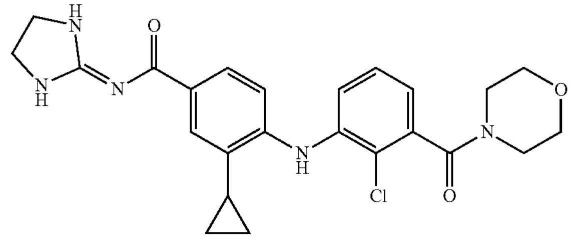 [SMILES: O=C(N=C1NCCN1)c1ccc(Nc2cccc(C(=O)N3CCOCC3)c2Cl)c(C2CC2)c1] |
| 5 | 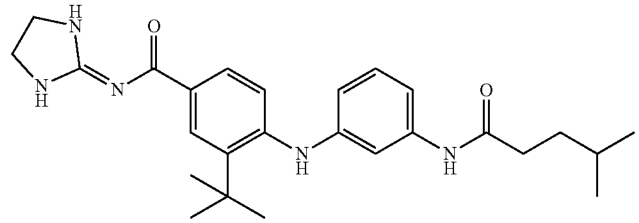 [SMILES: CC(C)CCC(=O)Nc1cccc(Nc2ccc(C(=O)N=C3NCCN3)cc2C(C)(C)C)c1] |
| 6 | 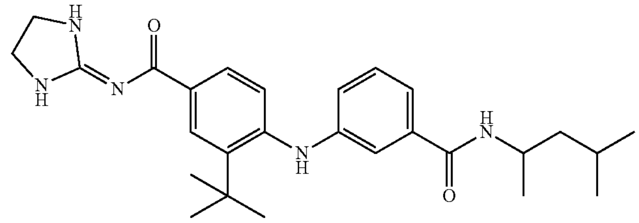 [SMILES: CC(C)CC(C)NC(=O)c1cccc(Nc2ccc(C(=O)N=C3NCCN3)cc2C(C)(C)C)c1] |
| 7 | 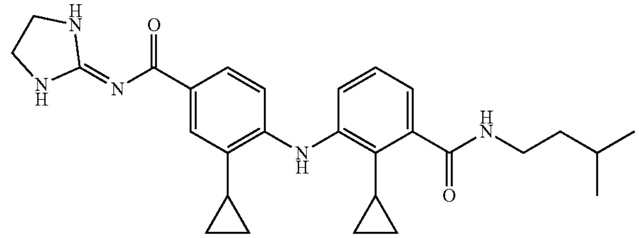 [SMILES: CC(C)CCNC(=O)c1cccc(Nc2ccc(C(=O)N=C3NCCN3)cc2C2CC2)c1C1CC1] |

-continued
| No | Structure |
| --- | --- |
| 8 | 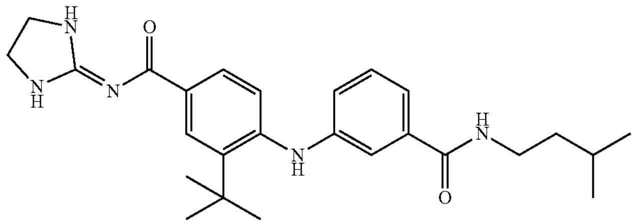 [SMILES: CC(C)CCNC(=O)c1cccc(Nc2ccc(C(=O)N=C3NCCN3)cc2C(C)(C)C)c1] |
| 9 | 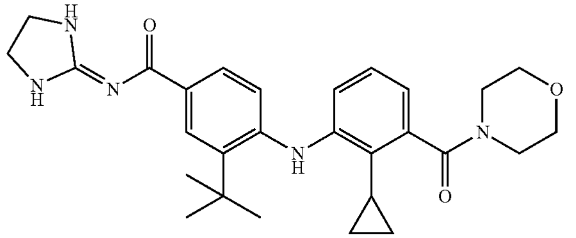 [SMILES: CC(C)(C)c1cc(C(=O)N=C2NCCN2)ccc1Nc1cccc(C(=O)N2CCOCC2)c1C1CC1] |
| 10 | 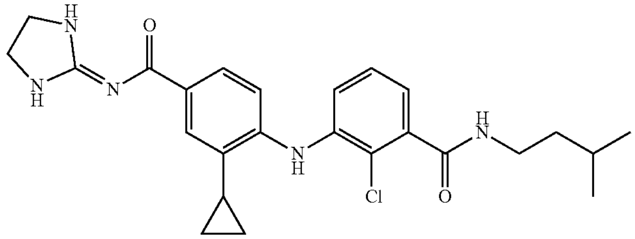 [SMILES: CC(C)CCNC(=O)c1cccc(Nc2ccc(C(=O)N=C3NCCN3)cc2C2CC2)c1Cl] |
| 11 | 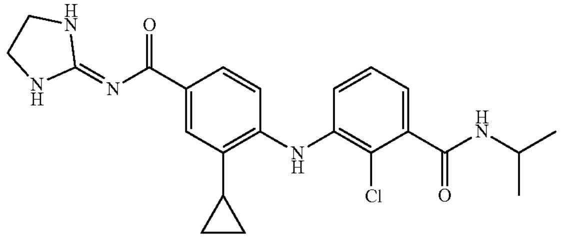 [SMILES: CC(C)NC(=O)c1cccc(Nc2ccc(C(=O)N=C3NCCN3)cc2C2CC2)c1Cl] |
| 12 | 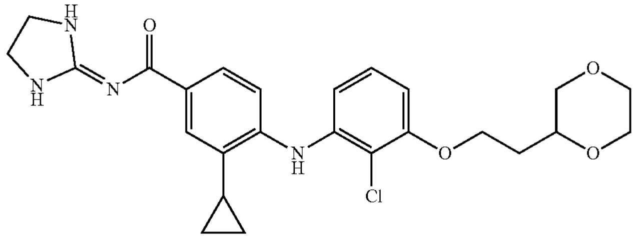 [SMILES: O=C(N=C1NCCN1)c1ccc(Nc2cccc(OCCC3COCCO3)c2Cl)c(C2CC2)c1] |
| 13 | 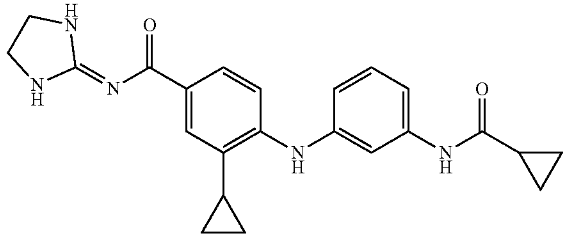 [SMILES: O=C(N=C1NCCN1)c1ccc(Nc2cccc(NC(=O)C3CC3)c2)c(C2CC2)c1] |

-continued
| No | Structure |
|---|---|
| 14 | 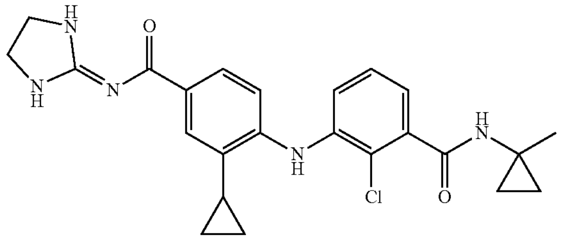 [SMILES: CC1(NC(=O)c2cccc(Nc3ccc(C(=O)N=C4NCCN4)cc3C3CC3)c2Cl)CC1] |
| 15 | 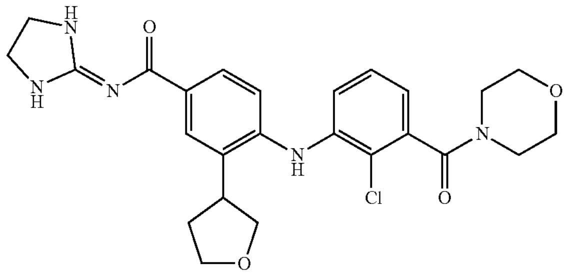 [SMILES: O=C(N=C1NCCN1)c1ccc(Nc2cccc(C(=O)N3CCOCC3)c2Cl)c(C2CCOC2)c1] |
| 16 | 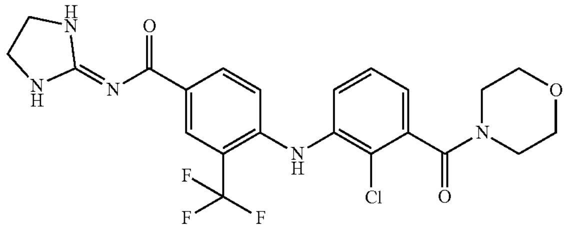 [SMILES: O=C(N=C1NCCN1)c1ccc(Nc2cccc(C(=O)N3CCOCC3)c2Cl)c(C(F)(F)F)c1] |
| 17 | 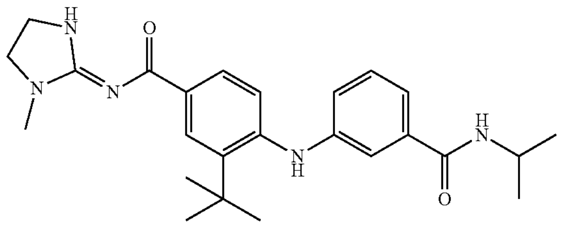 [SMILES: CC(C)NC(=O)c1cccc(Nc2ccc(C(=O)/N=C3\NCCN3C)cc2C(C)(C)C)c1] |
| 18 | 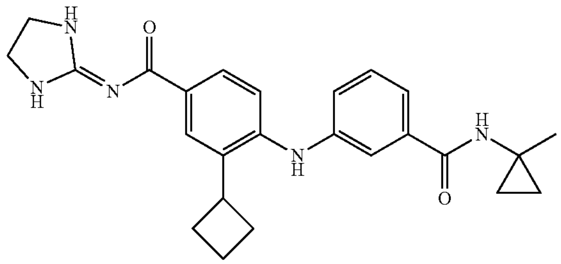 [SMILES: CC1(NC(=O)c2cccc(Nc3ccc(C(=O)N=C4NCCN4)cc3C3CCC3)c2)CC1] |
| 19 | 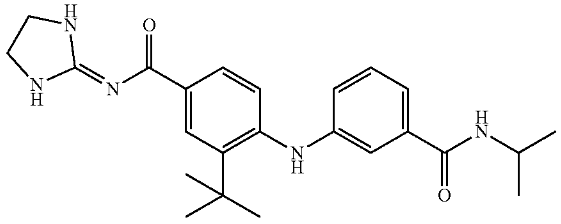 [SMILES: CC(C)NC(=O)c1cccc(Nc2ccc(C(=O)N=C3NCCN3)cc2C(C)(C)C)c1] |

-continued
| No | Structure |
| --- | --- |
| 20 | 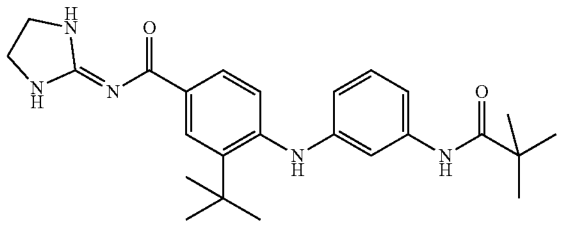 [SMILES: CC(C)(C)C(=O)Nc1cccc(Nc2ccc(C(=O)N=C3NCCN3)cc2C(C)(C)C)c1] |
| 21 | 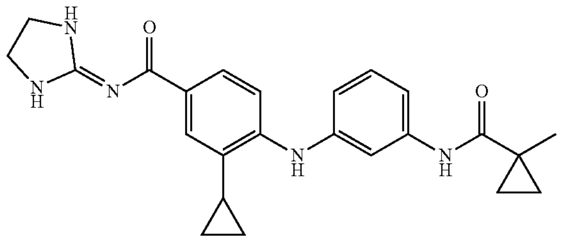 [SMILES: CC1(C(=O)Nc2cccc(Nc3ccc(C(=O)N=C4NCCN4)cc3C3CC3)c2)CC1] |
| 22 | 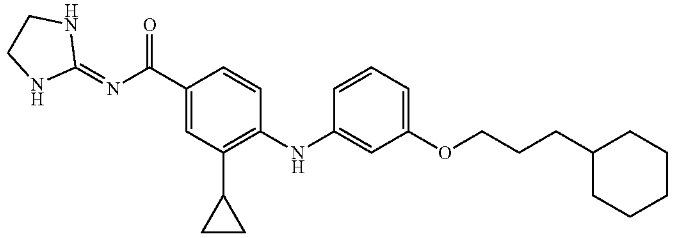 [SMILES: O=C(N=C1NCCN1)c1ccc(Nc2cccc(OCCCC3CCCCC3)c2)c(C2CC2)c1] |
| 23 | 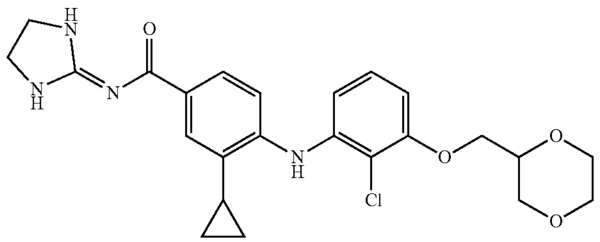 [SMILES: O=C(N=C1NCCN1)c1ccc(Nc2cccc(OCC3COCCO3)c2Cl)c(C2CC2)c1] |
| 24 | 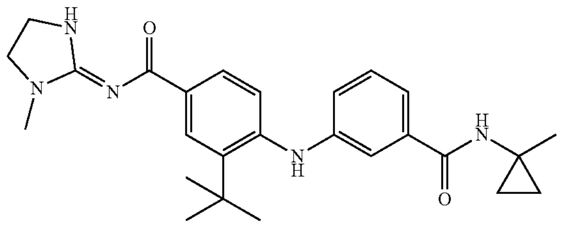 [SMILES: CN1CCN/C1=N\C(=O)c1ccc(Nc2cccc(C(=O)NC3(C)CC3)c2)c(C(C)(C)C)c1] |
| 25 | 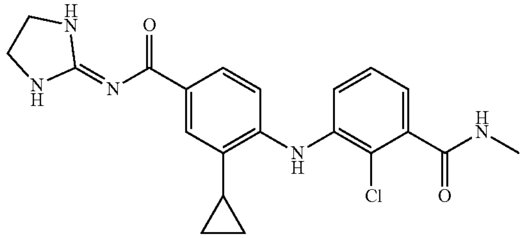 [SMILES: CNC(=O)c1cccc(Nc2ccc(C(=O)N=C3NCCN3)cc2C2CC2)c1Cl] |

-continued
| No | Structure |
|---|---|
| 26 | 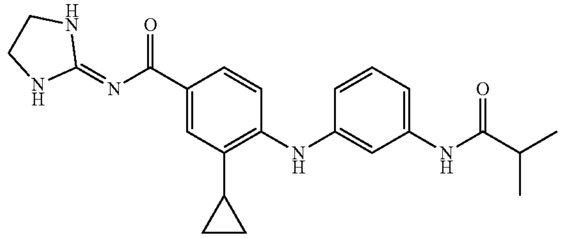 [SMILES: CC(C)C(=O)Nc1cccc(Nc2ccc(C(=O)N=C3NCCN3)cc2C2CC2)c1] |
| 27 | 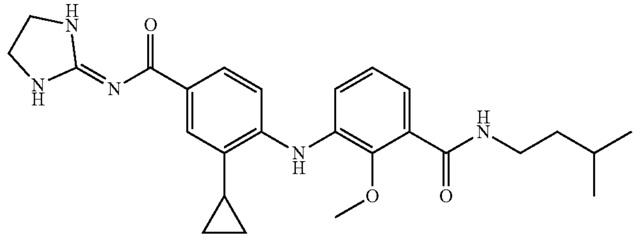 [SMILES: COc1c(Nc2ccc(C(=O)N=C3NCCN3)cc2C2CC2)cccc1C(=O)NCCC(C)C] |
| 28 | 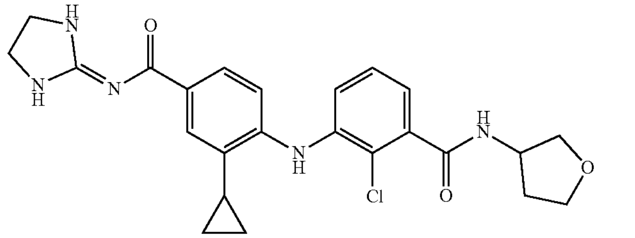 [SMILES: O=C(N=C1NCCN1)c1ccc(Nc2cccc(C(=O)NC3CCOC3)c2Cl)c(C2CC2)c1] |
| 29 | 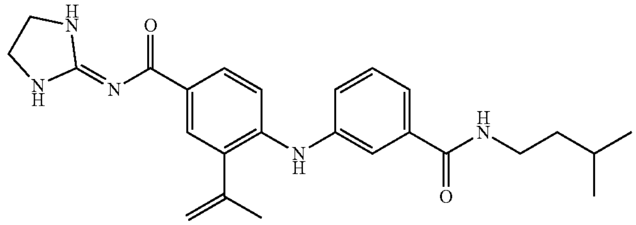 [SMILES: C=C(C)c1cc(C(=O)N=C2NCCN2)ccc1Nc1cccc(C(=O)NCCC(C)C)c1] |
| 30 | 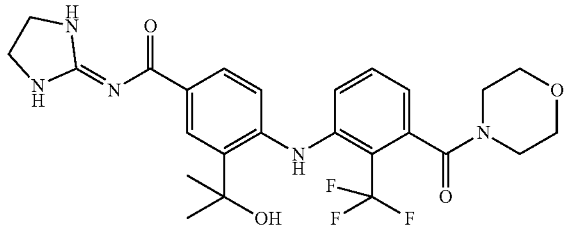 [SMILES: CC(C)(O)c1cc(C(=O)N=C2NCCN2)ccc1Nc1cccc(C(=O)N2CCOCC2)c1C(F)(F)F] |
| 31 | 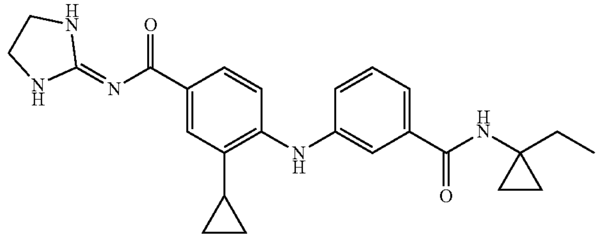 [SMILES: CCC1(NC(=O)c2cccc(Nc3ccc(C(=O)N=C4NCCN4)cc3C3CC3)c2)CC1] |

-continued
| No | Structure |
|---|---|
| 32 | 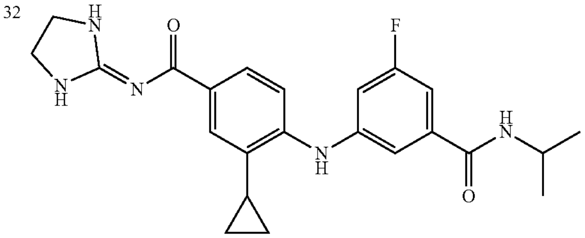 |
| 33 | 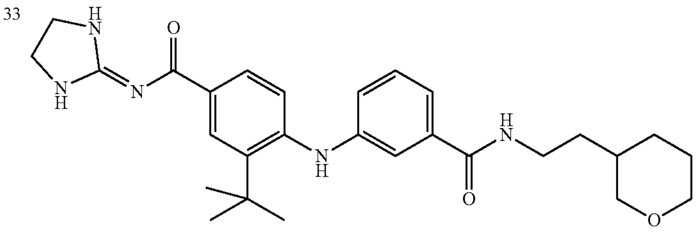 |
| 34 | 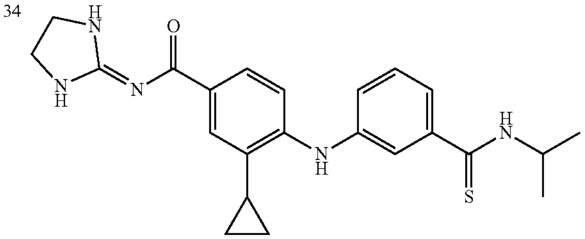 |
| 35 | 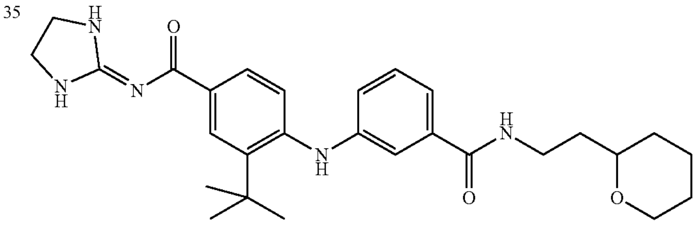 |
| 36 | 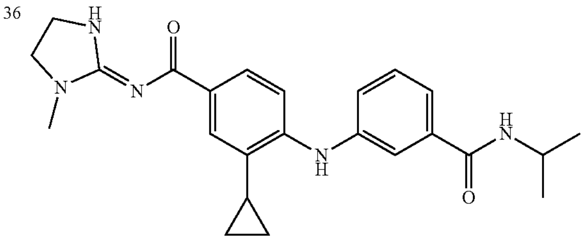 |
| 37 | 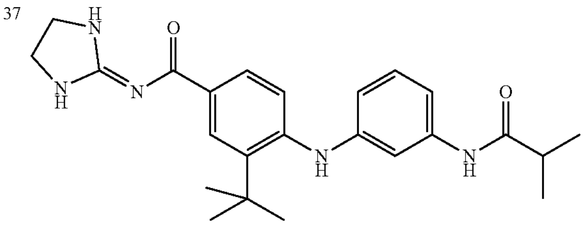 |

-continued
| No | Structure |
|---|---|
| 38 | 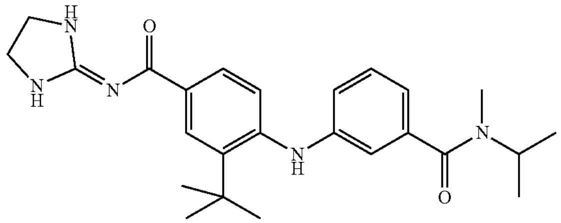 [SMILES: CC(C)N(C)C(=O)c1cccc(Nc2ccc(C(=O)N=C3NCCN3)cc2C(C)(C)C)c1] |
| 39 | 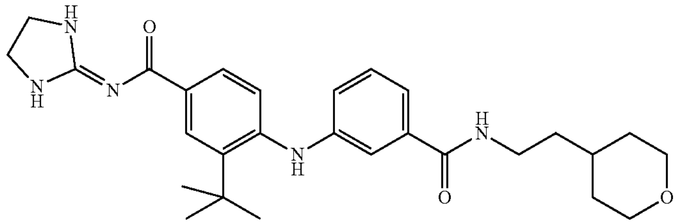 [SMILES: CC(C)(C)c1cc(C(=O)N=C2NCCN2)ccc1Nc1cccc(C(=O)NCCC2CCOCC2)c1] |
| 40 | 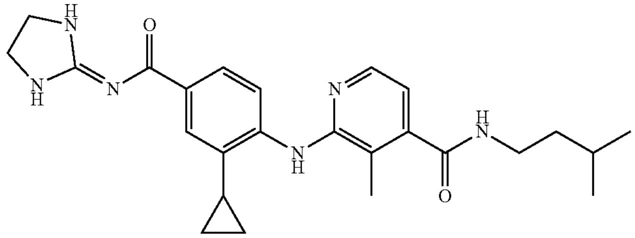 [SMILES: Cc1c(C(=O)NCCC(C)C)ccnc1Nc1ccc(C(=O)N=C2NCCN2)cc1C1CC1] |
| 41 | 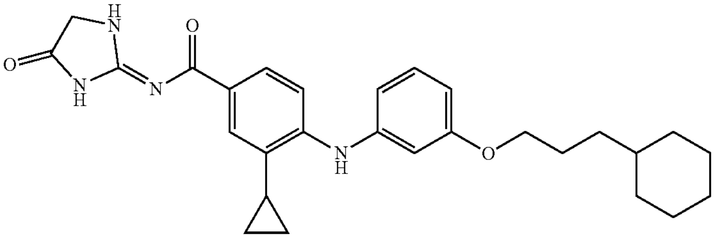 [SMILES: O=C1CN/C(=N\C(=O)c2ccc(Nc3cccc(OCCCC4CCCCC4)c3)c(C3CC3)c2)N1] |
| 42 | 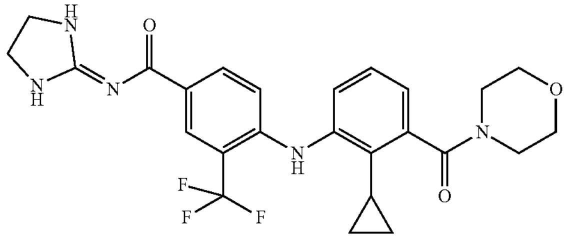 [SMILES: O=C(N=C1NCCN1)c1ccc(Nc2cccc(C(=O)N3CCOCC3)c2C2CC2)c(C(F)(F)F)c1] |
| 43 | 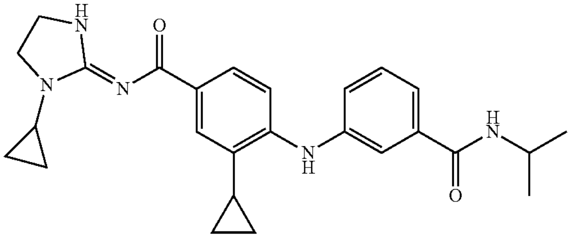 [SMILES: CC(C)NC(=O)c1cccc(Nc2ccc(C(=O)/N=C3\NCCN3C3CC3)cc2C2CC2)c1] |

-continued
| No | Structure |
| --- | --- |
| 44 | 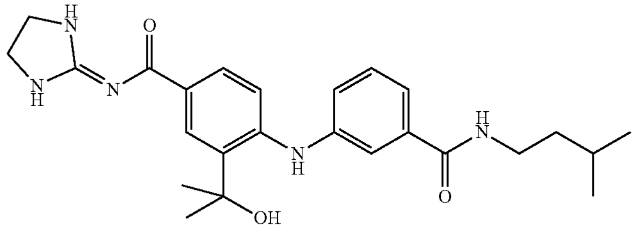 [SMILES: CC(C)CCNC(=O)c1cccc(Nc2ccc(C(=O)N=C3NCCN3)cc2C(C)(C)O)c1] |
| 45 | 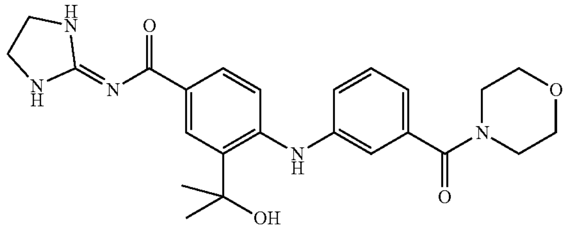 [SMILES: CC(C)(O)c1cc(C(=O)N=C2NCCN2)ccc1Nc1cccc(C(=O)N2CCOCC2)c1] |
| 46 | 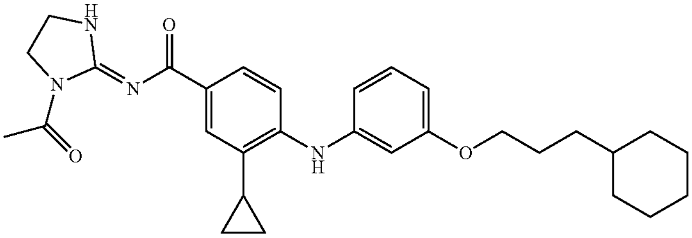 [SMILES: CC(=O)N1CCN/C1=N\C(=O)c1ccc(Nc2cccc(OCCCC3CCCCC3)c2)c(C2CC2)c1] |
| 47 | 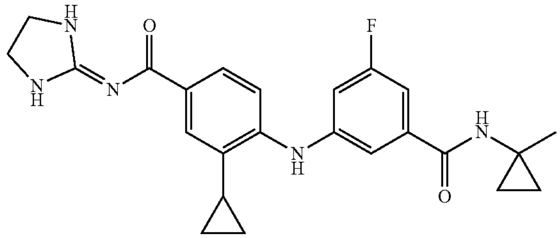 [SMILES: CC1(NC(=O)c2cc(F)cc(Nc3ccc(C(=O)N=C4NCCN4)cc3C3CC3)c2)CC1] |
| 48 | 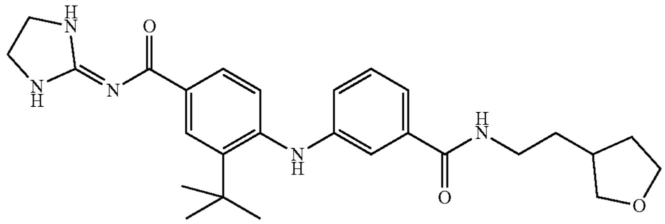 [SMILES: CC(C)(C)c1cc(C(=O)N=C2NCCN2)ccc1Nc1cccc(C(=O)NCCC2CCOC2)c1] |
| 49 | 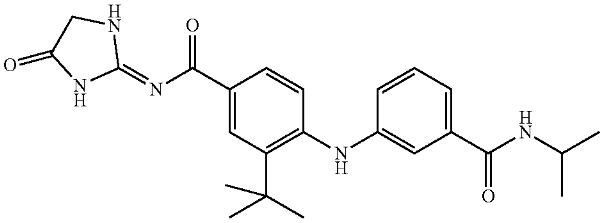 [SMILES: CC(C)NC(=O)c1cccc(Nc2ccc(C(=O)/N=C3\NCC(=O)N3)cc2C(C)(C)C)c1] |

-continued
| No | Structure |
| --- | --- |
| 50 | 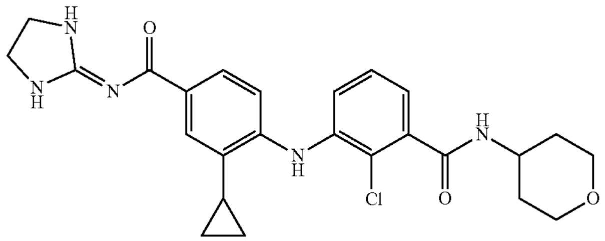 [SMILES: O=C(N=C1NCCN1)c1ccc(Nc2cccc(C(=O)NC3CCOCC3)c2Cl)c(C2CC2)c1] |
| 51 | 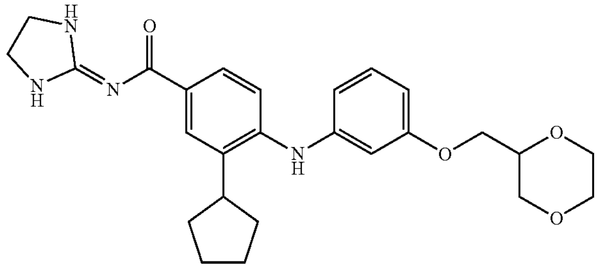 [SMILES: O=C(N=C1NCCN1)c1ccc(Nc2cccc(OCC3COCCO3)c2)c(C2CCCC2)c1] |
| 52 | 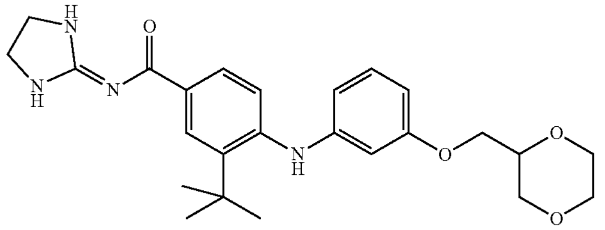 [SMILES: CC(C)(C)c1cc(C(=O)N=C2NCCN2)ccc1Nc1cccc(OCC2COCCO2)c1] |
| 53 | 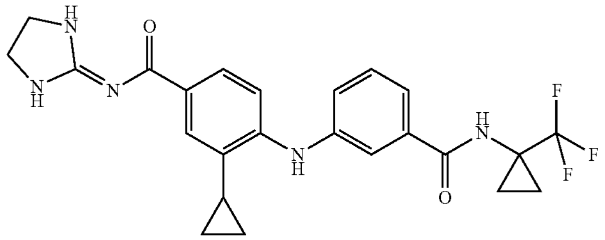 [SMILES: O=C(N=C1NCCN1)c1ccc(Nc2cccc(C(=O)NC3(C(F)(F)F)CC3)c2)c(C2CC2)c1] |
| 54 | 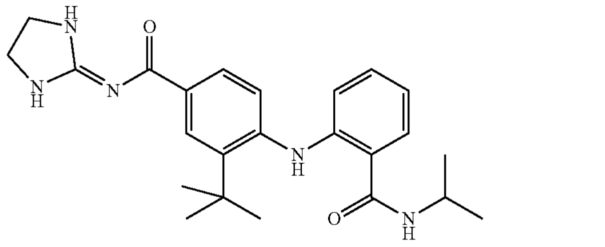 [SMILES: CC(C)NC(=O)c1ccccc1Nc1ccc(C(=O)N=C2NCCN2)cc1C(C)(C)C] |
| 55 | 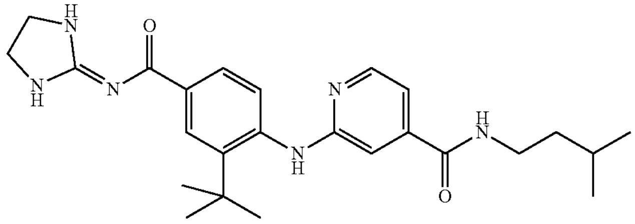 [SMILES: CC(C)CCNC(=O)c1ccnc(Nc2ccc(C(=O)N=C3NCCN3)cc2C(C)(C)C)c1] |

-continued
| No | Structure |
|---|---|
| 56 | 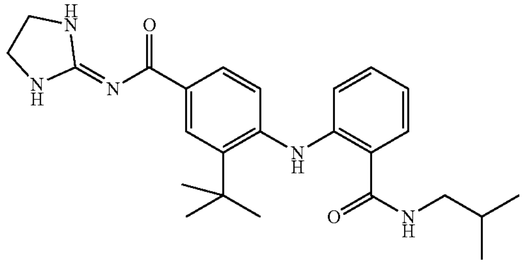 [SMILES: CC(C)CNC(=O)c1ccccc1Nc1ccc(C(=O)N=C2NCCN2)cc1C(C)(C)C] |
| 57 | 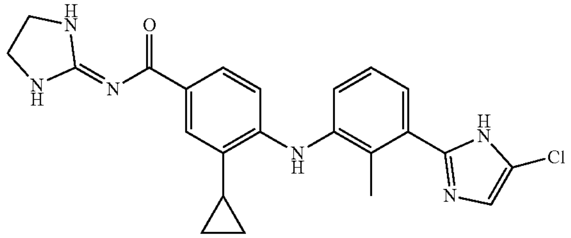 [SMILES: Cc1c(Nc2ccc(C(=O)N=C3NCCN3)cc2C2CC2)cccc1-c1ncc(Cl)[nH]1] |
| 58 | 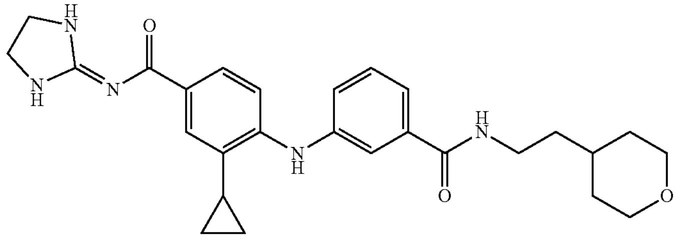 [SMILES: O=C(N=C1NCCN1)c1ccc(Nc2cccc(C(=O)NCCC3CCOCC3)c2)c(C2CC2)c1] |
| 59 | 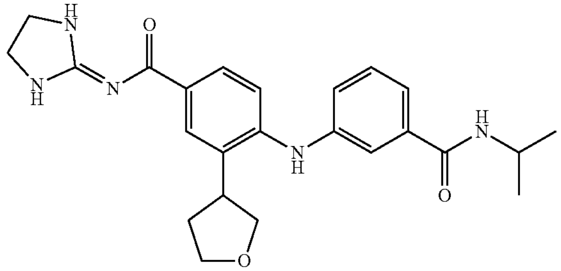 [SMILES: CC(C)NC(=O)c1cccc(Nc2ccc(C(=O)N=C3NCCN3)cc2C2CCOC2)c1] |
| 60 | 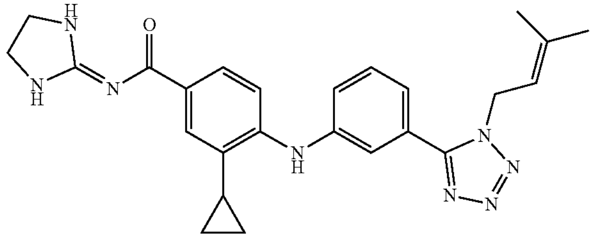 [SMILES: CC(C)=CCn1nnnc1-c1cccc(Nc2ccc(C(=O)N=C3NCCN3)cc2C2CC2)c1] |
| 61 | 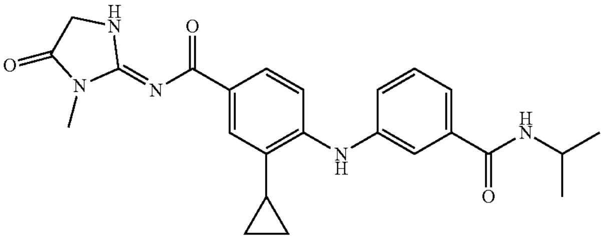 [SMILES: CC(C)NC(=O)c1cccc(Nc2ccc(C(=O)/N=C3\NCC(=O)N3C)cc2C2CC2)c1] |

-continued
| No | Structure |
|---|---|
| 62 | 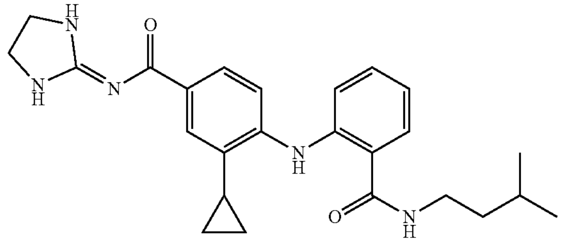 |
| 63 | 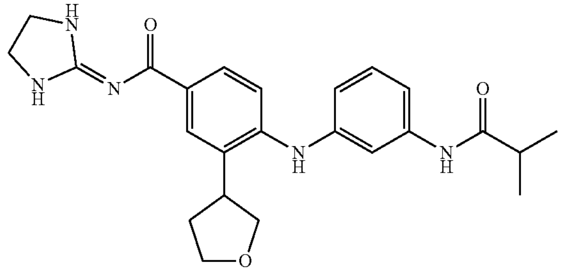 [SMILES: CC(C)C(=O)Nc1cccc(Nc2ccc(C(=O)N=C3NCCN3)cc2C2CCOC2)c1] |
| 64 | 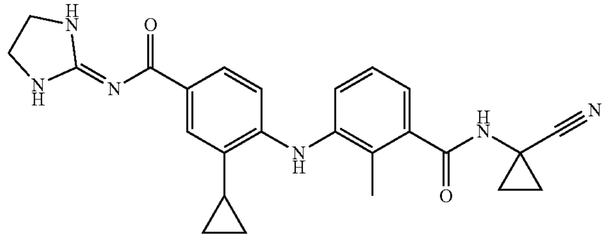 [SMILES: Cc1c(Nc2ccc(C(=O)N=C3NCCN3)cc2C2CC2)cccc1C(=O)NC1(C#N)CC1] |
| 65 | 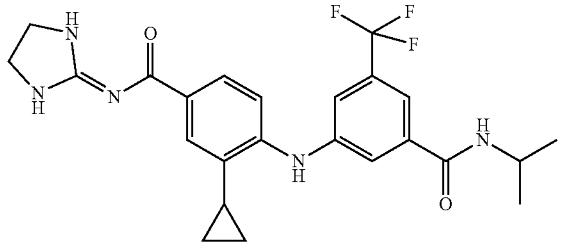 [SMILES: CC(C)NC(=O)c1cc(Nc2ccc(C(=O)N=C3NCCN3)cc2C2CC2)cc(C(F)(F)F)c1] |
| 66 | 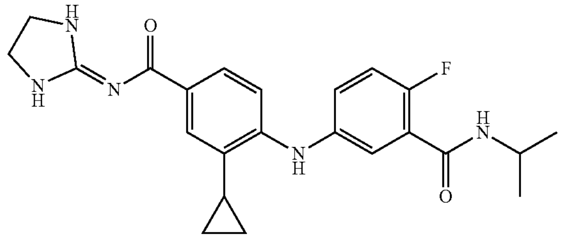 [SMILES: CC(C)NC(=O)c1cc(Nc2ccc(C(=O)N=C3NCCN3)cc2C2CC2)ccc1F] |
| 67 | 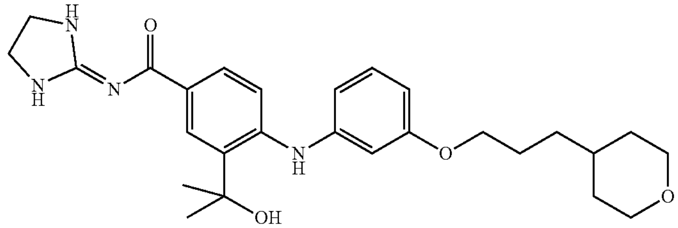 [SMILES: CC(C)(O)c1cc(C(=O)N=C2NCCN2)ccc1Nc1cccc(OCCCC2CCOCC2)c1] |

-continued
| No | Structure |
|---|---|
| 68 | 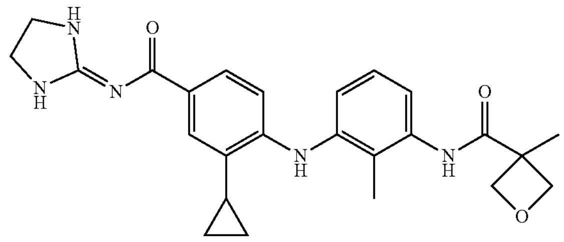 [SMILES: Cc1c(NC(=O)C2(C)COC2)cccc1Nc1ccc(C(=O)N=C2NCCN2)cc1C1CC1] |
| 69 | 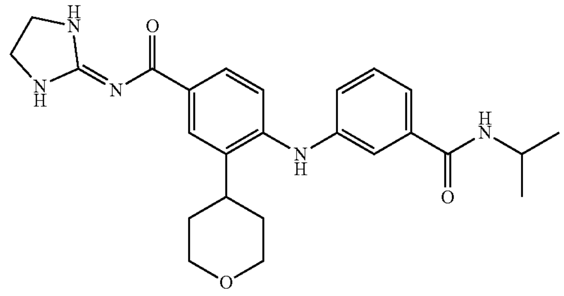 [SMILES: CC(C)NC(=O)c1cccc(Nc2ccc(C(=O)N=C3NCCN3)cc2C2CCOCC2)c1] |
| 70 | 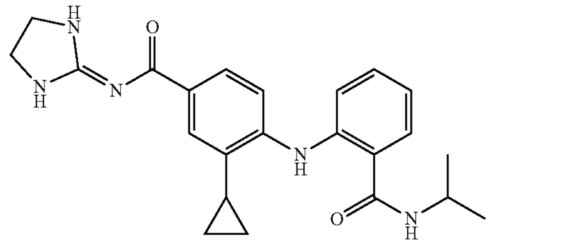 [SMILES: CC(C)NC(=O)c1ccccc1Nc1ccc(C(=O)N=C2NCCN2)cc1C1CC1] |
| 71 | 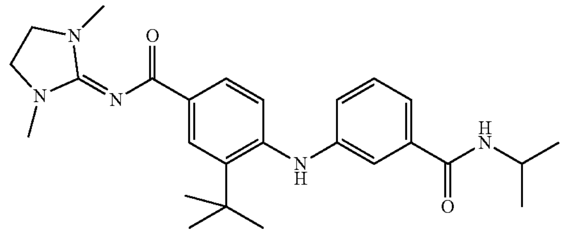 [SMILES: CC(C)NC(=O)c1cccc(Nc2ccc(C(=O)N=C3N(C)CCN3C)cc2C(C)(C)C)c1] |
| 72 | 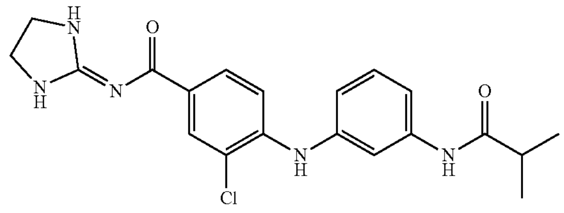 [SMILES: CC(C)C(=O)Nc1cccc(Nc2ccc(C(=O)N=C3NCCN3)cc2Cl)c1] |
| 73 | 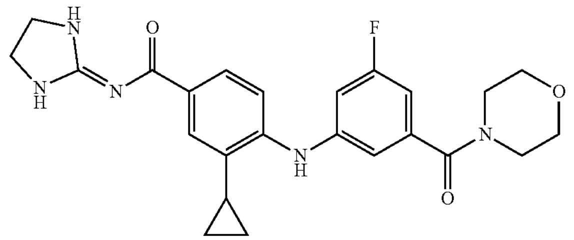 [SMILES: O=C(N=C1NCCN1)c1ccc(Nc2cc(F)cc(C(=O)N3CCOCC3)c2)c(C2CC2)c1] |

-continued
| No | Structure |
|---|---|
| 74 | 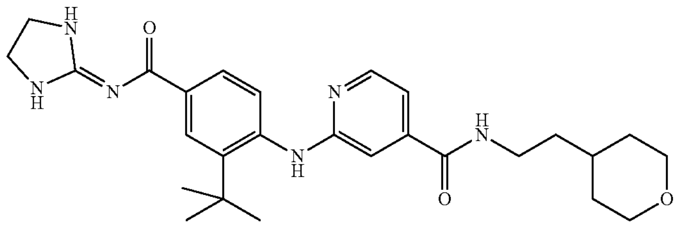 [SMILES: CC(C)(C)c1cc(C(=O)N=C2NCCN2)ccc1Nc1cc(C(=O)NCCC2CCOCC2)ccn1] |
| 75 | 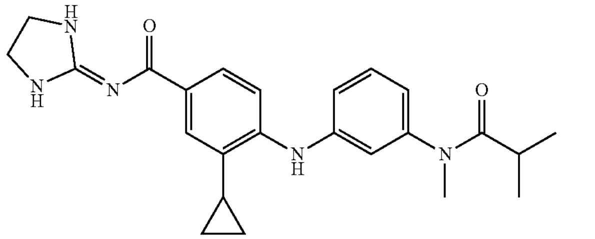 |
| 76 | 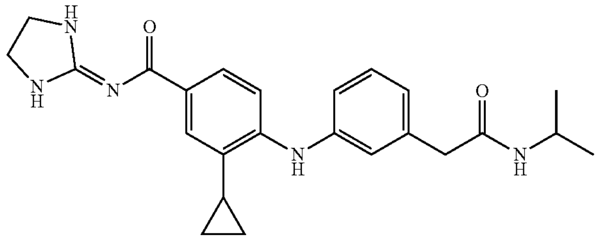 [SMILES: CC(C)NC(=O)Cc1cccc(Nc2ccc(C(=O)N=C3NCCN3)cc2C2CC2)c1] |
| 77 | 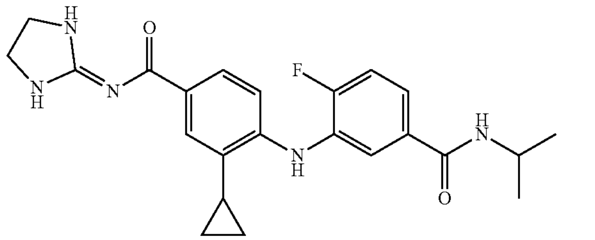 [SMILES: CC(C)NC(=O)c1ccc(F)c(Nc2ccc(C(=O)N=C3NCCN3)cc2C2CC2)c1] |
| 78 | 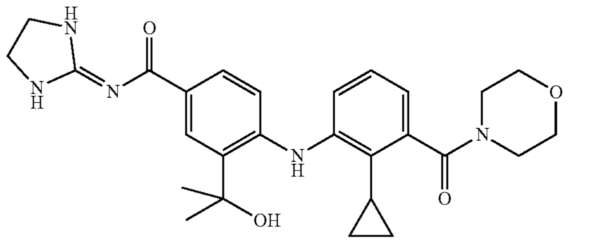 [SMILES: CC(C)(O)c1cc(C(=O)N=C2NCCN2)ccc1Nc1cccc(C(=O)N2CCOCC2)c1C1CC1] |
| 79 | 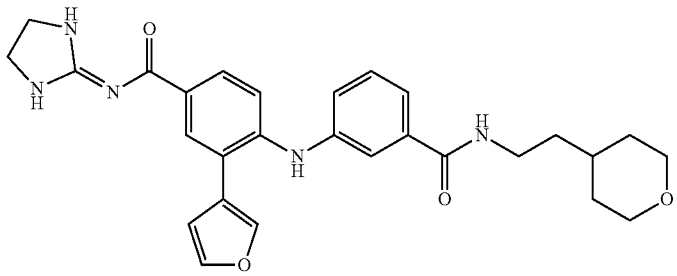 [SMILES: O=C(N=C1NCCN1)c1ccc(Nc2cccc(C(=O)NCCC3CCOCC3)c2)c(-c2ccoc2)c1] |

-continued
| No | Structure |
|---|---|
| 80 | 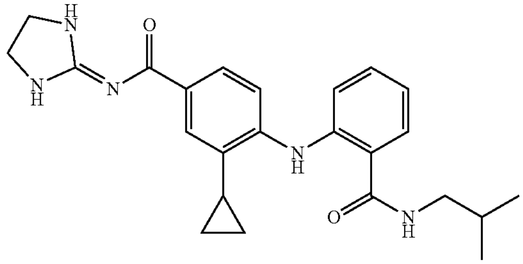 [SMILES: CC(C)CNC(=O)c1ccccc1Nc1ccc(C(=O)N=C2NCCN2)cc1C1CC1] |
| 81 | 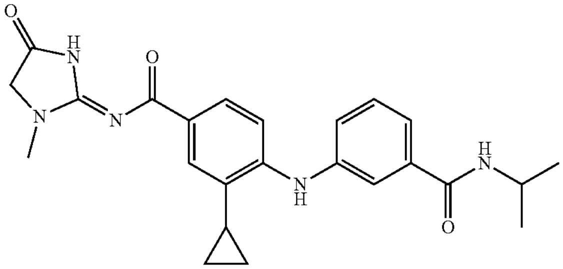 [SMILES: CC(C)NC(=O)c1cccc(Nc2ccc(C(=O)/N=C3\NC(=O)CN3C)cc2C2CC2)c1] |
| 82 | 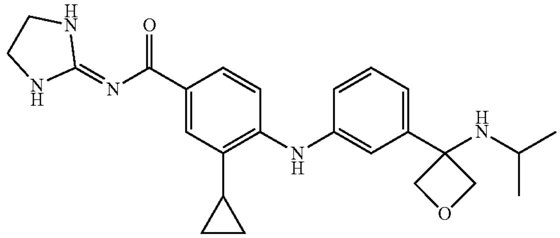 [SMILES: CC(C)NC1(c2cccc(Nc3ccc(C(=O)N=C4NCCN4)cc3C3CC3)c2)COC1] |
| 83 | 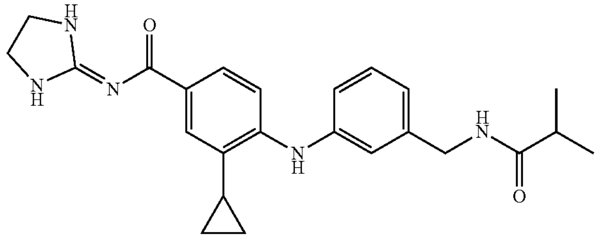 [SMILES: CC(C)C(=O)NCc1cccc(Nc2ccc(C(=O)N=C3NCCN3)cc2C2CC2)c1] |
| 84 | 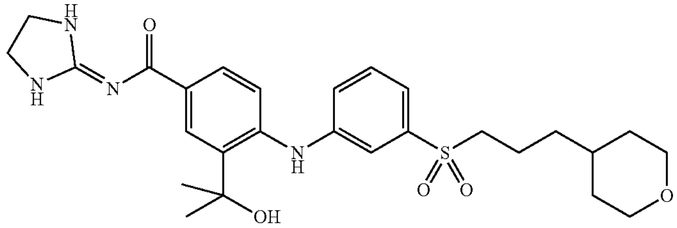 [SMILES: CC(C)(O)c1cc(C(=O)N=C2NCCN2)ccc1Nc1cccc(S(=O)(=O)CCCC2CCOCC2)c1] |
| 85 | 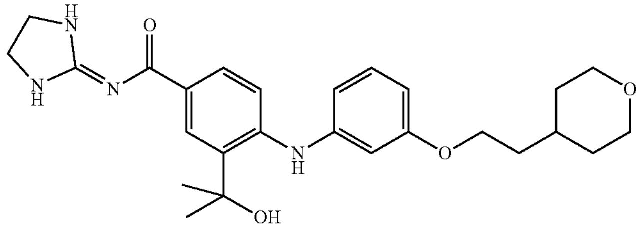 [SMILES: CC(C)(O)c1cc(C(=O)N=C2NCCN2)ccc1Nc1cccc(OCCC2CCOCC2)c1] |

-continued
| No | Structure |
| --- | --- |
| 86 | 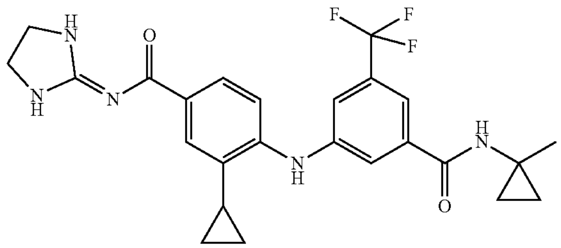 [SMILES: CC1(NC(=O)c2cc(Nc3ccc(C(=O)N=C4NCCN4)cc3C3CC3)cc(C(F)(F)F)c2)CC1] |
| 87 | 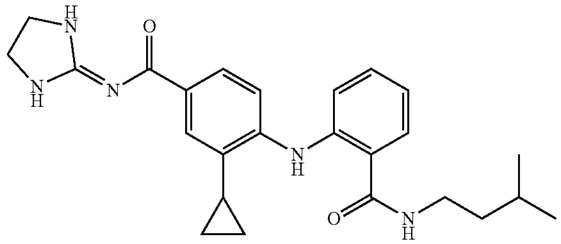 |
| 88 | 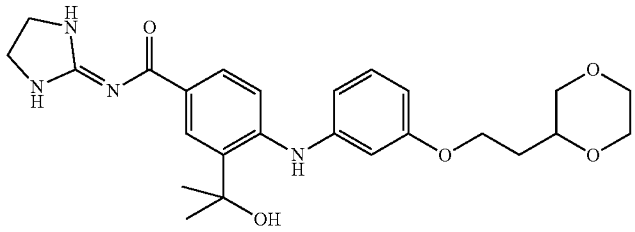 [SMILES: CC(C)(O)c1cc(C(=O)N=C2NCCN2)ccc1Nc1cccc(OCCC2COCCO2)c1] |
| 89 | 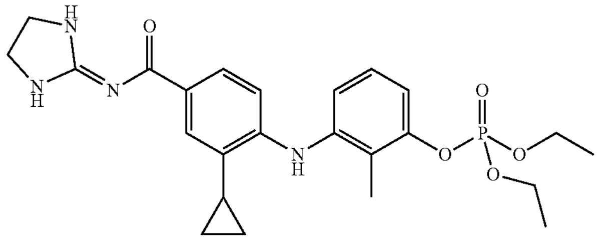 [SMILES: CCOP(=O)(OCC)Oc1cccc(Nc2ccc(C(=O)N=C3NCCN3)cc2C2CC2)c1C] |
| 90 | 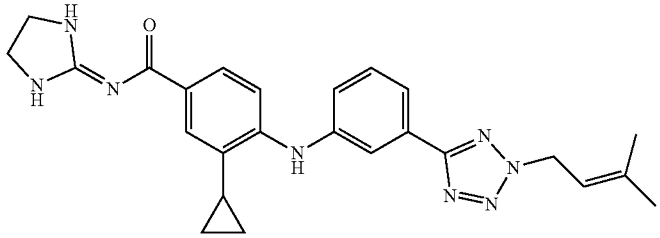 [SMILES: CC(C)=CCn1nnc(-c2cccc(Nc3ccc(C(=O)N=C4NCCN4)cc3C3CC3)c2)n1] |
| 91 | 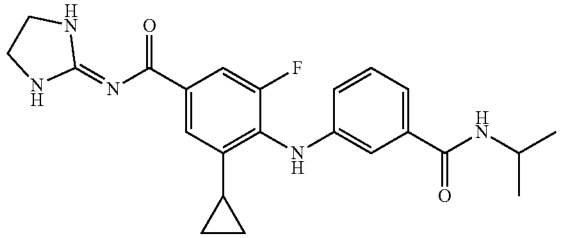 [SMILES: CC(C)NC(=O)c1cccc(Nc2c(F)cc(C(=O)N=C3NCCN3)cc2C2CC2)c1] |

-continued
| No | Structure |
|---|---|
| 92 | 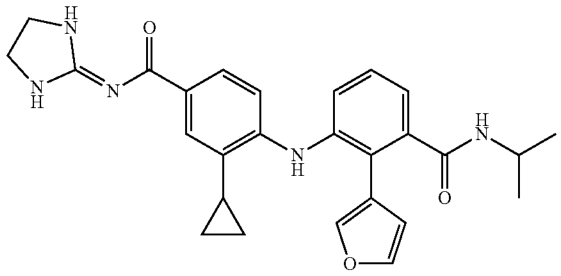 [SMILES: CC(C)NC(=O)c1cccc(Nc2ccc(C(=O)N=C3NCCN3)cc2C2CC2)c1-c1ccoc1] |
| 93 | 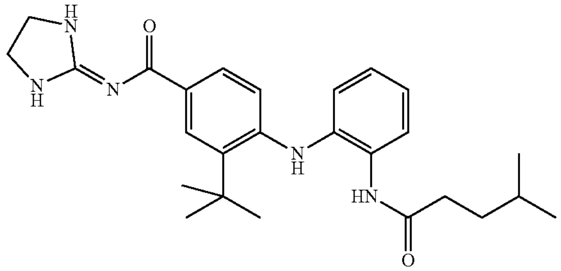 |
| 94 | 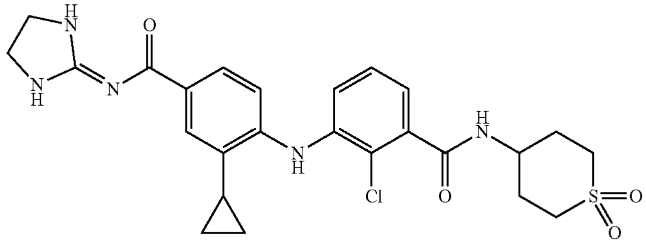 [SMILES: O=C(N=C1NCCN1)c1ccc(Nc2cccc(C(=O)NC3CCS(=O)(=O)CC3)c2Cl)c(C2CC2)c1] |
| 95 | 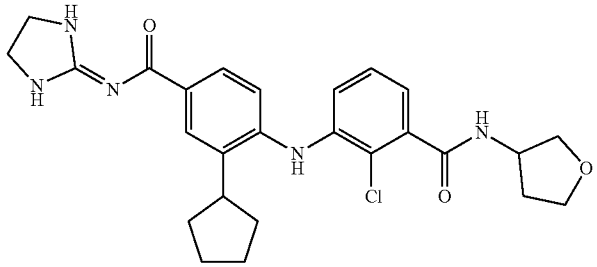 [SMILES: O=C(N=C1NCCN1)c1ccc(Nc2cccc(C(=O)NC3CCOC3)c2Cl)c(C2CCCC2)c1] |
| 96 | 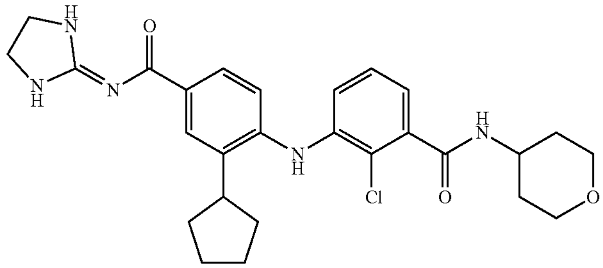 [SMILES: O=C(N=C1NCCN1)c1ccc(Nc2cccc(C(=O)NC3CCOCC3)c2Cl)c(C2CCCC2)c1] |

-continued
| No | Structure |
|---|---|
| 97 | 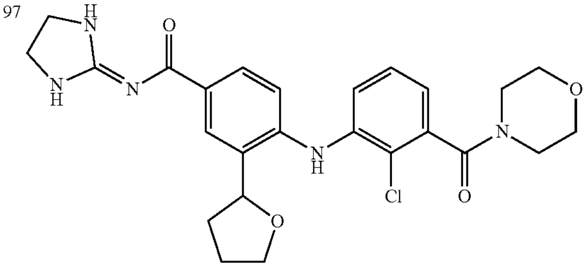 |
| 98 | 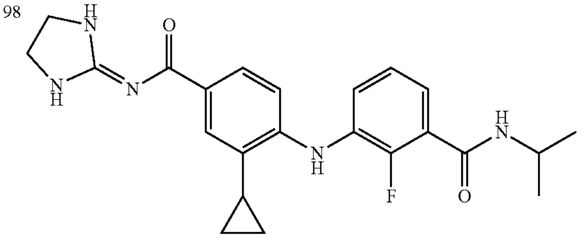 |
| 99 | 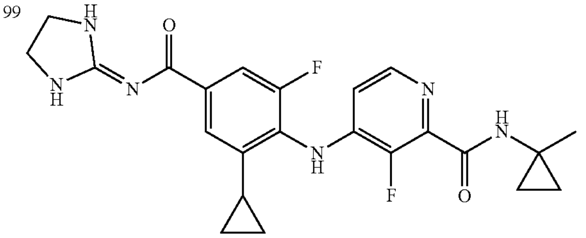 |
| 100 | 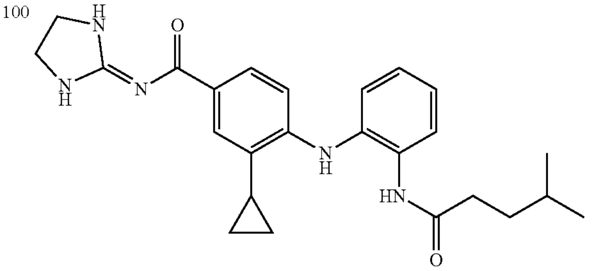 |
| 101 | 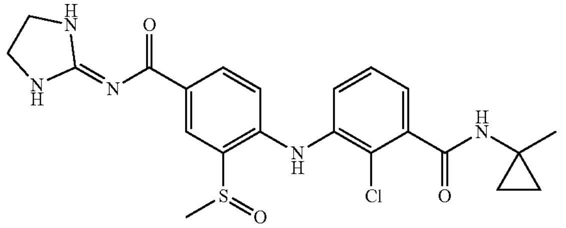 [SMILES: CS(=O)c1cc(C(=O)N=C2NCCN2)ccc1Nc1cccc(C(=O)NC2(C)CC2)c1Cl] |
| 102 | 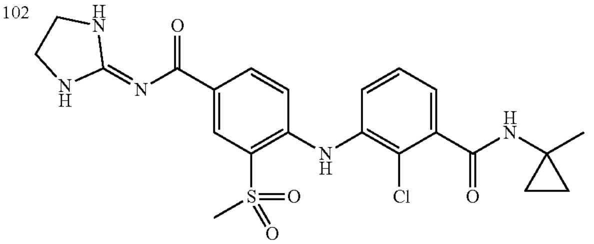 |

-continued
| No | Structure |
|---|---|
| 103 | 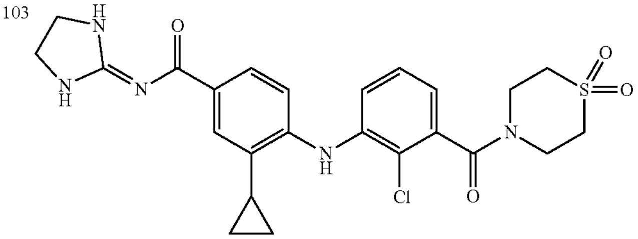 |
| 104 | 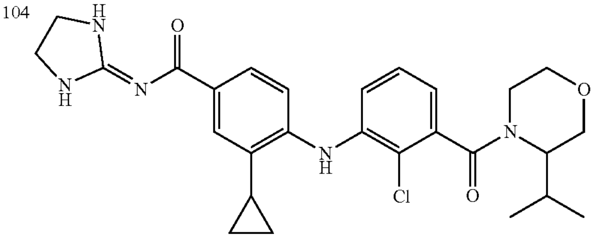 |
| 105 | 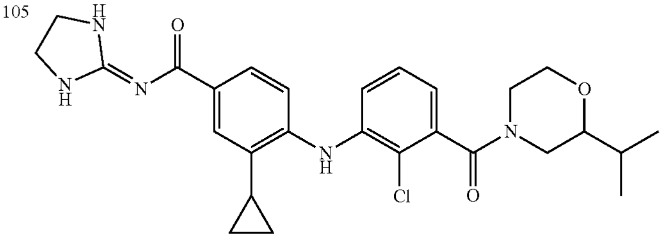 |
| 106 | 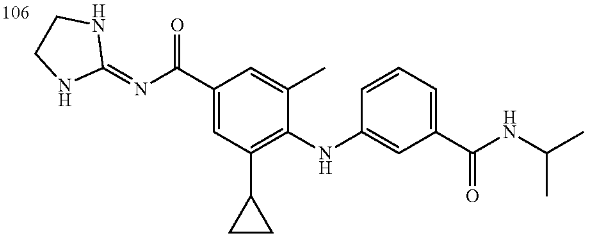 |
| 107 | 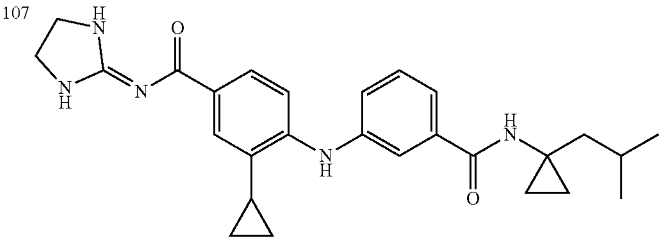 |
| 108 | 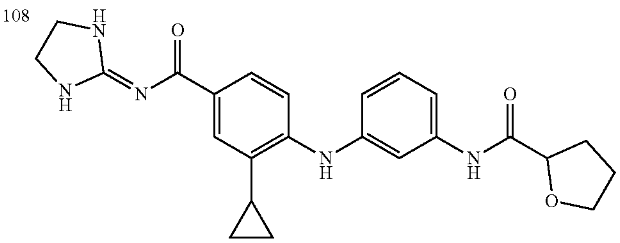 |

-continued
| No | Structure |
|---|---|
| 109 | 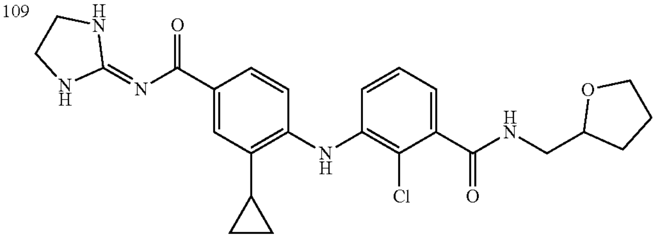 |
| 110 | 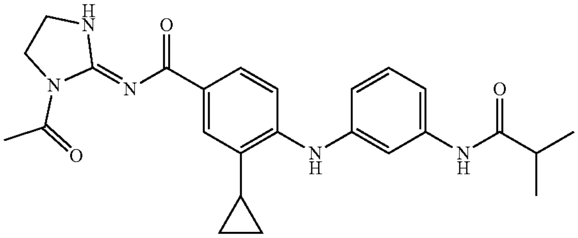 [SMILES: CC(=O)N1CCN/C1=N\C(=O)c1ccc(Nc2cccc(NC(=O)C(C)C)c2)c(C2CC2)c1] |
| 111 | 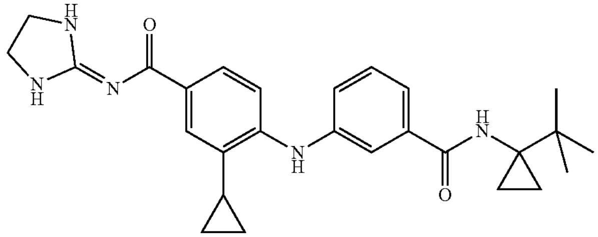 [SMILES: CC(C)(C)C1(NC(=O)c2cccc(Nc3ccc(C(=O)N=C4NCCN4)cc3C3CC3)c2)CC1] |
| 112 | 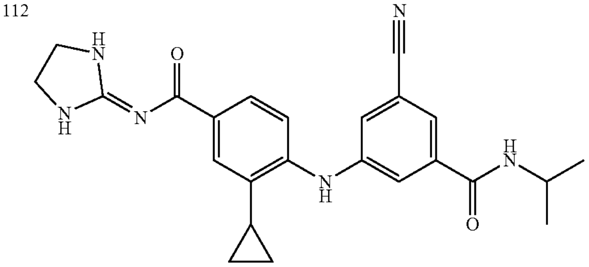 |
| 113 | 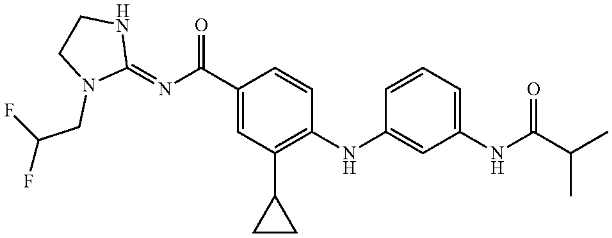 [SMILES: CC(C)C(=O)Nc1cccc(Nc2ccc(C(=O)/N=C3\NCCN3CC(F)F)cc2C2CC2)c1] |
| 114 | 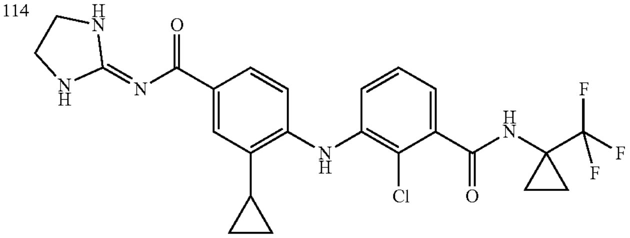 |

-continued
| No | Structure |
|---|---|
| 115 | 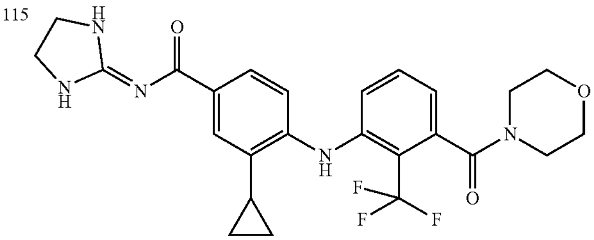 |
| 116 | 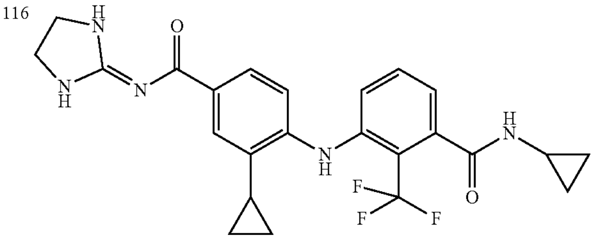 |
| 117 | 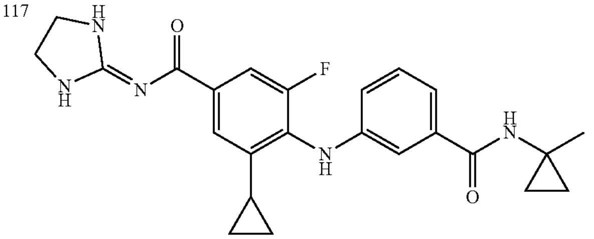 |
| 118 | 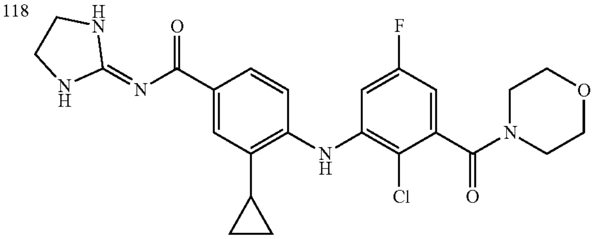 |
| 119 | 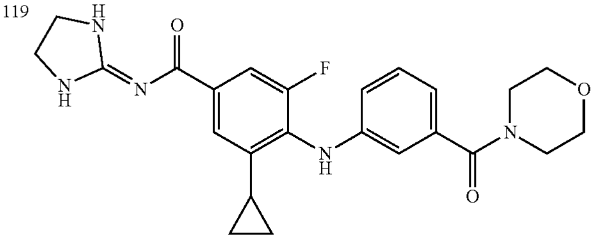 |
| 120 | 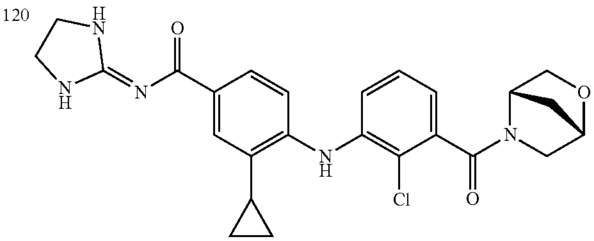 |

-continued
| No | Structure |
| --- | --- |
| 121 | 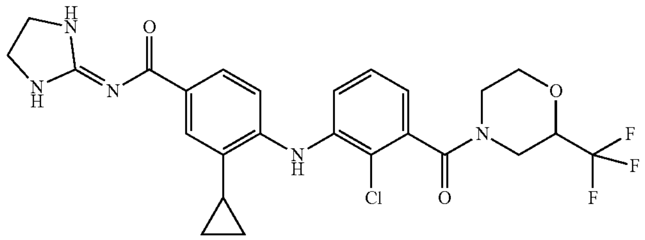 [SMILES: O=C(N=C1NCCN1)c1ccc(Nc2cccc(C(=O)N3CCOC(C(F)(F)F)C3)c2Cl)c(C2CC2)c1] |
| 122 | 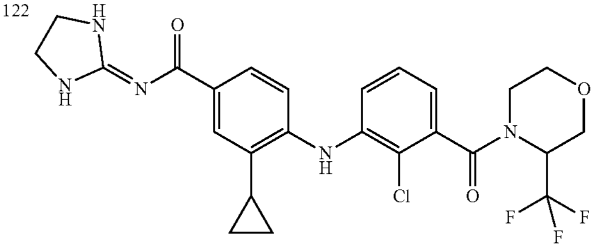 |
| 123 | 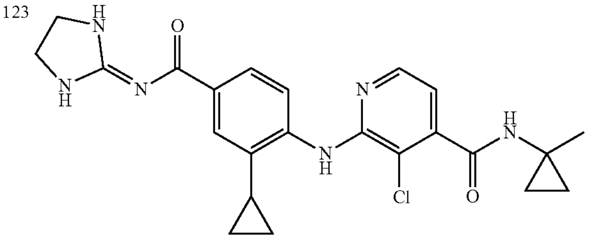 |
| 124 | 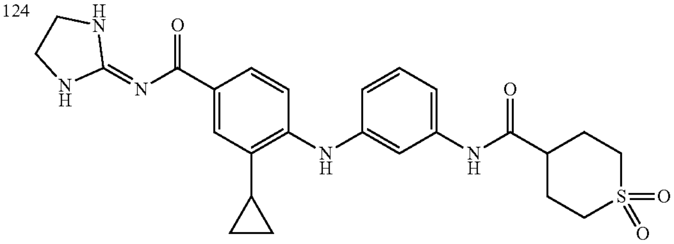 |
| 125 | 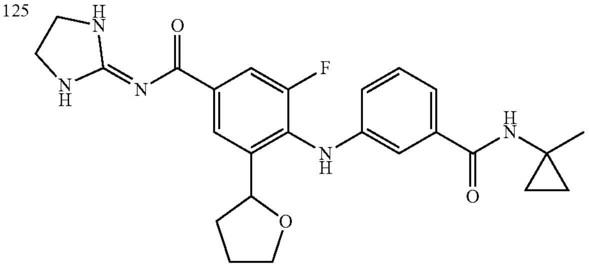 |
| 126 | 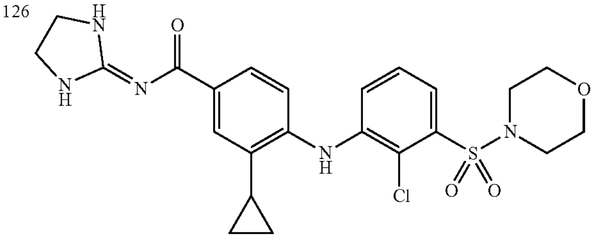 |

-continued
| No | Structure |
|---|---|
| 127 | 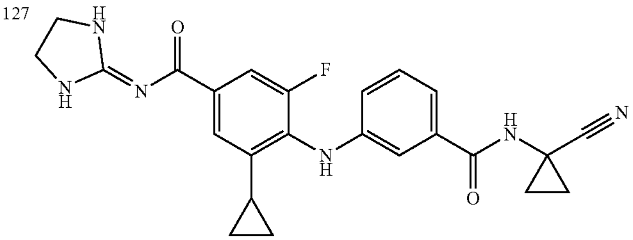 |
| 128 | 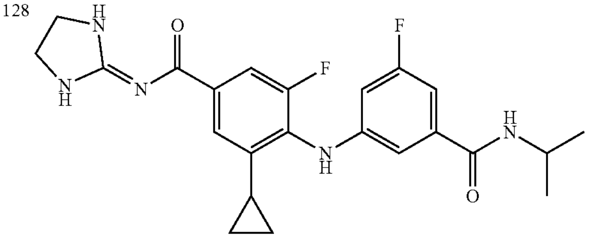 |
| 129 | 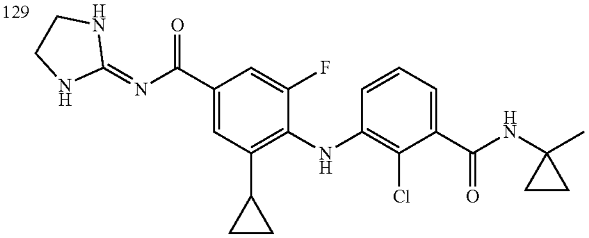 |
| 130 | 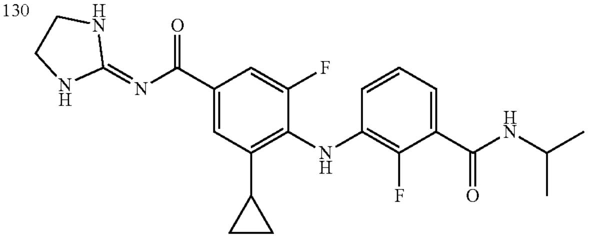 |
| 131 | 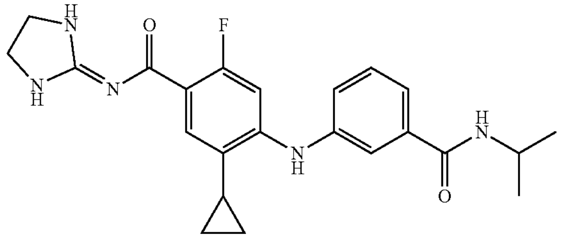 [SMILES: CC(C)NC(=O)c1cccc(Nc2cc(F)c(C(=O)N=C3NCCN3)cc2C2CC2)c1] |
| 132 | 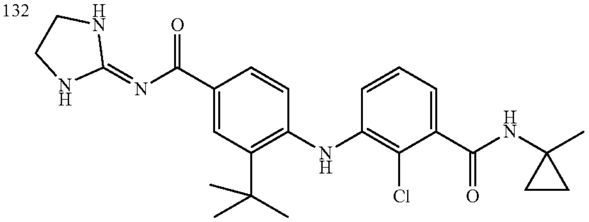 |

-continued
| No | Structure |
| --- | --- |
| 133 | 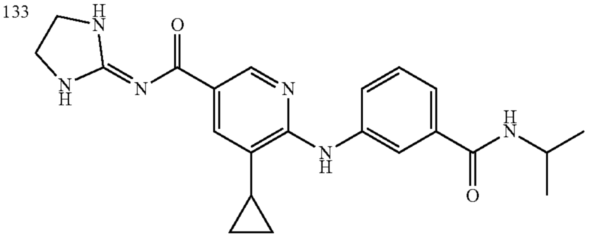 |
| 134 | 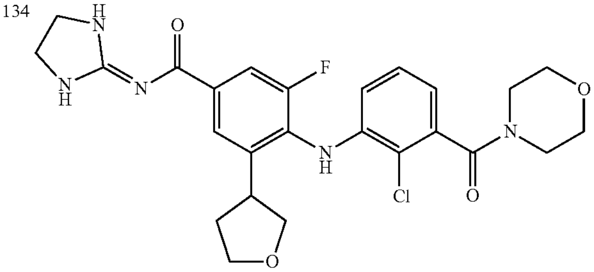 |
| 135 | 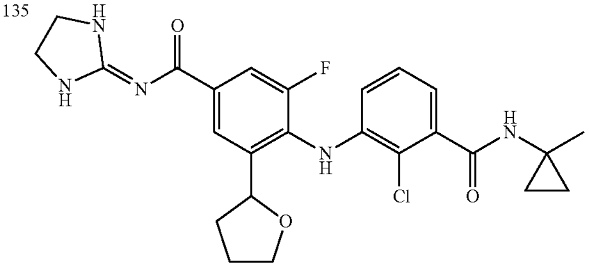 |
| 136 | 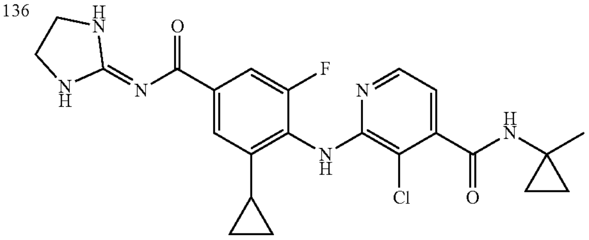 |
| 137 | 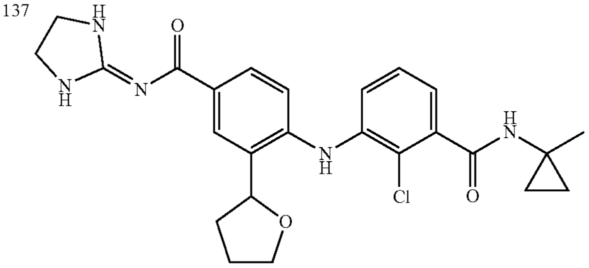 |
| 138 | 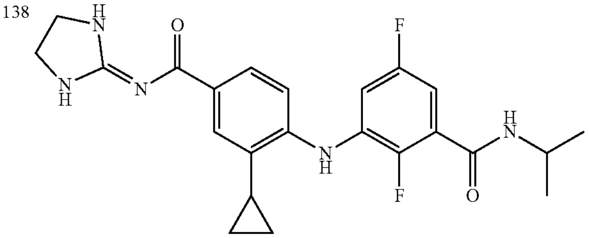 |

-continued
| No | Structure |
|---|---|
| 139 | 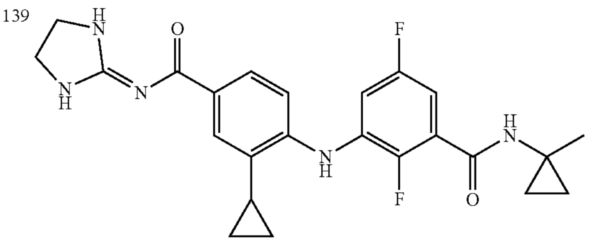 |
| 140 | 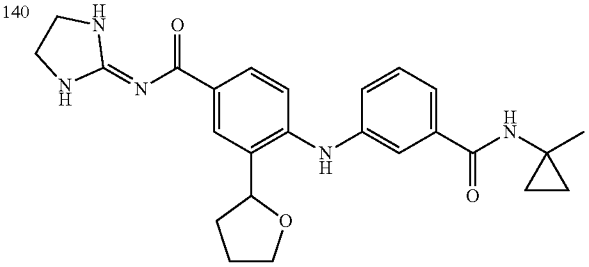 |
| 141 | 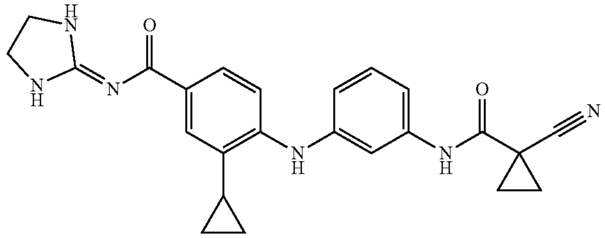 [SMILES: N#CC1(C(=O)Nc2cccc(Nc3ccc(C(=O)N=C4NCCN4)cc3C3CC3)c2)CC1] |
| 142 | 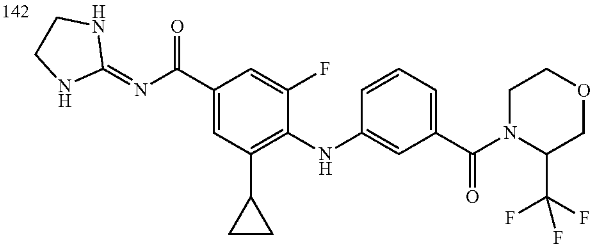 |
| 143 | 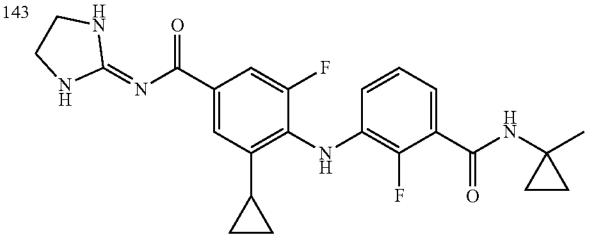 |
| 144 | 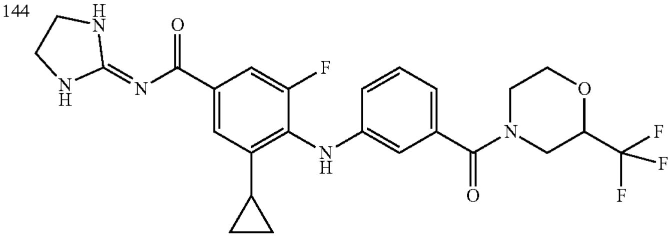

-continued
| No | Structure |
|---|---|
| 145 | 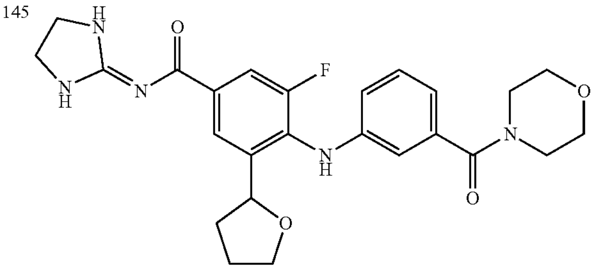 |
| 146 | 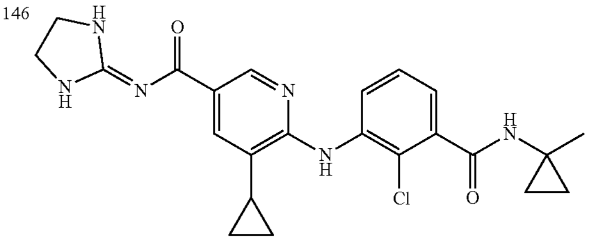 |
| 147 | 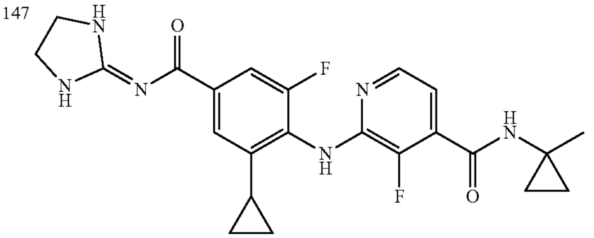 |
| 148 | 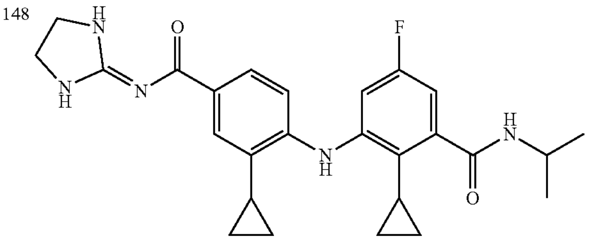 |
| 149 | 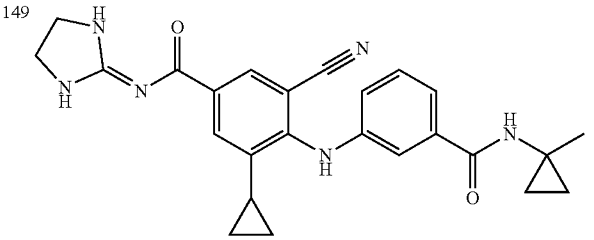 |
| 150 | 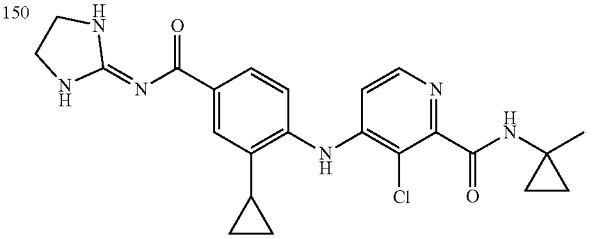 |

-continued
| No | Structure |
|---|---|
| 151 | 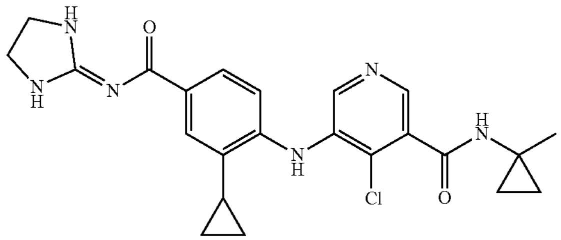 [SMILES: CC1(NC(=O)c2cncc(Nc3ccc(C(=O)N=C4NCCN4)cc3C3CC3)c2Cl)CC1] |
| 152 | 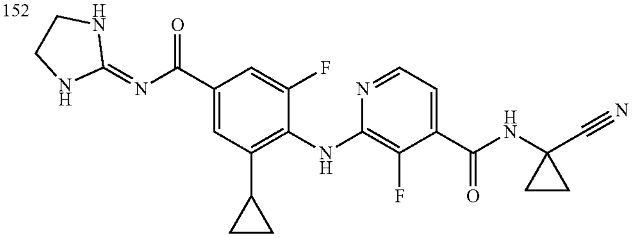 |
| 153 | 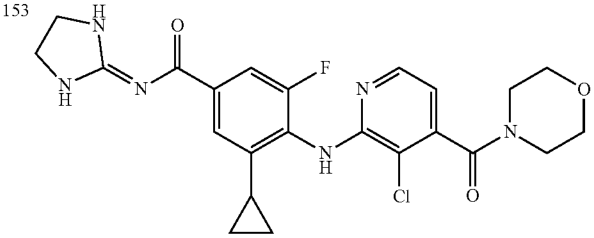 |
| 154 | 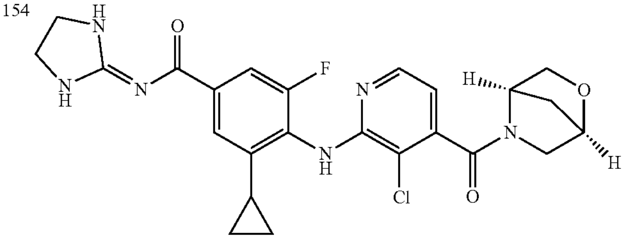 |
| 155 | 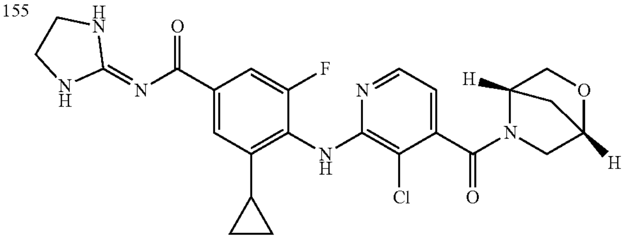 |
| 156 | 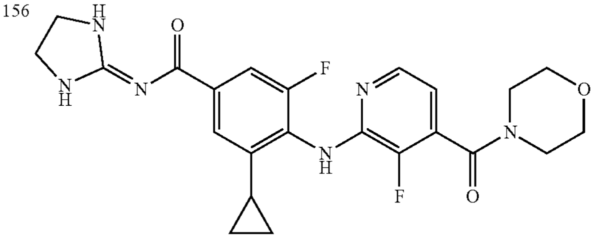 |

-continued
| No | Structure |
| --- | --- |
| 157 | 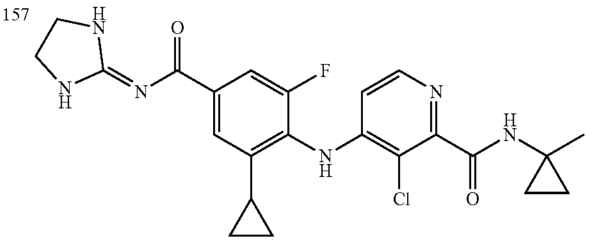 |
| 158 | 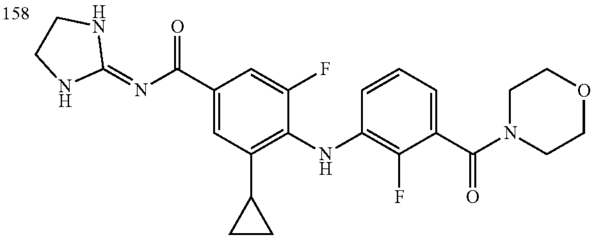 |
| 159 | 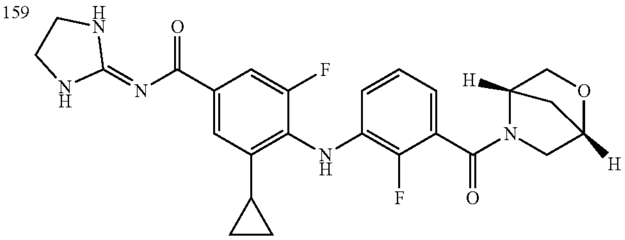 |
| 160 | 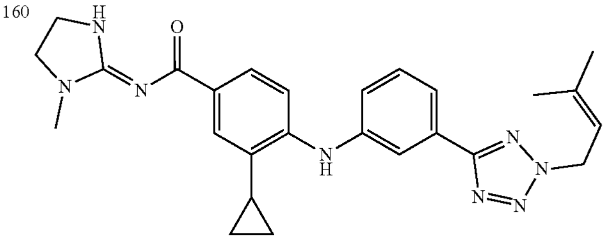 |
| 161 | 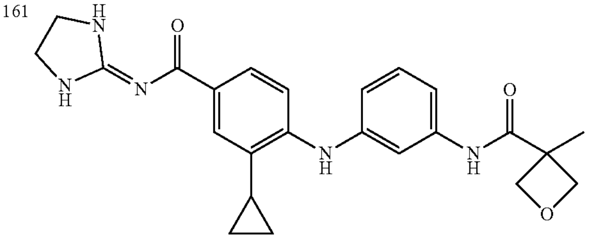 |
| 162 | 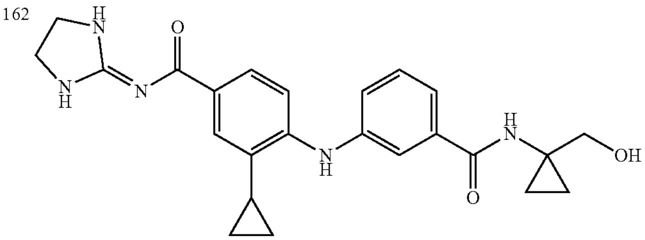 |

-continued
| No | Structure |
|---|---|
| 163 | 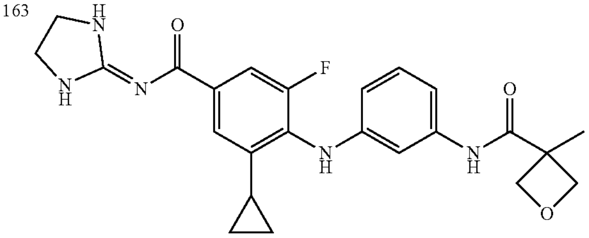 |
| 164 | 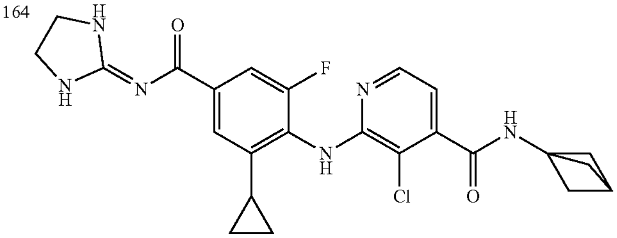 |
| 165 | 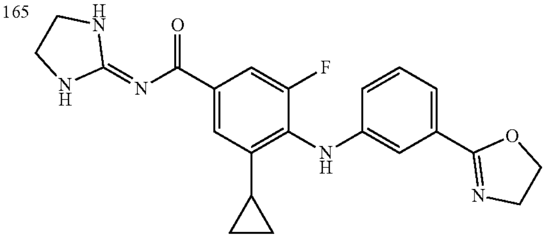 |
| 166 | 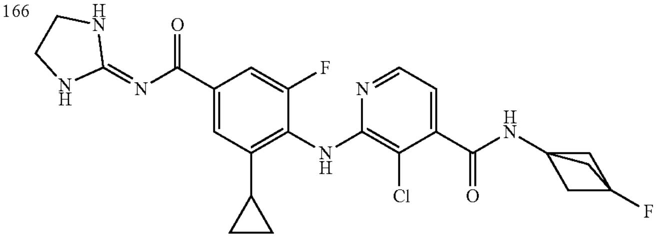 |
| 167 | 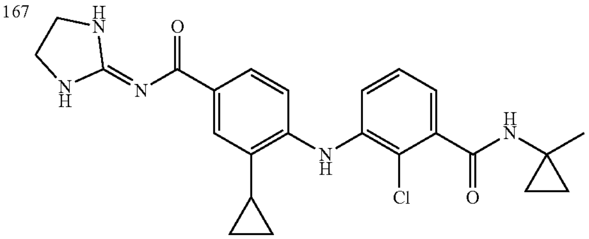 |
| 168 | 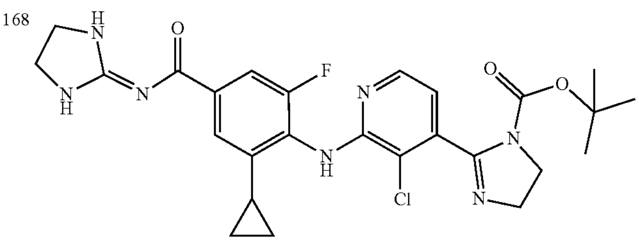 |

-continued
No Structure
169
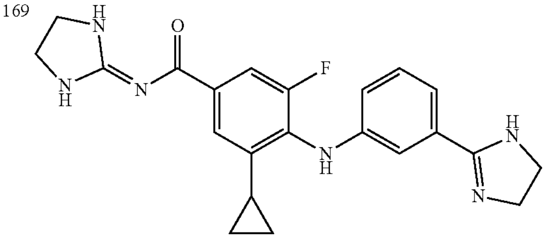
170
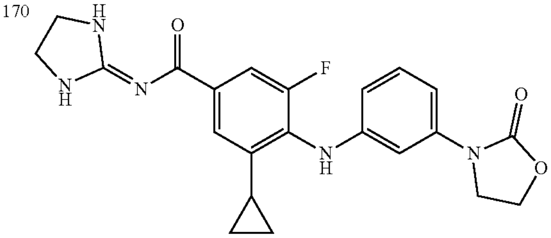
171
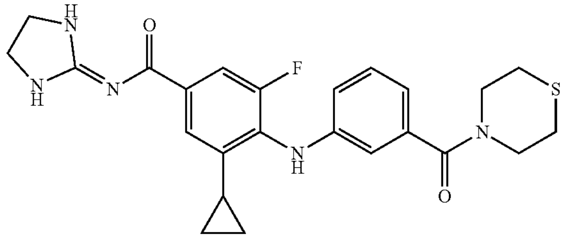 [SMILES: O=C(N=C1NCCN1)c1cc(F)c(Nc2cccc(C(=O)N3CCSCC3)c2)c(C2CC2)c1]
172
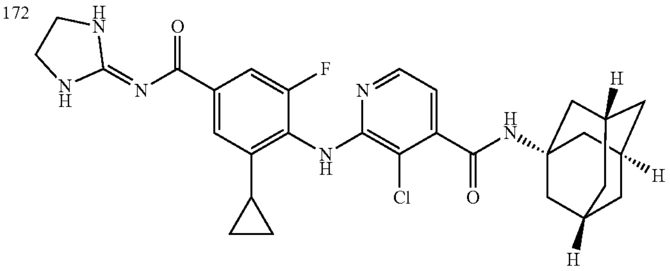
173
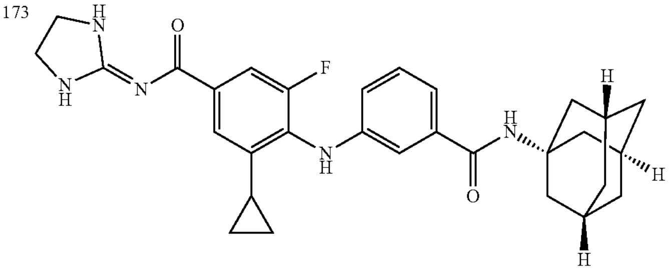
174
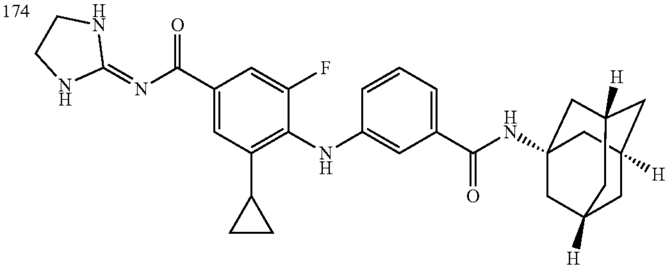

-continued
| No | Structure |
|---|---|
| 175 | 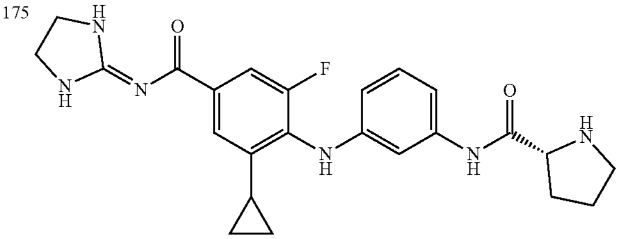 |
| 176 | 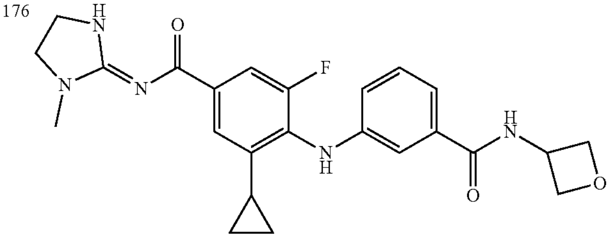 |
| 177 | 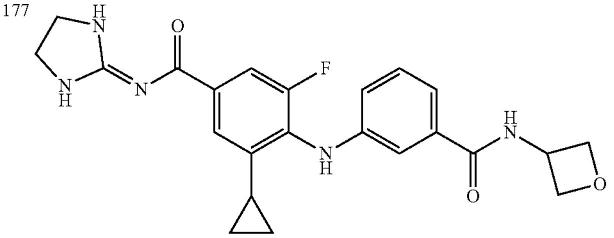 |
| 178 | 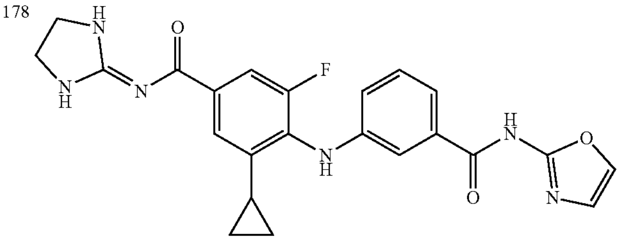 |
| 179 | 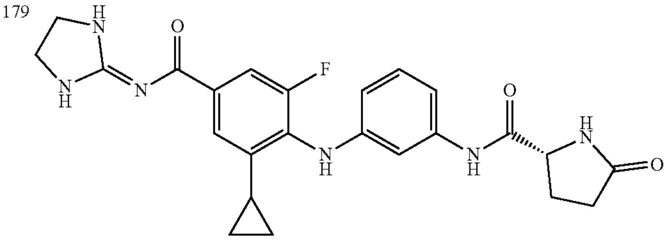 |
| 180 | 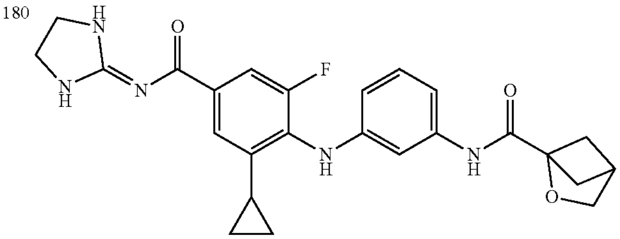 |

-continued
| No | Structure |
| --- | --- |
| 181 | 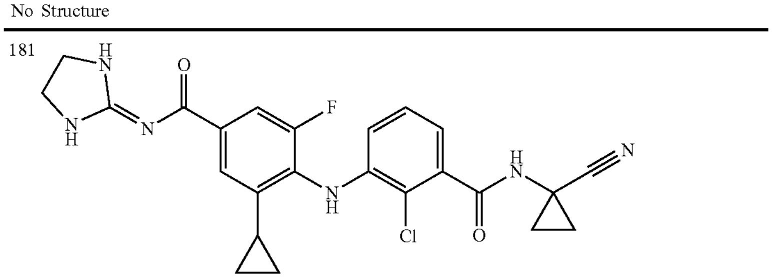 |
or a pharmaceutically acceptable salt thereof.
17. A compound selected from the group consisting of:
| | |
| --- | --- |
| 76 | 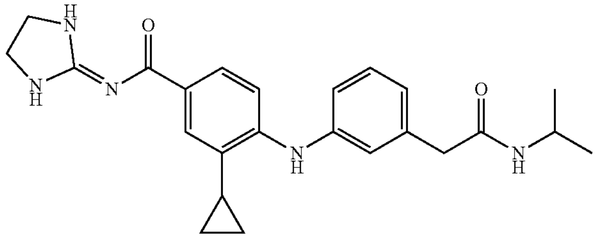 [SMILES: CC(C)NC(=O)Cc1cccc(Nc2ccc(C(=O)N=C3NCCN3)cc2C2CC2)c1] |
| 83 | 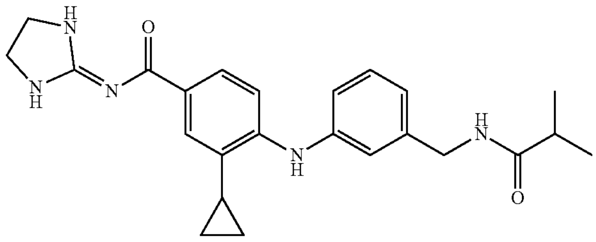 [SMILES: CC(C)C(=O)NCc1cccc(Nc2ccc(C(=O)N=C3NCCN3)cc2C2CC2)c1] |
| 166 | 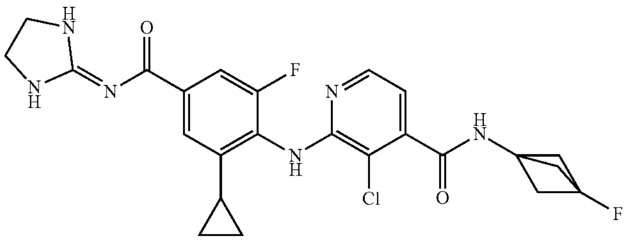 [SMILES: O=C(N=C1NCCN1)c1cc(F)c(Nc2nccc(C(=O)NC34CC(F)(C3)C4)c2Cl)c(C2CC2)c1] |

-continued and

171 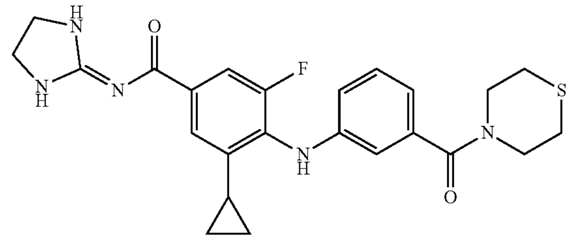 [SMILES: O=C(N=C1NCCN1)c1cc(F)c(Nc2cccc(C(=O)N3CCSCC3)c2)c(C2CC2)c1]

or a pharmaceutically acceptable salt thereof.

18. A method for treating respiratory syncytial virus (RSV) infection in a subject, the method comprising administering to the subject in need thereof a therapeutically effective quantity of at least one compound according to claim 17, or a pharmaceutically acceptable salt thereof.

19. A method for treating a ribonucleic acid (RNA) virus infection in a subject, the method comprising administering to the subject in need thereof a therapeutically effective quantity of at least one compound according to claim 17, or a pharmaceutically acceptable salt thereof.

* * * * *